(12) United States Patent
Allen et al.

(10) Patent No.: US 8,003,663 B2
(45) Date of Patent: Aug. 23, 2011

(54) PYRAZOLO[3,4-B]PYRIDINE COMPOUNDS, AND THEIR USE AS PDE4 INHIBITORS

(75) Inventors: David George Allen, Stevenage (GB); Rodger Phillip Barnett, Ware (GB); Reshma Manesh Chudasama, Stevenage (GB); Caroline Jane Day, Stevenage (GB); Christopher David Edlin, Stevenage (GB); Leanda Jane Kindon, Stevenage (GB)

(73) Assignee: Glaxo Group Limited, Middlesex (GB)

( * ) Notice: Subject to any disclaimer, the term of this patent is extended or adjusted under 35 U.S.C. 154(b) by 838 days.

(21) Appl. No.: 11/831,325

(22) Filed: Jul. 31, 2007

(65) Prior Publication Data
US 2008/0058369 A1   Mar. 6, 2008

(30) Foreign Application Priority Data

Aug. 1, 2006  (GB) .................................. 0615286.2
Apr. 5, 2007  (GB) .................................. 0706790.3
Jul. 30, 2007  (GB) .................................. 0714815.8

(51) Int. Cl.
*A61K 31/437*   (2006.01)
*C07D 471/04*   (2006.01)

(52) U.S. Cl. ........................................ 514/303; 546/119

(58) Field of Classification Search .................. 546/119; 514/303
See application file for complete search history.

(56) References Cited

U.S. PATENT DOCUMENTS

| | | | | |
|---|---|---|---|---|
| 3,200,123 | A | 8/1965 | Richardson et al. | 260/288 |
| 2008/0058369 | A1 | 3/2008 | Allen et al. | 514/303 |
| 2009/0318494 | A1 | 12/2009 | Allen et al. | 514/303 |
| 2009/0325952 | A1 | 12/2009 | Allen et al. | 514/234.2 |

FOREIGN PATENT DOCUMENTS

| | | |
|---|---|---|
| DE | 21 01 691 | 3/1972 |
| EP | 1 099 701 | 5/2001 |
| WO | WO 96/40640 | 12/1996 |
| WO | WO 97/48683 | 12/1997 |
| WO | WO 98/41508 | 9/1998 |
| WO | WO 00/69849 | 11/2000 |
| WO | WO 01/21577 | 3/2001 |
| WO | WO 01/62737 | 8/2001 |
| WO | WO 02/08221 | 1/2002 |
| WO | WO 2005/058892 | 6/2005 |
| WO | WO 2005/090348 | 9/2005 |
| WO | WO 2005/090353 | 9/2005 |
| WO | WO 2007/036733 | 4/2007 |

OTHER PUBLICATIONS

Szallasi, A., et. al, "Vanilloid (Capsaicin) Receptors and Mechanisms" Pharmacological Reviews, Williams and Wilkins Inc., Baltimore, MD, US, vol. 51, No. 2, 1999, pp. 159-211, XP001105620, ISSN: 0031-6997.
Wai, N. Chan, et al.: "Evaluation of a series of anticonvulsant 1,2,3,4-tetrahydroisoquinolinolinyl-benzamides", BioOrg. Med. Chem., vol. 8, 2000, pp. 2085-2094, XP002239649.
Hishashi shinkai: "4-aminoquinolines: novel nociceptin antagonists with analgesic activity" J. Med. Chem., vol. 43, No. 24, 2000, pp. 4667-4677, XP002239650.
Patent Abstracts of Japan, vol. 1999, No. 2, Feb. 26, 1999 & JP 10 291988 A (Fujisawa Pharmaceut Co. Ltd), Nov. 4, 1998.
J. Jaen et al. "Kyurenic acid derivatives inhibit the binding of Nerve Growth Factor (NGF) to the Low-Affinity p75 NGF receptor" J. Med. Chem., vol. 38, No. 22, 1995, pp. 4439-4445, XP002239651.
Formulary, Rolfumalist: A new phosphodiesterase 4 inhibitor for chronic obstructive pulmonary disease, (2010), pp. 1-10.
Takizawa, et al., Recent patents on inflammation & Allergy drug discovery (2007), 1, pp. 13-19.
Patani, et al. Chem.. Rev. (1996), 96 pp. 3147-3176.
Non Final Office Action dated Jan. 19, 2011; U.S. Appl. No. 12/375,685.
U.S. Appl. No. 12/375,685, filed Jan. 2009, Allen et al.

*Primary Examiner* — Patricia L Morris
(74) *Attorney, Agent, or Firm* — Nora L. Stein; Theodore R. Furman

(57) ABSTRACT

The invention provides N-{[1,6-diethyl-4-(tetrahydro-2H-pyran-4-ylamino)-1H-pyrazolo [3,4-b]pyridin-5-yl]methyl}-4-({8-[(2-hydroxyethyl) (methyl)amino] octanoyl}amino)benzamide, whose formula is

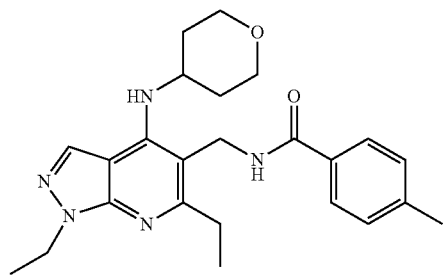

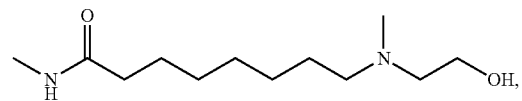

or a salt thereof, such as the monohydrochloride salt thereof. The invention also provides the use of the compound or salt as inhibitors of phosphodiesterase type IV (PDE4) and/or for the treatment and/or prophylaxis of inflammatory and/or allergic diseases such as chronic obstructive pulmonary disease (COPD), asthma, or rhinitis (e.g. allergic and/or non-allergic rhinitis).

8 Claims, No Drawings

PYRAZOLO[3,4-B]PYRIDINE COMPOUNDS, AND THEIR USE AS PDE4 INHIBITORS

The present invention relates to pyrazolo[3,4-b]pyridine compounds or salts thereof, processes for their preparation, intermediates usable in these processes, and pharmaceutical compositions containing the compounds or salts. The invention also relates to the use of the pyrazolo[3,4-b]pyridine compounds or salts thereof in therapy, for example as inhibitors of phosphodiesterase type IV (PDE4) and/or for the treatment and/or prophylaxis of inflammatory and/or allergic diseases such as chronic obstructive pulmonary disease (COPD), asthma, or rhinitis (e.g. allergic and/or non-allergic rhinitis).

BACKGROUND TO THE INVENTION

Phosphodiesterase 4 inhibitors (PDE4 inhibitors) may be useful in the treatment and/or prophylaxis of a variety of diseases/conditions, especially inflammatory and/or allergic diseases, in mammals such as humans, for example: chronic obstructive pulmonary disease (COPD) (e.g. chronic bronchitis and/or emphysema), asthma, rhinitis (e.g. allergic or non-allergic rhinitis), rheumatoid arthritis, atopic dermatitis, psoriasis, urticaria, allergic conjunctivitis, vernal conjunctivitis, eosinophilic granuloma, septic shock, inflammatory bowel disease (e.g. ulcerative colitis and/or Crohn's disease), reperfusion injury of the myocardium and/or brain, chronic glomerulonephritis, endotoxic shock, or adult respiratory distress syndrome, in mammals such as humans.

Chronic obstructive pulmonary disease (COPD) is often characterised by the presence of airflow obstruction due to chronic bronchitis and/or emphysema (e.g., see S. L. Wolda, *Emerging Drugs*, 2000, 5(3), 309-319).

PDE4 inhibitors, for example cilomilast and roflumilast, are thought to be effective in the treatment of COPD. For example, see S. L. Wolda, *Emerging Drugs*, 2000, 5(3), 309-319; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; A. M. Vignola, *Respiratory Medicine*, 2004, 98, 495-503; D. Spina, *Drugs*, 2003, 63(23), 2575-2594; and references cited in the aforementioned publications; G. Krishna et al., *Expert Opinion on Investigational Drugs*, 2004, 13(3), 255-267 (see especially pp. 259-261 and refs. 102-111 and 201 therein); and B. J. Lipworth, *The Lancet*, 2005, 365, 167-175.

The PDE4 inhibitor cilomilast (Ariflo™) at 15 mg orally twice daily appears to improve forced expiratory volume in 1s (FEV$_1$) in COPD patients (C. H. Compton et al., *The Lancet*, 2001, vol. 358, 265-270), and appears to have antiinflammatory effects in COPD patients (E. Gamble et al., *Am. J. Respir. Crit. Care Med.*, 2003, 168, 976-982). On cilomilast, see also R. D. Border et al., *Chest*, 2003, vol. 124 Suppl. 4, p. 170S (abstract) and J. D. Eddleston et al., *Am. J. Respir. Crit. Care Med.*, 2001, 163, A277 (abstract). The PDE4 inhibitor roflumilast appears to show small improvements in FEV$_1$ in COPD patients (see B. J. Lipworth, *The Lancet*, 2005, 365, 167-175, and refs 49-50 therein).

PDE4 inhibitors are thought to be effective in the treatment and/or prophylaxis of asthma (e.g. see M. A. Giembycz, *Drugs*, February 2000, 59(2), 193-212; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; P. J. Barnes, *Nature Reviews—Drug Discovery*, October 2004, 831-844; B. J. Lipworth, *The Lancet*, 2005, 365, 167-175; and references cited in the aforementioned publications).

The PDE4 inhibitor roflumilast, given orally at 500 ug once daily for 9 days, is reported to be effective in improving rhinal airflow during the treatment period (compared to placebo), in humans with histories of allergic rhinitis but asymptomatic at screening, and who were challenged with intranasal allergen provocation (pollen extracts) daily beginning the third day of treatment and each time approx. 2 hours after study drug administration (B. M. Schmidt et al., *J. Allergy & Clinical Immunology*, 108(4), 2001, 530-536).

PDE4 inhibitors may be effective in the treatment of rheumatoid arthritis (e.g. see H. J. Dyke et al., *Expert Opinion on Investigational Drugs*, January 2002, 11(1), 1-13; C. Burnouf et al., *Current Pharmaceutical Design*, 2002, 8(14), 1255-1296; and A. M. Doherty, *Current Opinion Chem. Biol.*, 1999, 3(4), 466-473; and references cited in these publications).

PDE4 inhibition has been suggested for the treatment of inflammatory bowel disease (e.g. ulcerative colitis and/or Crohn's disease), see K. H. Banner and M. A. Trevethick, *Trends Pharmacol. Sci.*, August 2004, 25(8), 430-436.

For the use of PDE4 inhibitors in atopic dermatitis, see for example:

J. M. Hanifin et al., "Type 4 phosphodiesterase inhibitors have clinical and in vitro anti-inflammatory effects in atopic dermatitis", *J. Invest. Dermatol.*, 1996, 107(1), 51-56; which reports reductions of inflammatory parameters in atopic dermatitis patients treated with PDE4 inhibitor CP80,633 (0.5% ointment, twice daily topical application);

C. E. M. Griffiths et al., "Randomized comparison of the type 4 phosphodiesterase inhibitor cipamfylline cream, cream vehicle and hydrocortisone 17-butyrate cream for the treatment of atopic dermatitis", *Br. J. Dermatol.*, 2002, 147(2), 299-307, which reports that cipamfylline (0.15%) cream is significantly more effective than vehicle, but significantly less effective than hydrocortisone 17-butyrate (0.1%) cream, in the treatment of atopic dermatitis patients;

T. C. Roos et al., "Recent advances in treatment strategies for atopic dermatitis", *Drugs*, 2004, 64(23), 2639-2666 (see e.g. page 2657 and refs. 201-209 therein);

A. M. Doherty, *Current Opinion Chem. Biol.*, 1999, 3(4), 466-473 (e.g. see p. 470); and H. J. Dyke et al., *Expert Opinion Invest. Drugs*, 2002, 11(1), 1-13 (e.g. see p. 7 and refs. 74, 75 and 76 cited therein);

and references cited in the above references.

For the use of the PDE4 inhibitors SB 207499 (cilomilast) and AWD 12-281 in mouse models of the allergic type of dermatitis, see W. Bäumer et al., *Eur. J. Pharmacol.*, 2002, 446, 195-200 and W. Bäumer et al., *J. Pharmacy Pharmacol.*, 2003, 55, 1107-1114.

WO 2004/056823 A1 (PCT/EP2003/014867, Glaxo Group Limited) discloses certain pyrazolo[3,4-b]pyridine compounds or salts thereof; and their use as PDE4 inhibitors.

WO 2004/024728 A2 (PCT/EP2003/011814, Glaxo Group Limited) discloses pyrazolo[3,4-b]pyridine compounds or salts thereof with a 4-NHR$^3$ group and a 5-C(O)—X group, according to the following formula, wherein X is NR$^4$R$^5$ or OR$^{5a}$, and R$^2$ is a hydrogen atom (H), methyl or C$_1$fluoroalkyl. These pyrazolo[3,4-b]pyridine compounds and salts are disclosed as being inhibitors of phosphodiesterase type IV (PDE4):

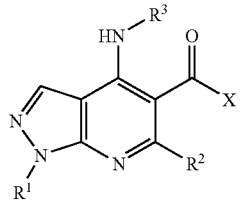

WO 2004/024728 has been reviewed, and WO 2004/056823 mentioned, in *Expert Opin. Ther. Patents,* 2005 (January edition), 15(1), 111-114.

Further pyrazolo[3,4-b]pyridine compounds or salts thereof, and their use as PDE4 inhibitors, are disclosed in patent publications WO 2005/058892 A1 (PCT/EP2004/014490), WO 2005/090348 A1 (PCT/GB2005/000983), WO 2005/090352 A1 (PCT/EP2005/003038), WO 2005/090353 A1 (PCT/GB2005/000976), WO 2005/090354 A1 (PCT/GB2005/000987) (all Glaxo Group Limited). Of these, WO 2005/090348 A1 discloses pyrazolo[3,4-b]pyridine compounds or salts thereof with a 4-NHR³ group and a 5-C(O)—NH—W group, according to the following formula, wherein W is Ar, —CR⁴R⁵Ar or a group (y) or (y1), and R² is $C_{2-6}$alkyl, $C_{3-6}$cycloalkyl or —(CH$_2$)$_n^4$C$_{3-6}$cycloalkyl:

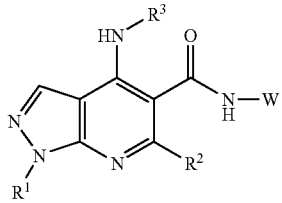

Copending patent application PCT/GB2006/003626, published on 5 Apr. 2007 as WO 2007/036733 A1, discloses pyrazolo[3,4-b]pyridine compounds of the following formula or salts thereof, and their use as PDE4 inhibitors:

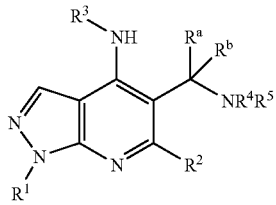

Copending patent application PCT/GB2006/003627, published on 5 Apr. 2007 as WO 2007/036734 A1, discloses N-{[1,6-diethyl-4-(tetrahydro-2H-pyran-4-ylamino)-1H-pyrazolo[3,4-b]pyridin-5-yl]methyl}-3-methyl-5-isoxazole-carboxamide or a salt thereof, and its use as PDE4 inhibitor.

THE INVENTION

We have now found new pyrazolo[3,4-b]pyridine compounds having a long side-chain containing a basic nitrogen atom, which compounds inhibit phosphodiesterase type IV (PDE4).

The present invention therefore provides a compound of formula (I) or a salt thereof (in particular, a pharmaceutically acceptable salt thereof):

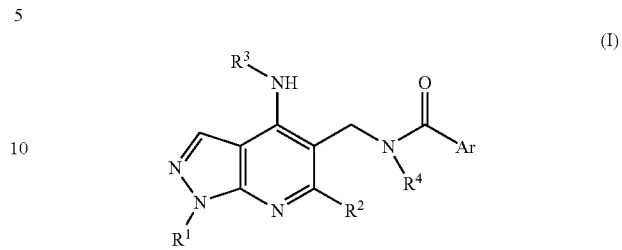

wherein Ar has the sub-formula (x):

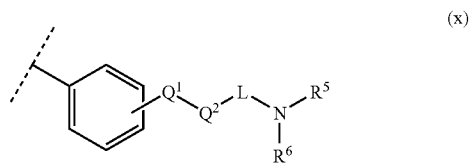

wherein:
$Q^1$ is NH or NMe, in which case $Q^2$ is —C(O)—, —S(O)$_2$—, —C(O)NH— or —C(O)NMe-;
or $Q^1$ is a bond or —O—, in which case $Q^2$ is a bond;
or $Q^1$ is —C(O)—, in which case $Q^2$ is NH or NMe;
or $Q^1$ is —S(O)$_2$—, in which case $Q^2$ is NH, NMe or a bond;
and L is (CH$_2$)$_n$ wherein n is 4, 5, 6, 7, 8, 9, 10, 11, 12 or 13;
or L is —(CH$_2$)$_{m^1}$-O—(CH$_2$)$_{m^2}$—, wherein it is the —(CH$_2$)$_{m^2}$— which is bonded to the NR⁵R⁶ group, and wherein m¹ is 1, 2, 3, 4, 5, 6, 7, 8 or 9, and m² is 2, 3, 4, 5, 6, 7, 8 or 9; provided that m¹+m² is 3, 4, 5, 6, 7, 8, 9, 10, 11 or 12, and provided that when m¹ is 1 then Q² is —C(O)—;
and R⁵ is a hydrogen atom (H), methyl, ethyl, n-propyl, iso-propyl, —CH$_2$CH$_2$OH, —CH$_2$CH(Me)OH, —CH$_2$CH$_2$CH$_2$OH, —CH$_2$CH$_2$OMe, or —CH$_2$CH$_2$CH$_2$OMe; and
R⁶ is $C_{1-4}$alkyl, or R⁶ is $C_{1-4}$alkyl substituted by one OH or OC$_{1-3}$alkyl (e.g. OMe) substituent which is not substituted at the alkyl carbon atom which is bonded to the nitrogen atom of the NR⁵R⁶ group (for example R⁶ can be —CH$_2$CH$_2$OH, —CH$_2$CH(Me)OH, —CH$_2$CH$_2$CH$_2$OH, —CH$_2$CH$_2$CH$_2$OH, —CH$_2$CH$_2$OMe, or —CH$_2$CH$_2$CH$_2$OMe);
or R⁵ and R⁶ taken together are —(CH$_2$)$_2$—X—(CH$_2$)$_2$—, —(CH$_2$)$_2$—X—(CH$_2$)$_3$—, —(CH$_2$)$_{p^1}$—, —CHR$^{7a}$—(CH$_2$)$_{p^2}$—, or —(CH$_2$)$_{p^3}$—CHR$^{7b}$—(CH$_2$)$_{p^4}$—; in which:
X is O or NR⁸ wherein R⁸ is a hydrogen atom (H) or $C_{1-3}$alkyl (e.g. H or methyl);
R$^{7a}$ is —CH$_2$OH, —CH$_2$OC$_{1-3}$alkyl (e.g. —CH$_2$OMe), —CH$_2$CH$_2$OH, —CH$_2$CH$_2$OC$_{1-3}$alkyl (e.g. —CH$_2$CH$_2$OMe), or $C_{1-3}$alkyl such as methyl (e.g. R$^{7a}$ can be —CH$_2$OH or preferably —CH$_2$OMe);
R$^{7b}$ is OH, OC$_{1-3}$alkyl (e.g. OMe), —CH$_2$OH, —CH$_2$OC$_{1-3}$alkyl (e.g. —CH$_2$OMe), —CH$_2$CH$_2$OH, —CH$_2$CH$_2$OC$_{1-3}$ alkyl (e.g. —CH$_2$CH$_2$OMe), or $C_{1-3}$alkyl such as methyl (e.g. R$^{7b}$ can be OH or OMe);
p¹ is 4, 5 or 6 (e.g. 4 or 5),
p² is 3, 4 or 5 (e.g. 3 or 4),
p³ is 1 or 2 and p⁴ is 2, 3 or 4 (e.g. 2 or 3), provided that p³+p⁴ is 3, 4 or 5 (e.g. 3 or 4);
and wherein:

$R^1$ is $C_{1-3}$alkyl, —$CH_2$—$C_{1-2}$-fluoroalkyl, or —$CH_2CH_2OH$;

$R^2$ is a hydrogen atom (H), methyl, ethyl, n-propyl, isopropyl, n-butyl, $C_{1-2}$-fluoroalkyl, cyclopropyl, cyclobutyl, or (cyclopropyl)methyl-;

$R^4$ is a hydrogen atom (H), methyl or ethyl; and $R^3$ is optionally substituted $C_{4-7}$cycloalkyl, or optionally substituted mono-unsaturated-$C_{5-7}$cycloalkenyl, or an optionally substituted heterocyclic group of sub-formula (aa), (bb) or (cc), or a bicyclic group of sub-formula (ee);

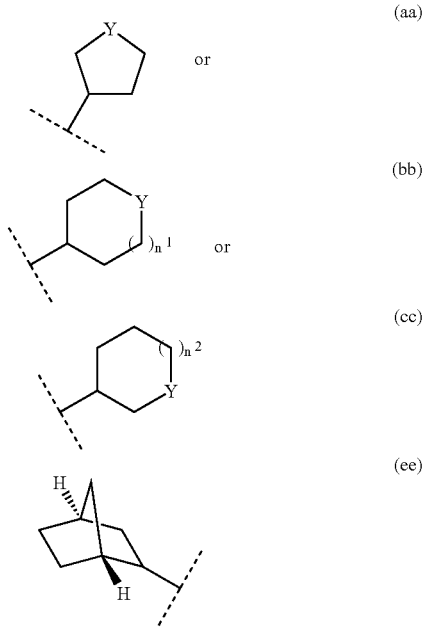

in which $n^1$ and $n^2$ independently are 1 or 2; and in which Y is O, S, $SO_2$, or $NR^{10}$; where $R^{10}$ is a hydrogen atom (H), methyl, $C(O)NH_2$, $C(O)$-methyl, or $C(O)$—$C_1$ fluoroalkyl;

and wherein, when $R^3$ is optionally substituted $C_{4-7}$cycloalkyl, then $R^3$ is $C_{4-7}$cycloalkyl optionally substituted on a ring carbon(s) with one or two substituents independently being: oxo (═O); OH; methoxy; $C_1$fluoroalkoxy; $NH_2$; $C_{1-2}$alkyl; $C_1$fluoroalkyl; —$CH_2OH$; —$CH(Me)OH$; —$CH_2CH_2OH$; —$CH_2NH_2$; —$C(O)OH$; —$C(O)NHR^{24}$ wherein $R^{24}$ is H or methyl; —$C(O)R^{25}$ wherein $R^{25}$ is methyl; fluoro; hydroxyimino (═N—OH); or ($C_{1-2}$ alkoxy)imino (═N—$OR^{26}$ where $R^{26}$ is $C_{1-2}$alkyl); and wherein any OH, methoxy, fluoroalkoxy or $NH_2$ substituent is not bonded to the $R^3$ ring carbon bonded to the —NH— group of formula (I);

and wherein, when $R^3$ is the optionally substituted heterocyclic group of sub-formula (aa), (bb) or (cc), then the heterocyclic group of sub-formula (aa), (bb) or (cc) is optionally substituted on a ring carbon(s) with one or two oxo (═O) substituents;

and wherein, when $R^3$ is optionally substituted mono-unsaturated-$C_{5-7}$cycloalkenyl, then the cycloalkenyl is optionally substituted on a ring carbon with one substituent being fluoro or methyl, and the $R^3$ ring carbon bonded to the —NH— group of formula (I) does not partake in the cycloalkenyl double bond;

and wherein:

when $R^3$ is the heterocyclic group of sub-formula (aa) and Y is $NR^{10}$, then $R^{10}$ is not C(O)-methyl, or C(O)—$C_1$fluoroalkyl; and when $R^3$ is the heterocyclic group of sub-formula (bb) and Y is $NR^{10}$, then $R^{10}$ is not methyl; and when $R^3$ is the heterocyclic group of sub-formula (cc), then Y is O, S, $SO_2$ or $NR^{10}$ wherein $R^{10}$ is H or methyl;

and wherein:

when $R^3$ is optionally substituted $C_{4-7}$cycloalkyl, then any —$C(O)NHR^{24}$ or —$C(O)R^{25}$ substituent on a ring carbon is: at the 3-position of a $R^3$ cyclobutyl ring; or at the 3- or 4-position of a $R^3$ cyclopentyl ring; or at the 4-position of a $R^3$ cyclohexyl ring; or at the 3-, 4-, 5- or 6-position of a $R^3$ cycloheptyl ring (wherein, in this connection, the 1-position of the $R^3$ cycloalkyl ring is deemed to be the connection point to the —NH— in formula (I), that is the ring atom connecting to the —NH— in formula (I));

and wherein:

when $R^3$ is optionally substituted $C_{4-7}$cycloalkyl, then any OH, methoxy, fluoroalkoxy, —$CH_2OH$, —$CH(Me)OH$, —$CH_2CH_2OH$, —$CH_2NH_2$, or —$C(O)OH$ substituent on a ring carbon is: at the 3-position of a $R^3$ cyclobutyl ring; or at the 3- or 4-position of a $R^3$ cyclopentyl ring; or at the 3-, 4- or 5-position of a $R^3$ cyclohexyl ring; or at the 3-, 4-, 5- or 6-position of a $R^3$ cycloheptyl ring.

In compounds, for example in the compounds of formula (I), an "alkyl" group or moiety may be straight-chain or branched. Alkyl groups, for example $C_{1-8}$alkyl or $C_{1-6}$alkyl or $C_{1-4}$alkyl or $C_{1-3}$alkyl or $C_{1-2}$alkyl, which may be employed include $C_{1-6}$alkyl or $C_{1-4}$alkyl or $C_{1-3}$alkyl or $C_{1-2}$alkyl such as methyl, ethyl, n-propyl, n-butyl, n-pentyl, or n-hexyl or any branched isomers thereof such as isopropyl, t-butyl, sec-butyl, isobutyl, 3-methylbutan-2-yl, 2-ethylbutan-1-yl, or the like.

A corresponding meaning is intended for "alkoxy", "alkylene", and like terms derived from alkyl. For example, "alkoxy" such as $C_{1-6}$alkoxy or $C_{1-4}$alkoxy or $C_{1-2}$alkoxy includes methoxy, ethoxy, propyloxy, and oxy derivatives of the alkyls listed above. "Alkylsulfonyl" such as $C_{1-4}$alkylsulfonyl includes methylsulfonyl (methanesulfonyl), ethylsulfonyl, and others derived from the alkyls listed above.

"Alkylsulfonyloxy" such as $C_{1-4}$alkylsulfonyloxy includes methanesulfonyloxy (methylsulfonyloxy), ethanesulfonyloxy, et al.

"Cycloalkyl", for example $C_{3-8}$cycloalkyl (e.g. $C_{4-7}$cycloalkyl), includes cyclopropyl, cyclobutyl, cyclopentyl, cyclohexyl, cycloheptyl, cyclooctyl, and the like. Suitably, a $C_{3-8}$cycloalkyl group can be $C_{3-6}$cycloalkyl or $C_{5-6}$cycloalkyl or $C_{4-7}$cycloalkyl or $C_{6-7}$cycloalkyl, that is contains a 3-6 membered or 5-6 membered or 4-7 membered or 6-7 membered carbocyclic ring.

"Fluoroalkyl" includes alkyl groups with one, two, three, four, five or more fluorine substituents, for example $C_{1-4}$fluoroalkyl or $C_{1-3}$fluoroalkyl or $C_{1-2}$fluoroalkyl such as monofluoromethyl, difluoromethyl, trifluoromethyl, pentafluoroethyl, 2,2,2-trifluoroethyl ($CF_3CH_2$—), 2,2-difluoroethyl ($CHF_2CH_2$—), 2-fluoroethyl ($CH_2FCH_2$—), etc.

"Fluoroalkoxy" includes $C_{1-4}$fluoroalkoxy or $C_{1-2}$fluoroalkoxy such as trifluoromethoxy, pentafluoroethoxy, monofluoromethoxy, difluoromethoxy, etc.

A halogen atom ("halo") present in compounds, for example in the compounds of formula (I), means a fluorine, chlorine, bromine or iodine atom ("fluoro", "chloro", "bromo" or "iodo"), for example fluoro, chloro or bromo.

When the specification states that atom or moiety A is "bonded" or "attached" to atom or moiety B, it means that atom/moiety A is directly bonded to atom/moiety B usually by means of a covalent bond or a double covalent bond, and excludes A being indirectly attached to B via one or more intermediate atoms/moieties (e.g. excludes A-C-B); unless it is clear from the context that another meaning is intended.

In the invention, Ar has the sub-formula (x).

Ar can be of sub-formula (x1), (x2) or (x3):

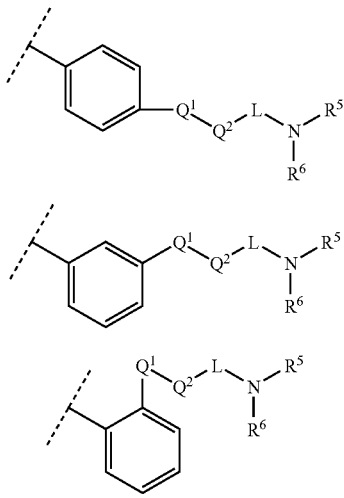

Ar can for example be of sub-formula (x1) or (x3). Preferably, Ar is of sub-formula (x1).

In one embodiment, $Q^1$ is NH or NMe (e.g. NH), in which case $Q^2$ is —C(O)—, —S(O)$_2$— or —C(O)NH— (e.g. —C(O)— or —S(O)$_2$—);

or $Q^1$ is a bond or —O—, in which case $Q^2$ is a bond;

or $Q^1$ is —C(O)—, in which case $Q^2$ is NH or NMe (e.g. NH);

or $Q^1$ is —S(O)$_2$—, in which case $Q^2$ is NH or NMe or a bond (e.g. NH or NMe such as NH).

In one embodiment, suitably, $Q^1$ is NH or NMe (e.g. NH), in which case $Q^2$ is —C(O)—;

or $Q^1$ is a bond, in which case $Q^2$ is a bond;

or $Q^1$ is —C(O)—, in which case $Q^2$ is NH or NMe (e.g. NH).

Suitably, $Q^1$ is NH or NMe (e.g. NH), in which case $Q^2$ is —C(O)—;

or $Q^1$ is a bond, in which case $Q^2$ is a bond.

L is (CH$_2$)$_n$ or L is —(CH$_2$)$_{m^1}$—O—(CH$_2$)$_{m^2}$—.

Typically, L is (CH$_2$)$_n$.

Suitably, n is 5, 6, 7, 8, 9, 10 or 11, such as 5, 6, 7, 8, 9 or 10.

Preferably, n is 6, 7, 8 or 9, such as 7.

$m^1$ can for example be 2, 3, 4, 5, 6, 7, 8 or 9. In particular, $m^1$ is 2, 3, 4, 5 or 6.

Suitably, $m^1$ is 3, 4 or 5. Preferably, $m^1$ is 4.

In particular, $m^2$ is 2, 3, 4, 5 or 6. Suitably, $m^2$ is 3, 4 or 5. Preferably, $m^2$ is 4.

$m^1+m^2$ can for example be 4, 5, 6, 7, 8, 9, 10, 11 or 12. In particular, $m^1+m^2$ is 4, 5, 6, 7, 8, 9 or 10.

Suitably, $m^1+m^2$ is 6, 7, 8, 9 or 10. Preferably, $m^1+m^2$ is 8.

In one embodiment, when L is (CH$_2$)$_n$, then:

$Q^1$ is NH or NMe (e.g. NH), in which case $Q^2$ is —C(O)—, —S(O)$_2$—, —C(O)NH— or —C(O)NMe- (e.g. —C(O)— or —S(O)$_2$—);

or $Q^1$ is a bond or —O— (e.g. a bond), in which case $Q^2$ is a bond;

or $Q^1$ is —C(O)—, in which case $Q^2$ is NH or NMe (e.g. NH);

or $Q^1$ is —S(O)$_2$—, in which case $Q^2$ is NH or NMe or a bond (e.g. NH or NMe such as NH);

and when L is —(CH$_2$)$_{m^1}$—O—(CH$_2$)$_{m^2}$—, then:

$Q^1$ is NH or NMe (e.g. NH), in which case $Q^2$ is —C(O)—;

or $Q^1$ is a bond or —O— (e.g. a bond), in which case $Q^2$ is a bond;

or $Q^1$ is —C(O)—, in which case $Q^2$ is NH or NMe (e.g. NH).

In one embodiment, when L is (CH$_2$)$_n$, then:

$Q^1$ is NH or NMe (e.g. NH), in which case $Q^2$ is —C(O)—, —S(O)$_2$—, —C(O)NH— or —C(O)NMe- (e.g. —C(O)— or —S(O)$_2$—);

or $Q^1$ is a bond or —O— (e.g. a bond), in which case $Q^2$ is a bond;

or $Q^1$ is —C(O)—, in which case $Q^2$ is NH or NMe (e.g. NH);

or $Q^1$ is —S(O)$_2$—, in which case $Q^2$ is NH or NMe or a bond (e.g. NH or NMe such as NH);

and when L is —(CH$_2$)$_{m^1}$—O—(CH$_2$)$_{m^2}$—, then:

$Q^1$ is a bond or —O— (e.g. a bond), in which case $Q^2$ is a bond.

In one embodiment, suitably, when L is (CH$_2$)$_n$, then:

$Q^1$ is NH or NMe (e.g. NH), in which case $Q^2$ is —C(O)—;

or $Q^1$ is a bond, in which case $Q^2$ is a bond;

or $Q^1$ is —C(O)—, in which case $Q^2$ is NH or NMe (e.g. NH);

and when L is —(CH$_2$)$_{m^1}$—O—(CH$_2$)$_{m^2}$—, then $Q^1$ is a bond, and $Q^2$ is a bond.

Suitably, when L is (CH$_2$)$_n$, then:

$Q^1$ is NH, in which case $Q^2$ is —C(O)—;

or $Q^1$ is a bond, in which case $Q^2$ is a bond;

and when L is —(CH$_2$)$_{m^1}$—O—(CH$_2$)$_{m^2}$—, then $Q^1$ is a bond, and $Q^2$ is a bond.

Suitably, (when $R^5$ and $R^6$ are not taken together), $R^5$ is a hydrogen atom (H), methyl, ethyl, n-propyl, isopropyl, or —CH$_2$CH$_2$OH. Preferably, $R^5$ is methyl, ethyl, n-propyl or isopropyl, such as methyl.

Suitably, (when $R^5$ and $R^6$ are not taken together), $R^6$ is —CH$_2$CH$_2$OH, —CH$_2$CH(Me)OH, —CH$_2$CH$_2$CH$_2$OH, —CH$_2$CH$_2$CH$_2$CH$_2$OH, —CH$_2$CH$_2$OMe, or —CH$_2$CH$_2$CH$_2$OMe. Preferably, $R^6$ is —CH$_2$CH$_2$OH.

In one embodiment, when $R^5$ and $R^6$ are taken together, then $R^5$ and $R^6$ taken together can be —(CH$_2$)$_2$—X—(CH$_2$)$_2$—, —(CH$_2$)$_{p^1}$—, —CHR$^{7a}$—(CH$_2$)$_{p^2}$—, or —(CH$_2$)$_{p^3}$—CHR$^{7b}$—(CH$_2$)$_{p^4}$—.

Suitably, when $R^5$ and $R^6$ are taken together, then $R^5$ and $R^6$ taken together are —(CH$_2$)$_2$—X—(CH$_2$)$_2$—, —(CH$_2$)$_{p^1}$—, or —CHR$^{7a}$—(CH$_2$)$_{p^2}$—.

$R^8$ can be for example a hydrogen atom (H) or methyl, such as methyl.

X is suitably O.

$R^{7a}$ can for example be —CH$_2$OH, —CH$_2$OMe, —CH$_2$CH$_2$OH, —CH$_2$CH$_2$OMe, or C$_{1-3}$alkyl such as methyl.

$R^{7a}$ is suitably —CH$_2$OH or preferably —CH$_2$OMe.

$R^{7b}$ can for example be OH, OMe, —CH$_2$OH, or —CH$_2$OMe or methyl.

$R^{7b}$ can for example be OH or OMe.

$p^1$ can suitably be 4 or 5, such as 4.

$p^2$ can suitably be 3 or 4, such as 3.

$p^4$ can suitably be 2 or 3, provided that $p^3+p^4$ is 3, 4 or 5.

$p^3+p^4$ can suitably be 3 or 4.

When $R^1$ is C$_{1-3}$alkyl or —CH$_2$—C$_{1-2}$fluoroalkyl, it can be straight-chained or branched. When $R^1$ is C$_{1-3}$alkyl then it can be methyl, ethyl, n-propyl, or isopropyl. When $R^1$ is —CH$_2$—C$_{1-2}$fluoroalkyl: then $R^1$ can for example be —CH$_2$—C$_1$fluoroalkyl such as 2,2,2-trifluoroethyl (CF$_3$CH$_2$—), 2,2-difluoroethyl (CHF$_2$CH$_2$—), or 2-fluoroethyl (CH$_2$FCH$_2$—).

In the invention, $R^1$ is C$_{1-3}$alkyl (e.g. methyl, ethyl or n-propyl), —CH$_2$—C$_{1-2}$fluoroalkyl or —CH$_2$CH$_2$OH. $R^1$ for example can be C$_{1-3}$alkyl, —CH$_2$—C$_1$fluoroalkyl, or —CH$_2$CH$_2$OH.

Suitably, $R^1$ is $C_{2-3}$alkyl (e.g. ethyl or n-propyl), —$CH_2$—$C_1$fluoroalkyl (e.g. $CF_3$—$CH_2$—) or —$CH_2CH_2OH$.

Preferably, $R^1$ is ethyl, n-propyl or —$CH_2CH_2OH$.

Most preferably, $R^1$ is ethyl.

$R^2$ can for example be a hydrogen atom (H), methyl, ethyl, n-propyl, isopropyl, $C_1$fluoroalkyl (such as $CF_3$ or $CHF_2$ or $CH_2F$), $C_2$fluoroalkyl such as $C_2F_5$ or $C_1$fluoroalkyl-$CH_2$— [e.g. 2,2,2-trifluoroethyl ($CF_3CH_2$—), 2,2-difluoroethyl ($CHF_2CH_2$—) or 2-fluoroethyl ($CH_2FCH_2$—)], or cyclopropyl.

$R^2$ can for example be methyl, ethyl, $C_1$fluoroalkyl (such as $CF_3$ or $CHF_2$ or $CH_2F$), or $C_2$fluoroalkyl such as $C_2F_5$ or $C_1$fluoroalkyl-$CH_2$— [e.g. 2,2,2-trifluoroethyl ($CF_3CH_2$—), 2,2-difluoroethyl ($CHF_2CH_2$—) or 2-fluoroethyl ($CH_2FCH_2$—)].

$R^2$ can for example be a hydrogen atom (H), methyl, ethyl or $C_1$fluoroalkyl (such as $CF_3$ or $CHF_2$ or $CH_2F$). Suitably, $R^2$ is a hydrogen atom (H), methyl or ethyl. Alternatively, suitably, $R^2$ is methyl, ethyl or $C_1$fluoroalkyl (such as $CF_3$ or $CHF_2$ or $CH_2F$).

Preferably, $R^2$ is methyl or ethyl.

Most preferably, $R^2$ is ethyl.

$R^4$ can for example be a hydrogen atom (H) or methyl.

Preferably, $R^4$ is a hydrogen atom (H).

Preferably, in $R^3$ there is one substituent on a ring carbon or no substituent on a ring carbon.

Preferably, $R^3$ is the optionally substituted $C_{4-7}$cycloalkyl or the optionally substituted heterocyclic group of sub-formula (aa), (bb) or (cc).

Optionally, when $R^3$ is optionally substituted $C_{4-7}$cycloalkyl, it is not unsubstituted cyclopentyl. In this case, suitably, $R^3$ is optionally substituted $C_{6-7}$cycloalkyl or optionally substituted cyclobutyl.

When $R^3$ is optionally substituted $C_{4-7}$cycloalkyl, it is suitably optionally substituted $C_{6-7}$cycloalkyl or optionally substituted cyclobutyl, preferably optionally substituted $C_6$cycloalkyl (i.e. optionally substituted cyclohexyl).

When $R^3$ is optionally substituted $C_{4-7}$cycloalkyl, then $R^3$ is $C_{4-7}$cycloalkyl (e.g. $C_{6-7}$cycloalkyl or cyclobutyl) optionally substituted on a ring carbon(s) with one or two substituents independently being (e.g. one substituent being): oxo (=O); OH; methoxy; $C_1$fluoroalkoxy (e.g. trifluoromethoxy or difluoromethoxy); $NH_2$; $C_{1-2}$alkyl such as methyl; $C_1$fluoroalkyl such as —$CH_2F$ or —$CHF_2$; —$CH_2OH$; —$CH(Me)OH$; —$CH_2CH_2OH$; —$CH_2NH_2$; —C(O)OH; —C(O)NHR$^{24}$ wherein $R^{24}$ is H or methyl (preferably H); —C(O)R$^{25}$ wherein $R^{25}$ is methyl; fluoro; hydroxyimino (=N—OH); or ($C_{1-2}$alkoxy)imino (=N—OR$^{26}$ where $R^{26}$ is $C_{1-2}$alkyl); and wherein any OH, methoxy, fluoroalkoxy or $NH_2$ substituent is not bonded to the $R^3$ ring carbon bonded to the —NH— group of formula (I).

When $R^3$ is optionally substituted $C_{4-7}$cycloalkyl, then $R^3$ can suitably be $C_{4-7}$cycloalkyl (e.g. $C_{6-7}$cycloalkyl or cyclobutyl) optionally substituted on a ring carbon(s) with one or two substituents independently being (e.g. one substituent being): oxo (=O); OH; $NH_2$; $C_{1-2}$alkyl such as methyl; $C_1$fluoroalkyl such as —$CH_2F$ or —$CHF_2$; —$CH_2OH$; —$CH(Me)OH$; —C(O)NHR$^{24}$ wherein $R^{24}$ is H or methyl (preferably H); —C(O)R$^{25}$ wherein $R^{25}$ is methyl; fluoro; hydroxyimino (=N—OH); or ($C_{1-2}$alkoxy)imino (=N—OR$^{26}$ where $R^{26}$ is $C_{1-2}$alkyl).

Preferably, when $R^3$ is optionally substituted $C_{4-7}$cycloalkyl, then $R^3$ is $C_{4-7}$cycloalkyl (e.g. $C_{6-7}$cycloalkyl or cyclobutyl) optionally substituted on a ring carbon(s) with one or two substituents independently being (e.g. one substituent being): oxo (=O); OH; methyl; —$CH_2F$; —$CHF_2$; —$CH_2OH$; —C(O)NHR$^{24}$ wherein $R^{24}$ is H; fluoro; hydroxyimino (=N—OH); or methoxyimino (=N—OR$^{26}$ where $R^{26}$ is methyl).

More preferably, when $R^3$ is optionally substituted $C_{4-7}$cycloalkyl, then $R^3$ is $C_{4-7}$cycloalkyl (e.g. $C_{6-7}$cycloalkyl or cyclobutyl) optionally substituted on a ring carbon(s) with one or two substituents independently being (e.g. one substituent being): oxo (=O); OH; methyl; —C(O)NHR$^{24}$ wherein $R^{24}$ is H; fluoro; or hydroxyimino (=N—OH).

Still more preferably, when $R^3$ is optionally substituted $C_{4-7}$cycloalkyl, then $R^3$ is $C_{4-7}$cycloalkyl (e.g. $C_{6-7}$cycloalkyl or cyclobutyl) optionally substituted on a ring carbon(s) with one or two substituents independently being (e.g. one substituent being): oxo (=O); OH; —C(O)NHR$^{24}$ wherein $R^{24}$ is H; or hydroxyimino (=N—OH).

In one optional embodiment, in $R^3$, the $C_{4-7}$cycloalkyl can be unsubstituted.

When $R^3$ is optionally substituted $C_{4-7}$cycloalkyl or optionally substituted $C_{5-7}$cycloalkenyl, e.g. optionally substituted ($C_{6-7}$cycloalkyl or cyclobutyl or $C_{5-7}$cycloalkenyl), such as optionally substituted $C_6$cycloalkyl (optionally substituted cyclohexyl) or optionally substituted cyclohexenyl, the one or two optional substituents on a ring carbon(s) if present suitably can comprise a substituent (for example is or are substituent(s)) at the 3-, 4- and/or 5-position(s), e.g. at the 3- and/or 4-position(s), of the $R^3$ cycloalkyl or cycloalkenyl ring.

(In this connection and generally herein, the 1-position of the $R^3$ ring, e.g. of the $R^3$ cycloalkyl or cycloalkenyl ring, is deemed to be the connection point to the —NH— in formula (I), that is the ring atom connecting to the —NH— in formula (I)).

Suitably, for $R^3$, and in particular when $R^3$ is optionally substituted $C_{4-7}$cycloalkyl or optionally substituted $C_{5-7}$cycloalkenyl, $R^3$ is not substituted (other than optionally by alkyl or fluoroalkyl) at the ring atom connecting to the —NH— in formula (I), and $R^3$ is not substituted (other than optionally by alkyl, fluoroalkyl or NHR$^{21}$) at the two ring atoms either side of (bonded to) the connecting atom. For example, suitably, for $R^3$, and in particular when $R^3$ is optionally substituted $C_{4-7}$cycloalkyl or optionally substituted $C_{5-7}$cycloalkenyl, $R^3$ is not substituted at the ring atom connecting to the —NH— in formula (I), and $R^3$ is not substituted at the two ring atoms either side of (bonded to) the connecting atom.

Suitably, for $R^3$, and in particular when $R^3$ is optionally substituted $C_{4-7}$cycloalkyl or optionally substituted $C_{5-7}$cycloalkenyl, the one or two optional $R^3$ ring-carbon substituents if present can comprise a substituent (for example is or are substituent(s)):

(a) at the 3-position of a $R^3$ cyclobutyl ring, or (b) at the 3- and/or 4-position(s) of a $R^3$ cyclopentyl or cyclopentenyl ring, or (c) at the 3-, 4- and/or 5-position(s) of a $R^3$ cyclohexyl or cyclohexenyl ring, or (d) at the 3-, 4-, 5- and/or 6-position(s) of a $R^3$ cycloheptyl or cycloheptenyl ring, and/or (f) at the 1-, 2- and/or highest-numbered-position(s) of a $R^3$ cycloalkyl or cycloalkenyl ring, for alkyl or fluoroalkyl substituent(s), and/or (g) at the 2- and/or highest-numbered-position(s) of a $R^3$ cycloalkyl or cycloalkenyl ring, for $NH_2$ or fluoro substituent(s).

When $R^3$ is optionally substituted $C_{4-7}$cycloalkyl, then any OH, methoxy, fluoroalkoxy, —$CH_2OH$, —CH(Me)OH, —$CH_2CH_2OH$, —$CH_2NH_2$, or —C(O)OH substituent on a ring carbon is: at the 3-position of a $R^3$ cyclobutyl ring; or at the 3- or 4-position of a $R^3$ cyclopentyl ring; or at the 3-, 4- or 5-position of a $R^3$ cyclohexyl ring (such as at the 3- or 5-position of a $R^3$ cyclohexyl ring especially for any OH substituent); or at the 3-, 4-, 5- or 6-position (e.g. 4- or 5-position) of a $R^3$ cycloheptyl ring. Suitably, when $R^3$ is optionally substituted $C_{4-7}$cycloalkyl, then any OH, methoxy, fluoroalkoxy, —$CH_2OH$, —$CH(Me)OH$, —$CH_2CH_2OH$ or —$CH_2NH_2$, or —C(O)OH substituent (or any OH substituent) on a ring carbon is at the 3- or 4-position of a $R^3$ cyclopentyl ring; or more suitably at the 3-, 4- or 5-position, such as at the 3- or 5-position, of a $R^3$ cyclohexyl ring.

When $R^3$ is optionally substituted $C_{4-7}$cycloalkyl, then any —$C(O)NHR^{24}$ or —$C(O)R^{25}$ substituent on a ring carbon is: at the 3-position of a $R^3$ cyclobutyl ring; or at the 3- or 4-position of a $R^3$ cyclopentyl ring; or at the 4-position of a $R^3$ cyclohexyl ring; or at the 3-, 4-, 5- or 6-position (e.g. 4- or 5-position) of a $R^3$ cycloheptyl ring. When $R^3$ is optionally substituted $C_{4-7}$cycloalkyl, then any —$C(O)NHR^{24}$ or —$C(O)R^{25}$ substituent, or any —$C(O)NHR^{24}$ substituent, on a ring carbon is suitably at the 3-position of a $R^3$ cyclobutyl ring or at the 4-position of a $R^3$ cyclohexyl ring. When $R^3$ is optionally substituted $C_{4-7}$cycloalkyl, it is preferable for any —$C(O)NHR^{24}$ substituent to be at the 4-position of a $R^3$ cyclohexyl ring.

When $R^3$ is optionally substituted $C_{4-7}$cycloalkyl, any $NH_2$ substituent on a ring carbon is at any position other than the 1-position (the ring atom connecting to the —NH— in formula (I)), e.g. at the 2-, 3-, 4-, 5-, 6- or 7-position. Suitably, any $NH_2$ substituent is at the 2-, 3-, 4-, 5- or 6-position, for example at the 3-, 4- or 5-position or at the 3- or 5-position, of a $R^3$ cyclohexyl ring.

When $R^3$ is optionally substituted $C_{4-7}$cycloalkyl or optionally substituted $C_{5-7}$cycloalkenyl, any alkyl or fluoroalkyl substituent on a ring carbon can for example be at the 1-, 2-, 3-, 4-, 5-, 6- or 7-position, for example at the 1-, 2-, 3-, 5- or 6-position, e.g. the 1-position, of the $R^3$ ring. Preferably, any such alkyl or fluoroalkyl substituent on a ring carbon is at the 1-, 2-, 3-, 5- or 6-position, or more preferably at the 1-, 3- or 5-position, of a $R^3$ cyclohexyl or cyclohexenyl ring.

When $R^3$ is optionally substituted $C_{4-7}$cycloalkyl or optionally substituted $C_{5-7}$cycloalkenyl, any fluoro substituent on a ring carbon can for example be at the 2-, 3-, 4-, 5-, 6- or 7-position, for example at the 2-, 3-, 4-, 5- or 6-position, such as at the 3- or 4-position, of the $R^3$ ring. Suitably, any fluoro substituent on a ring carbon is at the 3-, 4- or 5-position, in particular at the 4-position, of a $R^3$ cyclohexyl or cyclohexenyl ring.

When $R^3$ is optionally substituted $C_{4-7}$cycloalkyl, any oxo (=O), hydroxyimino (=N—OH); or ($C_{1-2}$alkoxy)imino (=N—$OR^{26}$) substituent on a ring carbon can for example be at the 3-, 4- or 5-position, e.g. at the 4-position, of the $R^3$ cycloalkyl (e.g. $C_{6-7}$cycloalkyl e.g. cyclohexyl, or cyclobutyl) ring. Any such substituent can for example be at the 3-position of a $R^3$ cyclobutyl ring or at the 4-position of a $R^3$ cyclohexyl ring. Preferably, any such substituent is at the 4-position of a $R^3$ cyclohexyl ring.

When $R^3$ is optionally substituted $C_{4-7}$cycloalkyl (e.g. $C_{6-7}$cycloalkyl or cyclobutyl, optionally substituted), then $R^3$ is suitably cyclohexyl (i.e. unsubstituted); or cycloheptyl (i.e. unsubstituted); or cyclohexyl substituted on a ring carbon by one substituent being oxo (=O), OH, $NH_2$, $C_{1-2}$alkyl, $C_1$fluoroalkyl such as —$CH_2F$ or —$CHF_2$, —$CH_2OH$, —CH(Me)OH, —$C(O)NHR^{24}$ wherein $R^{24}$ is H or methyl (preferably H), —$C(O)R^{25}$, fluoro, hydroxyimino (=N—OH), or ($C_{1-2}$alkoxy)imino (=N—$OR^{26}$ wherein $R^{26}$ is $C_{1-2}$alkyl); or cyclohexyl substituted by two fluoro substituents; or cyclobutyl (i.e. unsubstituted); or cyclobutyl substituted on a ring carbon with one substituent being oxo (=O), OH, methyl, —$CH_2F$, —$CHF_2$, —$CH_2OH$, —$C(O)NHR^{24}$ wherein $R^{24}$ is H or methyl (preferably H), fluoro, hydroxyimino (=N—OH), or methoxyimino (=N—$OR^{26}$ where $R^{26}$ is methyl). Preferably, when $R^3$ is optionally substituted $C_{4-7}$cycloalkyl (e.g. $C_{6-7}$cycloalkyl or cyclobutyl, optionally substituted), then $R^3$ is cyclohexyl (i.e. unsubstituted); or cycloheptyl (i.e. unsubstituted); or cyclohexyl substituted on a ring carbon by one substituent being oxo (=O), OH, $NH_2$, $C_{1-2}$alkyl, $C_1$fluoroalkyl such as —$CH_2F$ or —$CHF_2$, —$CH_2OH$, —$C(O)NHR^{24}$ wherein $R^{24}$ is H, fluoro, hydroxyimino (=N—OH), or (methoxy)imino (=N—$OR^{26}$ wherein $R^{26}$ is methyl); or cyclohexyl substituted by two fluoro substituents; or cyclobutyl (i.e. unsubstituted); or cyclobutyl substituted on a ring carbon with one substituent being oxo (=O), OH, methyl, —$CH_2F$, —$CHF_2$, —$CH_2OH$, —$C(O)NHR^{24}$ wherein $R^{24}$ is H, fluoro, hydroxyimino (=N—OH), or methoxyimino (=N—$OR^{26}$ where $R^{26}$ is methyl). More preferably, when $R^3$ is optionally substituted $C_{4-7}$cycloalkyl (e.g. $C_{6-7}$cycloalkyl or cyclobutyl, optionally substituted), then $R^3$ is cyclohexyl (i.e. unsubstituted); or cyclohexyl substituted on a ring carbon by one oxo (=O), hydroxyimino (=N—OH), —$C(O)NH_2$, methyl or OH substituent; or cyclobutyl substituted on a ring carbon by one —$C(O)NHR^{24}$ substituent wherein $R^{24}$ is H. The optional substituent can for example be at the 3- or 4-position of the $R^3$ cyclohexyl ring. Preferably, when $R^3$ is optionally substituted $C_{4-7}$cycloalkyl (e.g. $C_{6-7}$cycloalkyl or cyclobutyl, optionally substituted), then any OH substituent on a ring carbon is preferably at the 3-position of a $R^3$ cyclohexyl ring, and/or any oxo (=O), hydroxyimino (=N—OH), or ($C_{1-12}$alkoxy)imino (=N—$OR^{26}$) substituent on a ring carbon is preferably at the 4-position of a $R^3$ cyclohexyl ring or at the 3-position of a $R^3$ cyclobutyl ring, and/or any alkyl or fluoroalkyl substituent is preferably at the 1-, 3- or 5-position of a $R^3$ cyclohexyl ring.

When $R^3$ is optionally substituted cyclobutyl, then $R^3$ can preferably be cyclobutyl (i.e. unsubstituted) or more preferably 3-(aminocarbonyl)cyclobutyl (i.e. 3-(aminocarbonyl)cyclobutan-1-yl) (e.g. in a cis or trans configuration, preferably cis).

When $R^3$ is optionally substituted cyclopentyl, $R^3$ can for example be cyclopentyl (i.e. unsubstituted) or more suitably 3-hydroxy-cyclopentyl.

When $R^3$ is optionally substituted $C_{4-7}$cycloalkyl (e.g. optionally substituted $C_{6-7}$cycloalkyl or optionally substituted cyclobutyl), $R^3$ can for example be cyclobutyl (i.e. unsubstituted), 4-hydroxy-cyclohexyl (i.e. 4-hydroxycyclohexan-1-yl) (e.g. racemic or in a cis or trans configuration), 4-methylcyclohexyl (e.g. racemic), 2-aminocyclohexyl (e.g. racemic or in a cis or trans configuration, preferably trans), 4-aminocyclohexyl (e.g. racemic or in a cis or trans configuration, preferably racemic or cis), 3-oxocyclohexyl, 4-acetylcyclohexyl (e.g. racemic or in a cis or trans configuration, preferably racemic or cis), 4-(1-hydroxyethyl)cyclohexyl (e.g. racemic or in a cis or trans configuration with respect to the ring, preferably racemic or cis), or 3-(hydroxymethyl)cyclohexyl (e.g. racemic or in a cis or trans configuration).

However, when $R^3$ is optionally substituted $C_{4-7}$cycloalkyl (e.g. optionally substituted $C_{6-7}$cycloalkyl or optionally substituted cyclobutyl), $R^3$ is more preferably cyclohexyl (i.e. unsubstituted), cycloheptyl (i.e. unsubstituted), 3-hydroxycyclohexyl (i.e. 3-hydroxycyclohexan-1-yl) (e.g. racemic or in a cis or trans configuration, preferably racemic or cis), 4-oxo-cyclohexyl (i.e. 4-oxocyclohexan-1-yl), 4-(hydroxyimino)cyclohexyl (i.e. 4-(hydroxyimino)cyclohexan-1-yl), 4-($C_{1-2}$alkoxyimino)cyclohexyl, 4-(aminocarbonyl)cyclohexyl (i.e. 4-(aminocarbonyl)cyclohexan-1-yl) (e.g. racemic or in a cis or trans configuration, preferably racemic or cis), 1-methylcyclohexyl (e.g. racemic), 3-methylcyclohexyl (e.g. racemic), 4,4-(difluoro)cyclohexyl, 3-aminocyclohexyl (e.g. racemic or in a cis or trans configuration), 4-(hydroxymethyl) cyclohexyl (e.g. racemic or in a cis or trans configuration), or 3-(aminocarbonyl)cyclobutyl (i.e. 3-(aminocarbonyl)cyclobutan-1-yl) (e.g. racemic or in a cis or trans configuration, preferably cis).

A "cis configuration" in general includes mixtures of configurations wherein the cis configuration is the major component.

When $R^3$ is optionally substituted $C_{4-7}$cycloalkyl (e.g. optionally substituted $C_{6-7}$cycloalkyl or optionally substituted cyclobutyl), $R^3$ is still more preferably cyclohexyl (i.e. unsubstituted), 3-hydroxy-cyclohexyl (i.e. 3-hydroxycyclohexan-1-yl) (preferably racemic or in a cis configuration), 4-oxo-cyclohexyl (i.e. 4-oxocyclohexan-1-yl), 4-(hydroxyimino)cyclohexyl (i.e. 4-(hydroxyimino)cyclohexan-1-yl), 4-(aminocarbonyl)cyclohexyl (i.e. 4-(aminocarbonyl)cyclohexan-1-yl) (preferably racemic or in a cis configuration), or 3-(aminocarbonyl)cyclobutyl (i.e. 3-(aminocarbonyl)cyclobutan-1-yl) (preferably racemic or in a cis configuration).

When $R^3$ is optionally substituted mono-unsaturated-$C_{5-7}$ cycloalkenyl, suitably it is optionally substituted mono-unsaturated-$C_{5-6}$cycloalkenyl, preferably optionally substituted mono-unsaturated-$C_6$cycloalkenyl (i.e. optionally substituted mono-unsaturated-cyclohexenyl=optionally substituted cyclohexenyl). For example, the $R^3$ cyclohexenyl can be optionally substituted cyclohex-3-en-1-yl.

When $R^3$ is optionally substituted mono-unsaturated-$C_{5-7}$ cycloalkenyl, suitably the $R^3$ cycloalkenyl (e.g. cyclohexenyl) is substituted on a ring carbon with one fluoro substituent or is unsubstituted. For example, the $R^3$ optionally substituted cycloalkenyl can be cyclohex-3-en-1-yl (i.e. unsubstituted) or 4-fluoro-cyclohex-3-en-1-yl.

For $R^3$ cycloalkenyl, the optional substituent(s) on a ring carbon can for example be at the 1-, 2-, 3-, 4-, 5- or 6-position(s) of the cycloalkenyl ring.

When $R^3$ is the heterocyclic group of sub-formula (aa), (bb) or (cc), then Y is suitably O or $NR^{10}$. When $R^3$ is the heterocyclic group of sub-formula (aa) or (bb), then Y is preferably O or N—C(O)—NH$_2$.

$R^{10}$ can for example be a hydrogen atom (H), methyl, C(O)NH$_2$, C(O)-methyl or C(O)—C$_1$fluoroalkyl.

Suitably, $R^{10}$ is not methyl.

Suitably, $R^{10}$ is a hydrogen atom (H), C(O)NH$_2$, C(O)-methyl or C(O)—C$_1$fluoroalkyl (e.g. C(O)—CF$_3$). More suitably, $R^{10}$ is H, C(O)NH$_2$ or C(O)-methyl; in particular C(O) NH$_2$.

When $R^3$ is the heterocyclic group of sub-formula (aa), (bb) or (cc), then it is preferable that $R^3$ is the heterocyclic group of sub-formula (aa) or (bb), more preferably of sub-formula (bb).

In sub-formula (bb), $n^1$ is preferably 1. In sub-formula (cc), $n^2$ is preferably 1. That is, six-membered rings are preferred in the $R^3$ heterocyclic group.

In the invention, the $R^3$ heterocyclic group of sub-formula (aa), (bb) or (cc) is optionally substituted on a ring carbon with one or two (e.g. one) substituents being oxo (=O).

In the $R^3$ heterocyclic group of sub-formula (aa), (bb) or (cc), any oxo (=O) substituent on a ring carbon is suitably on a carbon atom bonded (adjacent) to Y. In one embodiment, any oxo (=O) substituent on a ring carbon can be on a carbon atom bonded (adjacent) to Y only when Y is O or NR$^{10}$, for example only when Y is NR$^{10}$.

In the $R^3$ heterocyclic group of sub-formula (aa), (bb) or (cc), any oxo (=O) substituent on a ring carbon can suitably be at the 2-, 3-, 4-, 5- or 6-position of the $R^3$ heterocyclic ring. For example any ring-carbon oxo (=O) substituent(s) can be: at the 2-, 4- or 5-position(s) (e.g. 2-position or 4-position, or two oxo substituents at 2- and 4-positions) of a $R^3$ heterocyclic group of sub-formula (aa), at the 2-, 4-, 5- or 6-position(s) (e.g. 4-position) of a six-membered $R^3$ heterocyclic group of sub-formula (cc) wherein $n^2$ is 1, at the 2-, 3-, 5-, 6- or 7-position(s) (e.g. 5-position) of a seven-membered $R^3$ heterocyclic group of sub-formula (bb) wherein $n^1$ is 2, or at the 2-, 4-, 5-, 6- or 7-position(s) (e.g. 2-position) of a seven-membered $R^3$ heterocyclic group of sub-formula (cc) wherein $n^2$ is 2.

(In this connection and generally herein, the 1-position of the $R^3$ heterocyclic ring is deemed to be the connection point to the —NH— in formula (I), that is the ring atom connecting to the —NH— in formula (I), and the remaining positions of the ring are then numbered so that the ring heteroatom takes the lowest possible number).

In the $R^3$ heterocyclic group of sub-formula (aa), (bb) or (cc), no substitution is allowed at the 1-position ring-carbon of the $R^3$ heterocyclic ring.

However, it is generally preferable that, in $R^3$, the heterocyclic group of sub-formula (aa), (bb) or (cc) is not substituted on a ring carbon (i.e. is not substituted on any ring carbon).

When $R^3$ is the heterocyclic group of sub-formula (aa) and Y is NR$^{10}$, then R$^{10}$ is not C(O)-methyl, or C(O)—C$_1$fluoroalkyl.

In one preferable embodiment, when $R^3$ is the heterocyclic group of sub-formula (aa), then Y is O, S, SO$_2$, NH or NC(O) NH$_2$ (in particular Y can be O, S, NH or NC(O)NH$_2$, such as NC(O)NH$_2$).

When $R^3$ is the heterocyclic group of sub-formula (bb) and Y is NR$^{10}$ (e.g. when NHR$^3$ is

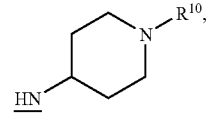

wherein the —NH— connection point of the NHR$^3$ group to the 4-position of the pyrazolopyridine of formula (I) is underlined), then R$^{10}$ is not methyl.

Therefore, when $R^3$ is the heterocyclic group of sub-formula (bb), then Y is O, S, SO$_2$ or NR$^{10}$ wherein R$^{10}$ is H, C(O)NH$_2$, C(O)-methyl or C(O)—C$_1$fluoroalkyl (e.g. C(O)—CF$_3$). When $R^3$ is the heterocyclic group of sub-formula (bb), then R$^{10}$ is preferably H, C(O)NH$_2$ or C(O)-methyl, for example C(O)NH$_2$ or C(O)-methyl, more preferably C(O)NH$_2$.

When $R^3$ is the heterocyclic group of sub-formula (cc), then Y is O, S, SO$_2$ or NR$^{10}$ wherein R$^{10}$ is H or methyl.

Suitably, when $R^3$ is the heterocyclic group of sub-formula (cc), then:
either Y is O, S, SO$_2$ or NR$^{10}$ wherein R$^{10}$ is H, or NHR$^3$ is of sub-formula (m4):

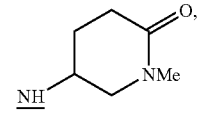

wherein the —NH— connection point of the NHR$^3$ group to the 4-position of the pyrazolopyridine of formula (I) is underlined.

Suitably, when R$^3$ is the heterocyclic group of sub-formula (cc), then Y is O, S, SO$_2$ or NR$^{10}$ wherein R$^{10}$ is H, or Y is O or NR$^{10}$ wherein R$^{10}$ is H.

In one embodiment, for sub-formula (bb) and/or for sub-formula (cc), Y is O or NR$^{10}$.

When R$^3$ is optionally substituted C$_{4-7}$cycloalkyl (e.g. optionally substituted C$_{6-7}$cycloalkyl or optionally substituted cyclobutyl) or optionally substituted mono-unsaturated-C$_{5-7}$cycloalkenyl or an optionally substituted heterocyclic group of sub-formula (aa), (bb) or (cc), then a substituent on a ring carbon can be racemic or in the cis or trans configuration with respect to the —NH— group of formula (I) to which R$^3$ is attached (bonded). A cis or trans configuration includes mixtures of configurations wherein the stated configuration is the major component. In this context, "racemic" refers to a mixture of isomers containing substantially equal amounts of the cis and trans configurations with respect to a substituent and the —NH— group on the R$^3$ ring, and in this context "racemic" does not refer to isomerism at atoms other than R$^3$ ring carbon atoms. For example, an OH or —C(O)NHR$^{24}$ substituent on C$_{6-7}$cycloalkyl or cyclobutyl can for example be in the cis configuration and/or a NH$_2$ substituent on C$_{6-7}$cycloalkyl can for example be racemic or in the cis or trans configuration, with respect to the —NH-group of formula (I) to which R$^3$ is attached (bonded), including mixtures of configurations wherein the stated configuration is the major component.

When R$^3$ is a bicyclic group of sub-formula (ee), then NHR$^3$ can be of sub-formula (c6) or (c7):

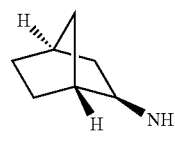
(c6)

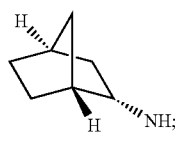
(c7)

wherein the —NH— connection point of the NHR$^3$ group to the 4-position of the pyrazolopyridine of formula (I) is underlined.

Preferably, NHR$^3$ is of sub-formula (a1), (b), (c), (c 1), (c 2), (c 3), (c 4), (c 5), (c 6), (c 7), (d), (e), (f), (g), (g2), (g4), (h), (i), (j), (k), (k1), (k2), (k3), (L), (m), (m1), (m3), (m4), (n), (o), (o1), (o2), (o3), (p), (p1), (p2), (p3), (p5), (p6), (p9), (p10), (p12), (p13), (p14), (p15), or (q):

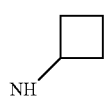
(a1)

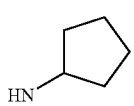
(b)

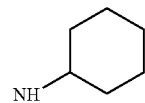
(c)

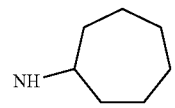
(c1)

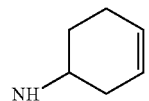
(c2)

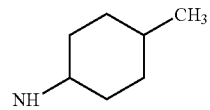
(c3)

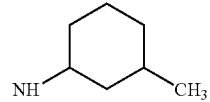
(c4)

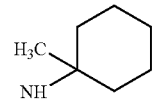
(c5)

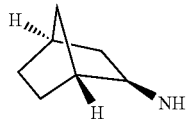
(c6)

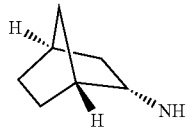
(c7)

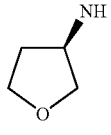
(d)

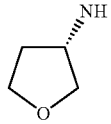
(e)

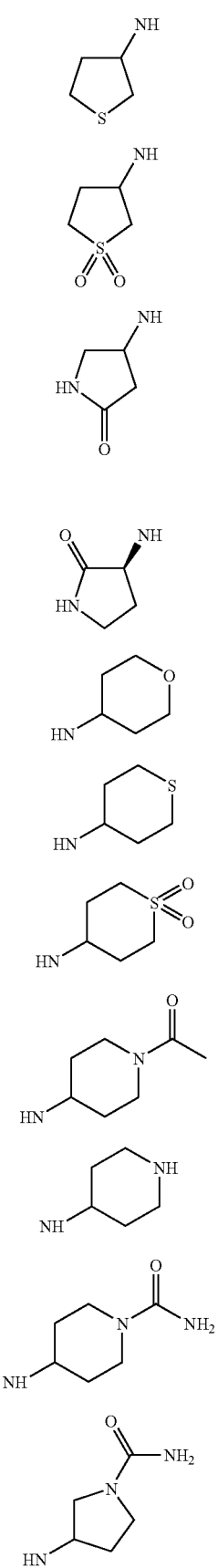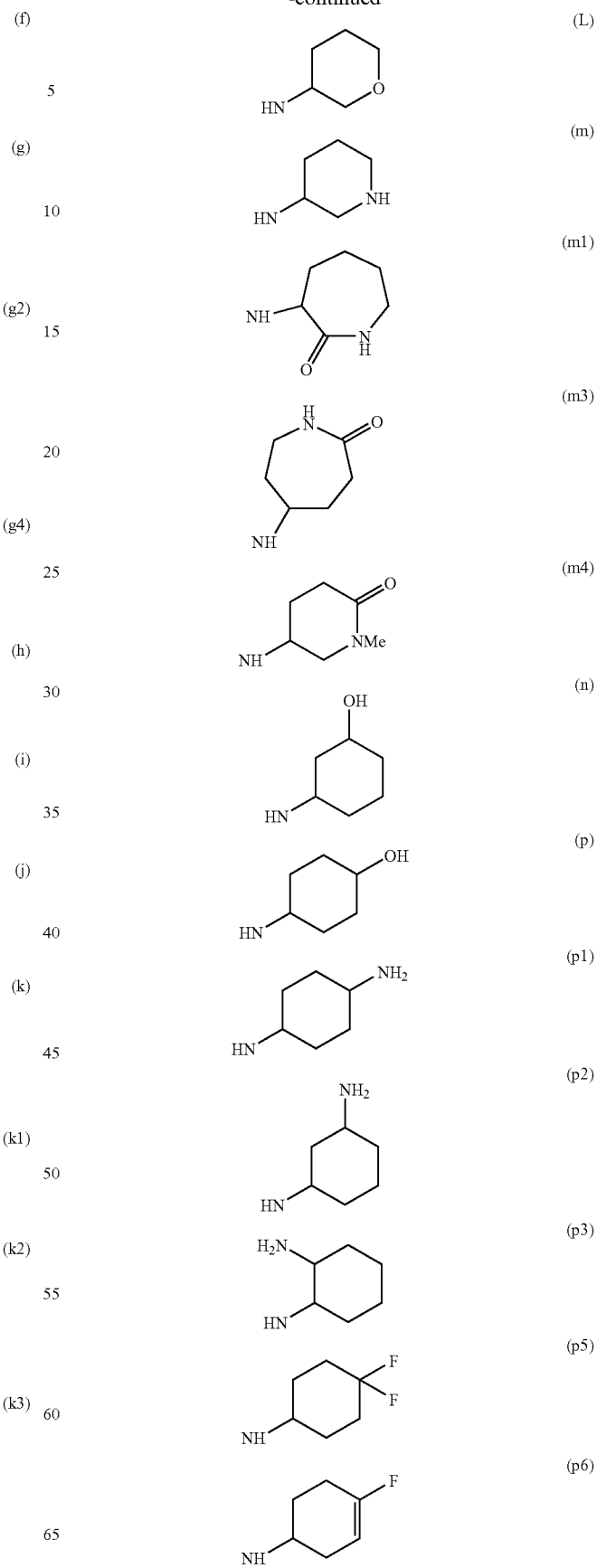

-continued (p9) 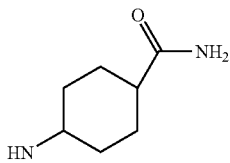

(p10) 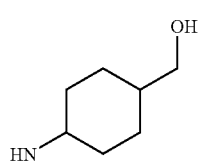

(p12) 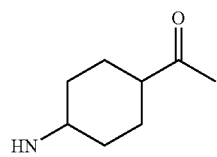

(p13) 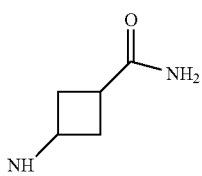

(p14) 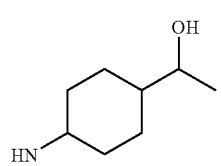

(p15) 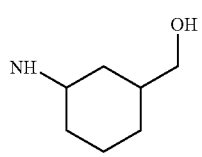

(q) 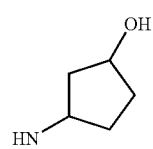

(o) 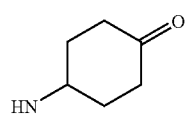

-continued (o1) 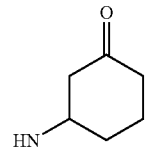

(o2) 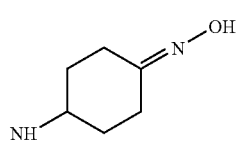

(o3) 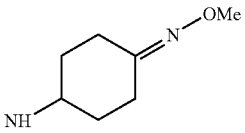

In the sub-formulae (a1) to (q) etc above, the —NH— connection point of the $NHR^3$ group to the 4-position of the pyrazolopyridine of formula (I) is underlined.

Preferably, $NHR^3$ is of sub-formula (c), (c1), (c 2), (c 3), (c 4), (c 5), (c 6), (c 7), (d), (e), (f), (g4), (h), (i), (j), (k), (k1), (k2), (k3), (L), (m), (m1), (m3), (m4), (n), (O), (o1), (o2), (o3), (p), (p2), (p5), (p6), (p9), (p10), (p12), (p13), (p14), (p15) or (q); or preferably $NHR^3$ is of sub-formula (a1), (c), (c1), (c 2), (c 3), (c 4), (c 5), (c 6), (c 7), (d), (e), (f), (g4), (h), (i), (j), (k), (k1), (k2), (k3), (L), (m), (m1), (m3), (m4), (n), (O), (o1), (o2), (o3), (p), (p1), (p2), (p5), (p6), (p9), (p10), (p12), (p13), (p14), (p15) or (q).

More preferably, $NHR^3$ is of sub-formula (c), (c1), (c 4), (c 5), (h), (i), (k), (k2), (k3), (m1), (n), (O), (o2), (o3), (p2), (p5), (p6), (p9), (p10), (p13) or (p15).

$NHR^3$ is more preferably of sub-formula (c), (h), (k), (k2), (k3), (n), (O), (o2), (p9) or (p13); still more preferably $NHR^3$ is (c), (h), (k2), (k3), (n), (O), (o2), (p9) or (p13).

Most preferably, $R^3$ is tetrahydro-2H-pyran-4-yl or 1-(aminocarbonyl)-4-piperidinyl; that is $NHR^3$ is most preferably of sub-formula (h) or (k2), as shown above, in particular of sub-formula (h).

When $NHR^3$ is of sub-formula (n), then it can be in the trans configuration. But preferably it is in the cis configuration, i.e. preferably it is a cis-(3-hydroxycyclohexan-1-yl) amino group (including mixtures of configurations wherein the cis configuration is the major component), or it is racemic.

When $NHR^3$ is of sub-formula (p9), then it can be in the trans configuration. But preferably it is in the cis configuration, i.e. preferably it is a cis-[4-(aminocarbonyl)cyclohexan-1-yl]amino group (including mixtures of configurations wherein the cis configuration is the major component), or it is racemic.

When $NHR^3$ is of sub-formula (p12), then it can be in the trans configuration. But, preferably, it is in the cis configuration, i.e. preferably $NHR^3$ is a cis-[4-acetylcyclohexan-1-yl] amino group (including mixtures of configurations wherein the cis configuration is the major component), or it is racemic.

When $NHR^3$ is of sub-formula (p13), then it can be in the trans configuration. But, preferably, it is in the cis configuration, i.e. preferably $NHR^3$ is a cis-[3-(aminocarbonyl)cyclobutan-1-yl]amino group (including mixtures of configurations wherein the cis configuration is the major component), or it is racemic.

The $NHR^3$ group of sub-formula (p10), (p14) or (p15), independently, can for example be racemic; or it can be in the cis configuration with respect to the ring (including mixtures of configurations wherein the cis configuration is the major component).

Preferably, the compound of formula (I) or the salt thereof is:

N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, 4-[(1,6-diethyl-5-{[({4-[(8-{(2R)-2-[(methyloxy)methyl]-1-pyrrolidinyl}octanoyl)amino]phenyl}carbonyl)amino]methyl}-1H-pyrazolo[3,4-b]pyridin-4-yl)amino]-1-piperidinecarboxamide, 4-[(1,6-diethyl-5-{[({4-[(8-{(2S)-2-[(methyloxy)methyl]-1-pyrrolidinyl}octanoyl)amino]phenyl}carbonyl)amino]methyl}-1H-pyrazolo[3,4-b]pyridin-4-yl)amino]-1-piperidinecarboxamide, 4-({1,6-diethyl-5-[({[4-({8-[(2-hydroxyethyl)(methyl)amino]octanoyl}amino)phenyl]carbonyl}amino)methyl]-1H-pyrazolo[3,4-b]pyridin-4-yl}amino)-1-piperidinecarboxamide, N-{[1,6-diethyl-4-(tetrahydro-2H-pyran-4-ylamino)-1H-pyrazolo[3,4-b]pyridin-5-yl]methyl}-4-[(8-{(2R)-2-[(methyloxy)methyl]-1-pyrrolidinyl}octanoyl)amino]benzamide, N-{[1,6-diethyl-4-(tetrahydro-2H-pyran-4-ylamino)-1H-pyrazolo[3,4-b]pyridin-5-yl]methyl}-4-[(8-{(2S)-2-[(methyloxy)methyl]-1-pyrrolidinyl}octanoyl)amino]benzamide, N-{[1,6-diethyl-4-(tetrahydro-2H-pyran-4-ylamino)-1H-pyrazolo[3,4-b]pyridin-5-yl]methyl}-4-{[8-(4-morpholinyl)octanoyl]amino}benzamide, N-{[1,6-diethyl-4-(tetrahydro-2H-pyran-4-ylamino)-1H-pyrazolo[3,4-b]pyridin-5-yl]methyl}-4-{[8-(1-pyrrolidinyl)octanoyl]amino}benzamide, N-{[1,6-diethyl-4-(tetrahydro-2H-pyran-4-ylamino)-1H-pyrazolo[3,4-b]pyridin-5-yl]methyl}-4-[4-({4-[(2-hydroxyethyl)(methyl)amino]butyl}oxy)butyl]benzamide, N-{[1,6-diethyl-4-(tetrahydro-2H-pyran-4-ylamino)-1H-pyrazolo[3,4-b]pyridin-5-yl]methyl}-4-(4-{[4-(4-morpholinyl)butyl]oxy}butyl)benzamide, N-{[1,6-diethyl-4-(tetrahydro-2H-pyran-4-ylamino)-1H-pyrazolo[3,4-b]pyridin-5-yl]methyl}-4-(4-{[4-(1-pyrrolidinyl)butyl]oxy}butyl)benzamide, 4-[(1,6-diethyl-5-{[({4-[4-({4-[(2-hydroxyethyl)(methyl)amino]butyl}oxy)butyl]phenyl}carbonyl)amino]methyl}-1H-pyrazolo[3,4-b]pyridin-4-yl)amino]-1-piperidinecarboxamide, 4-({1,6-diethyl-5-[({[4-(4-{[4-(4-morpholinyl)butyl]oxy}butyl)phenyl]carbonyl}amino)methyl]-1H-pyrazolo[3,4-b]pyridin-4-yl}amino)-1-piperidinecarboxamide, 4-({1,6-diethyl-5-[({[4-(4-{[4-(1-pyrrolidinyl)butyl]oxy}butyl)phenyl]carbonyl}amino)methyl]-1H-pyrazolo[3,4-b]pyridin-4-yl}amino)-1-piperidinecarboxamide, N-{[1-ethyl-6-methyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, N-{[1-ethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, N-{[1,6-diethyl-4-(tetrahydro-2H-pyran-4-ylamino)-1H-pyrazolo[3,4-b]pyridin-5-yl]methyl}-4-[8-(4-morpholinyl)octyl]benzamide, N-{[1,6-diethyl-4-(tetrahydro-2H-pyran-4-ylamino)-1H-pyrazolo[3,4-b]pyridin-5-yl]methyl}-4-{8-[(2-hydroxyethyl)(methyl)amino]octyl}benzamide, N-{[1,6-diethyl-4-(tetrahydro-2H-pyran-4-ylamino)-1H-pyrazolo[3,4-b]pyridin-5-yl]methyl}-3-({8-[(2-hydroxyethyl)(methyl)amino]octanoyl}amino)benzamide, N-{[1,6-diethyl-4-(tetrahydro-2H-pyran-4-ylamino)-1H-pyrazolo[3,4-b]pyridin-5-yl]methyl}-2-({8-[(2-hydroxyethyl)(methyl)amino]octanoyl}amino)benzamide, N-{[1,6-diethyl-4-(tetrahydro-2H-pyran-4-ylamino)-1H-pyrazolo[3,4-b]pyridin-5-yl]methyl}-4-({6-[(2-hydroxyethyl)(methyl)amino]hexanoyl}amino)benzamide, N-{[1,6-diethyl-4-(tetrahydro-2H-pyran-4-ylamino)-1H-pyrazolo[3,4-b]pyridin-5-yl]methyl}-4-({7-[(2-hydroxyethyl)(methyl)amino]heptanoyl}amino)benzamide, N-{[1,6-diethyl-4-(tetrahydro-2H-pyran-4-ylamino)-1H-pyrazolo[3,4-b]pyridin-5-yl]methyl}-4-({10-[(2-hydroxyethyl)(methyl)amino]decanoyl}amino)benzamide, or N-{[1,6-diethyl-4-(tetrahydro-2H-pyran-4-ylamino)-1H-pyrazolo[3,4-b]pyridin-5-yl]methyl}-4-({11-[(2-hydroxyethyl)(methyl)amino]undecanoyl}amino)benzamide;

or a salt thereof such as a pharmaceutically acceptable salt thereof.

The structures of the above-listed specific compounds or salts, or embodiments (e.g. specific salts) thereof, are given in the Examples hereinafter.

In the most preferred embodiment of the invention, the compound of formula (I) or the salt thereof is: N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, whose formula is

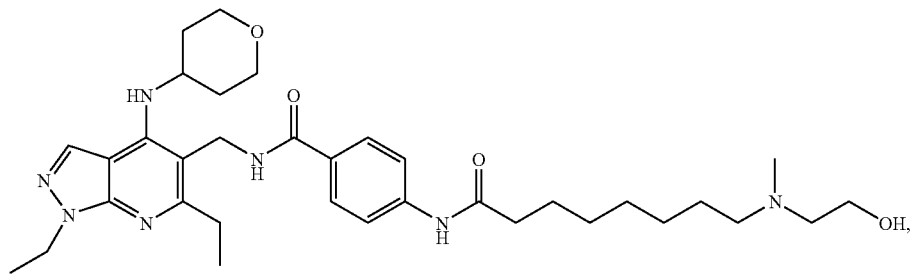

or a salt thereof (e.g. the compound or a pharmaceutically acceptable salt thereof).

Therefore, another preferred aspect of the invention provides N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, whose formula is

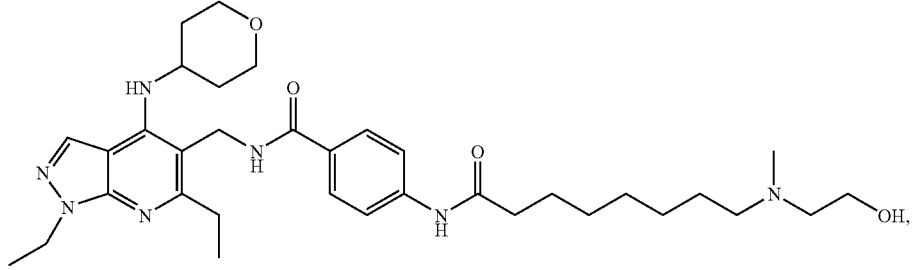

or a salt thereof (e.g. the compound or a pharmaceutically acceptable salt thereof).

See for Example 1A1, 1A2, 1A3, 1B, 1C, 1D, 1E, 1F, 1G, 1H1, 1H2, 1J1, or 1J2 disclosed herein. This above-illustrated compound or a salt thereof can be for inhaled or intranasal administration e.g. to a mammal such as a human, monkey, rodent (e.g. rat or mouse) or dog, in particular to a human.

This compound N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, encompassed by the presently invented compounds of formula (I), or a salt thereof (e.g. the monohydrochloride salt thereof), may be suitable for use via an inhaled route of administration, in particular as a PDE4 inhibitor. Preliminary tests appear to indicate that this specific compound or a salt thereof may exhibit a reasonable level of antiinflammatory efficacy and/or duration of action (2 or more hours duration of action after i.t. administration to the rat as an aqueous solution, and 4 hours duration of action after i.t. administration to the rat as a dry powder), when measured using an intratracheal (i.t.) rat LPS-induced neutrophilia model (see In Vivo Assay 1 hereinbelow), wherein LPS is lipopolysaccharide.

In one embodiment of the invention, the compound or salt can be N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a hydrochloride (e.g. monohydrochloride or dihydrochloride), hydrobromide (e.g. monohydrobromide or dihydrobromide), phosphate, succinate (e.g. hemisuccinate), fumarate (e.g. hemifumarate), 1-naphthoate, 1-hydroxy-2-naphthoate ("xinafoate") (e.g. mono-1-hydroxy-2-naphthoate), L-glutamate, camphorsulfonate (e.g. (+)-camphorsulfonate and/or 10-camphorsulfonate and/or mono-camphorsulfonate, e.g. mono-(+)-10-camphorsulfonate), or 1,5-naphthalenedisulfonate (e.g. hemi-1,5-naphthalenedisulfonate) salt thereof. This compound or the salt thereof can e.g. be for inhaled or intranasal administration e.g. to a mammal such as a human.

In particular, the compound or salt can be N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a hydrochloride (e.g. monohydrochloride or dihydrochloride), hydrobromide (e.g. monohydrobromide or dihydrobromide), or succinate (e.g. hemisuccinate) salt thereof. This compound or the salt thereof can be for inhaled or intranasal administration e.g. to a mammal such as a human.

Preferably, the compound or salt is a hydrochloride (e.g. monohydrochloride or dihydrochloride) salt of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, in particular the monohydrochloride salt.

It is currently thought that there are at least two solid forms of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride. The two currently known solid forms are:

a first, preferred, solid form (herein named "Form 1") which is thought to be a substantially-anhydrous solid form ("anhydrate") and which (e.g. from its XRPD spectrum) is thought to be crystalline, and a second, less-preferred, solid form (herein named "Form 2") which is thought to be a hydrated solid form ("hydrate") and which (e.g. from its XRPD spectrum) is thought to be crystalline.

Therefore, one preferable aspect of the invention provides crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate.

Suitably, the crystalline monohydrochloride Form 1 anhydrate is substantially free of (e.g. <30% w/w or <25% w/w or <20% w/w or <10% w/w or <5% w/w is present as) the crystalline monohydrochloride Form 2 hydrate. For example, suitably, the crystalline monohydrochloride Form 1 anhydrate is substantially free of (e.g. <30% w/w or <25% w/w or <20% w/w or <10% w/w or <5% w/w is present as) any other form of the monohydrochloride or dihydrochloride salt.

Suitably, the purity of the crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate is such that less than 30% w/w (e.g. less than 25% w/w, or less than 20% w/w, or less than 10% w/w, or less than 5% w/w) of the N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide hydrochloride salt is present as the crystalline monohydrochloride Form 2 hydrate.

Preferably, 70% w/w or more, or 75% w/w or more, or 80% w/w or more, or 90% w/w or more, or 95% w/w or more, of the N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide hydrochloride present is present as the N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate.

The crystalline monohydrochloride Form 2 hydrate is thought to have a greater propensity to take up water than the crystalline monohydrochloride Form 1 anhydrate, e.g. as the relative humidity (RH) increases. In addition, water is believed to be readily lost from the Form 2 hydrate (a) on heating to only slightly above room temperature and/or (b) on reduction in the relative humidity (RH) (e.g. water appears to be lost from the Form 2 hydrate when the RH is reduced to 0% RH).

Differential scanning calorimetry (DSC) data for the monohydrochloride Form 2 hydrate generally shows an endotherm, interpreted as water loss from the Form 2 hydrate, at temperatures only slightly above room temperature. In a DSC thermogram of one sample of the crystalline monohydrochloride Form 2 hydrate, measured using increasing temperature starting from about room temperature, amongst other thermal features, the following endotherms (interpreted to represent water loss events) were seen:
(i) a first endotherm/water loss event having an onset of very approximately 49° C. (a "broad" endotherm, i.e. seen at a broad temperature range starting from about 49° C. and ending at a higher temperature, possibly representing gradual water loss e.g. of unbound water), and
(ii) a second endotherm/water loss event having an onset of very approximately 97° C. (a "sharper" endotherm, possibly representing loss of bound water), although it is noted that the end of the first water loss event often merges into the start of the second water loss event.

These low-temperature water losses may pose developability risks for the crystalline monohydrochloride Form 2 hydrate, in that, for example, it is likely to be less suitable than the Form 1 anhydrate for micronisation (which may warm the drug substance), which micronisation may for example be carried out before formulation of the drug substance into an inhalable pharmaceutical composition.

In comparison, crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate typically shows a melt onset temperature in its DSC thermogram of very approximately 190-210° C. or above (depending on a variety of factors such as the impurity profile, sample preparation, prior micronisation, etc.), and generally has no significant thermal events (i.e. no or only minor thermal events), at lower temperatures.

In gravimetric vapour sorption studies conducted at 25° C., one sample of the crystalline monohydrochloride Form 1 anhydrate showed a moisture uptake as follows, measured as % weight gain over a selected relative humidity (RH) range as RH increases: about 0.5% weight gain when RH increased from 30% to 75%, and about 1.0% to about 1.1% weight gain when RH increased from 30% to 90%. This appears to show that the crystalline monohydrochloride Form 1 anhydrate has a non-negligible but small propensity to take up moisture as the RH increases, at least at 25° C.

Overall, the crystalline monohydrochloride Form 1 anhydrate is thought to be more suitable than the crystalline monohydrochloride Form 2 hydrate, e.g. for micronisation and/or for post-micronisation formulation into an inhalable pharmaceutical composition.

The crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate can be characterised for example by its X-ray powder diffraction (XRPD) spectrum. For example, the solid monohydrochloride salt prepared in Example 1A2 (synthesis first-mentioned herein) is thought to be crystalline monohydrochloride Form 1 anhydrate, and its detailed XRPD spectrum is disclosed at the end of Example 1A2 (first synthesis) herein.

The following four XRPD peaks of the crystalline monohydrochloride Form 1 anhydrate are thought to particularly distinguish the Form 1 anhydrate from the Form 2 hydrate: $5.1\pm0.1°$ 2θ (d-spacing ca. 17.3 Å), $10.7\pm0.1°$ 2θ (d-spacing ca. 8.3 Å), $23.1\pm0.1°$ 2θ (d-spacing ca. 3.9 Å), and $23.5\pm0.1°$ 2θ (d-spacing ca. 3.8 Å), the stated degrees two-theta values being when the XRPD spectrum is measured with a X-ray powder diffractometer using Cu Kα (copper K-alpha) radiation, a step size of 0.0167° 2θ or less, and a time per step of 31.75 seconds or more. The following additional two XRPD peaks of the crystalline monohydrochloride Form 1 anhydrate may also partially distinguish this Form 1 anhydrate from the Form 2 hydrate: $10.3\pm0.1°$ 2θ (d-spacing ca. 8.6 Å) and $17.5\pm0.1°$ 2θ (d-spacing ca. 5.1 Å), the stated degrees two-theta values being when the XRPD spectrum is measured with a X-ray powder diffractometer using Cu Kα (copper K-alpha) radiation, a step size of 0.0167° 2θ or less, and a time per step of 31.75 seconds or more; however, there are thought to be shoulders or low intensity peaks of another form in fairly close proximity that make these latter-mentioned two peaks slightly less distinguishing than the first-mentioned four XRPD peaks of the crystalline monohydrochloride Form 1 anhydrate.

In contrast, one sample of the less-preferred crystalline monohydrochloride Form 2 hydrate had an XRPD spectrum comprising peaks at substantially the following degrees 2θ (degrees 2-theta) values and d-spacings: $3.9\pm0.1°$ 2θ (d-spacing ca. 22.4 Å), $7.8\pm0.1°$ 2θ (d-spacing ca. 11.4 Å), $8.9\pm0.1°$ 2θ (d-spacing ca. 10.0 Å), $11.7\pm0.1°$ 2θ (d-spacing ca. 7.6 Å), $13.5\pm0.1°$ 2θ (d-spacing ca. 6.6 Å), $13.9\pm0.1°$ 2θ (d-spacing ca. 6.4 Å), $15.6\pm0.1°$ 2θ (d-spacing ca. 5.7 Å), $16.0\pm0.1°$ 2θ (d-spacing ca. 5.5 Å), $18.1\pm0.1°$ 2θ (d-spacing ca. 4.9 Å), $19.5\pm0.1°$ 2θ (d-spacing ca. 4.6 Å), $20.7\pm0.1°$ 2θ (d-spacing ca. 4.3 Å), $21.4\pm0.1°$ 2θ (d-spacing ca. 4.2 Å), $22.5\pm0.1°$ 2θ (d-spacing ca. 3.9 Å), $22.9\pm0.1°$ 2θ (d-spacing ca. 3.9 Å), $24.4\pm0.1°$ 2θ (d-spacing ca. 3.6 Å), and $25.4\pm0.1°$ 2θ (d-spacing ca. 3.5 Å), the stated degrees two-theta values being when the XRPD spectrum is measured with a X-ray powder diffractometer using Cu Kα (copper K-alpha) radiation, a step size of 0.0167° 2θ or less, and a time per step of 31.75 seconds or more. Of these Form 2 hydrate peaks, the following three XRPD peaks are thought to distinguish the crystalline monohydrochloride Form 2 hydrate from the Form 1 anhydrate $3.9\pm0.1°$ 2θ, $8.9\pm0.1°$ 2θ, and $11.7\pm0.1°$ 2θ, the stated degrees two-theta values being when the XRPD spectrum is measured with a X-ray powder diffractometer using Cu Kα (copper K-alpha) radiation, a step size of 0.0167° 2θ or less, and a time per step of 31.75 seconds or more.

Therefore, in particular, the crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate can be characterised by having an X-ray powder diffraction (XRPD) spectrum comprising two, three or all (e.g. three or all, e.g. all) of the following peaks at substantially the following degrees 2θ (degrees two-theta) values:

5.1±0.1°, 10.7±0.1°, 23.1±0.1°, 23.5±0.1°, wherein the XRPD spectrum is measured with a X-ray powder diffractometer using Cu Kα (copper K-alpha) radiation, a step size of 0.0167° 2θ or less, and a time per step of 31.75 seconds or more (and preferably using a sample mounted on a silicon wafer plate, e.g. a silicon wafer zero background plate, and/or e.g. as a layer of powder).

Alternatively, the crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate can be characterised by having an X-ray powder diffraction (XRPD) spectrum comprising four, five or all (e.g. five or all, e.g. all) of the following peaks at substantially the following degrees 2θ (degrees two-theta) values:

5.1±0.1°, 10.3±0.1°, 10.7±0.1°, 17.5±0.1°, 23.1±0.1°, 23.5±0.1°, wherein the XRPD spectrum is measured with a X-ray powder diffractometer using Cu Kα (copper K-alpha) radiation, a step size of 0.0167° 2θ or less, and a time per step of 31.75 seconds or more (and preferably using a sample mounted on a silicon wafer plate, e.g. a silicon wafer zero background plate, and/or e.g. as a layer of powder).

Alternatively, the crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate can be characterised by having an X-ray powder diffraction (XRPD) spectrum comprising 6 or more, or 9 or more, or 12 or more, or 15 or more, or all, of the following peaks at substantially the following degrees 2θ (degrees two-theta) values:

5.1±0.1°, 7.8±0.1°, 10.3±0.1°, 10.7±0.1°, 14.3±0.1°, 15.2±0.1°, 17.5±0.1°, 18.6±0.1°, 18.8±0.1°, 19.7±0.1°, 20.3±0.1°, 21.4±0.1°, 21.9±0.1°, 22.4±0.1°, 23.1±0.1°, 23.5±0.1°, 24.0±0.1°, and wherein the XRPD spectrum also comprises two, three or all (e.g. three or all) of the following peaks at substantially the following degrees 2θ (degrees two-theta) values:

5.1±0.1°, 10.7±0.1°, 23.1±0.1°, 23.5±0.1°, wherein the XRPD spectrum is measured with a X-ray powder diffractometer using Cu Kα (copper K-alpha) radiation, a step size of 0.0167° 2θ or less, and a time per step of 31.75 seconds or more (and preferably using a sample mounted on a silicon wafer plate, e.g. a silicon wafer zero background plate, and/or e.g. as a layer of powder).

Alternatively or additionally, the crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate can be characterised for example by its solid-form infrared (IR) spectrum.

The monohydrochloride Form 1 anhydrate can for example be characterised by a solid-form IR spectrum (e.g. as measured using an FT-IR spectrometer such as a Nicolet Avatar 360 FT-IR spectrometer, and/or e.g. as measured at 4 cm$^{-1}$ or 2 cm$^{-1}$ resolution) comprising 7 or more, or 10 or more, or 15 or more, or 18 or more, or all, of the following peaks:

3252, 2938, 2857, 1688, 1639, 1598, 1571, 1526, 1503, 1437, 1407, 1355, 1304, 1254, 1185, 1162, 1139, 1123, 1086, 1035, 1014, 988, 964, 860, 820 and 770 cm$^{-1}$, with a variation allowed for each peak of ±2 cm$^{-1}$ such as ±1 cm$^{-1}$, provided that the IR spectrum comprises a peak at 1639 (±2 or ±1) cm$^{-1}$.

The solid-form IR spectrum of the monohydrochloride Form 1 anhydrate includes a band at 1639 (±2 or ±1) cm$^{-1}$ which is thought to be capable of distinguishing from the IR spectrum of the solid-from monohydrochloride Form 2 hydrate. The monohydrochloride Form 2 hydrate includes an apparently-characteristic band at 1623 (±2 or ±1) cm$^{-1}$ which is not present in the Form 1 anhydrate IR spectrum. For example, representative solid-form IR spectrum peaks of a sample of the monohydrochloride Form 2 hydrate include: 3244, 2940, 2858, 1677, 1623, 1602, 1569, 1526, 1510, 1444, 1407, 1353, 1309, 1257, 1227, 1165, 1137, 1085, 1048, 1011, 995, 961 and 860 cm$^{-1}$ (with each peak being ±2 or ±1 cm$^{-1}$).

Alternatively or additionally, the crystalline N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate can be characterised for example by its solid-form Raman spectrum.

The monohydrochloride Form 1 anhydrate can for example be characterised by a solid-form Raman spectrum comprising 5 or more, or 7 or more, or 10 or more, or all, of the following peaks:

2937, 1671, 1643, 1608, 1563, 1502, 1439, 1343, 1304, 1253, 1191, 1123, 1015, 864 and 826 cm$^{-1}$, with a variation allowed for each peak of ±2 cm$^{-1}$ such as ±1 cm$^{-1}$, provided that the Raman spectrum comprises a peak at 1643 (±2 or ±1) cm$^{-1}$.

In comparison, representative solid-form Raman spectrum peaks of a sample of the monohydrochloride Form 2 hydrate include: 2937, 1684, 1607, 1572, ca. 1435 (broad), 1353, 1312, 1255, 1227, 1191, 1126, 1081, 1011, 886, 824, 634, 515 and 332 cm$^{-1}$ (with each peak being ±2 or ±1 cm$^{-1}$).

In an alternative embodiment of the invention, the compound of formula (I) or the salt thereof is for example a phosphate, fumarate (e.g. hemifumarate or monofumarate, such as hemifumarate), 1-hydroxy-2-naphthoate ("xinafoate") (e.g. mono- or di-1-hydroxy-2-naphthoate, such as mono-1-hydroxy-2-naphthoate=mono-xinafoate), or (+)-camphorsulfonate [e.g. (+)-10-camphorsulfonate, or mono- or di-(+)-camphorsulfonate, e.g. mono- or di-(+)-10-camphorsulfonate] salt of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide. This salt can e.g. be for inhaled or intranasal administration e.g. to a mammal such as a human.

In an alternative separate embodiment of the invention, the compound of formula (I) or the salt thereof does not include, and/or is not, N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, whose formula is

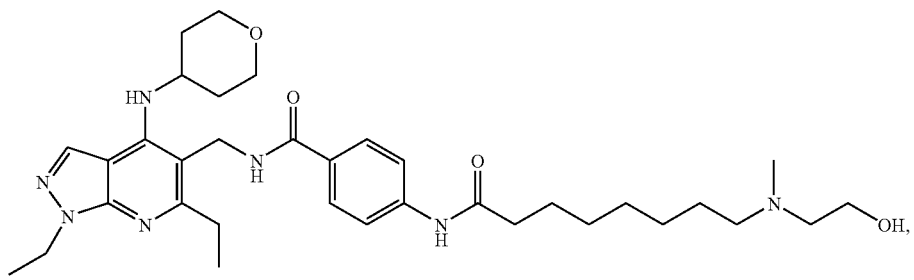

or a salt thereof.

In one preferred embodiment of the invention, the compound of formula (I) or the salt thereof is: 4-({1,6-diethyl-5-[({[4-(4-{[4-(4-morpholinyl)butyl]oxy}butyl)phenyl]carbonyl}amino)methyl]-1H-pyrazolo[3,4-b]pyridin-4-yl}amino)-1-piperidinecarboxamide, whose formula is

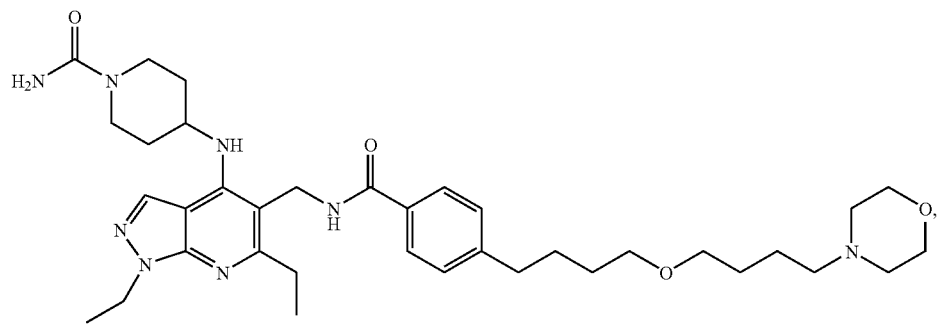

or a salt thereof (e.g. the compound or a pharmaceutically acceptable salt thereof).

In an alternative separate embodiment of the invention, the compound of formula (I) or the salt thereof does not include, and/or is not, 4-({1,6-diethyl-5-[({[4-(4-{[4-(4-morpholinyl)butyl]oxy}butyl)phenyl]carbonyl}amino)methyl]-1H-pyrazolo[3,4-b]pyridin-4-yl}amino)-1-piperidinecarboxamide, whose formula is

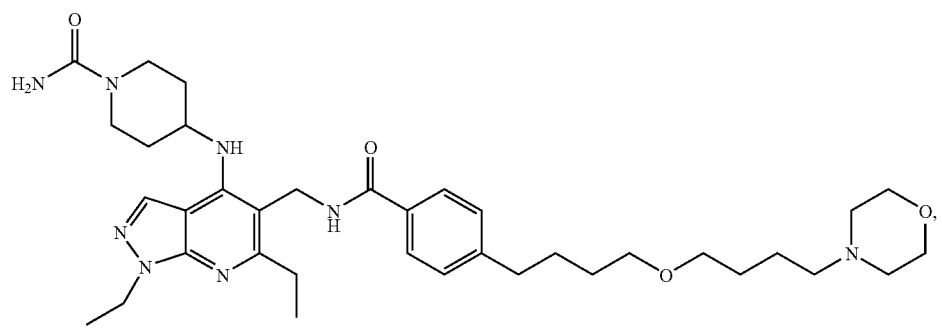

or a salt thereof.

Salts, Solvates, Isomers, Tautomeric Forms, Molecular Weights, Etc.

Because of their potential use in medicine, the salts of the compounds of formula (I) are preferably pharmaceutically acceptable. Suitable pharmaceutically acceptable salts can include acid addition salts, or less commonly (e.g. if a C(O)OH group is present in the compound) base addition salts.

In one embodiment, a pharmaceutically acceptable acid addition salt is optionally formed by mixing of a compound of formula (I) with a pharmaceutically acceptable inorganic or organic acid (such as hydrobromic, hydrochloric, sulfuric, nitric, phosphoric, succinic, maleic, formic, acetic, propionic, fumaric, citric, tartaric, lacetic, benzoic, 1-naphthoic, 1-hydroxy-2-naphthoic ("xinafoic"), salicylic, glutamic such as L-glutamic, aspartic, para-toluenesulfonic, benzenesulfonic, methanesulfonic, ethanesulfonic, naphthalenesulfonic such as 2-naphthalenesulfonic, naphthalenedisulfonic such as 1,5-naphthalenedisulfonic, camphorsulfonic (e.g. 10-camphorsulfonic), 1,2,4-benzenetricarboxylic, hydroxyethylidene-1,1-diphosphonic, or hexanoic acid), optionally in a suitable solvent such as an organic solvent, to give the salt which is usually isolated for example by crystallisation and filtration. The organic solvent used in the pharmaceutically acceptable acid addition salt formation process may e.g. be anhydrous or water-containing. Depending on the properties of and/or suitabilities for use with the compound of formula (I), the organic solvent may be for example selected from methanol, ethanol (e.g. anhydrous), n-propanol (propan-1-ol, e.g. anhydrous), isopropanol (IPA, propan-2-ol, e.g. substantially anhydrous IPA or IPA:water mixtures such as IPA containing about 1-2% water), butanol, pentan-1-ol (e.g. substantially anhydrous), ethyl acetate, methyl isobutyl ketone (MIBK), chloroform, dichloromethane, toluene, or mixtures thereof. A pharmaceutically acceptable inorganic or organic acid can for example be: hydrobromic, hydrochloric, sulfuric, nitric, phosphoric, succinic, maleic, 1-naphthoic, 1-hydroxy-2-naphthoic ("xinafoic"), glutamic such as L-glutamic, para-toluenesulfonic, benzenesulfonic, methanesulfonic, ethanesulfonic, naphthalenesulfonic such as 2-naphthalenesulfonic, naphthalenedisulfonic such as 1,5-naphthalenedisulfonic, camphorsulfonic (e.g. 10-camphorsulfonic and/or (+)-camphorsulfonic), 1,2,4-benzenetricarboxylic, or hydroxyethylidene-1,1-diphosphonic acid.

A pharmaceutically acceptable acid addition salt of a compound of formula (I) can comprise or be for example a hydrobromide (e.g. monohydrobromide or dihydrobromide), hydrochloride (e.g. monohydrochloride or dihydrochloride), sulfate, nitrate, phosphate, succinate (e.g. hemisuccinate), maleate, formate, acetate, propionate, fumarate (e.g. hemifumarate), citrate, tartrate, lactate, benzoate, 1-naphthoate, 1-hydroxy-2-naphthoate ("xinafoate") (e.g. mono-1-hydroxy-2-naphthoate), salicylate, glutamate such as L-glutamate, aspartate, para-toluenesulfonate (e.g. mono- or di-para-toluenesulfonate), benzenesulfonate, methanesulfonate (e.g. mono- or di-methanesulfonate), ethanesulfonate, naphthalenesulfonate (e.g. 2-naphthalenesulfonate), naphthalenedisulfonate (e.g. 1,5-naphthalenedisulfonate), camphorsulfonate (e.g. 10-camphorsulfonate and/or (+)-camphorsulfonate, e.g. mono-(+)-10-camphorsulfonate), 1,2,4-benzenetricarboxylate, hydroxyethylidene-1,1-diphosphonate, or hexanoate salt.

In one embodiment, a pharmaceutically acceptable base addition salt is optionally formed by reaction of a compound of formula (I) with a suitable inorganic or organic base (e.g. triethylamine, ethanolamine, triethanolamine, choline, arginine, lysine or histidine), optionally in a suitable solvent such as an organic solvent, to give the base addition salt which is usually isolated for example by crystallisation and filtration.

Other suitable pharmaceutically acceptable salts include pharmaceutically acceptable metal salts, for example pharmaceutically acceptable alkali-metal or alkaline-earth-metal salts such as sodium, potassium, calcium or magnesium salts; in particular pharmaceutically acceptable metal salts of one or more carboxylic acid moieties that may be present in the compound of formula (I).

Other non-pharmaceutically acceptable salts, e.g. oxalates or trifluoroacetates, may be used, for example in the isolation of compounds of the invention, and are included within the scope of this invention.

The invention includes within its scope all possible stoichiometric and non-stoichiometric forms of the salts of the compounds of formula (I).

Also included within the scope of the invention are all solvates, hydrates and complexes of compounds and salts of the invention.

Certain compounds or salts included in the present invention may be present as isomers. The present invention includes within its scope all such isomers, including racemates, enantiomers and mixtures thereof.

In the compounds or salts, pharmaceutical compositions, uses, methods of treatment/prophylaxis, methods of preparing, etc. according to the present invention, where a defined isomeric configuration e.g. stereochemical configuration is described or claimed, the invention includes a mixture comprising (a) a major component of the compound or salt which is in the described or claimed configuration, together with (b) one or more minor components of the compound or salt which is/are not in the described or claimed configuration. Preferably, in such a mixture, the major component of the compound or salt which is in the described or claimed configuration represents 70% or more, or 75% or more, more preferably 85% or more, still more preferably 90% or more, yet more preferably 95% or more, yet more preferably 98% or more, of the total amount of compound or salt present in the mixture on a molarity basis.

The percentage of one isomeric/stereochemical component in a mixture of different isomeric/stereochemical components, and if appropriate enantiomeric and/or diastereomeric excesses, can be measured using techniques known in the art. Such methods include the following:

(1) Measurement using NMR (e.g. $^1$H NMR) spectroscopy in the presence of chiral agent. One can measure a nuclear magnetic resonance (NMR) spectrum (preferably a $^1$H NMR spectrum, and/or a solution-phase NMR spectrum e.g. in CDCl$_3$ or D6-DMSO solvent) of the compound/salt mixture in the presence of a suitable chiral agent which "splits" the NMR peaks of a given atom in different isomers into different peak positions. The chiral agent can be: i) an optically pure reagent which reacts with the compound/salt e.g. to form a mixture of diastereomers, ii) a chiral solvent, iii) a chiral molecule which forms a transient species (e.g. diastereomeric species) with the compound/salt, or iv) a chiral shift reagent. See e.g. J. March, "Advanced Organic Chemistry", 4th edn., 1992, pages 125-126 and refs. 138-146 cited therein. A chiral shift reagent can be a chiral lanthanide shift reagent such as tris[3-trifluoroacetyl-d-camphorato]europium-(111) or others as described in Morrill, "Lanthanide Shift Reagents in Stereochemical Analysis", VCH, New York, 1986. Whatever the chiral agent is that is used, usually, the relative integrals (intensities) for the NMR peaks of a given atom or group in different isomers can provide a measurement of the relative amounts of each isomer present.

(2) Measurement using chiral chromatography, especially on an analytical scale. A suitable chiral column which separates the different isomeric components can be used to effect separation, e.g. using gas or liquid chromatography such as HPLC, and/or e.g. on an analytical scale. The peaks for each isomer can be integrated (area under each peak); and a comparison or ratio of the integrals for the different isomers present can give a measurement of the percentage of each isomeric component present. See for example: "Chiral Chromatography", Separation Science Series Author: T. E. Beesley and R. P. W. Scott, John Wiley & Sons, Ltd., Chichester, UK, 1998, electronic Book ISBN: 0585352690, Book ISBN: 0471974277.

(3) Separation of pre-existing diastereomeric mixtures which are compounds/salts of the invention can be achieved (usually directly, without derivatisation) using separation techniques such as gas or liquid chromatography. Diastereomeric ratios and/or excesses can thereby be derived e.g. from the relative peak areas or relative separated masses.

(4) Conversion with a chiral/optically-active agent and subsequent separation of the resulting isomers, e.g. diastereomers. Conversion can be via derivatisation of a derivatisable group (e.g. —OH, —NHR) on the compound/salt with an optically-active derivatising group (e.g. optically active acid chloride or acid anhydride); or can be via formation of an acid or base addition salt of the compound by treatment of the compound with an optically-active acid or base, such as + or – di-para-toluoyl tartaric acid. After derivatisation, separation of the resulting isomers e.g. diastereomers, can be using gas or liquid chromatography (usually non-chiral); or (especially with isomeric salts) can be by selective crystallisation of a single isomeric e.g. diastereoisomeric salt. Determination of isomeric ratios and/or excesses can be using chromatography peak areas or measurement of mass of each separated isomer.

See e.g. J. March, "Advanced Organic Chemistry", 4th edn., 1992, pages 120-121 and 126, and refs. 105-115 and 147-149 cited therein.

(5) Measurement of optical activity [alpha] of mixture and comparison with optical activity of pure isomer [alpha]$_{max}$ if available (e.g. see J. March, "Advanced Organic Chemistry", 4th edn., 1992, page 125 and refs. 138-139 cited therein). This assumes a substantially linear relationship between [alpha] and concentration.

Certain of the groups, e.g. heteroaromatic ring systems, included in compounds of formula (I) or their salts may exist in one or more tautomeric forms. The present invention includes within its scope all such tautomeric forms, including mixtures.

Synthetic Process Routes

The following non-limiting processes can generally be used to prepare the compounds of formula (I):

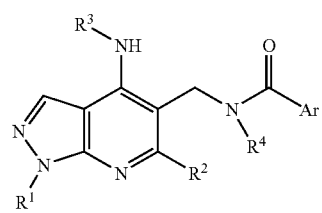

(I)

wherein Ar has the sub-formula (x):

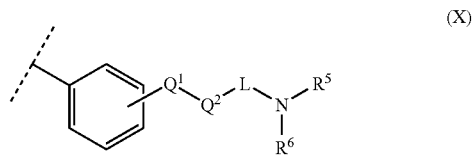

(X)

Some of the following synthetic processes may be exemplified for compounds of Formula (I) with particular Ar groups (in particular embodiments within the Ar sub-formula (x)) and/or with particular substitution patterns e.g. particular values of $Q^1$ and $Q^2$ and L. However, at least some of these processes are likely to be able to be usable with appropriate modification(s), e.g. modification(s) of starting materials and reagents, which modification(s) may be extensive, for making other compounds of Formula (I).

Process 1A (For example, the compounds or salts whose names and/or chemical structures are given in and which are the products of Examples 1A1, 1A2, 1A3, 1B, 1C, 1D, 1E, 1F, 1G, 1H1, 1H2, 1J1, 1J2, 3, 4, 9, 11, 12, 17, 18, 25, 26 and 29 to 34, may optionally be prepared by this Process 1A).

Compounds of formula (II), which are compounds of formula (I) wherein Ar has sub-formula (x), $Q^1$ is NH, $Q^2$ is —C(O)—, and L is $(CH_2)_n$, wherein $R^1$, $R^2$, $R^3$, $R^4$, $R^5$, $R^6$, and n are as defined herein, or salts thereof, can be prepared by reaction (substitution) of a compound of formula (III), wherein $X^1$ is a suitable leaving group such as mesylate (methanesulfonate), tosylate (p-toluenesulfonate) or a halogen atom, in particular a halogen atom such as preferably a bromine atom, and wherein $R^1$, $R^2$, $R^3$, $R^4$ and n are as defined herein, with an amine of formula (IV), wherein $R^5$ and $R^6$ are as defined herein. Suitable conditions for the reaction include heating in a suitable solvent such as N,N-dimethylformamide, in the presence of a suitable base (e.g. a base having a low nucleophilicity such that it does not substantially displace the $X^1$ leaving group) such as N,N-diisopropylethylamine, e.g. heating at a suitable temperature such as about 70-90° C. e.g. about 80-85° C. Alternative conditions include heating under microwave irradiation in a suitable solvent such as N,N-dimethylformamide, e.g. at a suitable temperature such as about 140° C.

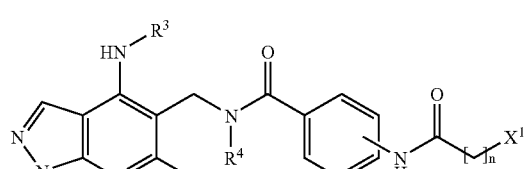

(III)

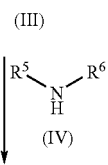

(IV)

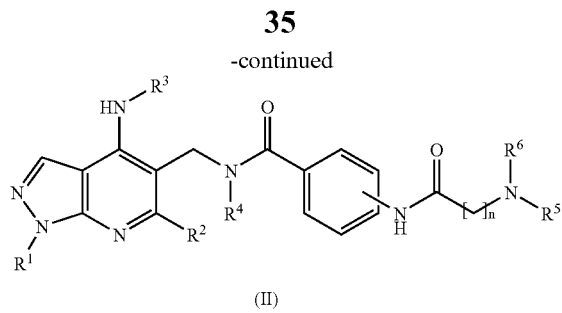

(II)

In general, the amines of formula (IV) are either commercially available (for example in some cases from Aldrich), known in the literature, or may be prepared e.g. by conventional means.

Compounds of formula (III), wherein $R^1$, $R^2$, $R^3$, $R^4$, $X^1$, and n are as defined herein (in particular where $X^1$=Br), typically may be prepared from compounds of formula (V), wherein $R^1$, $R^2$, $R^3$ and $R^4$ are as defined herein, by reaction with a suitable acylating agent (VI), wherein $X^1$ and n are as defined herein (in particular where $X^1$=Br) and $X^2$ represents a halogen atom such as a chlorine or bromine atom, preferably a chlorine atom. Suitable conditions include carrying out the reaction in a suitable anhydrous solvent such as dichloromethane or chloroform, in the presence of a suitable base such as N,N-diisopropylethylamine or triethylamine, at a suitable temperature such as from 0° C. to room temperature, and suitably under nitrogen.

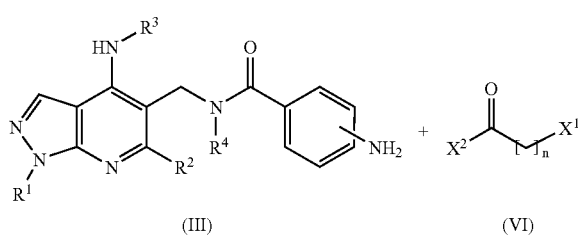

(III)    (VI)

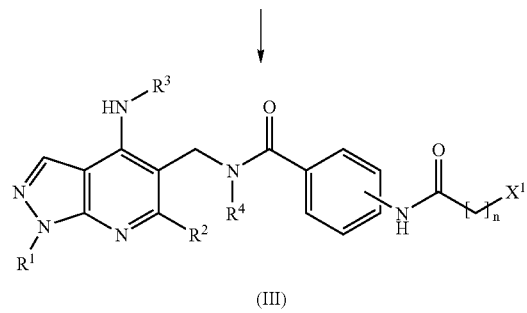

(III)

Compounds of formula (VI), wherein $X^1$, $X^2$ and n are as defined herein, typically can be prepared from compounds of formula (VII), wherein $X^1$ and n are as defined herein (in particular where $X^1$=Br), by reaction with for example thionyl chloride (for $X^2$=Cl), phosphoryl chloride (for $X^2$=Cl), or phosphoryl bromide (for $X^2$=Br) (preferably thionyl chloride for $X^2$=Cl), or other suitable reagents e.g. as described in R. C. Larock, *Comprehensive Organic Transformations*, $2^{nd}$ Ed, Wiley, 1999. Suitable conditions for $X^2$=Cl include the use of thionyl chloride, e.g. at room temperature, optionally in a suitable non-aqueous (e.g. anhydrous) aprotic organic solvent such as toluene.

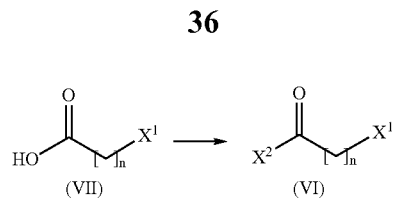

(VII)    (VI)

Compounds of formula (V), wherein $R^1$, $R^2$, $R^3$ and $R^4$ are as defined herein, can generally be prepared from compounds of formula (VIII), wherein $R^1$, $R^2$, $R^3$ and $R^4$ are as defined herein, and $X^3$ is a protecting group, by deprotection.

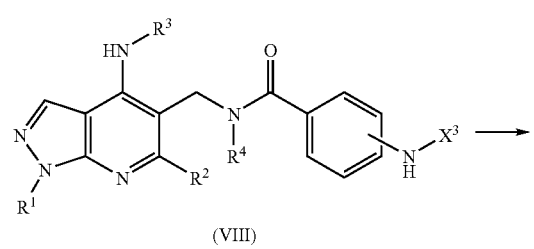

(VIII)

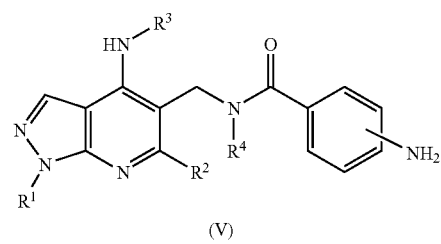

(V)

$X^3$ can be a nitrogen protecting group e.g. as described in T. W. Greene and P. G. M Wuts *Protecting Groups in Organic Synthesis*, Wiley 1999. Suitably, $X^3$ is tert-butoxycarbonyl ('BOC'). When $X^3$ is the BOC protecting group, standard methods (e.g. as described in Greene) can be used for the deprotection reaction (VIII) to (V), for example treatment with a solution of hydrogen chloride in 1,4-dioxane such as 4M HCl in 1,4-dioxane, e.g. at room temperature.

Compounds of formula (VIII), wherein $R^1$, $R^2$, $R^3$ and $R^4$ are as defined herein, and $X^3$ is a protecting group such as BOC, may typically be prepared by reaction between compounds of formula (IX), wherein $R^1$, $R^2$, $R^3$ and $R^4$ are as defined herein, and compounds of formula (X) wherein $X^3$ is as defined herein such as BOC and $X^4$ is a suitable leaving group.

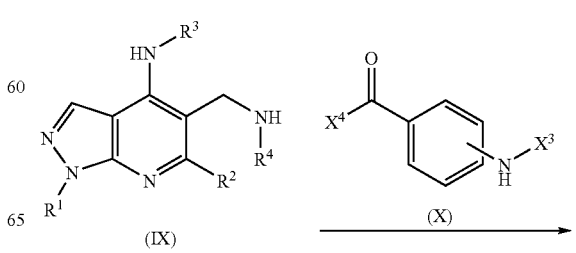

(IX)    (X)

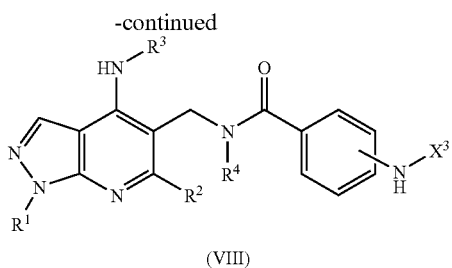

(VIII)

The activated compound (the compound of formula (X)) can for example be an activated ester and $X^4$ the leaving group thereof. For example the leaving group $X^4$ can be of sub-formula (bt):

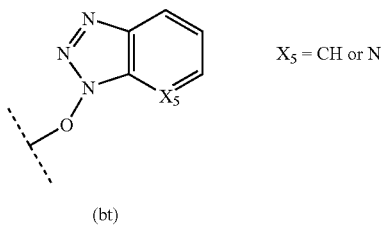

(bt)

The activated compound of formula (X), e.g. wherein $X^4$ is of sub-formula (bt), can be formed from the carboxylic acid of formula (Xa), wherein $X^3$ is as defined herein such as BOC:

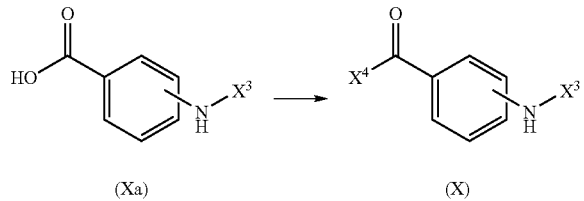

In one embodiment the activated compound of formula (X) wherein $X^4$ is of sub-formula (bt) is formed from the carboxylic acid of formula (Xa) by the following reaction (a). In this reaction (a), the carboxylic acid (Xa) is reacted with a suitable organic di-substituted carbodiimide, such as 1-ethyl-3-(3'-dimethylaminopropyl)carbodiimide [also named 1-(3-dimethylaminopropyl)-3-ethylcarbodiimide] or a salt thereof such as the hydrochloride salt thereof (EDC), or such as N,N'-dicyclohexylcarbodiimide (DCC), followed by reaction of the resulting product with 1-hydroxybenzotriazole (when $X_5$ is CH) or 1-hydroxy-7-azabenzotriazole (when $X_5$ is N). In one embodiment, this reaction (a), to form (X) wherein $X^4$ is of sub-formula (bt) from (Xa), is carried out in a suitable organic solvent e.g. an aprotic organic solvent (preferably anhydrous) such as N,N-dimethylformamide or acetonitrile, e.g. under anhydrous conditions and/or e.g. at a suitable temperature such as room temperature (e.g. about 18 to about 25° C.). In one optional embodiment, this reaction (a) is carried out in the presence of a tertiary amine base such as N,N-diisopropylethylamine ($^iPr_2NEt$=DIPEA).

In another embodiment, the activated compound of formula (X) wherein $X^4$ is of sub-formula (bt) is formed from the carboxylic acid of formula (Xa) by the following reaction (b). In reaction (b), the carboxylic acid (Xa) is reacted with a suitable 1-hydroxybenzotriazole-based or 1-hydroxy-7-azabenzotriazole-based coupling agent, such as (i), (ii), (iii) or (iv):

(i) O-(benzotriazol-1-yl)-N,N,N',N'-tetramethyluronium hexafluorophosphate (also called HBTU; when $X_2$ is CH), or (ii) 2-(1H-benzotriazol-1-yl)-1,1,3,3-tetramethyluronium tetrafluoroborate (TBTU; when $X_2$ is CH), or (iii) O-(7-azabenzotriazol-1-yl)—N,N,N',N'-tetramethyluronium hexafluorophosphate (HATU, when $X_2$ is N), or (iv) (benzotriazol-1-yloxy)-trispyrrolidinophosphonium hexafluorophosphate (PyBOP; when $X_2$ is CH)).

In one optional embodiment, this reaction (b), to form (X) wherein $X^4$ is of sub-formula (bt) from (Xa), is carried out in the presence of a tertiary amine base such as N,N-diisopropylethylamine ($^iPr_2NEt$=DIPEA). In one embodiment, this reaction (b) is usually carried out in the presence of a solvent such as an aprotic organic solvent (e.g. anhydrous solvent) such as N,N-dimethylformamide or acetonitrile, e.g. under anhydrous conditions and/or at a suitable temperature such as room temperature (e.g. about 18 to about 25° C.).

In one alternative embodiment, an activated compound of formula (X) is the product (adduct) formed from the reaction of the carboxylic acid of formula (Xa) with a suitable organic di-substituted carbodiimide (e.g. R'—N=C=N—R") [wherein the carbodiimide can e.g. be 1-(3-dimethylaminopropyl)-3-ethylcarbodiimide or a salt thereof such as the hydrochloride salt thereof (EDC), or dicyclohexylcarbodiimide (DCC)]. In this case, in the activated compound of formula (X) being the carboxylic acid-carbodiimide adduct, $X^4$ is —O—C(NHR')=N—R" or —O—C(NHR")=N—R'. This is the situation e.g. when the carbodiimide is reacted with the carboxylic acid (Xa) without 1-hydroxybenzotriazole or 1-hydroxy-7-azabenzotriazole being present. In one embodiment, this reaction is carried out in a suitable organic solvent e.g. an aprotic organic solvent (preferably anhydrous) such as N,N-dimethylformamide or acetonitrile, e.g. under anhydrous conditions and/or e.g. at a suitable temperature such as room temperature (e.g. about 18 to about 25° C.). In one optional embodiment, this reaction (a) is carried out in the presence of a tertiary amine base such as N,N-diisopropylethylamine ($^iPr_2NEt$=DIPEA).

In another alternative embodiment, the activated compound of formula (X) is for example the acid chloride (wherein $X^4$ is Cl). In one embodiment, this acid chloride is for example formed from the corresponding carboxylic acid (Xa) either (a) by reaction with thionyl chloride, either in an organic solvent such as chloroform or without solvent, or (b) by reaction with oxalyl chloride in N,N-dimethyloformamide (e.g. catalytic DMF in dichloromethane or in DMF solvent). When an acid chloride within formula (X) is used to prepare the compound of formula (VIII), the reaction with amine (IX) is usually carried out in the presence of a tertiary amine base such as N,N-diisopropylethylamine ($^iPr_2NEt$=DIPEA) and/or in a suitable aprotic organic solvent (e.g. anhydrous solvent) such as acetonitrile or dichloromethane, for example at room temperature (e.g. about 18 to about 25° C.). Note: this acid chloride method may not be ideal for Boc-protected compounds.

Compounds of formula (IX), wherein $R^1$, $R^2$ and $R^3$ are as defined herein and $R^4$ represents hydrogen, can be prepared by hydrogenation of an azide compound of formula (XI), wherein $R^1$, $R^2$ and $R^3$ are as defined herein, in the presence of a suitable catalyst such as a palladium catalyst, e.g. palladium on carbon, in a suitable solvent such as ethanol, e.g. at a suitable temperature such as room temperature:

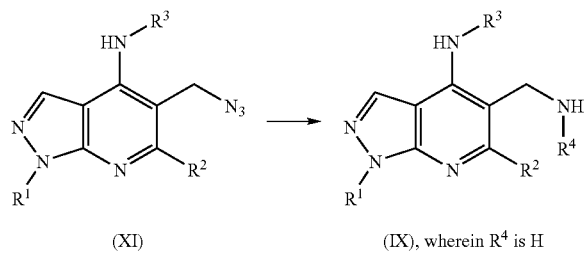 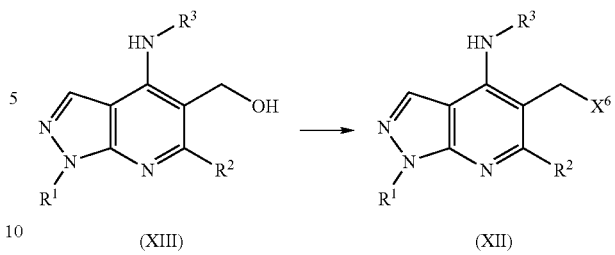

(XI)     (IX), wherein $R^4$ is H     (XIII)     (XII)

Compounds of formula (XI), wherein $R^1$, $R^2$ and $R^3$ are as defined herein, may be prepared from compounds of formula (XII), wherein $R^1$, $R^2$ and $R^3$ are as defined herein and wherein $X^6$ is a leaving group such as a halogen atom, mesylate (methanesulfonate), tosylate (p-toluenesulfonate), or triflate (trifluoromethanesulfonate) (suitably a halogen atom such as a chlorine atom).

For example the compounds of formula (XII), e.g. wherein $X^6$ is Cl, can be reacted with an azide salt such as sodium, lithium or potassium azide, in a suitable solvent such as dimethylsulfoxide such as dry DMSO, e.g. at a suitable temperature such as room temperature, to give compounds of formula (XI).

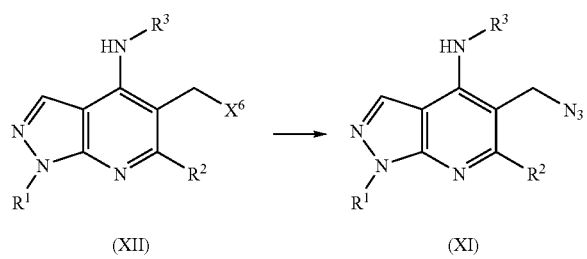

(XII)     (XI)

Compounds of formula (XII) or acid addition salts thereof (e.g. sulfonate such as benzenesulfonate or methanesulfonate salt thereof), wherein $R^1$, $R^2$ and $R^3$ and $X^6$ are as defined herein (e.g. wherein $X^6$ is Cl, mesylate, tosylate or triflate), can be prepared by reaction of compounds of formula (XIII), wherein $R^1$, $R^2$ and $R^3$ are as defined herein, with a suitable reagent such as thionyl chloride (for when $X^6$ is Cl), oxalyl chloride (for when $X^6$ is Cl), methanesulfonyl chloride or methanesulfonic anhydride (for when $X^6$ is mesylate), or para-toluenesulfonyl chloride or para-toluenesulfonic anhydride (for when $X^6$ is tosylate), preferably thionyl chloride. Suitable conditions, for when $X^6$ is Cl, include reacting with thionyl chloride in a suitable non-aqueous (e.g. anhydrous) aprotic organic solvent such as toluene or anisole (methoxybenzene), e.g. with heating to ca. 60-90° C. such as to ca. 85° C. (e.g. with toluene), or e.g. at 20±5° C. (e.g. with anisole), and optionally also in the presence of an anhydrous aryl (e.g. phenyl), alkyl (e.g. methyl) or trifluoromethyl sulfonic acid, such as benzenesulfonic acid or methanesulfonic acid (e.g. to prepare the sulfonate such as benzenesulfonate salt of (XII), e.g. when $X^6$ is Cl, for example to try to improve the stability of the "benzylic" chloride). Alternative conditions include reacting compounds of formula (XIII) with thionyl chloride and methanesulfonic acid or benzenesulfonic acid in a suitable non-aqueous (e.g. anhydrous) aprotic organic solvent such as dichloromethane, e.g. at a suitable temperature such as room temperature.

Preferably, in the process, the compound of formula (XII) or the acid addition salt thereof (e.g. sulfonate such as benzenesulfonate or methanesulfonate salt thereof, and/or e.g. when $X^6$ is Cl) is not isolated. Rather, it is preferably left in solution, optionally with partial or full exchange of solvents. The solution of the compound of formula (XII) or the acid addition salt thereof (e.g. when $X^6$ is Cl) can be reacted directly in the next step.

Alternatively, compounds of formula (XI) wherein $R^1$, $R^2$ and $R^3$ are as defined herein can be prepared directly from compounds of formula (XIII) wherein $R^1$, $R^2$ and $R^3$ are as defined herein.

For example, compounds of formula (XI) may be prepared by reacting compounds of formula (XIII) with an azide salt, e.g. sodium azide, in the presence of a halogenating agent such as carbon tetrabromide and a phosphine such as triphenylphosphine under suitable conditions, such as N,N-dimethylformamide, e.g. at a suitable temperature such as between 0° C. and room temperature (see e.g. Toyota et. al. *Journal of Organic Chemistry*, 2000, 65(21), 7110-7113).

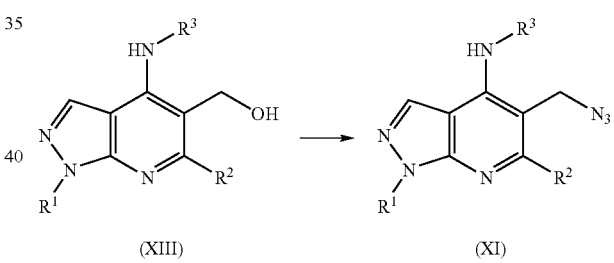

(XIII)     (XI)

This route, (XIII) to (XI) directly, may be suitable for where $R^3$ is a urea-containing group [such as a N-aminocarbonyl-piperidinyl or N-aminocarbonyl-pyrrolidinyl group within sub-formula (bb) or (aa), that is wherein $NHR^3$ is of sub-formula (k2) or (k3)], because it is noted that these $R^3$ urea-containing groups may not be tolerant of thionyl chloride which may be used in converting (XIII) to (XII) wherein $X^6$ is Cl and thence to (XI).

In another alternative embodiment of particular interest, an amine compound of formula (IX) or a salt thereof (e.g. HCl salt thereof), wherein $R^1$, $R^2$ and $R^3$ are as defined herein and $R^4$ is as defined herein (in particular where $R^4$ is a hydrogen atom), may usually be prepared directly from a compound of formula (XII) or an acid addition salt thereof, wherein $R^1$, $R^2$ and $R^3$ and $X^6$ are as defined herein, without first converting to an azide compound of formula (XI). For example, in compound (XII) or the acid addition salt thereof, $X^6$ can in particular be a chlorine atom. When $X^6$ is a chlorine atom, a suitable acid addition salt such as an arylsulfonate, alkylsulfonate or trifluoromethylsulfonate salt (in particular a benzenesulfonate or methanesulfonate salt) of the compound of formula (XII) can for example be used, in particular when $R^1$ and $R^2$ are ethyl and when $R^3$ is of the sub-formula (h) that is when $R^3$ is tetrahydro-2H-pyran-4-yl.

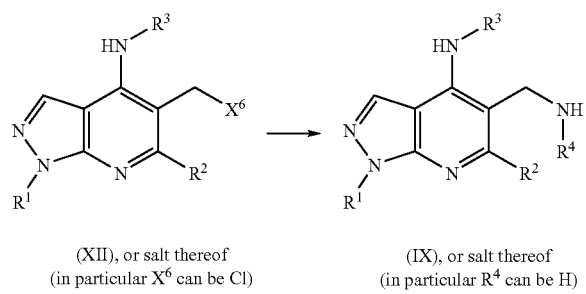

(XII), or salt thereof
(in particular $X^6$ can be Cl)

(IX), or salt thereof
(in particular $R^4$ can be H)

This reaction, converting the compound (XII) or the acid addition salt thereof (e.g. sulfonate such as benzenesulfonate salt) to the amine compound (IX) or the salt thereof (e.g. HCl salt), may for example be carried out under suitable conditions, for example by reaction of a compound of formula (XII) or an acid addition salt thereof with an aminating agent. When $R^4$ represents a hydrogen atom, and optionally for example when $X^6$ is a chlorine atom, a suitable aminating agent may be used, e.g. an alkali-metal hexamethyldisilazide such as lithium hexamethyldisilazide, sodium hexamethyldisilazide or potassium hexamethyldisilazide (in particular lithium hexamethyldisilazide), in a suitable non-aqueous non-alcohol (aprotic) organic solvent (e.g. anhydrous solvent) such as tetrahydrofuran (THF), for example at a suitable temperature such as about 25 to about 50° C., for example ca. 30-45° C. or ca. 30-40° C. The compound (XII) or the salt thereof is suitably added slowly to a mixture or solution of the alkali-metal hexamethyldisilazide (e.g. lithium hexamethyldisilazide) in the aprotic organic solvent (e.g. THF), to try to minimise alkylation of any in-situ deprotected amine (IX) by the compound (XII) or the salt thereof. The reaction with the suitable aminating agent (e.g. with the alkali-metal hexamethyldisilazide) is suitably followed by treatment with an aqueous acid such as aqueous hydrochloric acid (e.g. 2-10M, e.g. about 5M), for example at a suitable temperature such as from 0° C. to room temperature, for example at 5-15° C. or ca. 10° C. In one particular embodiment, a solution of the produced amine (IX) or the salt thereof in an organic solvent (suitably in an organic solvent having a low water miscibility, such as comprising 2-methyl-THF or a mixture of sec-butanol and isopropanol) is extracted with aqueous base, such as concentrated (e.g. ca. 32% w/w) NaOH solution, to form the amine compound (IX) as the "free base". Optionally, a mono-acid-addition salt, e.g. monohydrochloride, of the amine (IX) can be formed by mixing the "free base" amine compound (IX) (e.g. in an organic solvent such as comprising 2-methyl-THF or a mixture of sec-butanol and isopropanol) with about 1 equivalent (e.g. 1.03 equiv.) of a suitable acid such as HCl (e.g. aqueous hydrochloric acid such as concentrated aq. HCl e.g. ca. 36% w/w aq. HCl), preferably under conditions such that the mono-acid-addition salt, e.g. monohydrochloride, of the amine (IX) crystallises from a or the organic solvent present.

In one particular simplified embodiment of the conversion of compound (XII) or a salt thereof to amine compound (IX) or a salt thereof, when $X^6$ is a chlorine atom in the compound of formula (XII) and when $R^4$ is a hydrogen atom in the compound of formula (IX), the precursor alcohol compound of formula (XIII) or a salt thereof is converted into the amine of formula (IX) or a salt thereof, via the compound of formula (XII) or a salt thereof, without substantially purifying and/or without substantially isolating the compound of formula (XII) or the salt thereof wherein $X^6$ is a chlorine atom (Cl). In this embodiment, the compound of formula (XII) or the salt thereof wherein $X^6$ is a chlorine atom can for example be in the form of the benzenesulfonate salt, in particular when $R^1$ and $R^2$ are ethyl and when $R^3$ is of the sub-formula (h) that is when $R^3$ is tetrahydro-2H-pyran-4-yl. In the first step, conversion of compound (XIII) to compound (XII) or a salt thereof wherein $X^6$ is Cl is optionally carried out using thionyl chloride in a suitable non-aqueous (e.g. anhydrous) aprotic organic solvent such as anisole or toluene, e.g. at 20±5° C. or with heating to ca. 60-90° C., and optionally in the presence of an organic sulfonic acid such as benzenesulfonic acid to prepare the sulfonate e.g. benzenesulfonate salt of (XII), wherein $X^6$ is Cl. The second step, the compound (XII) or the salt thereof (wherein $X^6$ is Cl), dissolved and/or suspended in anisole and/or toluene, is optionally converted to compound (IX) or a salt thereof wherein $R^4$ is H, e.g. as described elsewhere hereinabove or hereinbelow. See Intermediate 7A herein for a specific example of this two-step reaction:

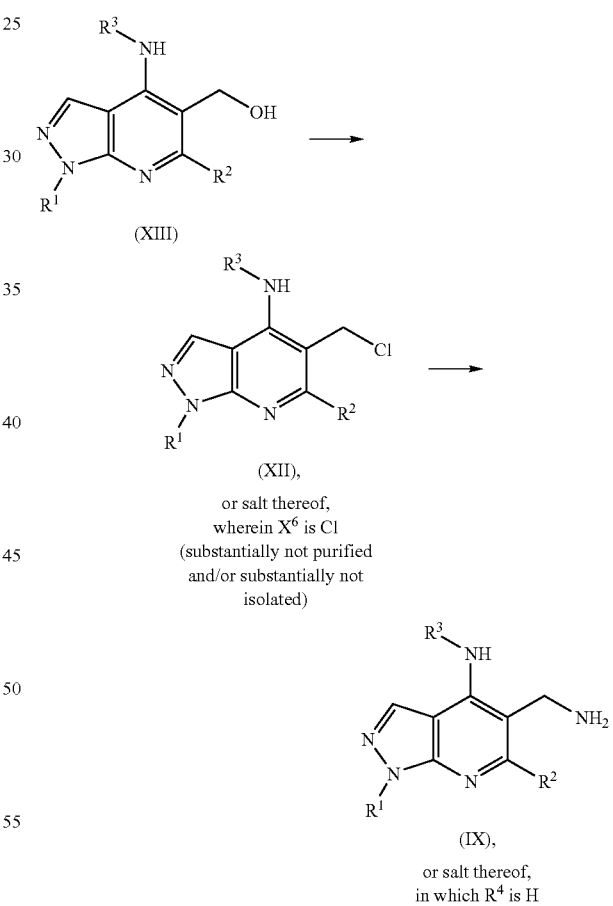

(XIII)

(XII),
or salt thereof,
wherein $X^6$ is Cl
(substantially not purified
and/or substantially not
isolated)

(IX),
or salt thereof,
in which $R^4$ is H

Compounds of formula (XIII), wherein $R^1$, $R^2$, and $R^3$ are as defined herein, can be prepared by reaction of compounds of formula (XIV), wherein $R^1$, $R^2$ and $R^3$ are as defined herein, and wherein $X^7$ is an alkyl group such as a $C_{1-6}$ or $C_{1-4}$ alkyl (e.g. straight-chain alkyl) group e.g. in particular ethyl, with a suitable reducing agent in a suitable solvent, e.g. at a suitable temperature.

One suitable reducing agent is lithium borohydride, in which case:

- a suitable solvent can for example comprise or be an aprotic organic solvent (e.g. anhydrous) such as tetrahydrofuran (THF, e.g. dry), optionally mixed with toluene (e.g. dry), or THF alone;
- and (for lithium borohydride), preferably, dry methanol (e.g. 3 to 15 equivalents, e.g. about 9 equivalents, but preferably not in very large excess) can be used, in particular in admixture with the suitable aprotic organic solvent such as THF, to speed up the reduction reaction;
- and/or (for lithium borohydride) a suitable reaction temperature can be from room temperature to the reflux temperature, e.g. about 50 to about 75° C., e.g. about 60 to about 70° C., e.g. 63-69° C. or 64-68° C.

Another reducing agent is di-iso-butylaluminium hydride (e.g. solution in toluene), in which case: a suitable solvent is dichloromethane and/or toluene, and/or a suitable reaction temperature can be about 0° C.

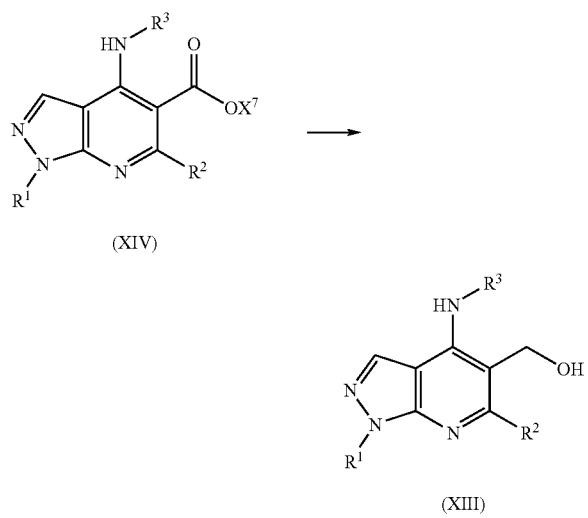

Compounds of formula (XIV), wherein $R^1$, $R^2$ and $R^3$ and $X^7$ are as defined herein, may be prepared by reaction of a compound of formula (XV) with an amine of formula $R^3NH_2$, for example generally according to the method described by Yu et. al. in *J. Med. Chem.*, 2001, 44, 1025-1027. The reaction is preferably carried out in the presence of a base such as triethylamine or N,N-diisopropylethylamine, and/or in an organic solvent such as ethanol, dioxane, 1-methyl-2-pyrrolidinone (NMP) or acetonitrile. The reaction may require heating e.g. to ca. 60-180° C., for example at 115° C.:

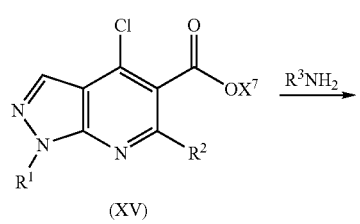

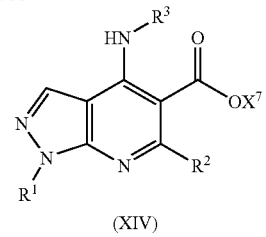

When $R^3$ is the N-aminocarbonyl-piperidinyl or N-aminocarbonyl-pyrrolidinyl group within sub-formula (bb) or (aa), that is wherein $NHR^3$ is of sub-formula (k2) or (k3), the compound of formula (XIV) can be prepared by reacting a compound of formula (XIVa), wherein $R^1$, $R^2$ and $X^7$ are as defined herein and $n^3=0$ or 1, or a salt thereof (e.g. a hydrochloride salt thereof) with a urea-forming reagent capable of converting the (4-piperidinyl)amino or (3-pyrrolidinyl)amino group in the compound of formula (XIVa) into a [(1-aminocarbonyl)-4-piperidinyl]amino group or [(1-aminocarbonyl)-3-pyrrolidinyl]amino group as in the below-illustrated embodiment of formula (XIV) respectively:

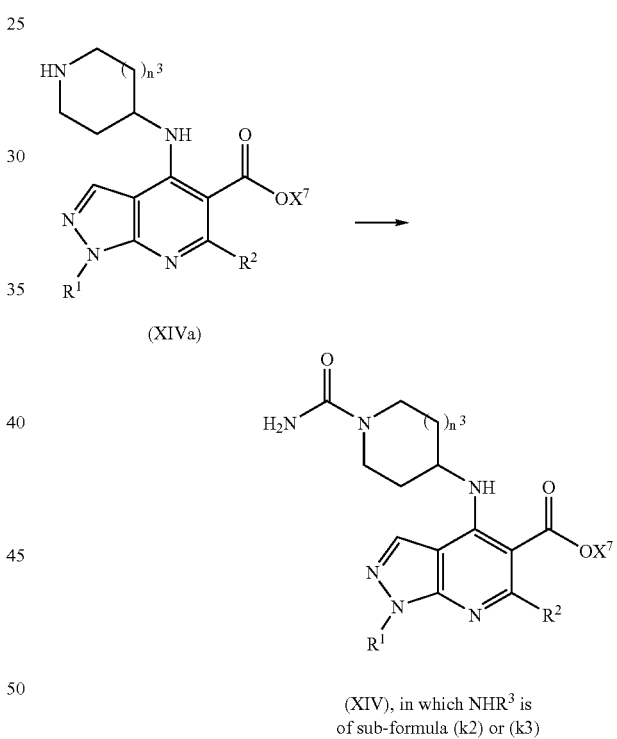

The urea-forming reagent may be benzyl isocyanate (followed later by debenzylation e.g. reductive debenzylation), or preferably the urea-forming reagent is a tri($C_{1-4}$alkyl)silyl isocyanate such as a tri($C_{1-2}$alkyl)silyl isocyanate, preferably trimethylsilyl isocyanate. The conversion of the compound (XIVa) or salt thereof to the compound (XIV) is in one embodiment carried out in the presence of a suitable base such as N,N-diisopropylethylamine, in a suitable solvent such as dichloromethane or chloroform, at a suitable temperature such as at room temperature or at the reflux temperature of the solvent.

Compound (XIVa), wherein $R^1$, $R^2$, $X^7$ and $n^3$ are as defined herein, or a salt thereof, can be prepared from compound (XIVb), wherein $R^1$, $R^2$, $X^7$ and $n^3$ are as defined herein and Prot is a nitrogen protecting group such as (tert-butyloxy)carbonyl, by removal of the nitrogen protecting group. For example, removal of the (tert-butyloxy)carbonyl group can be effected under suitable acidic conditions, such as with hydrogen chloride (e.g. 4M) in a suitable solvent such as 1,4-dioxane:

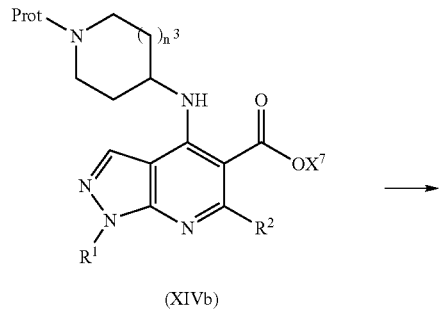

(XIVb)

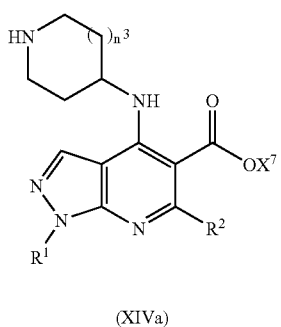

(XIVa)

Compound (XIVb), wherein $R^1$, $R^2$, and $n^3$ are as defined herein, $X^7$ is ethyl and Prot is (tert-butyloxy)carbonyl, can be prepared by reaction of a compound of formula (XV), wherein $R^1$ and $R^2$ are as defined herein and $X^7$=ethyl, with 1,1-dimethylethyl 4-amino-1-piperidinecarboxylate (e.g. commercially available from AstaTech, Philadelphia, USA) or 1,1-dimethylethyl 3-amino-1-pyrrolidinecarboxylate (e.g. commercially available from Aldrich). The reaction is optionally carried out in the presence of a base such as triethylamine or N,N-diisopropylethylamine, optionally in a suitable organic solvent such as acetonitrile, at a suitable temperature such as 60-100° C. (e.g. 80-90° C.):

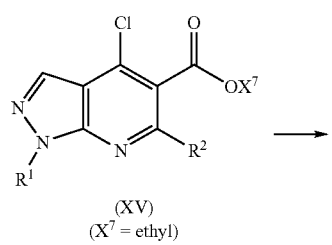

(XV)
($X^7$ = ethyl)

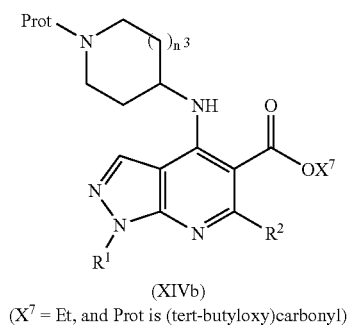

(XIVb)
($X^7$ = Et, and Prot is (tert-butyloxy)carbonyl)

Compounds of formula (XV), wherein $R^1$, $R^2$, and $X^7$ are as defined herein can be prepared by reaction of compounds of formula (XVI), wherein $R^1$ is as defined herein, with a dialkyl (1-chloroalkylidene)propanedioate of formula (XVII) (which is $(R^2)(Cl)C=C(CO_2X^7)_2$, wherein $R^2$ and $X^7$ are as defined herein; for example a diethyl (1-chloroalkylidene)propanedioate for when $X^7$ is Et; and e.g. $R^2$ can be Et), followed by reaction with phosphorous oxychloride ($POCl_3$). Suitable conditions for reaction of compounds of formula (XVI) with a dialkyl (1-chloroalkylidene)propanedioate of formula (XVII) include heating, for example in a suitable solvent such as toluene, and for example in the presence of a suitable base such as triethylamine, e.g. at a suitable temperature such as the reflux temperature of the solvent. Suitable conditions for the reaction of the intermediate [formed from (XVI) and the dialkyl (1-chloroalkylidene)propanedioate (XVIII)] with phosphorous oxychloride ($POCl_3$) can include heating, e.g. heating at the reflux temperature of phosphorous oxychloride.

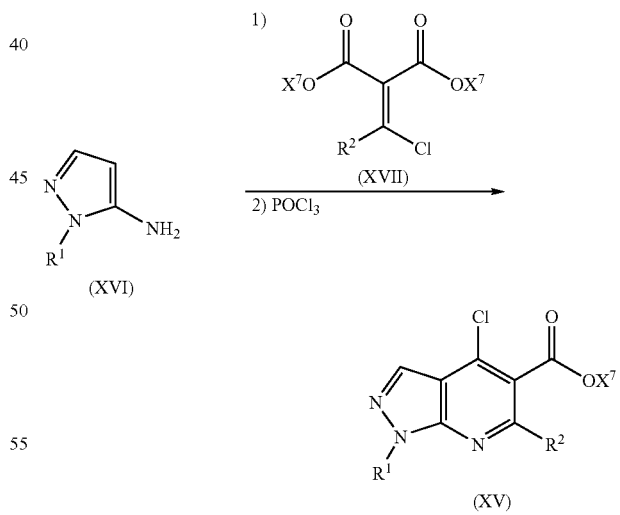

In one embodiment, a compound of formula (XVII), wherein $R^2$ and $X^7$ are as defined herein, is prepared by reaction of a compound of formula (XVIII), wherein $R^2$ and $X^7$ are as defined herein, with phosphorus oxychloride ($POCl_3$) in the presence of a suitable base such as tributylamine, at a suitable temperature such as ca. 80-130° C., for example ca. 100-120° C.

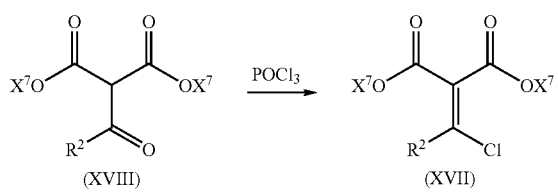

In one embodiment, a compound of formula (XVIII), wherein $R^2$ and $X^7$ are as defined herein, is prepared by reaction of a dialkyl malonate of formula (XIX), wherein $X^7$ is as defined herein, with magnesium chloride (suitably anhydrous) and a suitable non-aqueous base such as triethylamine, in a suitable solvent (e.g. anhydrous solvent) such as acetonitrile, at a suitable temperature such as ca. 5-10° C., followed by addition of an acid chloride of formula (XX), for example propanoyl chloride when $R^2$ is ethyl, at a suitable temperature such as between 10° C. and room temperature. In one embodiment, the reaction is for example carried out under anhydrous conditions:

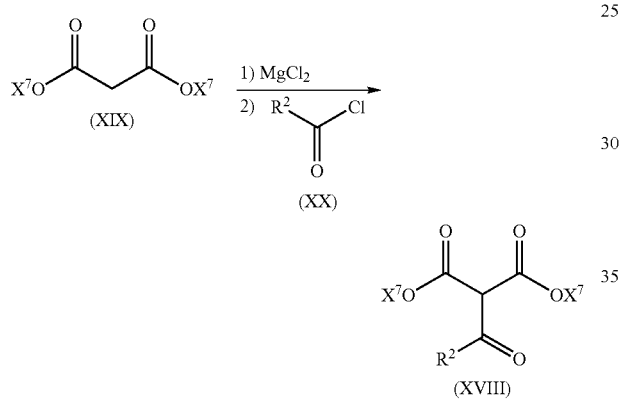

Generally, many of the compounds of formulae (XIX) and (XX) are either known compounds or may be prepared e.g. by conventional means. For example, the compound of formula (XIX) where $X^7$ is ethyl, and the compound of formula (XX) where $R^2$ represents methyl or ethyl, are commercially available, e.g. from Aldrich or elsewhere.

For examples of syntheses of compounds (XVIII) and compounds (XVII), in which $R^2$ is cyclopropyl, n-propyl, ethyl, cyclobutyl and (cyclopropyl)methyl-, see for example Intermediates 1, 3 to 6 and 7 to 11 on pages 60-62 of WO 2005/090348 A1 (Glaxo Group Limited).

In an alternative embodiment, a compound of formula (XV), wherein $R^1$, $R^2$ and $X^7$ are as defined herein, is prepared by reaction of a compound of formula (XVI), wherein $R^1$ is as defined herein, with a compound of formula (XXI), wherein $R^2$ and $X^7$ are as defined herein, with heating, followed by reaction with phosphorous oxychloride, again with heating (e.g. see Yu et. al. in *J. Med. Chem.*, 2001, 44, 1025-1027). Compounds of formula (XXI) can for example be diethyl [(ethyloxy)methylidene]propanedioate (wherein $R^2$ is H and $X^7$ is Et, available from Aldrich) or diethyl [1-(ethyloxy)ethylidene]propanedioate (wherein $R^2$ is Me and $X^7$ is Et, see Eur. Pat. Appl. (1991), EP 413918 A2).

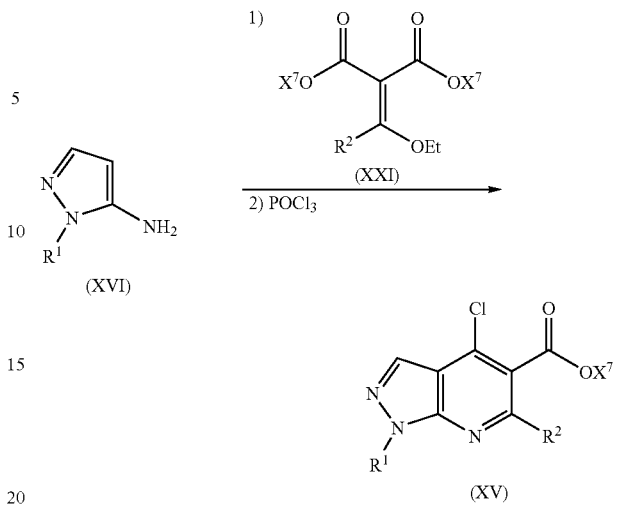

Where the desired amino pyrazole of formula (XVI) is not commercially available, in one alternative embodiment, a method of preparation of (XVI) comprises reaction of 3-hydrazinopropanenitrile (available from Lancaster Synthesis) with a suitable aldehyde of formula $R^{40}$CHO in a suitable solvent such as ethanol, with heating, followed by reduction with, for example sodium in a suitable solvent such as t-butanol. $R^{40}$ should be chosen so as to contain one less carbon atom than $R^1$, for example $R^{40}$=methyl will afford $R^1$=ethyl. See also the method(s) described by Dorgan et. al. in *J. Chem. Soc., Perkin Trans.* 1, 1980, (4), 938-942:

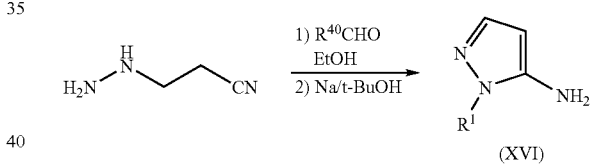

In an alternative less-preferred embodiment of Process 1A, the 4-chloro substituent in the compound of formula (XV) is replaced by another halogen atom, such as a bromine atom, or by another suitable leaving group which is displaceable by an amine of formula $R^3NH_2$. The leaving group can, for example, be a straight-chain alkoxy group —$OR^{35}$ being —OMe, —OEt or —OPr", or a group —O—S(O)$_2$—$R^{37}$, wherein $R^{37}$ is methyl, CF$_3$, or phenyl or 4-methyl-phenyl. The reaction is optionally carried out with or without solvent. The reaction may require heating.

In one embodiment, a compound of formula (XI), wherein $R^1$ and $R^2$ are as defined herein and $R^3$ represents the N-aminocarbonyl-piperidinyl or N-aminocarbonyl-pyrrolidinyl group of sub-formula (bb) or (aa), e.g. wherein NHR$^3$ is of sub-formula (k2) or (k3), is alternatively prepared from a compound of formula (XXXVIII), wherein $R^1$ and $R^2$ are as defined herein, $n^3$ is 0 or 1, and Prot represents a suitable nitrogen protecting group such as tert-butoxycarbonyl. Conditions can include:

suitable acidic conditions (for N-deprotection) such as hydrogen chloride in a suitable solvent such as 1,4-dioxane at a suitable temperature such as room temperature, followed by reacting the resultant N-deprotected piperidine/pyrrolidine with a urea-forming reagent (e.g. trimethylsilyl isocyanate) so as to convert the (4-piperidinyl)amino or (3-pyrrolidinyl)amino group in the compound into a [(1-aminocarbonyl)-4-piperidinyl]amino group or [(1-aminocarbonyl)-3-pyrrolidinyl]amino group in the below-illustrated embodiment of formula (XI) respectively [optional urea-forming conditions can include: carrying out the reaction in the presence of a suitable base such as N,N-diisopropylethylamine, in a suitable solvent such as dichloromethane or chloroform, at a suitable temperature such as at room temperature or at the reflux temperature of the solvent.].

(XXXVIII)

(XI), in which NHR³ is of sub-formula (k2) or (k3)

In one embodiment, a compound of formula (XXXVIII), wherein R¹ and R², n³ and Prot are as defined herein, is prepared from a compound of formula (XXXIX), wherein R¹ and R², n³ and Prot are as defined herein. Conditions can include reaction of a compound of formula (XXXIX) with an azide such as sodium azide and a halogenating agent such as carbon tetrabromide, in the presence of a suitable phosphine such as triphenylphosphine, in a suitable solvent such as N,N,-dimethylformamide, at a suitable temperature such as between 0° C. and room temperature.

(XXXIX)

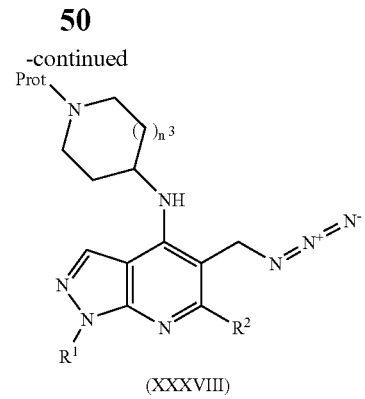

(XXXVIII)

In one embodiment, a compound of formula (XXXIX), wherein R¹ and R², n³ and Prot are as defined herein, is prepared from a compound of formula (XL), wherein R¹ and R², n³ Prot and X⁷ are as defined herein, by reduction with a suitable reducing agent such as lithium borohydride, in a suitable solvent such as a mixture of tetrahydrofuran and methanol, at a suitable temperature such as at the reflux temperature of the solvent.

(XL)

(XXXIX)

In one embodiment, a compound of formula (XL), wherein R¹ and R², n³ Prot and X⁷ are as defined herein, is prepared from compounds of formula (XV), wherein R¹, R², and X⁷ are as defined herein, by reaction of a compound of formula (XV) with an amine of formula (XLI), wherein Prot and n³ are as defined herein. The reaction is optionally carried out in the presence of a base such as triethylamine or N,N-diisopropylethylamine, and/or in an organic solvent such as ethanol, dioxane, 1-methyl-2-pyrrolidinone (NMP) or acetonitrile. The reaction may require heating e.g. to ca. 60-180° C., for example at 120° C.:

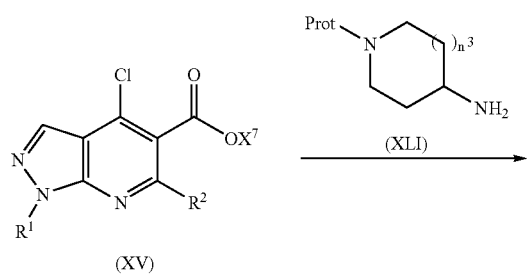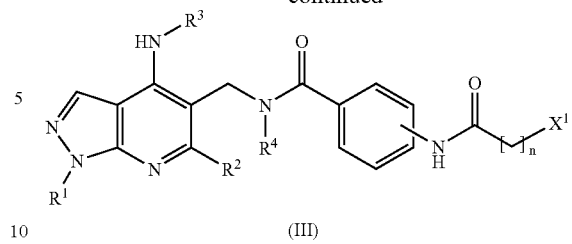

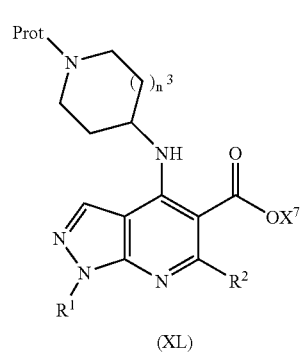

Process 1A—Alternative Embodiment 1A 1

(For example, Examples 1A1, 1A2, 1B, 1C, 3, 4, 9, 11, 12, 17, 18, 25, 26 and 29 to 34 may optionally be prepared by Process 1A alternative embodiment 1A1).

As an alternative embodiment within Process 1A, as the penultimate step, compounds of formula (III), wherein $R^1$, $R^2$, $R^3$, $R^4$, n and $X^1$ are as defined herein, may also be prepared by reaction between compounds of formula (IX), wherein $R^1$, $R^2$, $R^3$ and $R^4$ are as defined herein, and compounds of formula (XXVI), wherein $X^1$ and n are as described herein and $X^9$ is a suitable leaving group, preferably a halogen atom such as a chlorine atom; suitable conditions include stirring in a suitable anhydrous solvent such as dichloromethane, in the presence of a base such as triethylamine, at a suitable temperature such as between 0° C. and room temperature, for example between 0° C. and 10° C.

Compounds of formula (XXVI), wherein $X^1$, n and $X^9$ are as described herein, may be prepared from carboxylic acids of formula (XXVII), wherein $X^1$ and n are as described herein, by treatment with a suitable activating agent such as thionyl chloride, phosphoryl chloride or other reagents as described in R. C. Larock, *Comprehensive Organic Transformations*, Wiley, $2^{nd}$ Ed., 1999. For example when $X^9$ is chlorine compounds of formula (XXVI) may be prepared from compounds of formula (XXVII) by heating with thionyl chloride at a suitable temperature such as 100° C.

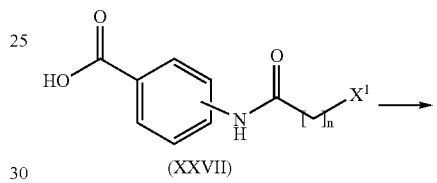

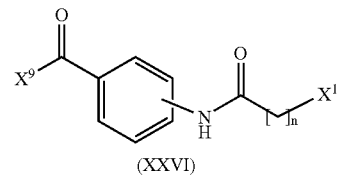

Compounds of formula (XXVII), wherein $X^1$ and n are as described herein, may be prepared by hydrolysis of compounds of formula (XXV), wherein $X^1$, n and $X^8$ are as described herein. Preferably $X^8$ is tert-butyl and the formation of compounds of formula (XXVII) from compounds of formula (XXV) can be achieved by treatment with a suitable acid such as 4M hydrogen chloride in a suitable solvent such as 1,4-dioxane, at a suitable temperature such as room temperature.

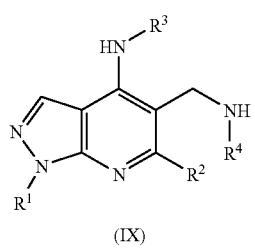

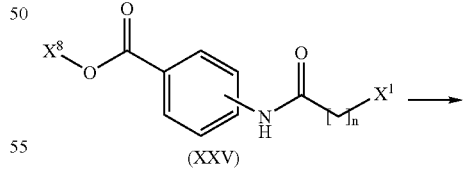

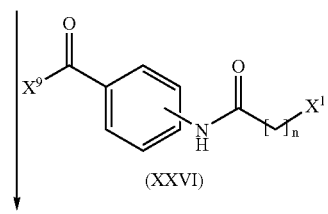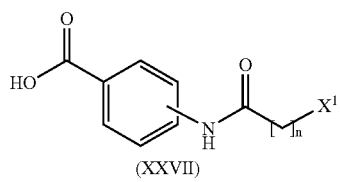

Compounds of formula (XXV) may be prepared as described herein.

Process 1B (For example, the compounds or salts whose names and/or chemical structures are given in and which are the products of Examples 1A1, 1A2, 1A3, 1B, 1C, 1D, 1E, 1F, 1G, 1H1, 1H2, 1J1, 1J2, 3, 4, 9, 11, 12, 17, 18, 25, 26 and 29 to 34, may optionally be prepared by Process 1B. Process 1B is a process of particular interest for the preparation of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a salt thereof e.g. this compound or a hydrochloride salt thereof, e.g. see Example 1B first preparation and/or Example 1A2 alternative preparation no. 1).

In the embodiment which is "Process 1B", a compound of formula (II) or a salt thereof, wherein $R^1$, $R^2$, $R^3$, $R^4$, $R^5$, $R^6$ and n are as defined herein (in particular when $R^4$ is a hydrogen atom), is prepared by reaction of a compound of formula (IX) or a salt thereof (e.g. a HCl salt thereof, e.g. monohydrochloride salt thereof), wherein $R^1$, $R^2$, $R^3$ and $R^4$ are as defined herein (in particular when $R^4$ is a hydrogen atom), with a compound of formula (XXII) or a salt thereof, wherein $R^5$, $R^6$ and n are as defined herein and $X^4$ is a suitable leaving group (e.g. wherein $X^4$ is as described hereinbelow). [As described above, a compound of formula (II) is a compound of formula (I) wherein Ar has sub-formula (x), $Q^1$ is NH, $Q^2$ is —C(O)—, and L is $(CH_2)_n$.]

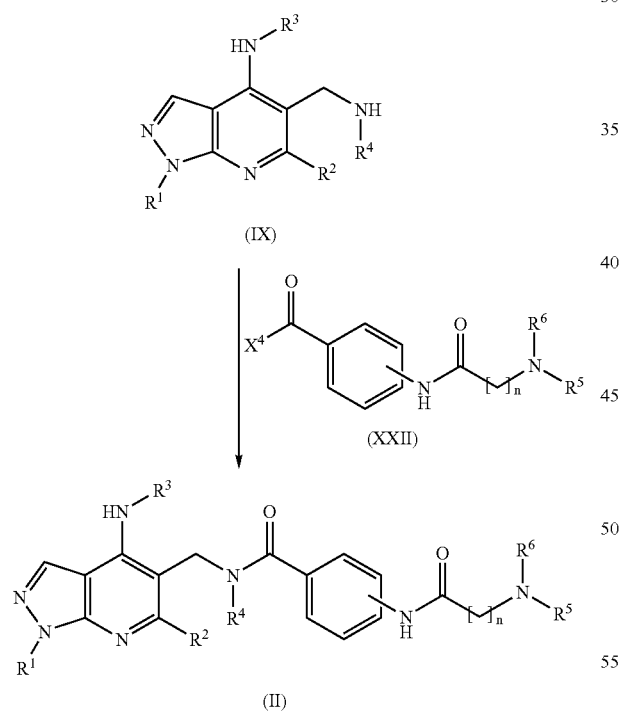

For various processes for the preparation of an amine compound of formula (IX) or a salt thereof (e.g. a HCl salt thereof), in particular for when $R^4$ is a hydrogen atom, and for processes for the preparation of the precursor intermediates usable to prepare the amine (IX) or a salt thereof, see the processes already extensively disclosed under the heading "Process 1A" hereinabove.

The compound of formula (XXII) or salt thereof can for example be a suitable activated carboxylic acid derivative wherein the leaving group $X^4$ is the leaving group of said activated carboxylic acid derivative. In the case of this activated carboxylic acid derivative, the leaving group $X^4$ can for example be of sub-formula (bt):

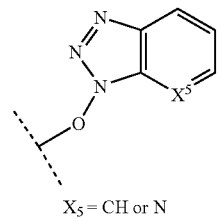

$X_5$ = CH or N

In the case of this activated carboxylic acid derivative, the leaving group $X^4$ can alternatively be for example —O—C(NHR')=N—R" or —O—C(NHR")=N—R', wherein R' and R" are the substituents (which may be the same or different) of an organic (di-substituted) carbodiimide reagent R'—N=C=N—R" which may have been used to prepare (XXII) or a salt thereof from the corresponding carboxylic acid.

The leaving group $X^4$ can alternatively be, for example, a chlorine atom (Cl), a bromine atom (Br), 1-imidazolyl, or t-Bu-C(O)—O—.

Preferably, the compound of formula (XXII) or the salt thereof (for example the suitable activated carboxylic acid derivative) is not isolated. Preferably, it is reacted with the amine of formula (IX) or the salt thereof to prepare the compound of formula (II) or the salt thereof, directly after formation of the compound of formula (XXII) or the salt thereof and without isolation of said compound (XXII) or salt.

A compound of formula (XXII), wherein $R^5$, $R^6$, n and $X^4$ are as defined herein, or a salt thereof can be formed from a carboxylic acid of formula (XXIII) or a salt (e.g. acid addition salt such as a HCl salt) thereof, wherein $R^5$, $R^6$, and n are as defined herein.

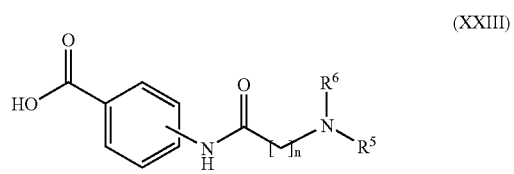

In one embodiment, a compound of formula (XXII) or a salt thereof, wherein the leaving group $X^4$ is of sub-formula (bt), is prepared from the corresponding carboxylic acid of formula (XXIII) or a salt thereof by the following reaction (a). In this reaction (a), the carboxylic acid (XXIII) or salt is reacted with a suitable organic carbodiimide e.g. organic di-substituted carbodiimide, such as 1-ethyl-3-(3'-dimethylaminopropyl)carbodiimide [also named 1-(3-dimethylaminopropyl)-3-ethylcarbodiimide] or a salt thereof such as a hydrochloride salt thereof (EDC), or such as N,N'-dicyclohexylcarbodiimide (DCC), followed by reaction of the resulting product with 1-hydroxybenzotriazole (when $X_5$ is CH) or 1-hydroxy-7-azabenzotriazole (when $X_5$ is N).

In an alternative embodiment, a compound of formula (XXII) or a salt thereof, wherein the leaving group $X^4$ is of sub-formula (bt), is prepared from the corresponding carboxylic acid of formula (XXIII) or a salt thereof by the following reaction (b). In this reaction (b), the carboxylic acid (XXIII) or salt is reacted with a suitable 1-hydroxybenzotriazole-based or 1-hydroxy-7-azabenzotriazole-based coupling agent, such as (i), (ii), (iii) or (iv):
(i) O-(benzotriazol-1-yl)-N,N,N',N'-tetramethyluronium hexafluorophosphate (also called HBTU, when $X_2$ is CH), or
(ii) 2-(1H-benzotriazol-1-yl)-1,1,3,3-tetramethyluronium tetrafluoroborate (TBTU, when $X_2$ is CH), or
(iii) O-(7-azabenzotriazol-1-yl)-N,N,N',N'-tetramethyluronium hexafluorophosphate (HATU, when $X_2$ is N), or
(iv) (benzotriazol-1-yloxy)-trispyrrolidinophosphonium hexafluorophosphate (PyBOP, when $X_2$ is CH).

In one embodiment, this reaction (b) is carried out in the presence of a base e.g. a tertiary amine base such as N,N-diisopropylethylamine ($^iPr_2NEt$=DIPEA), and/or usually in the presence of a solvent such as an aprotic organic solvent (e.g. anhydrous solvent) such as N,N-dimethylformamide or acetonitrile, e.g. under anhydrous conditions and/or at a suitable temperature such as room temperature (e.g. about 18 to about 25° C.).

Reaction (a) of the carboxylic acid (XXIII) or a salt thereof with the suitable organic carbodiimide (e.g. DCC; or more preferably 1-(3-dimethylaminopropyl)-3-ethylcarbodiimide or a salt thereof such as a hydrochloride salt thereof) to prepare compound (XXII) or a salt thereof, in particular in the presence of 1-hydroxybenzotriazole, followed by reaction of the resulting compound (XXII) or the salt thereof with the amine of formula (IX) or the salt thereof, can be carried out as follows:
  in the presence of a suitable organic solvent (preferably anhydrous or at least substantially dry), such as one or more $C_{1-7}$alkyl alcohols (in particular one or more $C_{4-6}$alkyl alcohols, such as pentanol, e.g. pentan-1-ol or pentan-2-ol, or butanol, e.g. butan-2-ol or butan-1-ol, or hexanol e.g. hexan-1-ol), N,N-dimethylformamide (DMF), N,N-dimethylacetamide, 1-methyl-2-pyrrolidinone (NMP), acetonitrile, tetrahydrofuran (e.g. anhydrous), dichloromethane, or a mixture of any of these (e.g. N,N-dimethylacetamide and pentan-1-ol, or NMP and pentan-1-ol); and/or
  at a suitable temperature such as about room temperature (e.g. about 15 to about 25° C., or about 18 to about 25° C.); and/or
  under an inert atmosphere such as nitrogen; and/or
  in the presence of a non-aqueous base such as solid potassium carbonate (e.g. having about 325 mesh particle size), solid sodium carbonate, or a non-aqueous tertiary amine base such as N,N-diisopropylethylamine ($^iPr_2NEt$=DIPEA) or triethylamine; and/or
  using an aqueous alkaline (e.g. concentrated aqueous alkaline) extraction of a or the organic phase (e.g. using conc. aq. NaOH or conc. aq. KOH), after the reaction which has prepared compound (II) or a salt thereof [this extraction may help to decrease the amount of certain possible reaction byproducts (e.g. ester byproducts, e.g. when the solvent comprises an alcohol and/or when the starting material compound (XXII) or (XXIII) or a salt thereof contains an alcoholic OH group in the $R^5$ and/or $R^6$ group) that might perhaps be formed during preparation of the product (II) or the salt thereof].

In particular where the compound of formula (II) or the salt thereof is N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a salt thereof, reaction (a) of the carboxylic acid (XXIII) or a salt thereof with the suitable organic carbodiimide (e.g. DCC; or more preferably 1-(3-dimethylaminopropyl)-3-ethylcarbodiimide or a salt thereof such as a hydrochloride salt thereof) to prepare the compound (XXII) or a salt thereof, in particular in the presence of 1-hydroxybenzotriazole, followed by reaction of the resulting compound (XXII) or the salt thereof with the amine of formula (IX) or the salt thereof, can be in particular carried out:
  in the presence of a hydrochloride salt (eg monohydrochloride) (e.g. solid e.g. crystalline) of an amine compound of formula (IX); and/or
  in the presence of a suitable organic solvent (preferably anhydrous or at least substantially dry) being or comprising an organic solvent with low water-miscibility such as one or more $C_{4-6}$alkyl alcohols (such as pentanol, e.g. pentan-1-ol or pentan-2-ol, or butanol, e.g. butan-2-ol or butan-1-ol, or hexanol e.g. hexan-1-ol) (e.g. to allow aqueous extractions more easily, e.g. see below); and/or
  at a suitable temperature such as about room temperature (e.g. about 15 to about 25° C., or about 18 to about 25° C.); and/or
  under an inert atmosphere such as nitrogen; and/or
  in the presence of a non-aqueous inorganic base such as solid potassium carbonate (e.g. having about 325 mesh particle size) or solid sodium carbonate, and for a solid base preferably with rapid stirring (e.g. about 160 rpm); and/or
  using an aqueous alkaline (e.g. concentrated aqueous alkaline) extraction of a or the organic phase (e.g. using conc. aq. NaOH or conc. aq. KOH), after the reaction which has prepared compound (II) or a salt thereof [this extraction may help to decrease the amount of certain possible reaction byproducts (e.g. ester byproducts, e.g. when the solvent comprises an alcohol and/or due to the starting material compound (XXII) or (XXIII) or the salt thereof generally containing a 2-hydroxyethyl group) that might perhaps be formed during preparation of the N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or the salt thereof]; and/or
  using an aqueous acidic extraction of a or the organic phase (e.g. using aq. HCl) after the reaction to prepare (II) or a salt thereof, and optionally after an aqueous alkaline extraction which may be present, with the amount of aqueous acid used in the acid extraction being such that the pH of the aqueous phase is adjusted to pH 5.75±0.25 [e.g. to decrease the amount of certain possible basic byproducts and/or basic impurities that might perhaps be present, for example after preparation of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide].

See e.g. Example 1A2 (alternative preparation no. 1, plant method), for one example of the above reaction conditions to prepare N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide before conversion to the monohydrochloride salt thereof.

Where a salt of the compound of formula (II) (or (I)) is prepared, in one embodiment this is salt optionally prepared after the preparation of the compound (II) or (I) and without isolation of said compound, e.g. by crystallisation of the salt directly from essentially the same or similar organic solvent as that used in the reaction to prepare the compound (II) or (I) (e.g. the organic solvent can be one or more $C_{4-6}$alkyl alcohols, such as pentanol e.g. pentan-1-ol), e.g. by salt crystallisation from the reaction mixture. In one embodiment, this salt crystallisation is optionally done:

(i) by conversion if necessary of the compound (II) or (I) and/or the salt thereof, prepared from the reaction and/or extraction thereof, into substantially wholly the "free base" form, e.g. by aqueous alkaline extraction of the non-extracted or previously-extracted reaction mixture; and/or (ii) by optional reduction of the volume of and/or heating of the reaction solvent, if necessary or desirable, e.g. after preparation of compound (II) or (I) and after aqueous extraction of the reaction mixture, and/or (iii) by mixing an appropriate amount of an appropriate acid such as HCl with the reaction mixture (e.g. ca. 1 mole equivalent of HCl to prepare a monohydrochloride salt, e.g. using 2-10M aq. HCl, e.g. 4-6 M aq. HCl); and/or (iv) by optional mixing with the reaction solvent of an organic "antisolvent" capable of crystallising the salt of the compound (II) or (I) from the organic solvent-antisolvent mixture, typically followed by cooling of the mixture and/or isolation eg by filtration of the crystallised salt. In particular, depending on the solubility properties of the salt of the compound, tert-butyl methyl ether (TBME) is optionally used as such an antisolvent, especially for preparing a salt of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide (e.g. the HCl salt e.g. monohydrochloride salt thereof).

See e.g. Example 1A2 (alternative preparation no. 1, plant method), for one specific example of the above salt preparation conditions, in the preparation of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino] octanoyl}amino)benzamide monohydrochloride.

In one alternative embodiment of when the compound of formula (XXII) or salt is a suitable activated carboxylic acid derivative, the compound of formula (XXII) or a salt thereof is the product (adduct) formed from the reaction of the carboxylic acid of formula (XXII) or salt thereof with a suitable organic carbodiimide e.g. organic di-substituted carbodiimide (e.g. R'—N=C=N—R") [e.g. wherein the carbodiimide can be 1-(3-dimethylaminopropyl)-3-ethylcarbodiimide or a salt thereof such as a hydrochloride salt thereof (EDC), or N,N'-dicyclohexylcarbodiimide (DCC)]. In this case, in the compound of formula (XXII) or salt which is the carboxylic acid-carbodiimide adduct, the leaving group $X^4$ is —O—C(NHR')=N—R" or —O—C(NHR")=N—R', wherein R' and R" are the substituents (which may be the same or different) of the organic (di-substituted) carbodiimide reagent used. This is the situation for example when the carbodiimide is reacted with the carboxylic acid (XXIII) or a salt thereof without 1-hydroxybenzotriazole or 1-hydroxy-7-azabenzotriazole being present. In one embodiment, this reaction is carried out in a suitable organic solvent e.g. an aprotic organic solvent (preferably anhydrous) such as N,N-dimethylformamide or acetonitrile, e.g. under anhydrous conditions and/or e.g. at a suitable temperature such as room temperature (e.g. about 18 to about 25° C.). In one optional embodiment, this reaction is carried out in the presence of a tertiary amine base such as N,N-diisopropylethylamine ($^iPr_2NEt$=DIPEA).

In another alternative embodiment, the compound of formula (XXII) or salt thereof is for example the acid chloride (in which case, the leaving group $X^4$ is a chlorine atom (Cl)). In one embodiment, this acid chloride is for example prepared from the corresponding carboxylic acid (XXIII) or a salt thereof by reaction with oxalyl chloride, usually in a suitable organic solvent (e.g. anhydrous) such as DMF or dichloromethane (e.g. dichloromethane or another solvent together with a catalytic amount of DMF), and/or e.g. under anhydrous conditions, and/or e.g. at room temperature or at or below 20° C. When an acid chloride of formula (XXII) wherein $X^4$ is Cl, or a salt thereof, is used to prepare the compound of formula (II) or (I), the reaction with amine (IX) or a salt thereof is usually carried out in the presence of a tertiary amine base such as N,N'-diisopropylethylamine ($^iPr_2NEt$=DIPEA) and/or in a suitable aprotic organic solvent (e.g. anhydrous solvent) such as acetonitrile or dichloromethane, for example at room temperature (e.g. about 18 to about 25° C.).

In the compound (XXII) or a salt thereof, further alternative values of the leaving group $X^4$ include a bromine atom (Br), 1-imidazolyl (e.g. as prepared from the acid (XXIII) or salt using carbonyl diimidazole), and t-Bu-C(O)—O— (e.g. as prepared from the acid (XXIII) or salt using t-Bu-C(O)—Cl).

Compounds of formula (XXIII), wherein $R^5$, $R^6$ and n are as defined herein, can for example typically be formed by hydrolysis of esters of formula (XXIV), wherein $R^5$, $R^6$, and n are as defined herein and $X^8$ is an alkyl group, such as ethyl or preferably tert-butyl. The hydrolysis may be achieved under suitable conditions, such as by reaction with 4M hydrogen chloride in 1,4-dioxane (e.g. for when $X^8$ is tert-butyl but usually not when $X^8$ is ethyl), at a suitable temperature such as room temperature, optionally in dry dichloromethane.

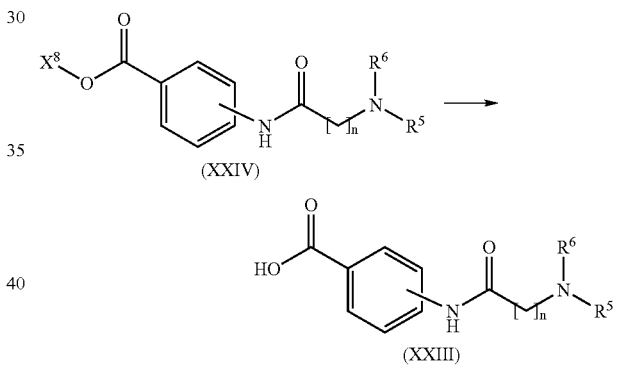

Compounds of formula (XXIV), wherein $R^5$, $R^6$ n and $X^8$ are as defined herein, can for example typically be formed by substitution of compounds of formula (XXV), wherein $X^8$ and n are as defined herein and $X^1$ is a leaving group as defined herein (e.g. for $X^1$ as defined in Process 1A hereinabove, e.g. $X^1$ can be a bromine atom), with an amine of formula (IV), wherein $R^5$ and $R^6$ are as defined herein, optionally in the presence of a suitable base such as N,N-diisopropylethylamine, in a suitable solvent such as N,N-dimethylformamide, at a suitable temperature such as between room temperature and 100° C., for example at about 60° C.

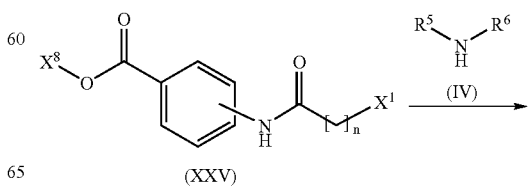

-continued

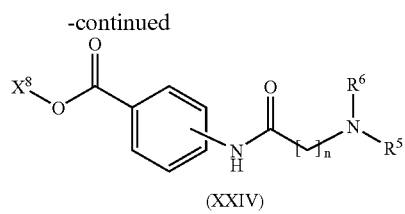

(XXIV)

Compounds of formula (XXV), wherein $X^8$ and $X^1$ and n are as defined herein, can for example typically be formed from compounds of formula (XXVI), wherein $X^8$ is as defined herein, by reaction with a suitable acylating agent (VI), wherein $X^1$, $X^2$ and n are as defined herein e.g. hereinabove (e.g. for $X^1$ and $X^2$ as defined in Process 1A hereinabove, e.g. $X^1$ can be a bromine atom and/or $X^2$ can be a chlorine atom). Suitable conditions include carrying out the reaction in a suitable anhydrous solvent such as dichloromethane or chloroform, in the presence of a suitable non-aqueous base e.g. a tertiary amine base such as N,N-diisopropylethylamine or triethylamine, at a suitable temperature such as between 0° C. and room temperature, e.g. under anhydrous conditions.

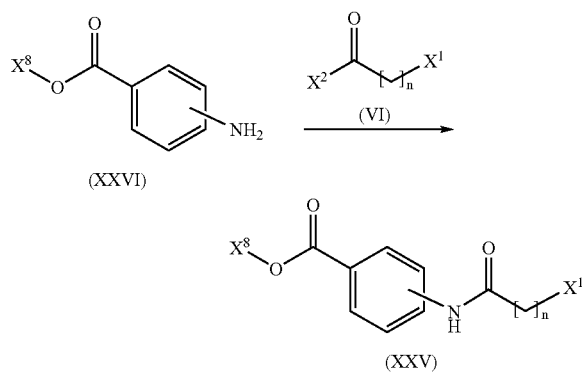

Compounds of formula (XXVI) are generally either commercially available, known in the literature or may be prepared e.g. by conventional means. For example ethyl 4-aminobenzoate ($X^8$ is ethyl) is commercially available, for example from Aldrich. Preferably $X^8$ is tert-butyl; for example tert-butyl 4-aminobenzoate and tert-butyl 3-aminobenzoate are commercially available, for example from Fluka.

Process 1C (For example, the compounds or salts prepared/preparable in Examples 1A1, 1A2, 1A3, 1B, 1C, 1D, 1E, 1F, 1G, 1H1, 1H2, 1J1, 1J2, 3, 4, 9, 11, 12, 17, 18, 25, 26 and 29 to 34 may optionally be prepared by Process 1C. Process 1C is a process which is of interest for the preparation of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a salt thereof, e.g. this compound or a hydrochloride salt thereof such as a monohydrochloride).

In Process 1C, a compound of formula (XLII), wherein $R^1$, $R^2$, $R^3$, $R^4$ and n are as defined herein (in particular when $R^4$ is a hydrogen atom), and wherein $R^{5'}$ is a hydrogen atom (H), methyl, ethyl, n-propyl, or isopropyl (e.g. methyl), and wherein $R^{6'}$ is $C_{1-4}$alkyl substituted by one OH substituent (e.g. wherein $R^{6'}$ is —CH$_2$CH$_2$OH, —CH$_2$CH(Me)OH, —CH$_2$CH$_2$CH$_2$OH, or —CH$_2$CH$_2$CH$_2$CH$_2$OH, in particular wherein $R^{6'}$ is —CH$_2$CH$_2$OH), which is one embodiment of a compound of formula (I), or a salt thereof, is prepared by deprotection of a compound of formula (XLIII) or a salt thereof, wherein $R^1$, $R^2$, $R^3$, $R^4$ and n are as defined herein (in particular when $R^4$ is a hydrogen atom), wherein $R^{5'}$ is a hydrogen atom (H), methyl, ethyl, n-propyl, or isopropyl (e.g. methyl), and wherein $R^{6\text{-}prot}$ is $C_{1-4}$alkyl substituted by one protected OH substituent O-Prot' (e.g. wherein $R^{6\text{-}prot}$ is —CH$_2$CH$_2$—O-Prot', —CH$_2$CH(Me)-O-Prot', —CH$_2$CH$_2$CH$_2$—O-Prot', or —CH$_2$CH$_2$CH$_2$CH$_2$—O-Prot', in particular wherein $R^{6\text{-}prot}$ is —CH$_2$CH$_2$—O-Prot').

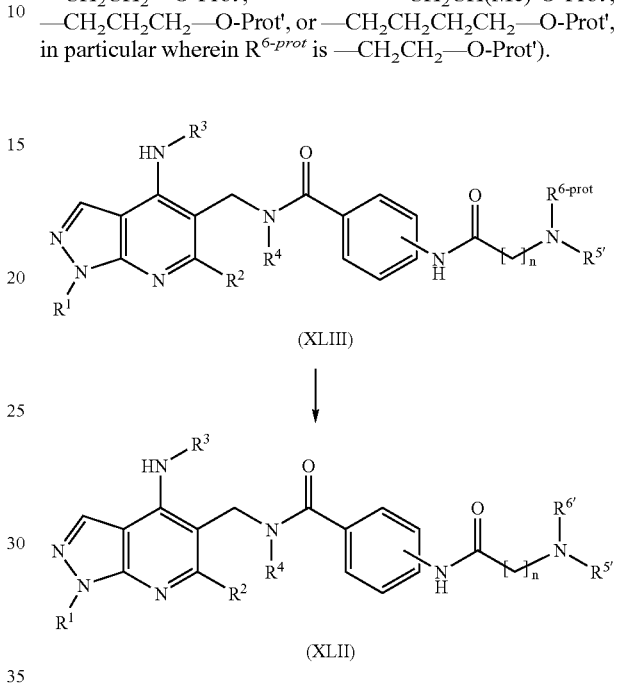

For example, O-Prot' can be any protected OH group which is deprotectable by treatment with acid or base or fluoride ions. In particular, O-Prot' can be —OC(O)—C$_{1-6}$alkyl such as OAc (acetate), OC(O)—CF$_3$, —OC(O)aryl such as —OC(O)-phenyl, or —O-(tri-organo)silyl such as O-trialkylsilyl such as O-TBDMS (tert-butyldimethylsilyloxy) or O-TMS (trimethylsilyloxy).

Deprotection of the compound of formula (XLIII) or the salt thereof can be via standard OH-deprotection conditions, e.g. using acid or more preferably base in particular strong base such as strong inorganic base (e.g. NaOH or KOH, e.g. aqueous and/or ethanolic NaOH or KOH, in particular concentrated (e.g. 5-12M or 10-11M) aqueous NaOH or KOH) for deprotection where O-Prot' is —OC(O)—C$_{1-6}$alkyl such as OAc (acetate) or —OC(O)—CF$_3$ or —OC(O)aryl. Deprotection mediated by base, e.g. where O-Prot' is —OC(O)—C$_{1-6}$alkyl or —OC(O)—CF$_3$ or —OC(O)aryl, can in particular be carried out under heating (e.g. at ca. 40-60° C. such as ca. 50° C.) and/or in the presence of an organic solvent such as a C$_{1-7}$alcohol for example a C$_{4-6}$alcohol e.g. pentanol such as pentan-1-ol. Where O-Prot' is O-trialkylsilyl such as O-TBDMS or O-TMS, this can be deprotected sometimes by acid or more usually by fluoride ions such as by use of tetra-n-butylammonium fluoride. For other OH-protecting groups and their chemistry, see Theadora Green, "Protective Groups in Organic Synthesis".

Compounds of formula (XLIII) or salts thereof can typically be formed by the following reaction of an amide of formula (XLV) or a salt thereof, wherein $R^4$ and n are as defined herein (in particular wherein $R^4$ is a hydrogen atom), $R^{5'}$ is a hydrogen atom (H), methyl, ethyl, n-propyl, or isopropyl (e.g. methyl), and $R^{6-prot}$ is as defined herein, with a compound of formula (XLIV) or an acid addition salt thereof (e.g. a sulfonate salt thereof, e.g. methanesulfonate or benzenesulfonate salt of (XLIV)), wherein $X^{11}$ is a suitable leaving group such as mesylate (methanesulfonate), tosylate (p-toluenenesulfonate), triflate (trifluoromethanesulfonate), or a chlorine, bromine or iodine atom (in particular a chlorine atom). Compounds of formula (XLIV), where $X^{11}$ is mesylate, tosylate, triflate, or a chlorine, bromine or iodine atom, are generally thought to be potent electrophiles.

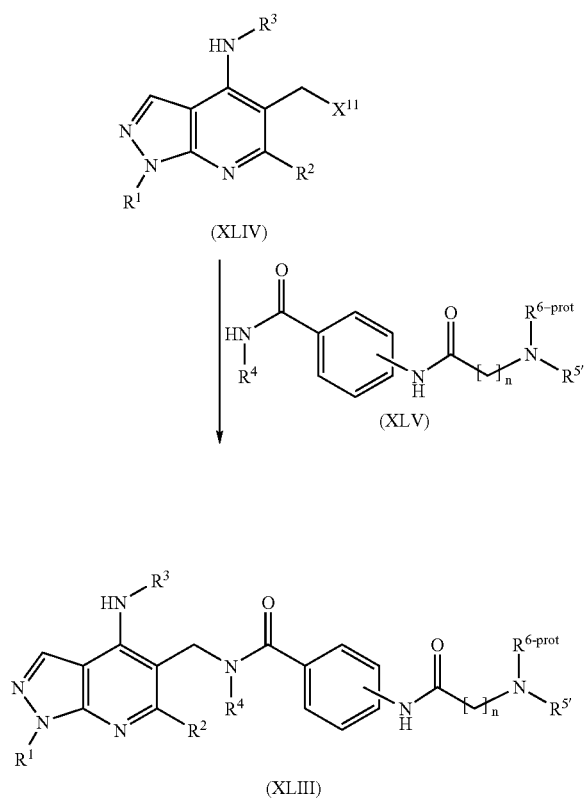

Conditions can include heating compound (XLIV) or the acid addition salt thereof (e.g. a sulfonate salt thereof, e.g. methanesulfonate or benzenesulfonate salt of (XLIV)) and compound (XLV) or a salt thereof together, e.g. at ca. 50-100° C. or ca. 60-80° C., e.g. at ca. 60° C., for example in a suitable solvent, such as N-methyl-2-pyrrolidinone (that is 1-methyl-2-pyrrolidinone, also called NMP), dimethyl sulfoxide, ethyl acetate, n-propyl acetate, chloroform, diethylene glycol dimethyl ether ["diglyme", $(CH_3OCH_2CH_2)_2O$], N,N-dimethylformamide (DMF), tetrahydrofuran (THF), or mixtures thereof. Suitably, the solvent can be NMP, dimethyl sulfoxide, ethyl acetate, n-propyl acetate, chloroform, diethylene glycol dimethyl ether, or mixtures thereof. Preferably, the solvent is 1-methyl-2-pyrrolidinone (NMP).

Due to its reactivity, the compound of formula (XLIV) or the acid addition salt thereof (e.g. sulfonate salt thereof, e.g. methanesulfonate or benzenesulfonate salt of (XLIV)), wherein $X^{11}$ is a suitable leaving group such as mesylate (methanesulfonate), tosylate (p-toluenenesulfonate), triflate (trifluoromethanesulfonate), or a chlorine, bromine or iodine atom (in particular a chlorine atom), is preferably not isolated; e.g. it can be prepared in solution and used directly in solution (with or without partial or full solvent replacement), e.g. by being used in THF and/or NMP solution, in the next step (i.e. reaction with the amide of formula (XLV) or the salt thereof).

The compound of formula (XLIV) or the acid addition salt thereof can for example be prepared as described in Process 1A herein. However, when $X^{11}$ is Cl, see the detailed scheme below marked "Scheme—Process 1C (to Example 1A2)", an embodiment intended e.g. for the preparation of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a salt thereof such as the monohydrochloride thereof, for some modified processes/reagents/reaction conditions leading to the relevant acid addition salt (e.g. methanesulfonate salt) of the compound of formula (XLIV) wherein $R^1$ and $R^2$ are both ethyl, $R^3$ is tetrahydro-2H-pyran-4-yl, and $X^{11}$ is Cl. See in particular Stages 1c, 1d, 2a, and 2b within that Scheme for alternative reagents and/or reaction conditions. For specific examples of these modified processes/reagents/reaction conditions, see Intermediate 2B (for Stage 1c preparation), Intermediate 2C (for Stage 1d preparation), Intermediate 3 (alternative preparation) (for Stage 2a preparation), and Intermediate 4 (alternative preparation) (for Stage 2b preparation) as disclosed herein.

One preferred specific route within Process 1C, e.g. for the preparation of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a salt thereof, in particular the monohydrochloride salt thereof, is illustrated in "Scheme—Process 1C (to Example 1A2)" as follows:

Scheme—Process 1C (to Example 1A2)
(scheme follows on next page)

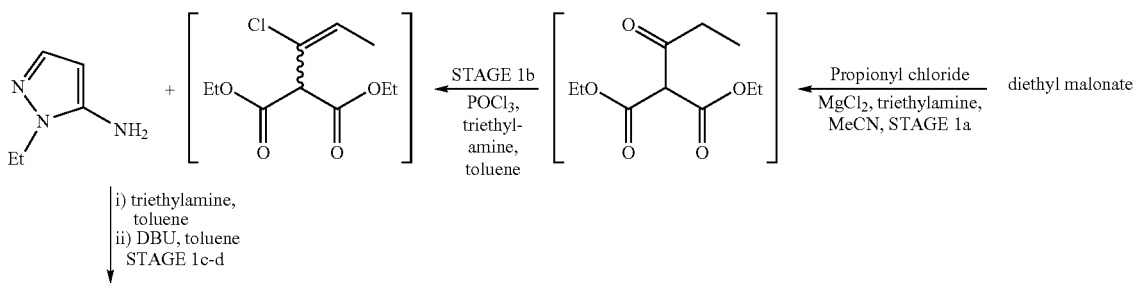

-continued
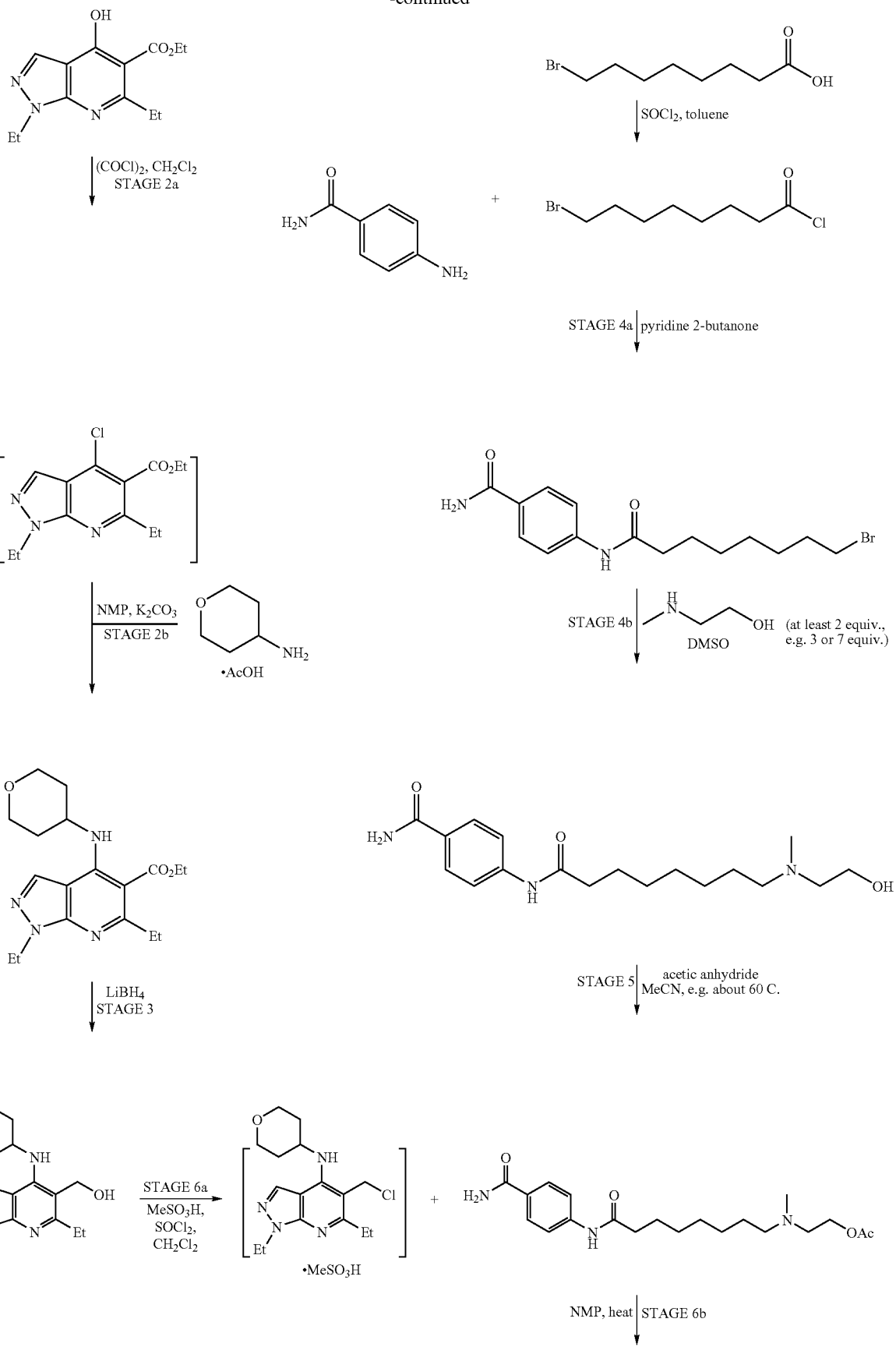

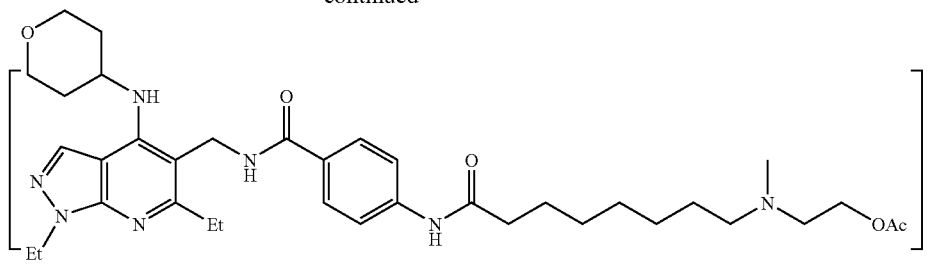

STAGE 7-8
i) aq. NaOH, pentan-1-ol
ii) HCl
iii) recrystallisation from pentan-1-ol

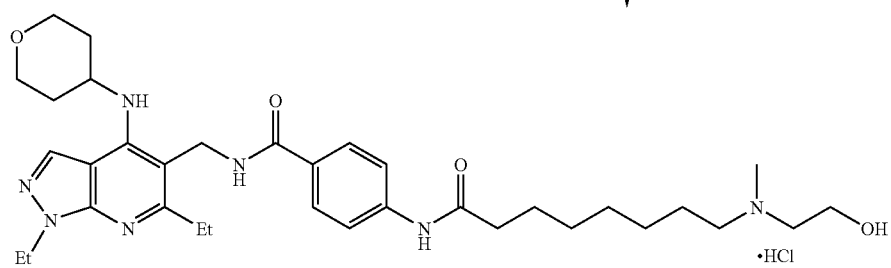

The final deprotection step in the specific route ["Scheme—Process 1C (to Example 1A2)"] shown above can preferably involve:
(i) extracting the acetyl-O-protected product within formula (XLIII) into n-pentanol (pentan-1-ol);
(ii) adding aqueous NaOH solution (e.g. ca. 2M to ca. 10M such as ca. 10M), optionally with heating e.g. at ca. 40-60° C. such as ca. 50° C., to cleave the acetate protecting group (whereupon the deprotected OH product (the "free base" compound within formula (XLII) and within formula (I)) stays in the n-pentanol phase); and
(iii) removing the aqueous phase (optionally after addition of water); and (iv) optionally (if a monoHCl salt is required) adding ca. 1 equivalent of aqueous HCl (eg ca. 5M aq. HCl) to produce the product, N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride.

As part of the general preparation of compounds of formula (XLII) or salts thereof, a compound of formula (XLV) or a salt thereof can for example be prepared by the following generalised route:

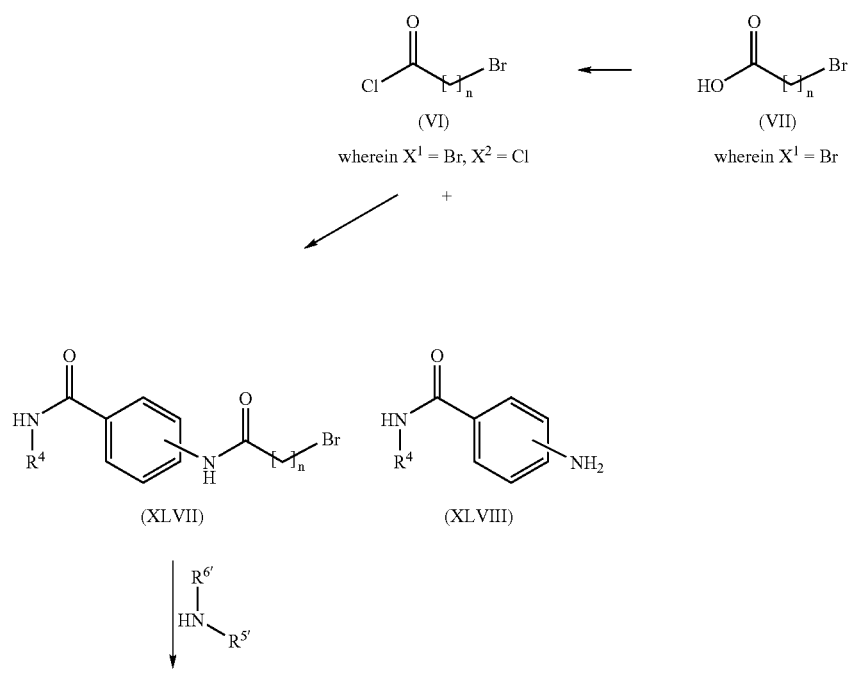

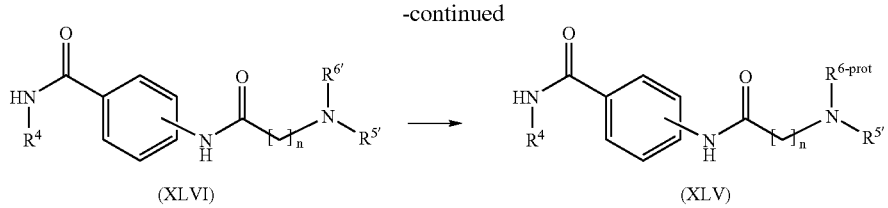

(XLVI) → (XLV)

Typical conditions and/or reagents for the protection of the OH group within $R^{6'}$ of compound (XLVI) ro a salt thereof, to form (XLV) or a salt thereof, can include conditions suitable for OH-protection with the OH-protecting group used. For example, where O-Prot' (within $R^{6\text{-}prot}$ of compound (XLV)) is OAc (acetate), acetic anhydride can be used, e.g. in a suitable solvent (e.g. anhydrous) such as acetonitrile, and/or in the presence of an organic base such as triethylamine, and/or e.g. with heating such as at ca. 60-90° C., for example heating at ca. 81-82° C. e.g. with acetonitrile solvent. Alternatively, acetyl chloride can be used for acetyl OH-protection. For other OH-protecting groups and their chemistry, see Theadora Green, "Protective Groups in Organic Synthesis".

Conditions and/or reagents for the coupling of the compound (XLVII) or a salt thereof with the amine $R^{5'}R^{6'}NH$ or a salt thereof to prepare compound (XLVI) or a salt thereof can include:

- using at least 2 equivalents (e.g. 3-10 equivalents, preferably 5-10 equivalents, such as 6-9 equivalents, e.g. ca. 7 equivalents) of the amine $R^{5'}R^{6'}NH$ [or if not then using another non-nucleophilic organic or inorganic base to remove the HBr formed in the reaction, such as pyridine, 2,6-dimethylpyridine, tri-n-butylamine, N,N-diisopropylethylamine ($^{i}Pr_2NEt=DIPEA$), or DABCO, or $K_2CO_3$ or $Na_2CO_3$], and/or
- using a suitable dipolar aprotic solvent such as dimethylsulfoxide, NMP, DMF, or dichloromethane (in particular dimethylsulfoxide), and/or
- either heating e.g. at ca. 40-80° C. or ca. 50-80° C. e.g. at ca. 60° C., or carrying out the reaction at room temperature.

Conditions and/or reagents for the coupling of the aminobenzamide or N-alkyl-(amino)benzamide compound (XLVIII) or a salt thereof with the specific acid chloride compound within formula (VI) will normally include generally anhydrous/dry conditions. and/or can optionally include:

- using a suitable organic or inorganic non-nucleophilic base such as pyridine, 2,6-dimethylpyridine, tri-n-butylamine, N,N-diisopropylethylamine ($^{i}Pr_2NEt=DIPEA$), or DABCO, or $K_2CO_3$ or $Na_2CO_3$ (in particular tri-n-butylamine or suitably pyridine), and/or
- using a suitable solvent (e.g. generally dry) such as a $C_{4-6}$ketone, a $C_{2-4}$alkyl acetate, $C_{1-3}$alkyl-CN, dichloromethane, chloroform, tetrahydrofuran or toluene; in particular 2-butanone (methyl ethyl ketone, MEK), pentanone such as 3-pentanone, n-propyl acetate, n-butyl acetate, acetonitrile, propionitrile ($CH_3CH_2$—CN), butyronitrile ($CH_3CH_2CH_2$—CN), dichloromethane, tetrahydrofuran or toluene; preferably 2-butanone or butyronitrile ($CH_3CH_2CH_2$—CN).

The compounds of formula (VI) wherein $X^1$ is Br and $X^2$ is Cl can be obtained by the skilled man, for example using process(es) as described elsewhere herein.

Process 1D

In Process 1D, in order to prepare a compound of formula (XLIIa), wherein $R^1$, $R^2$, $R^3$, $R^4$ and n are as defined herein (in particular when $R^4$ is a hydrogen atom), and wherein $R^{5''}$ and $R^{6''}$ are as defined herein for $R^5$ and $R^6$ respectively provided that there is no OH group in $R^{5''}$ or $R^{6''}$ or $[R^{5''}$ and $R^{6''}$ taken together] and provided that $R^8$ is not H, which is one embodiment of a compound of formula (I), or a salt thereof, an amide of formula (XLVa) or a salt thereof, wherein $R^4$ and n are as defined herein (in particular when $R^4$ is a hydrogen atom), and wherein $R^{5''}$ and $R^{6''}$ are as defined herein for $R^5$ and $R^6$ respectively provided that there is no OH group in $R^{5''}$ or $R^{6''}$ or $[R^{5''}$ and $R^{6''}$ taken together] and provided that $R^8$ is not H, can be reacted with a compound of formula (XLIV) or an acid addition salt thereof (e.g. a sulfonate salt thereof e.g. methanesulfonate or benzenesulfonate salt thereof), wherein $X^{11}$ is a suitable leaving group such as mesylate (methanesulfonate), tosylate (p-toluenenesulfonate), triflate (trifluoromethanesulfonate), or a chlorine, bromine or iodine atom (in particular a chlorine atom):

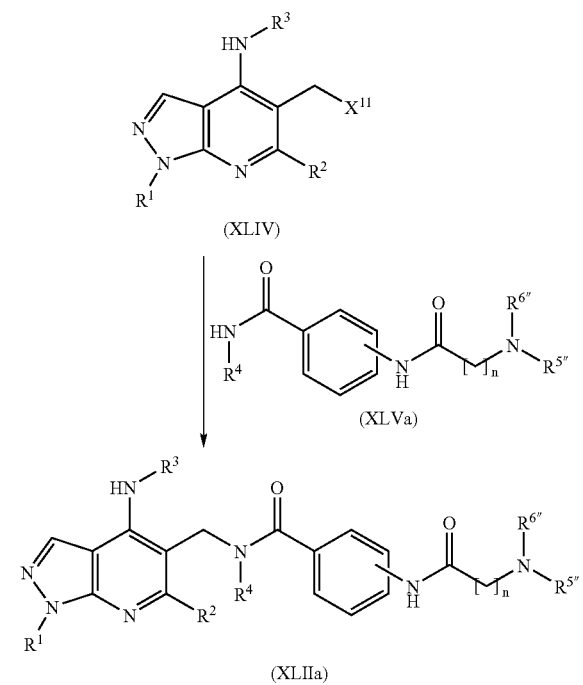

Compounds of formula (XLVa) are optionally prepared by a process analogous to that of compound (XLV) or (XLVI) in Process 1C (e.g. see above), but without the OH— protectionstep.

Process 3

In general terms, the Process 3 can be as follows:

A compound of formula (XXXa), wherein $R^1$, $R^2$, $R^3$, $R^4$ $R^5$, $R^6$, $m^1$, and $m^2$ are as defined herein (suitably, $m^1$ and $m^2$ are both 4), or a salt thereof, may typically be prepared by reaction by substitution of a compound of formula (XXXIa), or a salt thereof, wherein $R^1$, $R^2$, $R^3$, $R^4$, $X^1$, $m^1$, and $m^2$ are as defined herein, with an amine of formula (IV), or a salt thereof, wherein $R^5$ and $R^6$ are as defined herein. At least about 2 equivalents of the amine of formula (IV) or the salt thereof can be used. Suitable conditions include heating in a suitable solvent such as N,N-dimethylformamide, suitably in the presence of a suitable base e.g. organic tertiary amine base such as N,N-diisopropylethylamine, e.g. at a suitable temperature such as ca. 60-100° C. e.g. ca. 85° C. Alternative conditions include heating under microwave irradiation in a suitable solvent such as N,N-dimethylformamide, e.g. at a suitable temperature such as ca. 140-150° C.

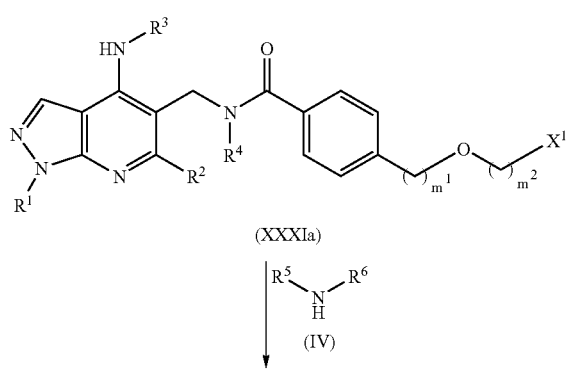

(XXXIa)

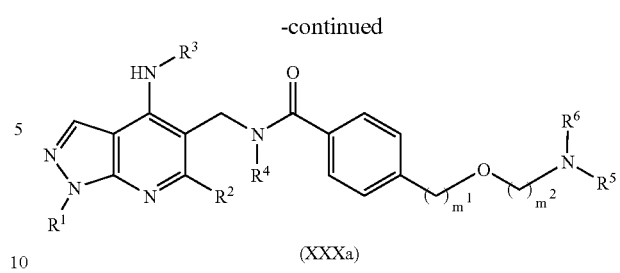

(XXXa)

For the suitable embodiment wherein $m^1$ and $m^2$ are both 4:

Compounds of formula (XXX), wherein $R^1$, $R^2$, $R^3$, $R^4$ $R^5$, and $R^6$ are as defined herein, or salts thereof, may typically be prepared by reaction by substitution of a compound of formula (XXXI), or a salt thereof, wherein $R^1$, $R^2$, $R^3$, $R^4$ and $X^1$ are as defined herein, with an amine of formula (IV), or a salt thereof wherein $R^5$ and $R^6$ are as defined herein. At least about 2 equivalents of the amine of formula (IV) or the salt thereof can be used. Suitable conditions include heating in a suitable solvent such as N,N-dimethylformamide, suitably in the presence of a suitable base e.g. organic tertiary amine base such as N,N-diisopropylethylamine, e.g. at a suitable temperature such as ca. 60-100° C. e.g. ca. 85° C. Alternative conditions include heating under microwave irradiation in a suitable solvent such as N,N-dimethylformamide, e.g. at a suitable temperature such as ca. 140-150° C.

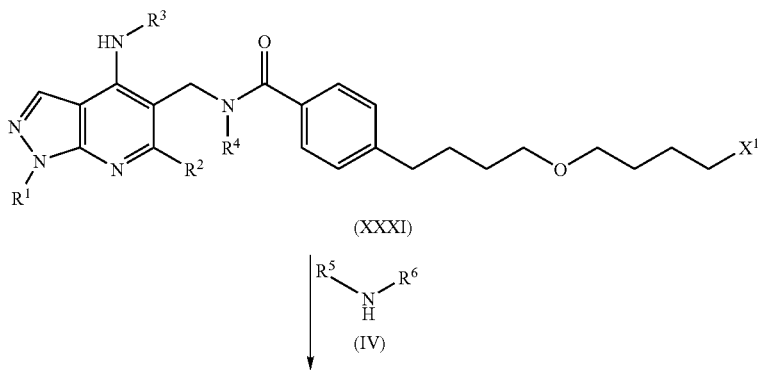

(XXXI)

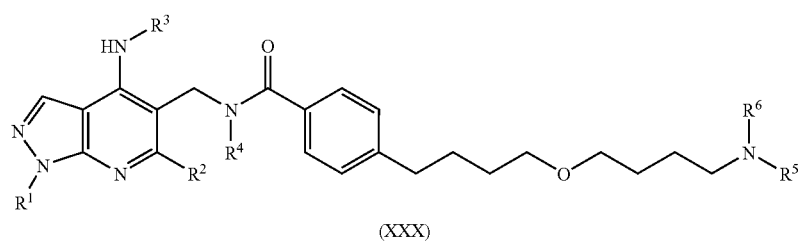

(XXX)

Compounds of formula (XXXI), wherein $R^1$, $R^2$, $R^3$, $R^4$ and $X^1$ are as defined herein, may typically be prepared by reaction between compounds of formula (IX), wherein $R^1$, $R^2$, $R^3$ and $R^4$ are as defined above, and compounds of formula (XXXIII) wherein $X^1$ and $X^4$ are as defined herein (e.g. $X^1$ can in particular be Br and/or $X^4$ can in particular be Cl).

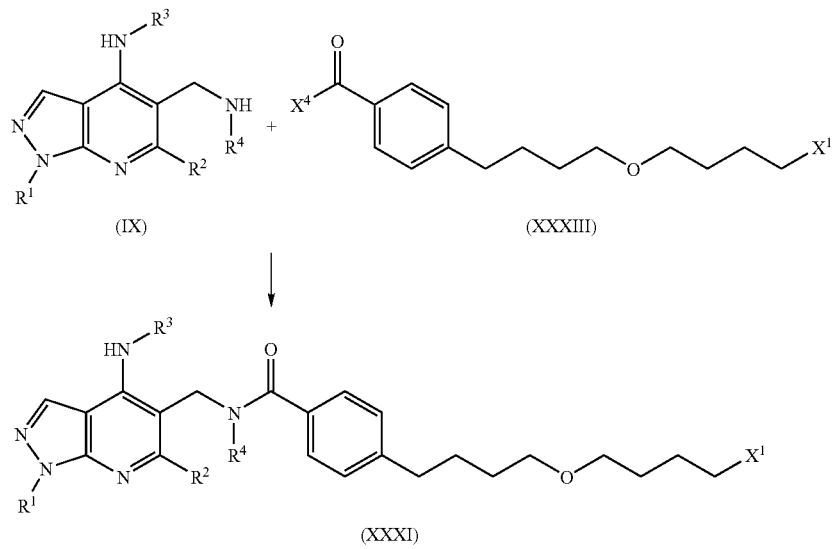

Compounds of formula (XXXIII) wherein $X^4$ is a chlorine atom (Cl) (and optionally wherein $X^1$ is Br) can e.g. be prepared as illustrated in Intermediates 26, 25, 24, 23, and/or 22 herein.

Alternatively, the activated compound (the compound of formula (XXXIII)) can for example be an activated carboxylic acid derivative wherein the leaving group $X^4$ is

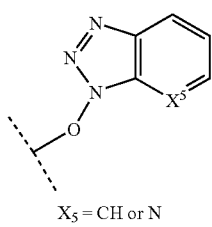

$X_5$ = CH or N

The latter activated compound of formula (XXXIII) can be formed from the carboxylic acid of formula (XXXIV), wherein $X^1$ is as defined above:

(a) by reaction of the carboxylic acid (XXXIV) with a suitable carbodiimide such as 1-ethyl-3-(3'-dimethylaminopropyl) carbodiimide [also named 1-(3-dimethylaminopropyl)-3-ethylcarbodiimide], or a salt thereof e.g. hydrochloride salt, preferably followed by reaction of the resulting product with 1-hydroxybenzotriazole, in a suitable solvent (preferably anhydrous) such as N,N-dimethylformamide or acetonitrile, e.g. at a suitable temperature such as room temperature (e.g. about 18 to about 25° C.); or:

(b) by reaction of the carboxylic acid (XXXIV) with 2-(1H-benzotriazole-1-yl)-1,1,3,3-tetramethyl uronium tetrafluoroborate or O-(7-azabenzotriazol-1-yl)-N,N,N',N'-tetramethyluronium hexafluorophosphate, e.g. in the presence of a base such as N,N-diisopropylethylamine, and/or usually in the presence of a solvent such as N,N-dimethylformamide or acetonitrile e.g. at a suitable temperature such as room temperature (e.g. about 18 to about 25° C.).

Compounds of formula (XXXIV), wherein $X^1$ is as defined herein, may for example be prepared by hydrolysis of an ester of formula (XXXV), wherein $X^1$ and $X^8$ are as defined herein. Conditions can include reaction with a base such as sodium hydroxide or potassium hydroxide in a suitable solvent such as aqueous ethanol or aqueous dioxane, or if $X^8$ is tert-butyl then 4M hydrogen chloride in dioxane can be used.

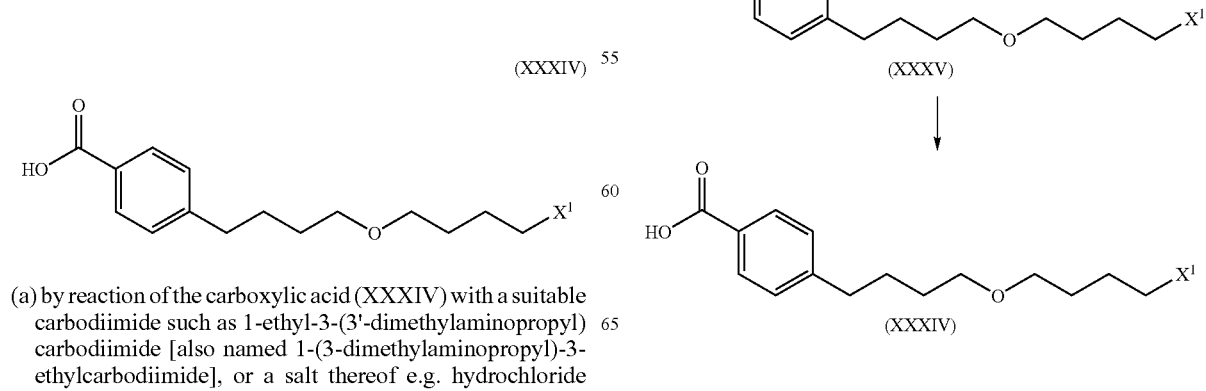

Compound of formula (XXXV), wherein $X^1$ and $X^8$ are as defined herein, may for example be prepared by reacting compounds of formula (XXXVI), wherein $X^8$ is as defined herein (e.g. where $X^8$=tert-butyl, can optionally be prepared according to Tetsuo Miwa et. al. *J. Org. Chem.* 1993, 58(7), 1696) with a suitable alkylating agent of formula (XXXVII), wherein $X^1$ is as defined herein.

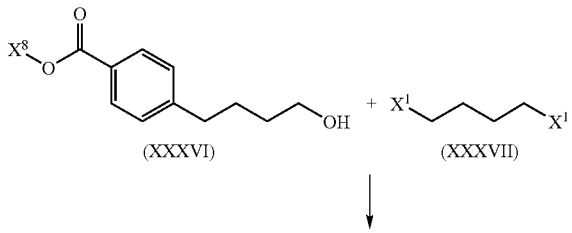

Process 4

Compounds of formula (XLII), wherein $R^1$, $R^2$, $R^3$, $R^4$, $R^5$ and $R^6$ are as defined herein, may typically be prepared by reaction by substitution of compounds of formula (XLIII) or a salt thereof, wherein $R^1$, $R^2$, $R^3$, $R^4$ and $X^1$ are as defined herein, with an amine of formula (IV) or a salt thereof, wherein $R^5$ and $R^6$ are as defined herein. Suitable conditions include heating in a suitable solvent such as N,N-dimethylformamide, suitably in the presence of a suitable base e.g. an organic tertiary amine base such as N,N-diisopropylethylamine, e.g. at a suitable temperature such as ca. 60-100° C. e.g. ca. 85° C. Alternative conditions include heating under microwave irradiation in a suitable solvent such as N,N-dimethylformamide, e.g. at a suitable temperature such as ca. 140-150° C.

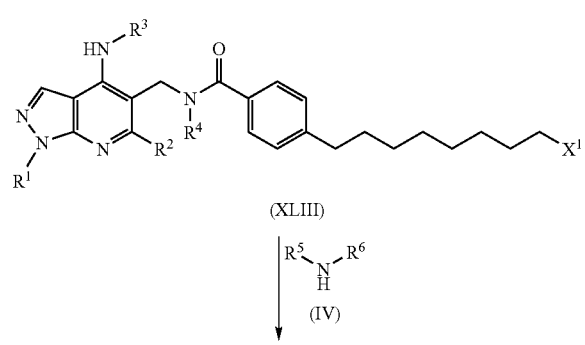

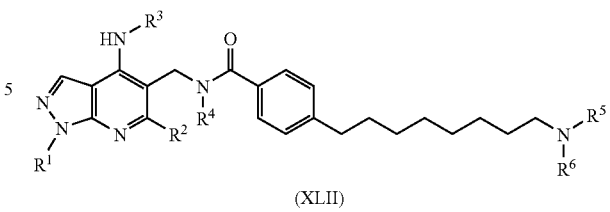

Compounds of formula (XLIII), wherein $R^1$, $R^2$, $R^3$, $R^4$ and $X^1$ are as defined above, may for example be prepared from compounds of formula (XLIV), wherein $R^1$, $R^2$, $R^3$ and $R^4$ are as defined above. For example, when $X^1$ represents a halogen atom such as a bromine atom, compounds of formula (XLIII) may be prepared from compounds of formula (XLIV) and a suitable halogenating agent such as carbon tetrabromide, in the presence of a suitable phosphine such as triphenylphosphine, in a suitable solvent such as dichloromethane, at a suitable temperature for example between 0° C. and room temperature.

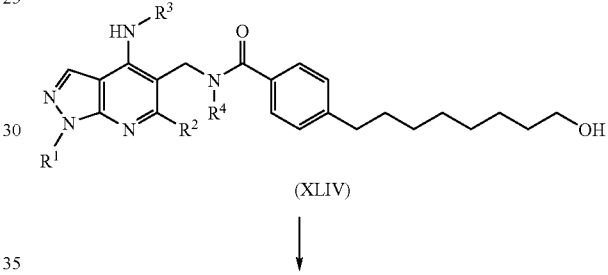

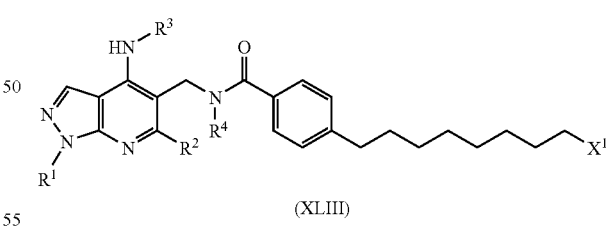

Compounds of formula (XLIV), wherein $R^1$, $R^2$, $R^3$ and $R^4$ are as defined above, may for example be prepared from compounds of formula (IX), wherein $R^1$, $R^2$, $R^3$ and $R^4$ are as defined above, and the compound of formula (XLV), in the presence of a suitable amide coupling reagent such as (1H-1,2,3-benzotriazol-1-yloxy)(tri-1-pyrrolidinyl)phosphonium hexafluorophosphate (available from Aldrich) and a suitable base such as N,N-diisopropylethylamine, in a suitable solvent such as anhydrous N,N-dimethylformamide, at a suitable temperature such as room temperature.

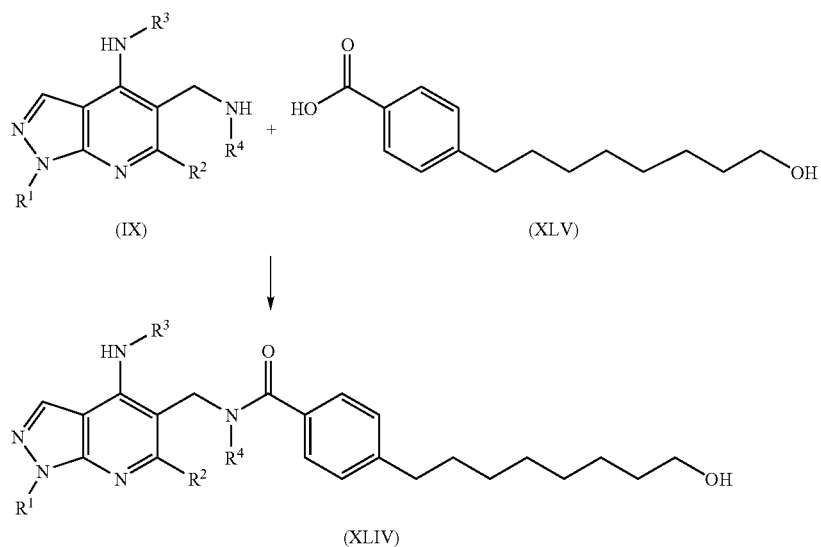

(IX) + (XLV) → (XLIV)

The compound of formula (XLV) is a known compound (e.g. can optionally be prepared according to K. Fukai JP11174621).

Process 5

Compounds of formula (XLVI), wherein $R^1$, $R^2$, $R^3$, $R^4$, $R^5$, $R^6$ and n are as defined herein, may typically be prepared by reaction by substitution of compounds of formula (XLVII) or a salt thereof, wherein $R^1$, $R^2$, $R^3$, $R^4$, $X^1$ and n are as defined herein, with an amine of formula (IV) or a salt thereof, wherein $R^5$ and $R^6$ are as defined herein. Suitable conditions include heating in a suitable solvent such as N,N-dimethylformamide, suitably in the presence of a suitable base e.g. an organic tertiary amine base such as N,N-diisopropylethylamine, e.g. at a suitable temperature such as ca. 60-100° C., e.g. ca. 85° C. Alternative conditions include heating under microwave irradiation in a suitable solvent such as N,N-dimethylformamide, e.g. at a suitable temperature such as ca. 140-150° C.

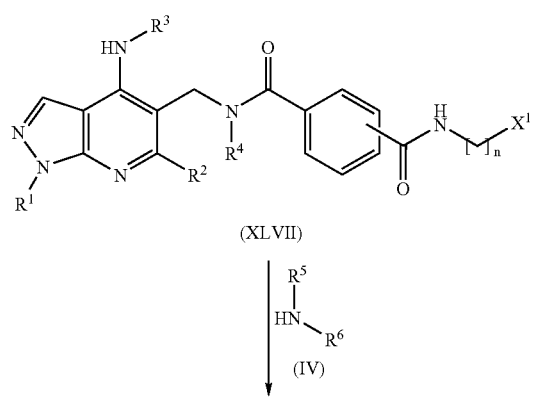

(XLVII)

↓ $R^5$ HN $R^6$ (IV)

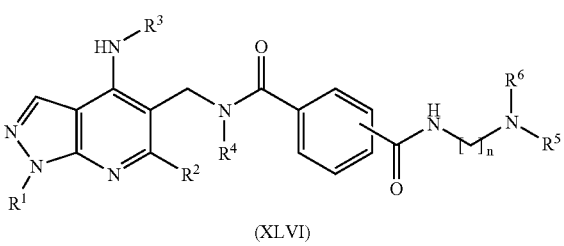

(XLVI)

Compounds of formula (XLVII), wherein $R^1$, $R^2$, $R^3R^4$, $X^1$ and n are as defined herein, may e.g. be prepared according to the following scheme:

(XLVII)

↑ CBr$_4$/PPh$_3$/CH$_2$Cl$_2$/ room temperature

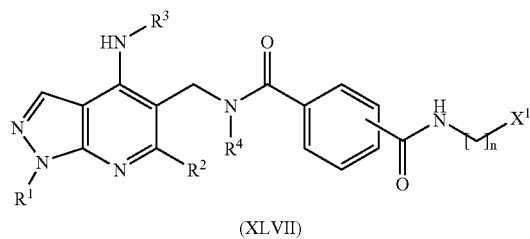

↑ EtN=C=N—(CH$_2$)$_3$NMe$_2$ Dimethylformamide/ room temperature

-continued

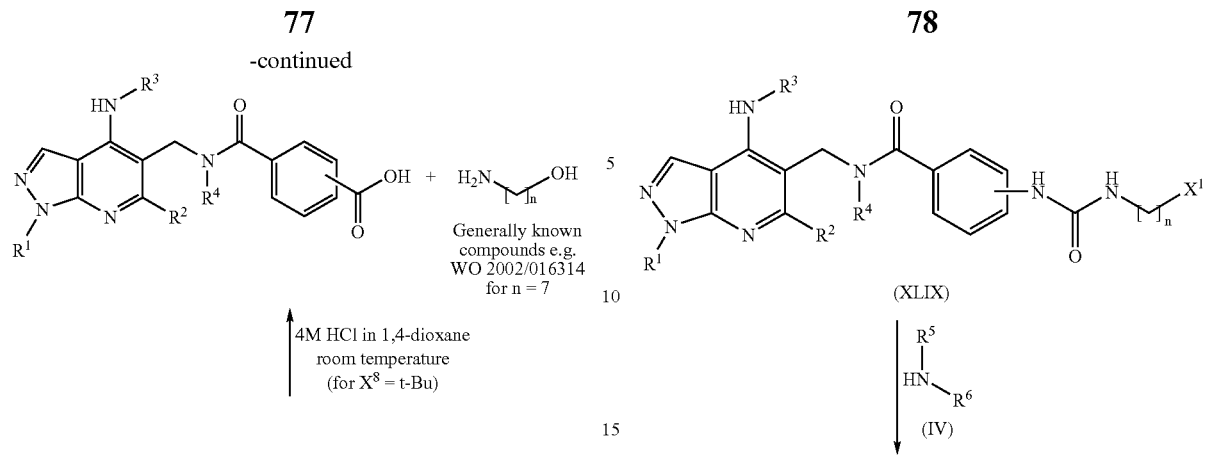

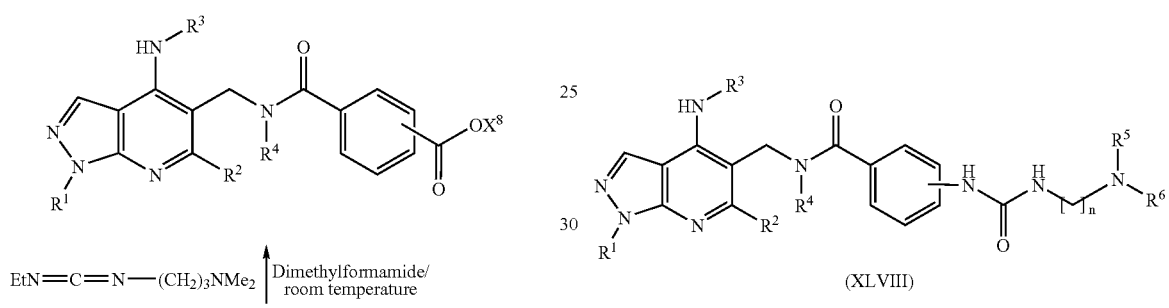

Process 6
Compounds of formula (XLVIII), wherein $R^1$, $R^2$, $R^3$, $R^4$, $R^5$, $R^6$ and n are as defined herein, may typically be prepared by reaction by substitution of compounds of formula (XLIX) or a salt thereof, wherein $R^1$, $R^2$, $R^3$, $R^4$, $X^1$ and n are as defined herein, with an amine of formula (IV) or a salt thereof, wherein $R^5$ and $R^6$ are as defined herein. Suitable conditions include heating in a suitable solvent such as N,N-dimethylformamide, suitably in the presence of a suitable base e.g. an organic tertiary amine base such as N,N-diisopropylethylamine, e.g. at a suitable temperature such as ca. 60-100° C. e.g. ca. 85° C. Alternative conditions include heating under microwave irradiation in a suitable solvent such as N,N-dimethylformamide, e.g. at a suitable temperature such as ca. 140-150° C.

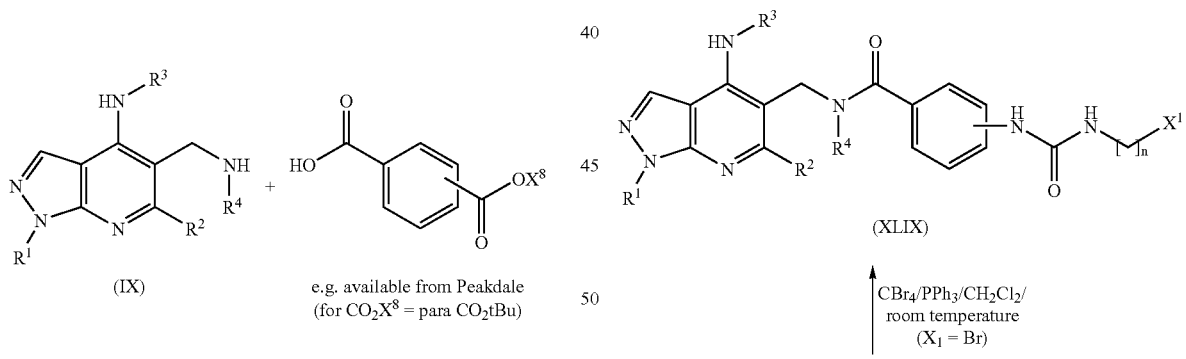

Compounds of formula (XLIX), wherein $R^1$, $R^2$, $R^3$, $R^4$, $X^1$ and n are as defined above, may for example be prepared according to the following scheme:

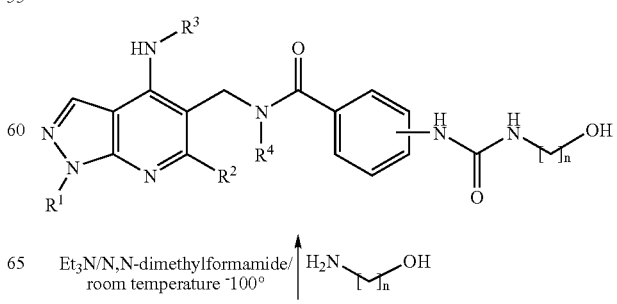

-continued

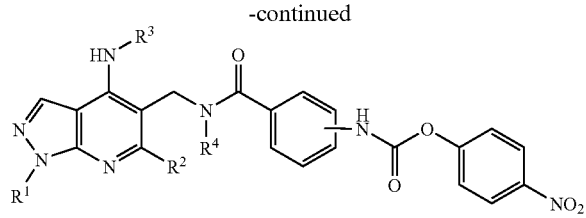

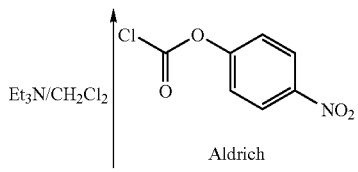

Aldrich

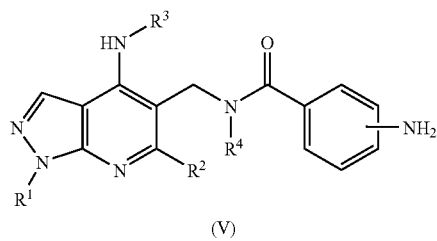

(V)

Process 7

Compounds of formula (L), wherein $R^1$, $R^2$, $R^3$, $R^4$, $R^5$, $R^6$ and n are as defined herein, may typically be prepared by reaction by substitution of a compound of formula (LI) or a salt thereof, wherein $R^1$, $R^2$, $R^3$, $R^4$, $X^1$ and n are as defined herein, with an amine of formula (IV) or a salt thereof, wherein $R^5$ and $R^6$ are as defined herein. Suitable conditions include heating in a suitable solvent such as N,N-dimethylformamide, suitably in the presence of a suitable base e.g. an organic tertiary amine base such as N,N-diisopropylethylamine, e.g. at a suitable temperature such as ca. 60-100° C. e.g. ca. 85° C. Alternative conditions include heating under microwave irradiation in a suitable solvent such as N,N-dimethylformamide, e.g. at a suitable temperature such as ca. 140-150° C.

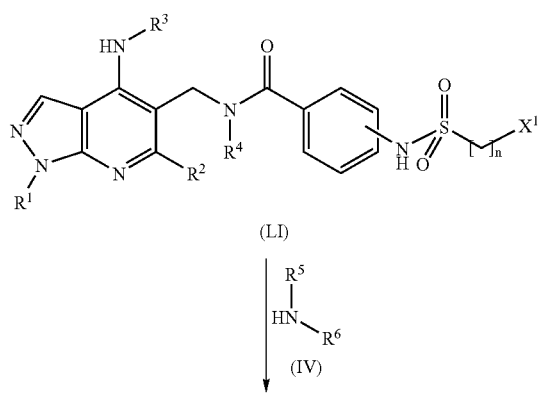

-continued

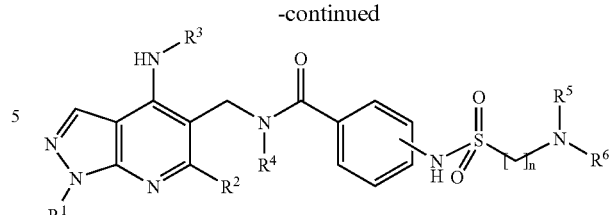

(L)

Compounds of formula (LI), wherein $R^1$, $R^2$, $R^3$, $R^4$, $X^1$ and n are as defined above, may e.g. typically be prepared according to the following scheme:

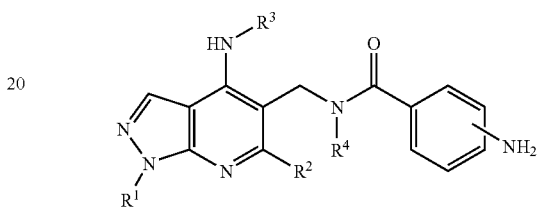

(V)

Et$_3$N/CH$_2$Cl$_2$/ room temperature e.g. for n = 7, $X^1$ = Br see WO 98/42660

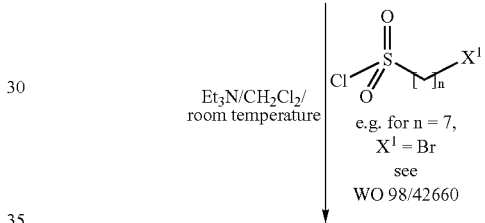

(LI)

Compounds of formula (V) may e.g. typically be prepared as described above.

Process 8

Compounds of formula (LII), wherein $R^1$, $R^2$, $R^3$, $R^4$, $R^5$, $R^6$ and n are as defined herein, may typically be prepared by reaction by substitution of a compound of formula (LIII) or a salt thereof, wherein $R^1$, $R^2$, $R^3$, $R^4$, $X^1$ and n are as defined herein, with an amine of formula (IV) or a salt thereof, wherein $R^5$ and $R^6$ are as defined herein. Suitable conditions include heating in a suitable solvent such as N,N-dimethylformamide, suitably in the presence of a suitable base e.g. an organic tertiary amine base such as N,N-diisopropylethylamine, e.g. at a suitable temperature such as ca. 60-100° C. e.g. ca. 85° C. Alternative conditions include heating under microwave irradiation in a suitable solvent such as N,N-dimethylformamide, e.g. at a suitable temperature such as ca. 140-150° C.

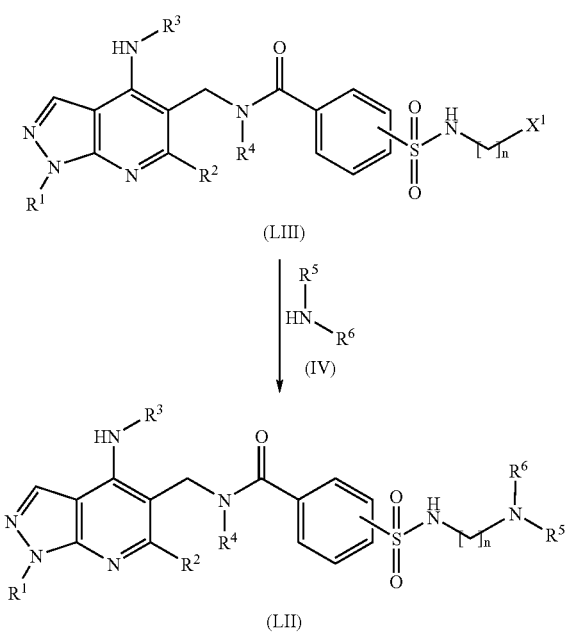

(LIII)

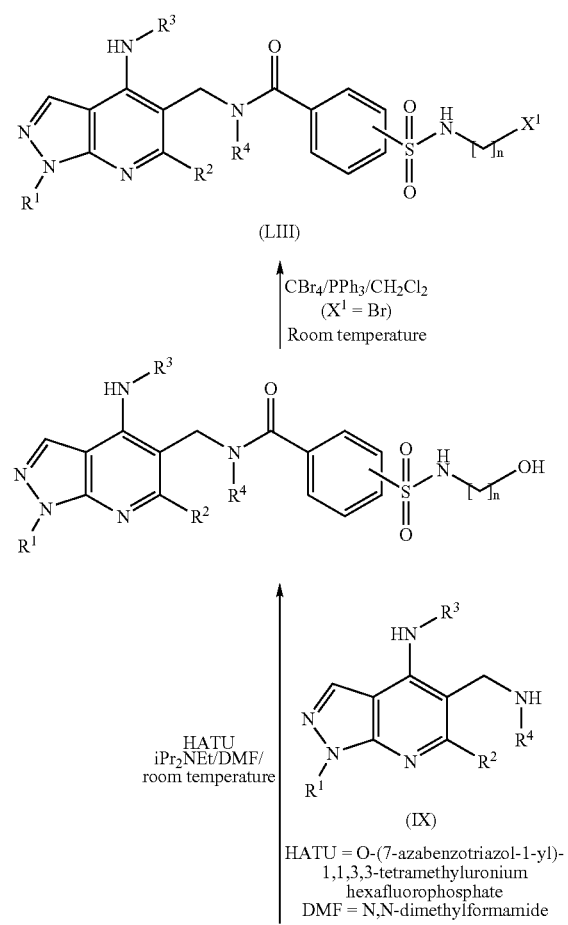

Compounds of formula (LIII), wherein $R^1$, $R^2$, $R^3$, $R^4$, $X^1$ and n are as defined above, may e.g. typically be prepared according to the following scheme:

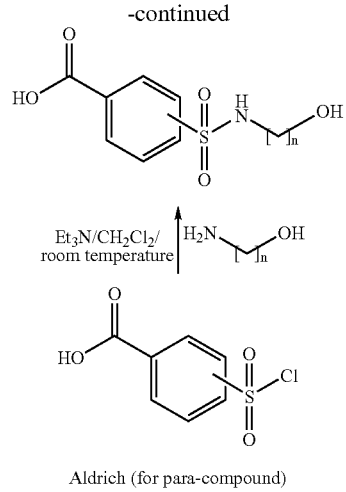

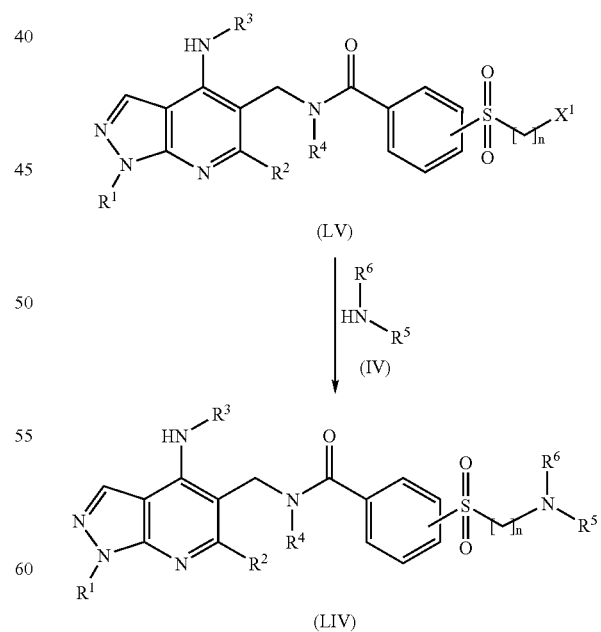

Process 9

Compounds of formula (LIV), wherein $R^1$, $R^2$, $R^3$, $R^4$, $R^5$, $R^6$ and n are as defined herein, may typically be prepared by reaction by substitution of a compound of formula (LV) or a salt thereof, wherein $R^1$, $R^2$, $R^3$, $R^4$, $X^1$ and n are as defined herein, with an amine of formula (IV) or a salt thereof, wherein $R^5$ and $R^6$ are as defined herein. Suitable conditions include heating in a suitable solvent such as N,N-dimethylformamide, suitably in the presence of a suitable base e.g. an organic tertiary amine base such as N,N-diisopropylethylamine, e.g. at a suitable temperature such as ca. 60-100° C. e.g. ca. 85° C. Alternative conditions include heating under microwave irradiation in a suitable solvent such as N,N-dimethylformamide, e.g. at a suitable temperature such as ca. 140-150° C.

Compounds of formula (LV) wherein $R^1$, $R^2$, $R^3$, $R^4$, $X^1$ and n are as defined above, may e.g. typically be prepared according to the following scheme:

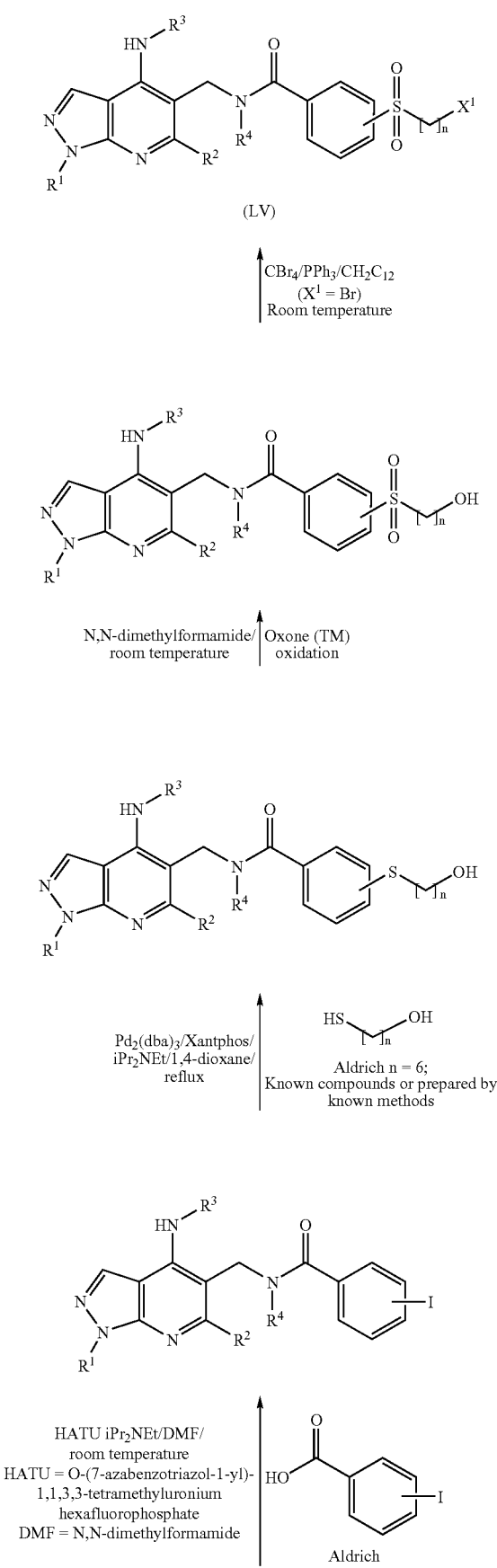

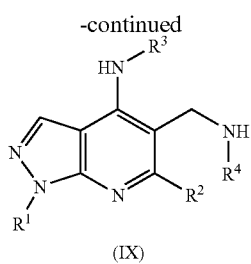

(IX)

Note: In the above scheme:
(a) Oxone™ is potassium peroxymonosulphate, which is 2KHSO$_5$.KHSO$_4$.K$_2$SO$_4$;
(b) Pd$_2$(dba)$_3$ is tris(dibenzylideneacetone)-dipalladium (0);
and (c) Xantphos is (9,9,-dimethyl-9H-xanthene-4,5-diyl)bis(diphenylphosphine).

Compound of formula (IX) may e.g. typically be prepared as described above.

Process 10

Compounds of formula (LVI), wherein $R^1$, $R^2$, $R^3$, $R^4$, $R^5$, $R^6$ and n are as defined herein, may e.g. typically be prepared by reaction by substitution of a compound of formula (LVII) or a salt thereof, wherein $R^1$, $R^2$, $R^3$, $R^4$, $X^1$ and n are as defined herein, with an amine of formula (IV) or a salt thereof, wherein $R^5$ and $R^6$ are as defined herein. Suitable conditions include heating in a suitable solvent such as N,N-dimethylformamide, suitably in the presence of a suitable base e.g. an organic tertiary amine base such as N,N-diisopropylethylamine, e.g. at a suitable temperature such as ca. 60-100° C. e.g. ca. 85° C. Alternative conditions include heating under microwave irradiation in a suitable solvent such as N,N-dimethylformamide, e.g. at a suitable temperature such as ca. 140-150° C.

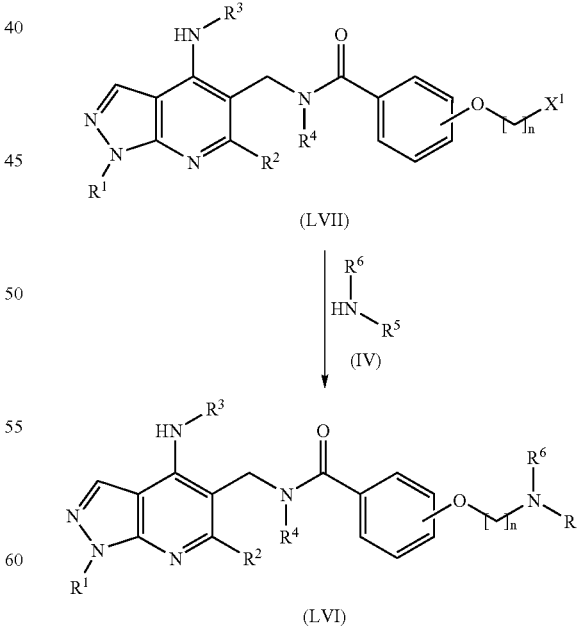

Compounds of formula (LVII) wherein $R^1$, $R^2$, $R^3$, $R^4$, $X^1$ and n are as defined above, may e.g. typically be prepared according to the following scheme:

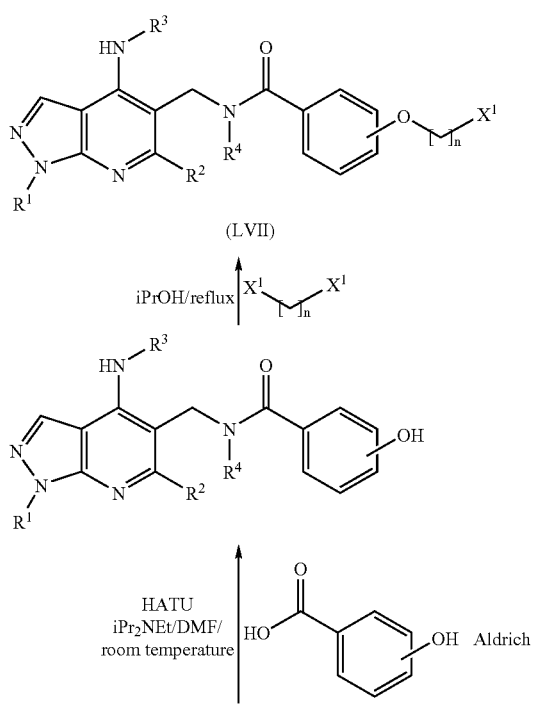

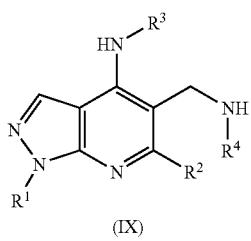

HATU = O-(7-azabenzotriazol-1-yl)-1,1,3,3-tetramethyluronium hexafluorophosphate
DMF = N,N-dimethylformamide Compounds of formula (IX) may e.g. be prepared as described above.

Process 11

Compounds of formula (XIV) wherein $R^2$ represents fluoroalkyl (for example trifluoromethyl) may e.g. typically be prepared according to the following scheme, followed by appropriate subsequent steps, e.g. as described in Process 1A or 1B or 1C:

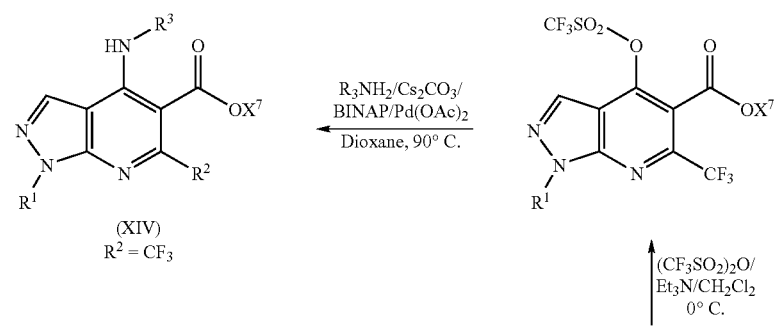

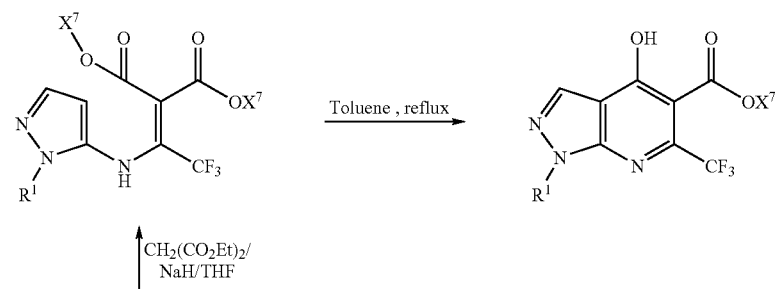

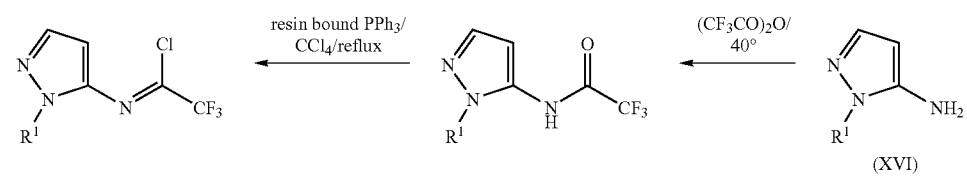

Process 12

Compounds of formula (IX) wherein $R^4$ represents methyl or ethyl may e.g. typically be prepared according to the following scheme, wherein $R^{4-C1}$ represents H when $R^4$ is methyl and $R^{4-C1}$ represents methyl when $R^4$ is ethyl; followed by appropriate subsequent steps, e.g. as described in Process 1A or 1B or 1C:

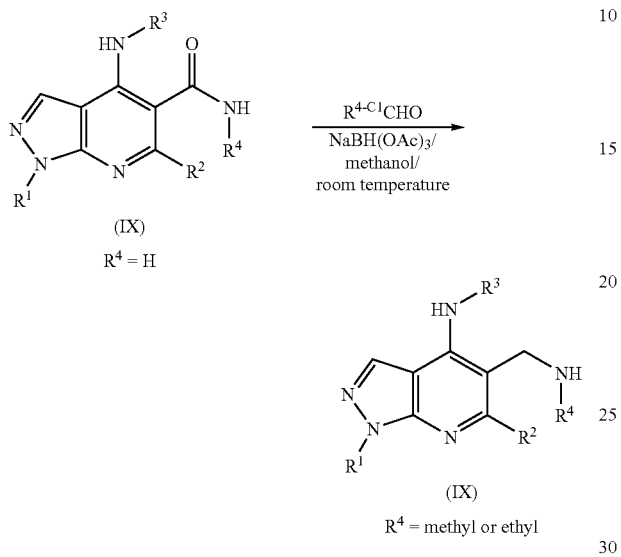

Process F: Conversion of One Compound of Formula (I), or a Salt Thereof into Another Compound of Formula (I) or a Salt Thereof In optional Process F, one compound of formula (I) or salt thereof (or a protected version thereof, such as an N-protected version thereof e.g. BOC-N-protected or benzyloxycarbonyl-N-protected version; or a derivative thereof such as an ester derivative thereof) is optionally converted into another compound of formula (I) or a salt thereof. This conversion reaction can for example occur within the $R^3$ group. This conversion optionally comprises or is one or more of the following processes F1 to F10:

F1. Conversion of a ketone into the corresponding oxime.
F2. An oxidation process. For example, the oxidation process can comprise or be oxidation of an alcohol to a ketone (e.g. using Jones reagent) or oxidation of an alcohol or a ketone to a carboxylic acid.
F3. A reduction process, for example reduction of a ketone or a carboxylic acid to an alcohol.
F4. Acylation, for example acylation of an amine (e.g. see Examples 329-349 and Example 353 of WO 2004/024728 A2 for suitable process details), or acylation of a hydroxy group.
F5. Alkylation, for example alkylation of an amine or of a hydroxy group.
F6. Hydrolysis, e.g. hydrolysis of an ester to the corresponding carboxylic acid or salt thereof (e.g. see Examples 351, 488, 489, 650, 651 of WO 2004/024728 A2 for suitable process details).
F7. Deprotection, e.g. deprotection of (e.g. deacylation of, or t-butyloxycarbonyl (BOC) removal from, or benzyloxycarbonyl removal from) an amine group. BOC deprotection is usually carried out under acidic conditions e.g. using hydrogen chloride in an organic solvent such as dioxan. Benzyloxycarbonyl deprotection is optionally carried out by hydrogenation.
F8. Formation of an ester or amide, for example from the corresponding carboxylic acid.
and/or
F9. Beckmann rearrangement of one compound of formula (I) into another compound of formula (I), for example using cyanuric chloride (2,4,6-trichloro-1,3,5-triazine) together with a formamide such as DMF, e.g. at room temperature (see L. D. Luca, *J. Org. Chem.*, 2002, 67, 6272-6274). The Beckmann rearrangement can for example comprise conversion of a compound of formula (I) wherein $NHR^3$ is of sub-formula (o2)

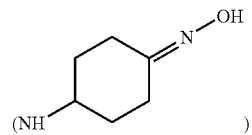

into a compound of formula (I) wherein $NHR^3$ is of sub-formula (m3)

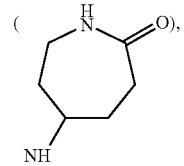

and process details can be for example as illustrated in Examples 658 and 659 of WO 2004/024728 A2.

Synthetic Process Summary

The present invention therefore also provides a process for preparing a compound of formula (I) or a salt (e.g. pharmaceutically acceptable salt) thereof:

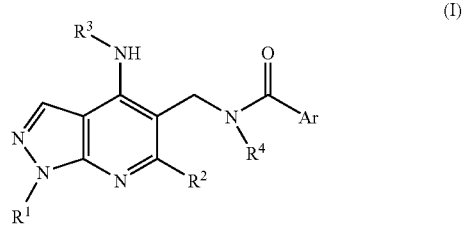

wherein Ar has the sub-formula (x):

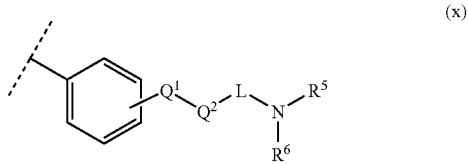

and wherein $R^1$, $R^2$, $R^3$, $R^4$, $R^5$, $R^6$, L, $Q^1$ and $Q^2$ are as defined herein, the process comprising:

(1A) to prepare a compound of formula (II), which are compounds of formula (I) wherein Ar has sub-formula (x), $Q^1$ is NH, $Q^2$ is —C(O)—, and L is $(CH_2)_n$, wherein $R^1$, $R^2$, $R^3$, $R^4$, $R^5$, $R^6$, and n are as defined herein, or a salt thereof, reaction (substitution) of a compound of formula (III), wherein $\lambda^1$ is a suitable leaving group such as mesylate (methanesulfonate), tosylate (p-toluenesulfonate) or a halogen atom (suitably a halogen atom, in particular a bromine atom), and $R^1$, $R^2$, $R^3$, $R^4$ and n are as defined herein, with an amine of formula (IV), wherein $R^5$ and $R^6$ are as defined herein:

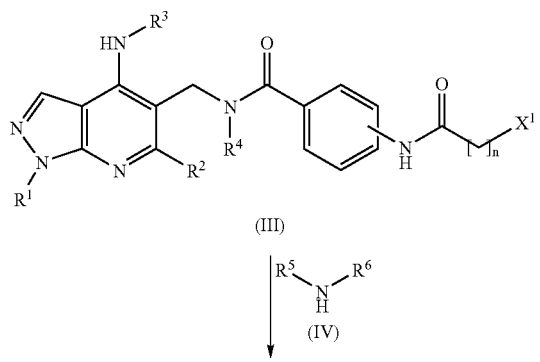

(III)

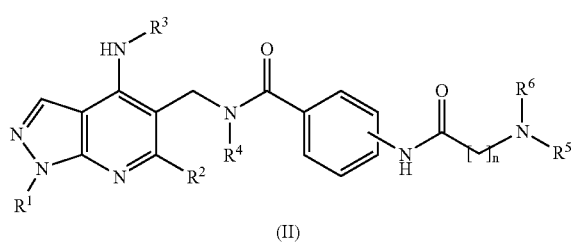

; or (1B) to prepare a compound of formula (II) or a salt thereof, wherein $R^1$, $R^2$, $R^3$, $R^4$, $R^5$, $R^6$ and n are as defined herein (in particular when $R^4$ is a hydrogen atom), reaction of a compound of formula (IX) or a salt thereof (e.g. a HCl salt thereof, e.g. monohydrochloride salt thereof), wherein $R^1$, $R^2$, $R^3$ and $R^4$ are as defined herein (in particular when $R^4$ is a hydrogen atom), with a compound of formula (XXII) or a salt thereof, wherein $R^5$, $R^6$ and n are as defined herein and $X^4$ is a suitable leaving group (e.g. wherein $X^4$ is as described herein):

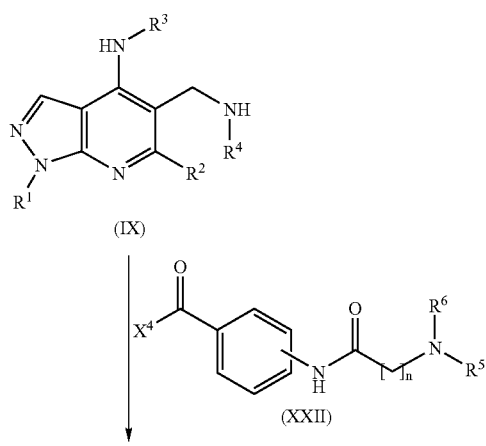

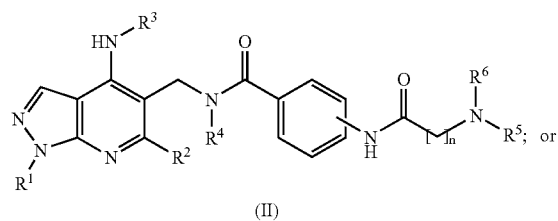

(II)

(1C) to prepare a compound of formula (XLII), wherein $R^1$, $R^2$, $R^3$, $R^4$ and n are as defined herein (in particular when $R^4$ is a hydrogen atom), and wherein $R^{5'}$ is a hydrogen atom (H), methyl, ethyl, n-propyl, or isopropyl (e.g. methyl), and wherein $R^{6'}$ is $C_{1-4}$alkyl substituted by one OH substituent (in particular wherein $R^{6'}$ is —$CH_2CH_2OH$), which is one embodiment of a compound of formula (I), or a salt thereof, by carrying out steps (1C)(i) and (1C)(ii):

(1C)(i) formation of a compound of formula (XLIII) or a salt thereof, wherein $R^1$, $R^2$, $R^3$, $R^4$ and n are as defined herein (in particular when $R^4$ is a hydrogen atom), wherein $R^{5'}$ is a hydrogen atom (H), methyl, ethyl, n-propyl, or isopropyl (e.g. methyl), and wherein $R^{6-prot}$ is $C_{1-4}$alkyl substituted by one OH substituent O-Prot' (in particular wherein $R^{6-prot}$ is —$CH_2CH_2$—O-Prot'), wherein O-Prot' is any protected OH group which is deprotectable by treatment with acid or base or fluoride ions [in particular, —OC(O)—$C_{1-6}$alkyl such as OAc (acetate), OC(O)—$CF_3$, —OC(O)aryl such as —OC(O)-phenyl, or —O-(tri-organo)silyl such as O-trialkylsilyl such as O-TBDMS (tert-butyldimethylsilyloxy) or O-TMS (trimethylsilyloxy)], by reaction of an amide of formula (XLV) or a salt thereof, wherein $R^4$ and n are as defined herein (in particular wherein $R^4$ is a hydrogen atom), $R^{5'}$ is a hydrogen atom (H), methyl, ethyl, n-propyl, or isopropyl (e.g. methyl), and $R^{6-prot}$ is as defined herein, with a compound of formula (XLIV) or an acid addition salt thereof (e.g. a sulfonate salt thereof e.g. methanesulfonate or benzenesulfonate salt thereof), wherein $X^{11}$ is a suitable leaving group such as mesylate (methanesulfonate), tosylate (p-toluenenesulfonate), triflate (trifluoromethanesulfonate), or a chlorine, bromine or iodine atom (in particular a chlorine atom):

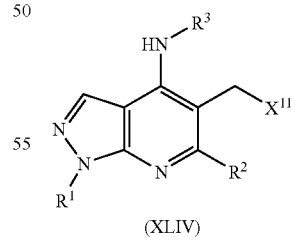

(XLIV)

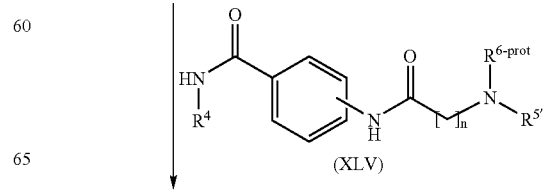

(XLV)

-continued

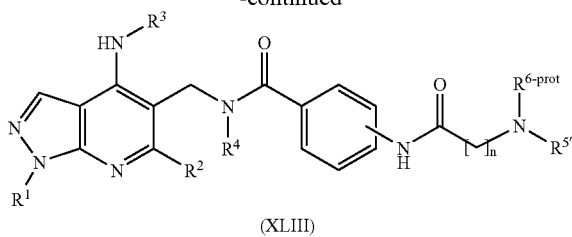

(XLIII)

, and then (1C)(ii) deprotection of the compound of formula (XLIII) or the salt thereof to prepare the prepare a compound of formula (XLII) or a salt thereof:

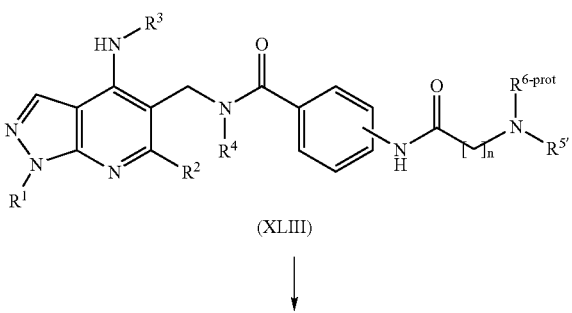

(XLIII)

↓

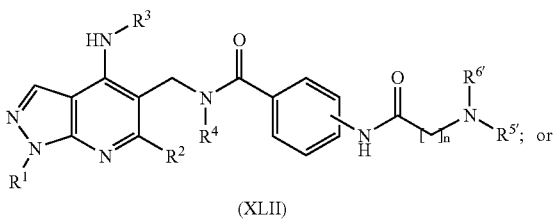

(XLII)

(1D) to prepare a compound of formula (XLIIa), wherein $R^1$, $R^2$, $R^3$, $R^4$ and n are as defined herein (in particular when $R^4$ is a hydrogen atom), and wherein $R^{5''}$ and $R^{6''}$ are as defined herein for $R^5$ and $R^6$ respectively provided that there is no OH group in $R^{5''}$ or $R^{6''}$ or [$R^{5''}$ and $R^{6''}$ taken together] and provided that $R^8$ is not H, which is one embodiment of a compound of formula (I), or a salt thereof, reaction of an amide of formula (XLVa) or a salt thereof, wherein $R^4$ and n are as defined herein (in particular when $R^4$ is a hydrogen atom), and wherein $R^{5''}$ and $R^{6''}$ are as defined herein for $R^5$ and $R^6$ respectively provided that there is no OH group in $R^{5''}$ or $R^{6''}$ or [$R^{5''}$ and $R^{6''}$ taken together] and provided that $R^8$ is not H, with a compound of formula (XLIV) or an acid addition salt thereof (e.g. a sulfonate salt thereof e.g. methanesulfonate or benzenesulfonate salt thereof), wherein $X^{11}$ is a suitable leaving group such as mesylate (methanesulfonate), tosylate (p-toluenenesulfonate), triflate (trifluoromethanesulfonate), or a chlorine, bromine or iodine atom (in particular a chlorine atom):

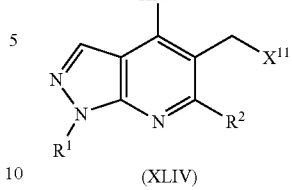

(XLIV)

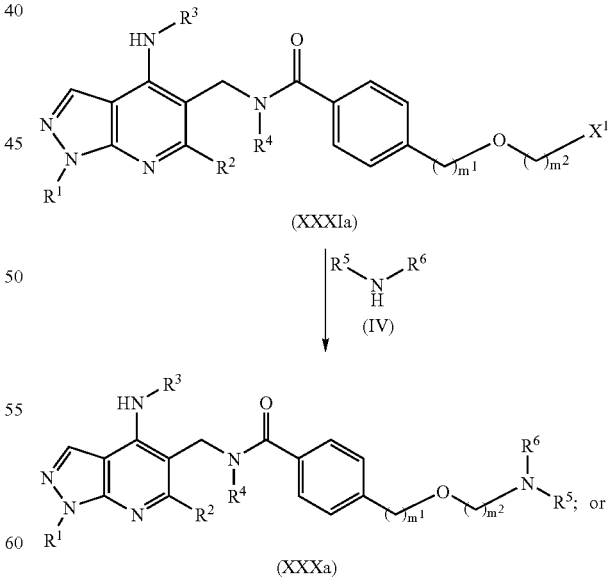

(XLIIa)

(3) to prepare a compound of formula (XXXa), wherein $R^1$, $R^2$, $R^3$, $R^4$ $R^5$, $R^6$, $m^1$, and $m^2$ are as defined herein (suitably, $m^1$ and $m^2$ can both be 4), or a salt thereof, reaction by substitution of a compound of formula (XXXIa), or a salt thereof, wherein $R^1$, $R^2$, $R^3$, $R^4$, $X^1$, $m^1$, and $m^2$ are as defined herein, with an amine of formula (IV), or a salt thereof, wherein $R^5$ and $R^6$ are as defined herein:

(XXXIa)

(IV)

(XXXa)

(4 to 10) a process according to the final step in the synthesis of the compound of formula (I) as described in Processes 4, 5, 6, 7, 8, 9, or 10 (as described herein, e.g. as described hereinabove); or (F) converting one compound of formula (I) or a salt thereof, or a protected version thereof or a derivative (e.g. ester derivative) thereof, into another compound of formula (I) or a salt thereof (e.g. as described in Process F hereinabove);

and, in the case of any of Process 1A, 1B, 1C, 1D, 3, or 4 to 10, or (F), optionally converting the compound of formula (I) into a salt thereof such as a pharmaceutically acceptable salt thereof;

or (G) to prepare a salt of a compound of formula (I), converting a compound of formula (I) into a salt thereof such as a pharmaceutically acceptable salt thereof.

Preferred, suitable or optional features of the steps in any of Processes 1A, 1B, 1C, 1D, 2A, or 3 to 10, or (F), independently of each other, can be as described above for such correspondingly-numbered and/or -lettered Processes, with all necessary changes being made.

The present invention also provides: (G) a process for preparing a pharmaceutically acceptable salt of a compound of formula (I) comprising conversion of the compound of formula (I) or a salt thereof into the desired pharmaceutically acceptable salt thereof. Such processes can for example be as described herein, e.g. as described in the Salts section above. For example, a pharmaceutically acceptable salt can be an acid addition salt, or less commonly (e.g. if a C(O)OH group is present in the compound) a base addition salt. In one embodiment, a pharmaceutically acceptable acid addition salt is optionally prepared by reaction of a compound of formula (I) with a suitable inorganic or organic acid (e.g. as described hereinabove).

The present invention also provides a compound of formula (I) or a salt thereof, prepared by (or obtainable by) a method as defined herein.

Medical Uses

The present invention also provides a compound of formula (I) or a pharmaceutically acceptable salt thereof for use as an active therapeutic substance in a mammal such as a human. The compound or salt can be for use in the treatment and/or prophylaxis of any of the diseases/conditions described herein (e.g. for use in the treatment and/or prophylaxis of an inflammatory and/or allergic disease in a mammal such as a human, monkey, rodent (e.g. rat or mouse) or dog, in particular in a human) and/or can be for use as a phosphodiesterase 4 (PDE4) inhibitor. "Therapy" may include treatment and/or prophylaxis.

Also provided is the use of a compound of formula (I) or a pharmaceutically acceptable salt thereof in the manufacture of a medicament (e.g. pharmaceutical composition) for the treatment and/or prophylaxis of any of the diseases/conditions described herein in a mammal such as a human, e.g. for the treatment and/or prophylaxis of an inflammatory and/or allergic disease in a mammal such as a human.

Also provided is a method of treatment and/or prophylaxis of any of the diseases/conditions described herein in a mammal (e.g. human) in need thereof, e.g. a method of treatment and/or prophylaxis of an inflammatory and/or allergic disease in a mammal (e.g. human) in need thereof, which method comprises administering to the mammal (e.g. human) a therapeutically effective amount of a compound of formula (I) as herein defined or a pharmaceutically acceptable salt thereof.

Phosphodiesterase 4 inhibitors may be useful in the treatment and/or prophylaxis of a variety of diseases/conditions, especially inflammatory and/or allergic diseases, in a mammal such as a human, for example: chronic obstructive pulmonary disease (COPD) (e.g. chronic bronchitis and/or emphysema), asthma, rhinitis (e.g. allergic and/or non-allergic rhinitis), rheumatoid arthritis, atopic dermatitis, psoriasis, urticaria, allergic conjunctivitis, vernal conjunctivitis, eosinophilic granuloma, septic shock, inflammatory bowel disease (e.g. ulcerative colitis and/or Crohn's disease), reperfusion injury of the myocardium and/or brain, chronic glomerulonephritis, endotoxic shock, or adult respiratory distress syndrome, in a mammal such as a human; in particular: chronic obstructive pulmonary disease (COPD) (e.g. chronic bronchitis and/or emphysema), asthma, rhinitis (e.g. allergic and/or non-allergic rhinitis), atopic dermatitis, psoriasis, urticaria, allergic conjunctivitis, vernal conjunctivitis, eosinophilic granuloma, inflammatory bowel disease (e.g. ulcerative colitis and/or Crohn's disease), or adult respiratory distress syndrome, in a mammal such as a human.

In the treatment and/or prophylaxis using the compound of formula (I) or the pharmaceutically acceptable salt thereof, the inflammatory and/or allergic disease can for example be chronic obstructive pulmonary disease (COPD), asthma, rhinitis (e.g. allergic and/or non-allergic rhinitis), atopic dermatitis or psoriasis, in a mammal (e.g. human). Preferably, the compound of formula (I) or the pharmaceutically acceptable salt thereof is for the treatment and/or prophylaxis of COPD, asthma or rhinitis (e.g. allergic and/or non-allergic rhinitis), in a mammal (e.g. human).

PDE4 inhibitors, for example cilomilast and roflumilast, are thought to be effective in the treatment of COPD. For example, see S. L. Wolda, *Emerging Drugs*, 2000, 5(3), 309-319; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; A. M. Vignola, *Respiratory Medicine*, 2004, 98, 495-503; D. Spina, *Drugs*, 2003, 63(23), 2575-2594; and references cited in the aforementioned publications; G. Krishna et al., *Expert Opinion on Investigational Drugs*, 2004, 13(3), 255-267 (see especially pp. 259-261 and refs. 102-111 and 201 therein); and B. J. Lipworth, *The Lancet*, 2005, 365, 167-175.

The PDE4 inhibitor cilomilast (Ariflo™) at 15 mg orally twice daily appears to improve forced expiratory volume in 1s ($FEV_1$) in COPD patients (C. H. Compton et al., *The Lancet*, 2001, vol. 358, 265-270), and appears to have anti-inflammatory effects in COPD patients (E. Gamble et al., *Am. J. Respir. Crit. Care Med.*, 2003, 168, 976-982). On cilomilast, see also R. D. Border et al., *Chest*, 2003, vol. 124 Suppl. 4, p. 170S (abstract) and J. D. Eddleston et al., *Am. J. Respir. Crit. Care Med.*, 2001, 163, A277 (abstract). The PDE4 inhibitor roflumilast appears to show small improvements in $FEV_1$ in COPD patients (see B. J. Lipworth, *The Lancet*, 2005, 365, 167-175, and refs 49-50 therein).

COPD is often characterised by the presence of airflow obstruction due to chronic bronchitis and/or emphysema (e.g., see S. L. Wolda, *Emerging Drugs*, 2000, 5(3), 309-319).

For treatment and/or prophylaxis of COPD or asthma in a mammal (e.g. human), inhaled or parenteral administration to the mammal of the compound of formula (I) or a pharmaceutically acceptable salt thereof can be used, preferably inhaled administration.

PDE4 inhibitors are thought to be effective in the treatment and/or prophylaxis of asthma (e.g. see M. A. Giembycz, *Drugs*, February 2000, 59(2), 193-212; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; P. J. Barnes,

*Nature Reviews—Drug Discovery*, October 2004, 831-844; B. J. Lipworth, *The Lancet*, 2005, 365, 167-175; and references cited in the aforementioned publications).

In one preferred embodiment, the compound of formula (I) or the pharmaceutically acceptable salt thereof is for the treatment and/or prophylaxis of rhinitis, such as allergic rhinitis (e.g. seasonal allergic rhinitis or perennial allergic rhinitis) and/or non-allergic rhinitis (e.g. vasomotor rhinitis or cold air rhinitis), in a mammal such as a human. One embodiment involves the treatment and/or prophylaxis of mixed allergic/non-allergic rhinitis in a mammal such as a human. By way of example, for rhinitis such as allergic and/or non-allergic rhinitis, intranasal or parenteral administration of the compound of formula (I) or a pharmaceutically acceptable salt thereof is optionally used.

The PDE4 inhibitor roflumilast, given orally at 500 ug once daily for 9 days, is reported to be effective in improving rhinal airflow during the treatment period (compared to placebo), in humans with histories of allergic rhinitis but asymptomatic at screening, and who were challenged with intranasal allergen provocation (pollen extracts) daily beginning the third day of treatment and each time approx. 2 hours after study drug administration (B. M. Schmidt et al., *J. Allergy & Clinical Immunology*, 108(4), 2001, 530-536).

PDE4 inhibitors may be effective in the treatment of rheumatoid arthritis (e.g. see H. J. Dyke et al., *Expert Opinion on Investigational Drugs*, January 2002, 11(1), 1-13; C. Burnouf et al., *Current Pharmaceutical Design*, 2002, 8(14), 1255-1296; and A. M. Doherty, *Current Opinion Chem. Biol.*, 1999, 3(4), 466-473; and references cited in these publications). For rheumatoid arthritis, parenteral administration is optionally used.

PDE4 inhibition has been suggested for the treatment of inflammatory bowel disease (e.g. ulcerative colitis and/or Crohn's disease), see K. H. Banner and M. A. Trevethick, *Trends Pharmacol. Sci.*, August 2004, 25(8), 430-436.

In one embodiment, the compound or salt can for example be for use in the treatment and/or prophylaxis of an inflammatory and/or allergic skin disease, such as atopic dermatitis or psoriasis, in a mammal such as a human.

In one optional embodiment, the treatment and/or prophylaxis is of atopic dermatitis in a mammal such as a human or pig, preferably in a human, in particular in a human aged 21 years or less, e.g. 18 years or less. For treatment and/or prophylaxis of atopic dermatitis in a mammal, external topical administration to the mammal of the compound of formula (I) or a pharmaceutically acceptable salt thereof (e.g. topical administration to the skin e,g. to skin affected by the atopic dermatitis) can be used, though alternatively oral or parenteral administration can be used. For treatment and/or prophylaxis of atopic dermatitis, inhaled administration is usually not suitable.

"Atopic dermatitis" has been proposed to include two general sub-classes: (1) an "allergic (extrinsic)" type of atopic dermatitis which generally occurs in the context of sensitization to environmental allergens and/or which is generally accompanied by elevated serum IgE levels; and (2) an "non-allergic (intrinsic)" type of atopic dermatitis generally with little or no detectable sensitization and/or generally with normal or low serum IgE levels (N. Novak et al., *J. Allergy Clin. Immunol.*, 2003, 112, 252-262; and T. C. Roos et al., Drugs, 2004, 64(23), 2639-2666, see e.g. pages 2640-2641). The compound of formula (I) or the pharmaceutically acceptable salt thereof can therefore be for the treatment and/or prophylaxis of allergic (extrinsic) atopic dermatitis and/or non-allergic (intrinsic) atopic dermatitis in a mammal (e.g. human or pig, preferably human).

"External topical" administration means topical administration to an external body part (i.e. excluding, for example, the lung or mouth, but including the lips), preferably excluding the eye.

"External topical" administration preferably is topical administration to the skin, for example to the skin of an arm, hand, leg, foot, head (e.g. face), neck and/or torso of a mammal such as a human. External topical administration can for example be to those parts of a mammal's skin affected by or susceptible to atopic dermatitis.

For the use of PDE4 inhibitors in atopic dermatitis, see for example:

- J. M. Hanifin et al., "Type 4 phosphodiesterase inhibitors have clinical and in vitro anti-inflammatory effects in atopic dermatitis", *J. Invest. Dermatol.*, 1996, 107(1), 51-56; which reports reductions of inflammatory parameters in atopic dermatitis patients treated with PDE4 inhibitor CP80,633 (0.5% ointment, twice daily topical application);
- C. E. M. Griffiths et al., "Randomized comparison of the type 4 phosphodiesterase inhibitor cipamfylline cream, cream vehicle and hydrocortisone 17-butyrate cream for the treatment of atopic dermatitis", *Br. J. Dermatol.*, 2002, 147(2), 299-307, which reports that cipamfylline (0.15%) cream is significantly more effective than vehicle, but significantly less effective than hydrocortisone 17-butyrate (0.1%) cream, in the treatment of atopic dermatitis patients;
- T. C. Roos et al., "Recent advances in treatment strategies for atopic dermatitis", *Drugs*, 2004, 64(23), 2639-2666 (see e.g. page 2657 and refs. 201-209 therein);
- A. M. Doherty, *Current Opinion Chem. Biol.*, 1999, 3(4), 466-473 (e.g. see p. 470); and
- H. J. Dyke et al., *Expert Opinion Invest. Drugs*, 2002, 11(1), 1-13 (e.g. see p. 7 and refs. 74, 75 and 76 cited therein);

and references cited in the above references.

For the use of the PDE4 inhibitors SB 207499 (cilomilast) and AWD 12-281 in mouse models of the allergic type of dermatitis, see W. Bäumer et al., *Eur. J. Pharmacol.*, 2002, 446, 195-200 and W. Bäumer et al., *J. Pharmacy Pharmacol.*, 2003, 55, 1107-1114.

Pharmaceutical Compositions, Routes of Administration, and Dosage Regimens

For use in medicine, the compounds or salts of the present invention are usually administered as a pharmaceutical composition.

The present invention therefore provides in a further aspect a pharmaceutical composition comprising a compound of formula (I) or a pharmaceutically acceptable salt thereof and one or more pharmaceutically acceptable carriers and/or excipients.

The pharmaceutical composition can be for use in the treatment and/or prophylaxis of any of the conditions described herein, for example chronic obstructive pulmonary disease (COPD), asthma, rhinitis (e.g. allergic rhinitis), atopic dermatitis or psoriasis in a mammal (e.g. human).

The invention also provides a method of preparing a pharmaceutical composition comprising a compound of formula (I), as herein defined, or a pharmaceutically acceptable salt thereof, and one or more pharmaceutically acceptable carriers and/or excipients, the method comprising mixing the compound or salt with the one or more pharmaceutically acceptable carriers and/or excipients.

The invention also provides a pharmaceutical composition prepared by said method.

The compounds of formula (I) or salts thereof and/or the pharmaceutical composition may be administered, for example, by inhaled, intranasal, external topical (e.g. skin topical), parenteral (e.g. intravenous, subcutaneous, or intramuscular), or oral administration, for example to a mammal such as a human. Inhaled administration involves topical administration to the lung e.g. by aerosol or dry powder composition.

Accordingly, the pharmaceutical composition can be suitable for (e.g. adapted for) inhaled, intranasal, external topical (e.g. skin topical), parenteral (e.g. intravenous, subcutaneous, or intramuscular), or oral administration, e.g. to a mammal such as a human. The pharmaceutical composition can for example be suitable for inhaled, intranasal or external topical (e.g. skin topical) administration, e.g. to a mammal such as a human.

Inhaled or intranasal administration, in particular inhaled administration, is generally a preferred route of administration. In particular, inhaled or intranasal administration is preferred for N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino) benzamide or a salt thereof such as the monohydrochloride salt thereof [e.g. which can be as prepared in Example 1A2 (monohydrochloride salt) or Example 1B ("free base")], and is thought to be preferred for 4-({1,6-diethyl-5-[({[4-(4-{[4-(4-morpholinyl)butyl]oxy}butyl)phenyl]carbonyl}amino) methyl]-1H-pyrazolo[3,4-b]pyridin-4-yl}amino)-1-piperidinecarboxamide or a salt thereof [e.g. which can be as prepared in Example 23 (formate salt) or Example 23A ("free base")].

Oral administration is generally not a preferred route of administration.

The pharmaceutical composition can optionally be in unit dose form. The unit dose form can for example be:
(a) a rupturable or peel-openable sealed dose container containing a dry powder inhalable pharmaceutical composition (e.g. a plurality of which are usually disposed inside a suitable inhalation device);
(b) a vial, ampoule or filled syringe for parenteral administration e.g. comprising a solution or suspension of the compound or pharmaceutically acceptable salt in a suitable carrier such as an aqueous carrier or e.g. containing a lyophilised parenteral pharmaceutical composition (the vial or ampoule can optionally be manufactured using a blow-fill-seal process); or
(c) a tablet or capsule for oral administration e.g. for oral administration to a human.

Alternatively, the composition can be in a form adapted for the administration of varying amounts of composition as desired by the user, such as a spreadable or sprayable external topical composition such as a cream, an ointment, a gel, or a liquid.

Pharmaceutical Compositions Suitable for Inhalable or Intranasal Administration, And Particle-size Reduction Pharmaceutical compositions suitable for (e.g. adapted for) intranasal or inhaled administration may conveniently be formulated as aerosols, solutions, suspensions, drops, gels or dry powders. Pharmaceutical compositions suitable for (e.g. adapted for) intranasal or inhaled administration may optionally be formulated with one or more pharmaceutically acceptable carriers and/or excipients such as an aqueous or non-aqueous vehicle, a suspending agent, a thickening agent, a wetting agent, an isotonicity adjusting agent, an antioxidant and/or a preservative.

For compositions suitable for intranasal or inhaled administration, the compound of formula (I) or a pharmaceutically acceptable salt thereof may typically be in a particle-size-reduced form, which may be prepared by conventional techniques, for example, micronisation and milling. Generally, the size-reduced (e.g. micronised) compound of formula (I) or a pharmaceutically acceptable salt thereof can be defined by a $D_{50}$ value of about 0.5 to 10 microns, such as of about 2 to 4 microns (for example as measured using laser diffraction).

Pharmaceutical Compositions Suitable for Intranasal Administration

In one embodiment, compositions comprising a compound of formula (I) or a pharmaceutically acceptable salt thereof are suitable for intranasal administration. In the composition for intranasal administration, a liquid vehicle such as an aqueous (liquid) vehicle is typically used. In the composition for intranasal administration, the compound of formula (I) or the salt thereof can be present, for example, as a suspension in a liquid vehicle (e.g. as a suspension in an aqueous (liquid) vehicle) and/or as a solution for example as an aqueous solution.

Intranasal compositions comprising a compound of formula (I) or a pharmaceutically acceptable salt thereof may permit the compound(s) to be delivered to all areas of the nasal cavities (the target tissue) and further, may permit the compound(s) to remain in contact with the target tissue for longer periods of time. One possible dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure up to two or three times each day, ideally once daily. Intranasal compositions can be for once daily administration.

Intranasal compositions may optionally contain one or more suspending and/or thickening agents, one or more preservatives, one or more wetting and/or solublising agents and/or one or more isotonicity adjusting agents as desired. Compositions suitable for intranasal administration may optionally further contain other excipients, such as antioxidants (for example sodium metabisulphite), taste-masking agents (such as menthol) and/or sweetening agents (for example dextrose, glycerol, saccharin and/or sorbitol).

A suspending and/or thickening agent, if included, will typically be present in the intranasal composition in an amount of from about 0.05 to about 5% w/w or from about 0.1 to about 5% w/w, such as from about 0.05 to about 1% w/w (e.g. about 0.1 to about 0.5% w/w, e.g. about 0.2% w/w, e.g. for xanthan gum) or from about 1% to about 3% w/w, based on the total weight of the composition. A suspending and/or thickening agent can include xanthan gum, microcrystalline cellulose (e.g. Avicel®), carboxymethylcellulose (e.g. carboxymethylcellulose sodium), veegum, tragacanth, bentonite, methylcellulose and polyethylene glycols; in particular xanthan gum, microcrystalline cellulose or carboxy methylcellulose sodium. A suspending and/or thickening agent of particular interest is xanthan gum, especially when the compound of formula (I) or the salt thereof is N-{[1,6-d]ethyl-4-(tetrahydro-2H-pyran-4-ylamino)-1H-pyrazolo[3,4-b]pyridin-5-yl]methyl}-4-({8-[(2-hydroxyethyl)(methyl)amino] octanoyl}amino)benzamide or a pharmaceutically acceptable salt thereof.

Suspending agents may also be included in compositions suitable for inhaled or oral liquid administration, as appropriate.

For stability purposes, intranasal compositions comprising a compound of formula (I) or a pharmaceutically acceptable salt thereof may be protected from microbial or fungal contamination and growth by inclusion of a preservative. Examples of pharmaceutically acceptable anti-microbial agents or preservatives may include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium ethylenediaminetetraacetate (EDTA, also called disodium edetate), and other anti-microbial agents such as chlorhexidine, chlorocresol, sorbic acid and its salts (such as potassium sorbate), polymyxin and sodium benzoate. In particular, the pharmaceutically acceptable anti-fungal agent or preservative can for example include potassium sorbate (e.g. 0.1% to 1% w/w, e.g. about 0.3% w/w) and/or disodium ethylenediaminetetraacetate (EDTA, also called disodium edetate) (e.g. 0.005% to 0.5% w/w, e.g. about 0.015% w/w). The preservative, if included, may be present in an amount of between about 0.001 and 1% (w/w), such as about 0.015% to 0.3% (w/w), based on the total weight of the composition. Preservatives may be included in compositions suitable for other routes of administration as appropriate.

Compositions which contain a suspended medicament may include a pharmaceutically acceptable wetting agent which functions to wet the particles of medicament to facilitate dispersion thereof in a or the aqueous phase of the composition. Typically, the amount of wetting agent used will not cause foaming of the dispersion during mixing. Examples of wetting agents include fatty alcohols, esters and ethers, such as polysorbate e.g. a polyoxyethylene sorbitan monooleate such as polyoxyethylene 20 sorbitan monooleate (polysorbate 80). The wetting agent may be present in intranasal compositions in an amount of between about 0.001 and 0.05% (w/w), for example about 0.025% (w/w), based on the total weight of the composition. Wetting agents may be included in compositions suitable for other routes of administration, e.g. for inhaled administration, as appropriate.

Compositions can alternatively or additionally contain a solublising agent, which generally functions to maintain the compound of formula (I) or salt in solution (e.g. aqueous solution) and/or to reduce the amount of precipitation of said compound or salt from solution (e.g. aqueous solution) and/or to decrease the rate of precipitation of said compound or salt from solution (e.g. aqueous solution). Such a solublising agent can include a polysorbate, for example a polyoxyethylene sorbitan monooleate such as polyoxyethylene 20 sorbitan monooleate (polysorbate 80) or polyoxyethylene 5 sorbitan monooleate (polysorbate 81), or polyoxyethylene 20 sorbitan monolaurate (polysorbate 20), or polyoxyethylene 20 sorbitan monopalmitate (polysorbate 40), or polyoxyethylene 20 sorbitan monostearate (polysorbate 60). [See The Handbook of Pharmaceutical Excipients 4th edition 2003 pp. 479-483 for polysorbates, and for an explanation of polyoxyethylene 20 sorbitan monooleate meaning it is the prepared at least in part by copolymerisation with about 20 moles of ethylene oxide for each mole of sorbitol and/or sorbitol anhydrides used.] The solubilising agent can be present in intranasal compositions in an amount of from about 0.25% to about 10% (w/w) such as about 1% to about 10% (w/w), for example about 1% to about 5% (w/w), based on the total weight of the composition.

An isotonicity adjusting agent may be included to achieve isotonicity with body fluids e.g. fluids of the nasal cavity, resulting in reduced levels of irritancy. The isotonicity adjusting agent can include sodium chloride, dextrose, xylitol or calcium chloride, in particular xylitol or dextrose. An isotonicity adjusting agent may be included in intranasal compositions in an amount of from about 0.1 to about 10% w/w, such as from about 1% to about 10% w/w or from about 2% to about 10% w/w, e.g. about 4 to about 5% (w/w), based on the total weight of the composition. Isotonicity adjusting agents may also be included in compositions suitable for other routes of administration, for example in compositions suitable for inhaled, oral liquid or parenteral administration, as appropriate. A isotonicity adjusting agent of particular interest is xylitol, especially when the compound of formula (I) or the salt thereof is N-{[1,6-d]ethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a pharmaceutically acceptable salt thereof.

Further, the intranasal compositions comprising a compound of formula (I) or a pharmaceutically acceptable salt thereof may be buffered by the addition of suitable buffering agents such as sodium citrate, citric acid, phosphates such as disodium phosphate (for example the dodecahydrate, heptahydrate, dihydrate and anhydrous forms) or sodium phosphate, or mixtures thereof, in particular sodium citrate and/or citric acid. Buffering agents may also be included in compositions suitable for other routes of administration as appropriate.

Compositions for administration topically to the nose or lung for example, for the treatment of rhinitis, include pressurised aerosol compositions (e.g. for inhaled administration/topical to the lung administration) and aqueous compositions for delivery to the nasal cavities by pressurised pump. Compositions which are non-pressurised and adapted to be administered topically to the nasal cavity are of particular interest. Suitable compositions contain water as the diluent or carrier for this purpose. Aqueous compositions for administration to the lung or nose may be provided with excipients such as buffering agents, tonicity modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in WO05/044354. The dispenser has a housing which houses a fluid discharge device having a compression pump mounted on a container for containing a fluid composition. The housing has at least one finger-operable side lever which is movable inwardly with respect to the housing to cam the container upwardly in the housing to cause the pump to compress and pump a metered dose of the composition out of a pump stem through a nasal nozzle of the housing. In one embodiment, the fluid dispenser is of the general type illustrated in FIGS. 30-40 of WO05/044354.

Particle Size Reduction of Compound of Formula (I) or Salt Thereof

In, for example, pharmaceutical compositions suitable for (e.g. adapted for) inhaled administration, the compound or salt of formula (I) can be in a particle-size-reduced form. The size-reduced form can for example be obtained or obtainable by micronisation. Micronisation usually involves subjecting the compound/salt to collisional and/or abrasional forces in a fast-flowing circular or spiral/vortex-shaped airstream often including a cyclone component. The particle size of the size-reduced (e.g. micronised) compound or salt can be defined by a D50 value of about 0.5 to about 10 microns, e.g. about 1 to about 7 microns or about 1 to about 5 microns (e.g. as measured using laser diffraction). For example, the compound or salt of formula (I) can have a particle size defined by: a D10 of about 0.3 to about 3 microns (e.g. about 0.4 to about 2 microns, or about 0.5 to about 1 microns), and/or a D50 of about 0.5 to about 10 microns or about 1 to about 7 microns or (e.g. about 1 to about 5 microns or about 1.5 to about 5 microns or about 1.5 to about 4 microns), and/or a D90 of about 1 to about 30 microns or about 2 to about 20 microns or about 2 to about 15 microns or about 3 to about 15 microns (e.g. about 2 to about 10 microns or about 4 to about 10 microns); for example as measured using laser diffraction.

In particle size measurements, D90, D50 and D10 respectively mean that 90%, 50% and 10% of the material is less than the micron size specified. D50 is the median particle size. DV90, DV50 and DV10 respectively mean that 90%, 50% and 10% by volume of the material is less than the micron size specified. DM90, DM50 and DM10 respectively mean that 90%, 50% and 10% by weight of the material is less than the micron size specified.

Laser diffraction measurement of particle size can use a dry method (wherein a suspension of the compound/salt in an airflow crosses the laser beam) or a wet method [wherein a suspension of the compound/salt in a liquid dispersing medium, such as isooctane or ca. 0.05% lecithin in isooctane or (e.g. if compound is soluble in isooctane) 0.1% Tween 80 in water, crosses the laser beam]. With laser diffraction, particle size is preferably calculated using the Fraunhofer calculation; and/or preferably a Malvern Mastersizer or Sympatec apparatus is used for measurement. For example, particle size measurement and/or analysis by laser diffraction can use any or all of (e.g. all of) the following apparatus and/or conditions: a Malvern Mastersizer 2000 version apparatus, a dispersing medium of isooctane or ca. 0.05% lecithin in isooctane or ca. 0.1% Tween 80 in water, a stirring speed of ca. 1500-2500 rpm, ca. 30 seconds to ca. 3 mins (e.g. ca. 30 seconds) sonification prior to final dispersion and analysis, a 300 RF (Reverse Fourier) lens, and/or the Fraunhofer calculation with Malvern software. In another example, particle size measurement and/or analysis by laser diffraction can use any or all of (e.g. all of) the following apparatus and/or conditions: a Malvern Mastersizer longbed version apparatus, a dispersing medium of ca. 0.1% Tween 80 in water, a stirring speed of ca. 1500 rpm, ca. 3 mins sonification prior to final dispersion and analysis, a 300 RF (Reverse Fourier) lens, and/or the Fraunhofer calculation with Malvern software.

An illustrative non-limiting example of a small-scale micronisation process is now given:

Micronisation Example: Micronisation of a Compound or Salt of One of the Examples Purpose: To micronise a compound or salt of one of the Examples (described hereinafter), e.g. in an amount of approximately 300-3000 mg (e.g. about 300-1000 mg) thereof, using a Jetpharma MC1 micronizer.

The parent (unmicronised) and micronised materials are analyzed for particle size by laser diffraction and crystallinity by PXRD.

| Micronisation Example: General Equipment and material | |
|---|---|
| Equipment/material | Description and specification |
| Jetpharma MC1 Micronizer | Nitrogen supply: Air tank with pressure resistant reinforced tubing (e.g. with 275 psi rate tubing) |
| Analytical balance | can e.g. be Sartorius Analytical |
| Top loader balance | can e.g. be Mettler PM400 or Sartorius L420P |
| Digital Caliper | can e.g. be VWR Electronic caliper |
| Materials to be micronised | a compound or salt of one of the Examples |

The Jetpharma MC1 Micronizer comprises a horizontal disc-shaped milling housing having: a tubular compound inlet (e.g. angled at ca. 30 degrees to the horizontal) for entry of a suspension of unmicronised compound of formula (I) or salt in a gasflow, a separate gas inlet for entry of gases, a gas outlet for exit of gases, and a collection vessel (micronizer container) for collecting micronised material. The milling housing has two chambers: (a) an outer annular chamber in gaseous connection with the gas inlet, the chamber being for receiving pressurised gas (e.g. air or nitrogen), and (b) a disc-shaped inner milling chamber within and coaxial with the outer chamber for micronising the input compound/salt, the two chambers being separated by an annular wall. The annular wall (ring R) has a plurality of narrow-bored holes connecting the inner and outer chambers and circumferentially-spaced-apart around the annular wall. The holes opening into the inner chamber are directed at an angle (directed part-way between radially and tangentially), and in use act as nozzles directing pressurised gas at high velocity from the outer chamber into the inner chamber and in an inwardly-spiral path (vortex) around the inner chamber (cyclone). The compound inlet is in gaseous communication with the inner chamber via a nozzle directed tangentially to the inner chamber, within and near to the annular wall/ring R. Upper and lower broad-diameter exit vents in the central axis of the inner milling chamber connect to (a) (lower exit) the collection vessel which has no air outlet, and (b) (upper exit) the gas outlet. Inside and coaxial with the tubular compound inlet and longitudinally-movable within it is positioned a venturi inlet (V) for entry of gases. The compound inlet also has a bifurcation connecting to an upwardly-directed material inlet port for inputting material.

In use, the narrow head of the venturi inlet (V) is preferably positioned below and slightly forward of the material inlet port, so that when the venturi delivers pressurised gas (e.g. air or nitrogen) the feed material is sucked from the material inlet port into the gas stream through the compound inlet and is accelerated into the inner milling chamber tangentially at a subsonic speed. Inside the milling chamber the material is further accelerated to a supersonic speed by the hole/nozzle system around the ring (R) (annular wall) of the milling chamber. The nozzles are slightly angled so that the acceleration pattern of the material is in the form of an inwardly-directed vortex or cyclone. The material inside the milling chamber circulates rapidly and particle collisions occur during the process, causing larger particles to fracture into smaller ones. "Centrifugal" acceleration in the vortex causes the larger particles to remain at the periphery of the inner chamber while progressively smaller particles move closer to the centre until they exit the milling chamber, generally through the lower exit, at low pressure and low velocity. The particles that exit the milling chamber are heavier than air and generally settle downward through the lower exit into the collection vessel (micronizer container), while the exhaust gas rises (together with a minority of small particles of micronised material) and escapes into the atmosphere at low pressure and low velocity. A filter sock can optionally be placed in the upper gas outlet to catch fine micronised material.

Micronisation Example: General Procedure:

The micronizer is assembled. The narrow head of the venturi inlet is positioned below and slightly forward of the material inlet port and is measured with a micro-caliper to make sure that it is inserted correctly. The grind (ring) (R) and venturi (V) pressures are adjusted according to the values specified in the experimental design (refer to experimental section below) by adjusting the valves on the pressure gauges on the micronizer. The setup is checked for leakage by observing if there is any fluctuation in the reading of the pressure gauges.

Note that the venturi (V) pressure is kept at least about 2 bars greater than the grind (ring) (R) pressure to prevent regurgitation of material, e.g. outwardly from the material inlet port.

Balance performance can be checked with calibration weights. Specified amount of the parent material (input material) is fed manually, generally quite slowly, into the input container of the micronizer using a spatula. The input container plus material is weighed. The equipment pressure is monitored during the micronization process.

[Note: As an optional variation of these procedures, input material may be passed through a sieve/screen (e.g. a 600 micron screen) prior to micronisation in order to de-aggregate the input material, if appropriate or desirable.]

Upon completion of the micronising run, the nitrogen supply is shut off and the micronised material is allowed to settle into the micronizer container. The Venturi pressure valve and the grind (ring) pressure valve can be closed. The micronised powder in the micronizer container (collection vessel) and the cyclone (above the recovery vessel) are collected together into a pre-weighed and labelled collection vial. Any fine micronised material which may have collected in any filter sock, which may have been optionally placed in the upper gas outlet of the microniser, can optionally be tapped down into the collection vessel or cyclone. The weight of the micronised material is recorded. The input container is generally re-weighed in order to calculate the amount of input material by difference. The micronizer can be disassembled and residual PDE4 compound on the micronizer inner surface can be rinsed e.g. with 70/30 isopropyl alcohol/water and collected into a flask. The micronizer can then be thoroughly cleaned, e.g. in a Lancer washing machine, and can be dried before subsequent runs are performed.

In one embodiment, one example of suitable micronisation conditions is: Material input amount about 300 mg to about 1000 mg; Venturi Pressure (V) about 4 to about 10 bar (e.g. about 4-6 bar, e.g. about 4-5 bar); Grind (Ring) Pressure (R) about 2 to about 6 bar (e.g. about 2 bar). Material feed rate can optionally be from about 70 to about 200 mg/min.

%yield=[(Material from collection vessel+Material from cyclone+optionally material from gas outlet)/Material input amount]×100.

MICRONISATION EXAMPLES CARRIED OUT

Micronisation Example 1

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride, substantially in the form of the Form 1 anhydrate thereof (e.g. which can be preparable in Example 1A2), was micronised, by manual feeding into the microniser venturi, using a general procedure and/or general apparatus generally similar or analogous to those described above, and generally using substantially the experimental equipment and parameters described below. The parent (unmicronised) material was analyzed for particle size by scanning electron microscopy (SEM).

Micronisation Example 1-Equipment and Process Details

| Micronisation Example 1 - Equipment and process details | |
|---|---|
| Equipment/material | Description and specification |
| Jetpharma MC1 Microniser | Nitrogen supply: Nitrogen cylinder with pressure resistant reinforced tubing |
| Analytical balance | e.g. Sartorius Analytical |
| Top loader balance | e.g. Sartorius L420P |
| Pre-micronisation screening of input material | The input material is thought not to have been passed through a screen before micronisation; but see below for screening performed during the process of micronisation. |

| Example no. | Material input amount (g) | Venturi Pressure (V) & Grind (ring) Pressure (R) (bar) | Particle Size Data (microns) (unmicronised material), SEM | Particle Size Data (microns) (micronised material), SEM | Recovery yield of micronised material* |
|---|---|---|---|---|---|
| 1 | 502 mg | V = ca. 5 bar (see below). | Agglomerates of equant | Primary equant particles | About 56%. 282 mg of |

Micronisation Example 1 - Equipment and process details (continued)

| | | | |
|---|---|---|---|
| R = 2 bar | primary particles. The primary particle size is generally about 5 microns or less | generally of about 2-4 microns or less particle size (e.g. generally about 2-3 microns or less). Some of the primary particles are present as loose agglomerates | micronised material collected |

Process notes for Micronisation Example 1: The Venturi Pressure V was initially 5 bar (with R=2 bar). In response to an apparently blocked venturi with material appearing to emit from the venturi, the process was stopped after 3 minutes micronisation, resumed again for a further 2 minutes and then stopped again. The process was restarted with V increased to 6 bar, but there was a blockage again with powder emitting from the venturi, so the process was stopped again after 1 minute; it appeared that there was a large lump of material which blew back. Apparently, the presence of aggregates (agglomerates) was blocking the venturi feed. Hence, the material was passed through a 355 micron screen (sieve), to attempt to break up significant agglomerates, and then micronisation was resumed, using V=5 bar and R=2 bar and feeding the cohesive screened material into the venturi using a brush rather than a spatula; there was no evidence of blow-back as the screened material was fed into the venturi. This final stage, micronising the screened material, lasted 7 minutes. The collected micronised material (282 g) appeared to be cohesive in nature, based on evidence of a residue on the venturi. There was some evidence of material present in the outlet; there was no major presence of material around the micronising ring.

Micronisation Example 2

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide hydrobromide (e.g. monohydrobromide, and/or e.g. which can be as prepared in Example 1D), fed manually into the venturi, was micronised, by manual feeding into the microniser venturi, using a general procedure and/or general apparatus generally similar or analogous to those described above, and generally using substantially the experimental equipment and parameters described below. The micronisation duration was about 5 minutes. The parent (unmicronised) material was analyzed for particle size by scanning electron microscopy (SEM).

Micronisation Example 2-Equipment and Process Details

| Equipment/material | Description and specification |
|---|---|
| Jetpharma MC1 Microniser | Nitrogen supply: Nitrogen cylinder with pressure resistant reinforced tubing |
| Analytical balance | e.g. Sartorius Analytical |
| Top loader balance | e.g. Sartorius L420P |
| Pre-micronisation screening of input material | Passed through 600 micron screen before micronisation, to try to de-aggregate visible lumps |

| Example no. | Material input amount (g) | Venturi Pressure (V) & Grind (ring) Pressure (R) (bar) | Particle Size Data (microns) (unmicronised material), SEM | Particle Size Data (microns) (micronised material), SEM | Recovery yield of micronised material* |
|---|---|---|---|---|---|
| 2 | 414.1 mg of quite cohesive screened material (weight micronised after screening 500 mg of raw input material) | V = 5 bar R = 2 bar | Agglomerates of equant primary particles. The primary particle size is generally: about 5 microns or less, or about 2-3 microns or less | Agglomerates of equant primary particles. Primary particle size is generally: about 1-5 microns, or about 2-3 microns or less | 59.5% based on input pre-screening; 71.8% based on input into microniser. 297.5 mg of micronised material collected. |

Micronisation Example 3

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide succinate (e.g. hemisuccinate and/or e.g. which can be as prepared in Example 1E) was micronised, by manual feeding into the microniser venturi, using a general procedure and/or general apparatus generally similar or analogous to those described above, and generally using substantially the experimental equipment and parameters described below. The parent (unmicronised) material was analyzed for particle size by scanning electron microscopy (SEM).

Micronisation Example 3 -Equipment and Process Details

| Equipment/material | Description and specification |
|---|---|
| Jetpharma MC1 Microniser | Nitrogen supply: Nitrogen cylinder with pressure resistant reinforced tubing |
| Analytical balance | e.g. Sartorius Analytical |
| Top loader balance | e.g. Sartorius L420P |
| Pre-micronisation screening of material | Not performed |

| Example no. | Material input amount (g) | Venturi Pressure (V) & Grind (ring) Pressure (R) (bar) | Particle Size Data (microns) (unmicronised material), SEM | Particle Size Data (microns) (micronised material), SEM | Recovery yield of micronised material* |
|---|---|---|---|---|---|
| 3 | 500 mg | V = ca. 4-5 bar (see below) R = 2 bar | Agglomerates of equant primary particles. The primary particle size is generally about 5 microns or less | Agglomerates (some of reduced size) made up of equant primary particles. Primary particle size is generally about 4-5 microns or less | about 60% yield. Either about 300 mg or about 380 mg of micronised material recovered. |

Process notes for Micronisation Example 3: The input material appeared to be reasonably free-flowing and not excessively aggregated or lumpy and so was not screened. The grind pressure (R) was 2 bar and the initial venturi pressure (V) was 4 bar, and the input material was fed manually to the microniser quickly, in an attempt to reduce the risk of rapid and excessive micronisation. After 5 minutes of the micronisation process, a change in noise was heard, and it was observed that there was a build-up of input material in the feed inlet funnel. The venturi pressure was increased to 5 bar, which cleared the powder in the feed funnel. There was no further recurrence of build-up/blockage in the feed funnel. At the end of the process, some fine material was noted in the filter outlet port. Micronised material was collected from the collecting pot and the outlet funnel. Micronised material did not appear to be excessively cohesive and was readily recovered. Micronisation process time=10 minutes.

Micronisation Example 4

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide (the "free base", e.g. which can be as prepared in Example 1B) was micronised, by manual feeding into the microniser venturi, using a general procedure and/or general apparatus generally similar or analogous to those described above, and generally using substantially the experimental equipment and parameters described below. The parent (unmicronised) material was analyzed for particle size by scanning electron microscopy (SEM).

Micronisation Example 4-Equipment and Process Details

| Equipment/material | Description and specification |
|---|---|
| Jetpharma MC1 Micronizer | Nitrogen supply: Nitrogen cylinder with pressure resistant reinforced tubing |
| Analytical balance | e.g. Sartorius Analytical |
| Top loader balance | e.g. Sartorius L420P |
| Pre-micronisation screening of input material | Passed through 600 micron screen before micronisation, to try to break up hard aggregates |

| Example no. | Material input amount (g) | Venturi Pressure (V) & Grind (ring) Pressure (R) (bar) | Particle Size Data (microns) (unmicronised material), SEM | Particle Size Data (microns) (micronised material), SEM | Recovery yield of micronised material* |
|---|---|---|---|---|---|
| 4 | 451 mg (weight available for micronising after screening 509.5 mg raw input material) | V = 5 bar R = 2 bar | Irregular particles of up to about 200 microns particle size | Equant particles of up to about 10 microns particle size | about 57%, based on material input to microniser. 257.6 mg of micronised material recovered. |

Micronisation Example 5

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride, substantially in the form of the Form 1 anhydrate thereof (e.g. which can be as prepared in Example 1A2 such as Example 1A2 alternative preparation no. 1, plant method), was micronised on a larger scale micronisation equipment, a 4 inch APTM microniser (available from APTM, Switzerland, "4 inch" referring to the diameter of the micronisation ring). Experimental parameters and procedures are substantially as described in the table and text below or similar, including automatic feeding of the input material into the microniser venturi. A detailed apparatus and method description is not described herein. The parent (unmicronised) material and the micronised material were analysed for particle size by a laser diffraction method; particle size data are thought to be substantially as given below.

| Material input amount (g) | Venturi Pressure (V) & Grinding pressure (G) (bar) | Particle Size Data (microns) (unmicronised material), laser diffraction | Particle Size Data (microns) (micronised material), laser diffraction | Recovery yield of micronised material |
|---|---|---|---|---|
| 800 g (divided into separate 443 g and 357 g lots) | V = ca. 7 bar G = ca. 5 bar | D50 = about 77.8 microns | D50 = about 2.48 microns | 721 g total net weight pre-sampling (about 90% yield) |

For Micronisation Example 5, the feed rate (i.e. the rate of feeding of the input material via a rotating screw feed into the venturi inlet of the microniser), was 14±2.5 g per minute. An automatic (not manual) feeder was used.

Inhaled administration involves topical administration to the lung, such as by aerosol or dry powder composition.

Aerosol Inhalable Compositions

An aerosol formulation (aerosol composition), e.g. for inhaled administration, can be either a suspension or a solution.

Aerosol formulations (aerosol compositions), e.g. for inhaled administration, can optionally comprise a solution or fine suspension of the compound of formula (I) or the pharmaceutically acceptable salt thereof (active substance) in a pharmaceutically acceptable aqueous or non-aqueous liquid (e.g. solvent).

An aerosol formulation (aerosol composition), e.g. for inhaled administration, generally can contain a compound of formula (I) or a pharmaceutically acceptable salt thereof and a suitable propellant (e.g. under pressure) such a suitable organic propellant such as a fluorocarbon or hydrofluorocarbon (HFC) or hydrogen-containing chlorofluorocarbon (HCFC) or a mixture thereof. A hydrofluorocarbon (HFC) propellant can comprise a hydrofluoroalkane, such as 1,1,1,2-tetrafluoroethane or 1,1,1,2,3,3,3-heptafluoropropane or a mixture thereof. Other propellants include chlorofluorocarbons (CFCs) such as dichlorodifluoromethane, trichlorofluoromethane or dichlorotetrafluoroethane.

An aerosol composition may optionally contain additional formulation excipient(s) such as a surfactant and/or a cosolvent. The surfactant can include, but is not limited to, oleic acid, lecithin, an oligolactic acid or derivative e.g. as described in WO94/21229 and/or WO98/34596. The cosolvent can for example comprise ethanol.

Aerosol formulations, e.g. for inhaled administration, can be presented e.g. as a dosage form, e.g. in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler, or MDI) which is intended for disposal once the contents of the container have been exhausted. The aerosol formulation dosage form can alternatively take the form of a pump-atomiser.

Dry Powder Inhalable Compositions

For pharmaceutical compositions suitable (e.g. adapted for) inhaled administration, the pharmaceutical composition may for example be a dry powder inhalable composition.

Dry powder inhalable compositions may take the form of capsules and cartridges of, for example, gelatine, or blisters of, for example, laminated aluminium foil, for use in an inhaler or insufflator. Dry powder inhalable compositions may be formulated comprising a powder mix of a compound of formula (I) or a pharmaceutically acceptable salt thereof and a suitable powder base such as lactose or starch.

A dry powder inhalable pharmaceutical composition can comprise a powder base such as lactose or starch, the compound of formula (I) or salt thereof (suitably in particle-size-reduced form, e.g. in micronised form), and optionally a ternary agent. The ternary agent can for example comprise L-leucine, mannitol, trehalose, magnesium stearate, calcium stearate and/or cellobiose octaacetate (e.g. alpha-D-isomer of cellobiose octaacetate, e.g. available from Aldrich). The ternary agent can in particular be magnesium stearate, e.g. magnesium stearate present in an amount of from about 0.05% to about 2% w/w or from about 0.1% to about 1% w/w or from about 0.1% to about 0.5% w/w, such as from about 0.1% to about 0.25% w/w or from about 0.25% to about 1% w/w, for example about 0.5% w/w magnesium stearate. For the use of magnesium stearate in dry powder inhalable compositions, see WO 00/28979 A1 (Skyepharma) and the corresponding publications U.S. Pat. No. 6,645,466 B1 and US 2004/0202616 A1; and/or see WO 00/53157 A1. For cellobiose octaacetate and storage stability, see WO 03/088943.

The dry powder inhalable composition can comprise a dry powder blend of lactose and the compound of formula (I) or salt thereof. The lactose can be lactose hydrate e.g. lactose monohydrate and/or can be inhalation-grade and/or fine-grade lactose. The particle size of the lactose can for example be defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. The particle size of the lactose can for example be defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose can be defined by 90% or more of the lactose particles being less than 100-200 microns in diameter, and/or 50% or more of the lactose particles being less than 40-70 microns in diameter. In particular, the particle size of the lactose can be about 2% to about 30% or about 3% to about 30% (e.g. 2% to 15%, or 7% to 11%, e.g. about 10%) (by weight or by volume) of the particles are less than 50 microns, or are less than 20 microns ("fines"), or are less than 15 microns ("fines"), in diameter.

For example, without limitation, one suitable inhalation-grade lactose is lactose (e.g. 10% fines (e.g. E9334), or 6% fines, or 7% fines, or 11% fines), obtainable from Friesland Foods Domo (formerly Borculo Domo Ingredients), Hanzeplein 25, 8017 JD Zwolle, Netherlands.

In the dry powder inhalable composition the compound of formula (I) or salt thereof can for example be present in about 0.1% to about 70% (e.g. about 0.1% to about 50%, about 0.1% to about 30%, or about 0.1% to about 20%, or about 0.1% to about 10%, such as about 0.4% to about 10%, e.g. about 1% to about 10%, e.g. about 1% to about 5%) by weight of the composition.

Illustrative non-limiting examples of dry powder inhalable compositions follow:

Dry Powder Composition Example 1-Dry Powder Lactose Blend Preparation

Using a size-reduced e.g. micronised form of the compound of formula (I) or salt thereof (e.g. as prepared in a Micronisation Example herein), a dry powder blend can, for example, be prepared by mixing the required amount of the compound/salt (e.g. 10 mg, 1% w/w) with inhalation-grade lactose containing 10% fines (e.g. 990 mg, 99% w/w) in a Teflon™ (polytetrafluoroethene) pot in a Mikro-dismembrator ball-mill (but without a ball bearing) at ¾ speed (ca. 2000-2500 rpm) for about 4 hours at each blend concentration. The Mikro-dismembrator (available from B. Braun Biotech International, Schwarzenberger Weg 73-79, D-34212 Melsungen, Germany; www.bbraunbiotech.com) comprises a base with an upwardly-projecting and sidewardly-vibratable arm to which is attached the Teflon™ pot. The vibration of the arm achieves blending.

Other blends can include: 10% w/w compound/salt (50 mg)+90% w/w lactose (450 mg, inhalation-grade lactose containing 10% fines).

Serial dilution of the 1% w/w blend can achieve e.g. 0.1% and 0.3% w/w blends.

Dry Powder Composition Example 2-Dry Powder Lactose Blend Preparations

Using a micronised form of the compound of formula (I) or salt thereof (e.g. as prepared in a Micronisation Example herein), the dry powder blend can, for example, be prepared by mixing (blending), in a high shear blender (such as an Aeromatic-Fielder Turbo Rapid Volume blender), the required amount of the compound/salt with inhalation-grade lactose, e.g. lactose (such as lactose monohydrate) containing from 2% to 15% w/w fines, such as 7% to 11% w/w fines.

Examples of the contents of these dry powder inhalable compositons are those which are in a dosage unit containing 12.5 mg total amount of dry powder inhalable compositon, which can have different constituents as follows:

Dry Powder Composition Example 2(A):
(i) 10 micrograms of the micronised compound of formula (I) or salt thereof (0.08% w/w of the formulation), plus
(ii) 12.49 mg of inhalation-grade lactose, containing from 7% to 11% lactose fines.

Dry Powder Composition Example 2(B):
(i) 50 micrograms of the micronised compound of formula (I) or salt thereof (0.4% w/w of the formulation), plus
(ii) 12.45 mg of inhalation-grade lactose, containing from 7% to 11% lactose fines.

Dry Powder Composition Example 2(C):
(i) 100 micrograms of the micronised compound of formula (I) or salt thereof (0.8% w/w of the formulation), plus
(ii) 12.4 mg of inhalation-grade lactose, containing from 7% to 11% lactose fines.

Dry Powder Composition Example 2(D):
(i) 500 micrograms of the micronised compound of formula (I) or salt thereof (4% w/w of the formulation), plus
(ii) 12.0 mg of inhalation-grade lactose, containing from 7% to 11% lactose fines.

Dry Powder Composition Example 2(E):
(i) 1000 micrograms of the micronised compound of formula (I) or salt thereof (8% w/w of the formulation), plus
(ii) 11.5 mg of inhalation-grade lactose, containing from 7% to 11% lactose fines.

Dry Powder Composition Example 2(F) with Magnesium Stearate Ternary Agent
(i) 50 micrograms of the micronised compound of formula (I) or salt thereof (0.4% w/w of the formulation), plus
(ii) 62.5 micrograms of magnesium stearate (0.5% w/w of the formulation), plus
(iii) 12.3875 mg of inhalation-grade lactose, containing from 7% to 11% lactose fines.

Dry Powder Composition Example 2(G) with Magnesium Stearate Ternary Agent
(i) 500 micrograms of the micronised compound of formula (I) or salt thereof (4% w/w of the formulation), plus
(ii) 62.5 micrograms of magnesium stearate (0.5% w/w of the formulation), plus
(iii) 11.9375 mg of inhalation-grade lactose, containing from 7% to 11% lactose fines.

Dry Powder Composition Example 2(H) with Magnesium Stearate Ternary Agent
(i) 1000 micrograms of the micronised compound of formula (I) or salt thereof (8% w/w of the formulation), plus
(ii) 62.5 micrograms of magnesium stearate (0.5% w/w of the formulation), plus
(iii) 11.4375 mg of inhalation-grade lactose, containing from 7% to 11% lactose fines.

In the above dry powder inhalable compositons (Dry Powder Composition Example 2(A) to 2(H)), the micronised compound of formula (I) or salt thereof is preferably N-{[1,6-d]ethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide or a salt thereof, such as the monohydrochloride salt thereof, e.g. the monohydrochloride Form 1 anhydrate thereof.

The above dry powder inhalable compositons (Dry Powder Composition Example 2(A) to 2(H)) can optionally be formed into a dosage unit as follows:
(a) encapsulated in a rupturable or openable capsule, or
(b) contained within sealed, rupturable or peel-openable, dose containers which are mounted longitudinally in a strip or ribbon which can be inside a suitable inhalation device (e.g. the DISKUS™ inhalation device, e.g. which can optionally be substantially as described in GB 2,242,134 A, see below).

Dry Powder Inhalation Devices

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container can be rupturable or peel-openable on demand and the dose, e.g. of the dry powder composition, can be administered by inhalation via a device such as the DISKUS™ device, marketed by GlaxoSmithKline. The DISKUS™ inhalation device can e.g. be substantially as described in GB 2,242,134 A. In such device at least one container for the pharmaceutical composition in powder form (the at least one container preferably being a plurality of sealed dose containers mounted longitudinally in a strip or ribbon) is defined between two members peelably secured to one another; the device comprises: means defining an opening station for the said at least one container; means for peeling the members apart at the opening station to open the container; and an outlet, communicating with the opened container, through which a user can inhale the pharmaceutical composition in powder form from the opened container.

See also WO 03/061743 A1 which discloses a medicament dispenser for use with plural elongate form medicament carriers, each having multiple distinct medicament dose portions carried thereby (e.g. as described in the claims thereof e.g. claim 1). See also WO 2007/012871 A1 which discloses a medicament dispenser for use with at least one medicament carrier carrying multiple distinct medicament portions (e.g. as described in the claims thereof e.g. claim 1).

Pharmaceutical Compositions Suitable for External Topical Administration

A pharmaceutical composition of the invention can for example be suitable for (e.g. adapted for) external topical (e.g. skin topical) administration, for example to a mammal such as a human. The pharmaceutical composition suitable for external topical administration can suitably be for the treatment and/or prophylaxis of atopic dermatitis in a mammal such as a human.

"External topical administration" is defined above under the "medical uses" section. External topical administration can for example be to those parts of the skin affected by or susceptible to the disease or condition e.g. atopic dermatitis, in particular in a mammal (e.g. human) suffering from or susceptible to atopic dermatitis.

An external-topical pharmaceutical composition, e.g. skin topical pharmaceutical composition, can for example be an ointment, a cream (usually an oil-in-water or water-in-oil pharmaceutical composition, usually an emulsion), an aqueous gel, or a microemulsion.

In the external-topical pharmaceutical composition, e.g. an ointment or an oil-in-water or water-in-oil composition, the compound of formula (I) or the pharmaceutically acceptable salt thereof can be present in 0.1% to 10%, such as 0.2% to 5%, or 0.5% to 5%, or 1% to 5%, or 0.5% to 3% (e.g. about 1% or about 2%), by weight of the composition (w/w).

In one optional embodiment, the compound of formula (I) or the pharmaceutically acceptable salt thereof can optionally be in a particle-size-reduced form, for example obtained or obtainable by micronisation. This can be, for example, for use in a pharmaceutical composition suitable for (e.g. adapted for) external topical (e.g. skin topical) administration. See the Particle size reduction sub-section herein, within the Inhalable pharmaceutical compositions section, for more details.

Aqueous solubility: A preliminary screen, which can aim to estimate roughly the aqueous solubility of a compound or salt of the invention, can include (as an approximate summary): (i) creating a ca. 10 mM solution of the compound in DMSO, (ii) diluting a portion of this DMSO solution by mixing about 19 parts by volume of pH 7.4 aqueous phosphate buffered saline (PBS) buffer with 1 part by volume of the ca. 10 mM DMSO solution, (iii) "filtering" the mixture with the aid of centrifugation, and then (iv) measuring the concentration of the dissolved compound in the "filtrate". Although some DMSO (about 5% by volume) is usually present in this solubility screen "filtrate", the results can be a very approximate estimate of aqueous solubility, e.g. at room temperature.

Lipophilicity: The clogP (calculated log of the octanol/water partition coefficient (P)) of a particular compound or salt of the invention can estimate the lipophilicity of the compound or salt.

Solubilising and/or skin-penetration-enhancing agents: In one embodiment, an external-topical pharmaceutical composition, e.g. an ointment or an oil-in-water cream or water-in-oil cream, suitably includes an agent which acts as a skin-penetration enhancer for and/or a solubiliser of the compound of formula (I) or the salt thereof. The skin-penetration-enhancing- and/or solubilising-agent can for example be propylene glycol, diethylene glycol monoethyl ether (e.g. TRANSCUTOL™) and/or caprylocaproyl macrogolglycerides (e.g. LABRASOL™), such as propylene glycol. The solubiliser and/or skin-penetration enhancer suitably does not comprise DMSO. The solubiliser and/or skin-penetration enhancer can be both a solubiliser and skin-penetration enhancer, and/or can for example be present in 0.5% to 50%, suitably 5% to 50%, more suitably 7% to 30%, for example 7% to 25%, such as about 10% to about 20% (e.g. about 10% or about 20%), by weight of the composition (w/w).

The skin-penetration enhancer is for delivery of the compound of formula (I) or salt thereof ("active agent" or "drug") through the skin. Solubilization of the drug also helps. The solubilising and/or skin-penetration-enhancing agents should ideally (a) be safe and/or tolerable, (b) have as low a potential for skin irritancy as possible consistent with being an effective skin penetration enhancer, and (c) be compatibile with the active pharmaceutical ingredient. Note that the agent can e.g. function both as a solubilising agent and a skin-penetration-enhancing agent.

Surfactants: An external-topical pharmaceutical composition, e.g. an ointment or in particular an oil-in-water cream or water-in-oil cream, can include a surfactant (e.g. as an emulsifier), for example for achieving emulsification of compositions having two or more phases. The total surfactant content can for example be 0.3% to 20%, e.g. 0.5% to 15% or 0.5% to 12% or 0.5% to 10% or 1% to 12% or 3% to 10%, by weight of the composition (w/w). The surfactant can for example comprise a nonionic surfactant such as one or more of the following: a polyoxyl $C_{12-22}$ alkyl ether (e.g. a polyoxyl $C_{12-18}$ alkyl ether such as polyoxyl cetyl ether or polyoxyl stearyl ether or polyoxyl lauryl ether) (e.g. present at 0.5% to 10% w/w, e.g. 2.5% to 10% w/w such as about 5% to about 8% w/w), glycerol monostearate (e.g. Arlacel 165 ™) (e.g. present at 0.5% to 10% w/w, e.g. about 2% w/w), sorbitan monostearate (e.g. Span 60 ™) (e.g. present at 0.05% to 10% w/w, e.g. about 1% w/w), and cetyl alcohol and/or stearyl alcohol (e.g. cetostearyl alcohol, e.g. wherein the total of any cetyl alcohol and any stearyl alcohol present is 0.5% to 15% w/w, e.g. 1% to 10% w/w such as 2% to 10% w/w or 5% to 10% w/w). Polyoxyl stearyl ether (steareth) can e.g. be a polyoxyl 2-21 stearyl ether, such as polyoxyl 2 stearyl ether (steareth-2), polyoxyl 10 stearyl ether (steareth-10), polyoxyl 20 stearyl ether (steareth-20) or polyoxyl 21 stearyl ether (steareth-21). Polyoxyl cetyl ether (ceteth) can e.g. be a polyoxyl 2-20 cetyl ether such as ceteth-2, ceteth-10 or ceteth-20. Polyoxyl alkyl ethers are also named polyoxyethylene alkyl ethers. Alternatively or additionally, the surfactant can for example comprise an ionic surfactantn such as sodium dodecyl sulfate (SDS)=sodium lauryl sulfate (e.g. SDS present at 0.3% to 2% w/w such as 0.5% to 1.5% w/w).

Ointments and creams (and oil phase): An external-topical pharmaceutical composition can be an ointment or an oil-in-water cream or water-in-oil cream. The ointment or cream typically contains an oil phase (oily ointment base). The oil phase (ointment base) typically comprises an oil and/or a fat, suitably of a consistency suitable for skin-spreadability.

In particular, an oil comprising or being white soft paraffin (white petrolatum) and/or a mineral oil (such as liquid paraffin) can be used. (Mineral oil can also be used as a solubiliser and/or emollient). The white soft paraffin (white petrolatum) can be of various grades, for example (for Penreco supplier) Penreco Regent White grade, Penreco Snow White grade, or Penreco Ultima White grade, in particular high melting point white soft paraffin (e.g. of Penreco Ultima White grade). Microcrystalline wax or beeswax or beeswax substitute can be used as an oil/fat in the oil phase.

Alternatively or additionally, one or more fats like straight or branched chain mono- or di-alkyl esters such as isopropyl myristate, isopropyl palmitate, diisopropyl adipate, isocetyl stearate, isostearyl isostearate, decyl oleate, butyl stearate, 2-ethylhexyl palmitate, propylene glycol diester of coconut fatty acids, or a mixed ester of 2-ethyl hexanoic acid with a blend of cetyl or stearyl alcohols (e.g. known as Crodamol CAP), may be used in the oil phase (some of these are also solubilisers and/or surfactants). These may be used singly or in combination depending on the properties required.

The oil phase (oily ointment base) can for example be present at:
  30% to 99.8% w/w (e.g. 50% to 99.5% w/w, e.g. 50% to 95% w/w, e.g. 60% to 95% w/w, e.g. 60% to 90% w/w) in an ointment (e.g. emulsion or homogeneous single phase);
  25% to 85% w/w (e.g. 35% to 70% w/w) in a water-in-oil cream (e.g. emulsion);
or
  5% to 60% w/w or 8% to 55% w/w (e.g. 10% to 45% w/w or 12% to 30% w/w) in an oil-in-water cream (e.g. emulsion).

Note that the w/w percentages for the oil phase (oily ointment base), mentioned above or in the example formulations below or generally herein, exclude the amount of any surfactant(s) present (except for compound(s) listed herein as fats which also have surfactant properties), and exclude the amount of any non-oil non-fat solubilising and/or skin-penetration-enhancing agents present.

Example ointments: As an example, an external-topical pharmaceutical composition can be an ointment comprising:
  the compound of formula (I) or pharmaceutically acceptable salt thereof present at 0.1% to 10% w/w (e.g. 0.2% to 5% w/w, or 0.5% to 5% w/w, or 0.5% to 3% w/w); and
  an oil phase (oily ointment base) present at 30% to 99.8% w/w or 50% to 99.5% w/w or 50% to 95% w/w or 60% to 95% w/w or 60% to 90% w/w (i.e. by weight of the composition).

For example, in the above example ointment, the oil phase or composition can suitably comprise white petrolatum present at 25% to 99.5% w/w or 45% to 99% w/w or 55% to 85% w/w (i.e. by weight of the composition). Optionally, additionally or alternatively, the oil phase or composition can comprise mineral oil (e.g. as solubiliser and emollient) present at 2.5% to 25% w/w such as 4% to 20% w/w (i.e. by weight of the composition)].

In the above example ointment, the ointment can optionally comprise one or more surfactants (e.g. polyoxyl stearyl ether, polyoxyl cetyl ether or cetostearyl alcohol) present in total at 0.5% to 10% w/w or 3% to 10% w/w.

In the above example ointment, the ointment can optionally comprise one or more agents acting as a skin-penetration enhancer (in particular acting as both a solubiliser and skin-penetration enhancer and/or in particular hydrophilic such as propylene glycol) present in total at 0.5% to 50% w/w, such as 5% to 50% w/w or 7% to 30% w/w.

In the above example ointment, the ointment can optionally comprise (a) one or more antioxidants (e.g. butylated hydroxyanisole), e.g. present in total at 0.001% to 2% w/w such as 0.02% to 2% w/w; and/or (b) one or more preservatives, e.g. present in total at 0.01% to 4% w/w such as 0.05% to 1% w/w (e.g. methylparaben present at 0.05% to 2% w/w and/or propylparaben present at 0.01% to 2% w/w).

The above example ointment composition, including the oil "phase" and an optional penetration enhancer, can optionally be a homogeneous single phase. However, in one embodiment of the above example ointment composition, e.g. when using propylene glycol or another hydrophilic solubiliser and penetration enhancer, the oil phase (oily ointment base) and a hydrophilic phase containing the hydrophilic solubiliser and penetration enhancer (e.g. propylene-glycol-containing phase) have been emulsified to form an ointment emulsion.

Ointment compositions having two phases can optionally be prepared using an emulsification process whereby the hydrophilic phase (e.g. propylene-glycol-containing phase) and oil phase are first prepared in separate vessels. The hydrophilic phase can optionally contain a penetration enhancer such as propylene glycol, and optionally some or all of the compound of formula (I) or salt thereof. The oil phase can optionally contain a surfactant. Temperatures of both phases are maintained at elevated temperatures, such as about 55-90° C. or in particular from above 70 to 90° C., the oil phase temperature being sufficiently high (e.g. from above 70 to 90° C.) to melt the oil phase. While hot, one phase is added to another while mixing, e.g. using a high shear mixer, to effect emulsification, e.g. keeping the temperature above 70° C. such as from above 70 to 90° C. The resulting ointment emulsion is allowed to cool, e.g. to about 15-35° C. such as to about 18-30° C., in particular while the agitation continues e.g. at lower speeds. The ointment emulsion can then optionally be dispensed from the manufacturing vessel and filled into primary packaging, for example tubes or sachets.

Optionally, an ointment can comprise a polyethylene glycol base, e.g. present at 25% to 99% w/w such as 50% to 98% w/w, instead of or as well as an oily ointment base.

Creams: An external-topical pharmaceutical composition can be a cream, e.g. a water-in-oil cream or an oil-in-water cream. Creams can sometimes be more fluid than ointments, can sometimes provide more moisture, and hence may in principle in certain cases allow for improved and/or good efficacy in patients with atopic dermatitis.

Water-in-oil creams: These usually have an increased aqueous content compared to ointments. In particular the water-in-oil cream can be a water-in-oil cream emulsion. That is, in particular, in the water-in-oil cream, an oil phase and an aqueous phase can have been emulsified to form a water-in-oil cream emulsion.

As an example, an external-topical pharmaceutical composition can be a water-in-oil cream (e.g. cream emulsion) comprising:
  the compound of formula (I) or pharmaceutically acceptable salt thereof present at 0.1% to 10% w/w (e.g. 0.2% to 5% w/w, or 0.5% to 5% w/w, or 0.5% to 3% w/w);
  an oil phase (oily ointment base) present at 25% to 85% w/w or 35% to 70% w/w [for example: comprising white petrolatum present at 25% to 75% w/w or 30% to 65% w/w (i.e. by weight of the composition), and/or comprising mineral oil (e.g. as solubiliser and emollient) present at 2.5% to 20% w/w or 4% to 15% w/w (i.e. by weight of the composition)];
  water present in 2% to 30% w/w, e.g. 5% to 25% or 10% to 22% w/w;
  one or more surfactants (e.g. polyoxyl stearyl ether) present in total at 0.5% to 12% w/w, such as 3% to 10% w/w; and in particular, one or more agents acting as a skin-penetration enhancer (e.g. acting as both a solubiliser and skin-penetration enhancer and/or e.g. hydrophilic such as propylene glycol) present in total at 0.5% to 50% w/w, such as 5% to 50% w/w or 7% to 30% w/w; and optionally, one or more antioxidants (e.g. butylated hydroxyanisole), e.g. present in total at 0.001 to 2% w/w such as 0.02 to 2% w/w; and optionally, one or more preservatives, e.g. present in total at 0.01 to 4% w/w such as 0.05 to 1% w/w (e.g. methylparaben present at 0.05 to 2% w/w and/or propylparaben present at 0.01 to 2% w/w).

Oil-in-water creams: These usually have an increased aqueous content compared to ointments and water-in-oil creams. In particular, the oil-in-water cream can be an oil-in-water cream emulsion. That is, preferably, in the oil-in-water cream, an oil phase and an aqueous phase have been emulsified to form an oil-in-water cream emulsion.

Examples of oil-in-water creams are high-occlusion creams, wherein, after topical administration to the skin, moisture loss from the skin and/or from the cream is reduced or limited by means of sufficiently high coverage of the skin and/or by providing a sufficient barrier at the site of application.

In particular, the oil-in-water cream can contain one or more emollients (hydrating agents), such as silicones (e.g. dimethicone, e.g. dimethicone 360 or dimethicone 20), a high-viscosity wax such as microcrystalline wax, and/or mineral oil. A sufficiently high water content is also preferred, for example wherein the water is present in 15% to 60% w/w, 20% to 50% w/w, or 25% to 40% w/w.

As an example, an external-topical pharmaceutical composition can be an oil-in-water cream (e.g. cream emulsion) comprising:

the compound of formula (I) or pharmaceutically acceptable salt thereof present at 0.1% to 10% w/w (e.g. 0.2% to 5% w/w, or 0.5% to 5% w/w, or 0.5% to 3% w/w);

an oil phase (oily ointment base), in particular containing one or more ingredients capable of acting as emollients, the oil phase being present at 5% to 60% w/w or 8% to 55% w/w or in particular 10% to 45% w/w or 12% to 30% w/w;

water present in 7% to 75% w/w or 7% to 60% w/w or 10% to 60% w/w, in particular 15% to 50% w/w or 20% to 40% w/w;

one or more surfactants present in total at 0.5% to 20% w/w, e.g. 3% to 15% w/w or 3% to 10% w/w; and preferably, one or more agents acting as a skin-penetration enhancer (e.g. acting as both a solubiliser and skin-penetration enhancer and/or e.g. hydrophilic such as propylene glycol) present in total at 0.5% to 50% w/w, preferably 5% to 50% w/w or 7% to 25% w/w; and optionally, one or more solubilisers (e.g. isopropyl myristate), e.g. present at 0.5% to 20% w/w, e.g. 3 to 12% w/w; and optionally, one or more buffers (e.g. citric acid and/or dibasic sodium phosphate), e.g. present in total at 0.05 to 5% w/w.

In the above example oil-in-water cream composition, the oil phase in particular can comprise mineral oil (e.g. as emollient and solubiliser) present at 15% to 50% w/w or 20% to 45% w/w (i.e. by weight of the composition), and/or comprises a high-viscosity wax such as microcrystalline wax (e.g. as emollient) present at 5% to 25% w/w such as 8% to 15% w/w, and/or comprises a silicone (such as dimethicone e.g. dimethicone 360 or dimethicone 20, e.g. as emollient) present at 0.5% to 20% such as 0.5% to 10% or 1% to 5% w/w.

In the above example oil-in-water cream composition, the one or more surfactants can in particular comprise: glycerol monostearate present at 0.5% to 10% w/w, and/or sorbitan monostearate present at 0.05% to 10% w/w, and/or [cetyl alcohol and/or stearyl alcohol] present in total at 0.1% to 15% or 1 to 10% w/w.

Cream emulsions, e.g. water-in-oil or oil-in-water cream emulsions, can be prepared by a process in which an aqueous phase is prepared, e.g. prepared before emulsification. The aqueous phase usually contains water and a solubiliser and/or skin-penetration enhancer such as propylene glycol, and optionally contains some or all of the compound of formula (I) or salt thereof, and/or optionally contains surfactant. The oil phase, e.g. containing white petrolatum and/or mineral oil, and/or optionally containing surfactant, can be prepared in a separate vessel. Temperatures of both phases are maintained at elevated temperatures, such as about 55-90° C. or in particular from above 70 to 90° C., the oil phase temperature being sufficiently high (e.g. from above 70 to 90° C.) to melt the oil phase. While hot, one phase is added to another while mixing, e.g. using a high shear mixer, to effect emulsification, in particular keeping the temperature above 70° C. such as from above 70 to 90° C. The resulting emulsion is allowed to cool, e.g. to about 15-35° C. such as to about 18-30° C., in particular while the agitation continues e.g. at lower speeds. The cream emulsion can then optionally be dispensed from the manufacturing vessel and filled into primary packaging, for example tubes or sachets.

Typically, a pharmaceutical composition of the invention suitable for external topical administration can be administered once daily, twice daily or more than twice daily, to external body part(s), e.g. on the skin such as at a site of diseased skin, e.g. skin suffering from atopic dermatitis.

Pharmaceutical Compositions Suitable for Parenteral or Oral Administration

A pharmaceutical composition suitable for (e.g. adapted for) parenteral (e.g. intravenous, subcutaneous, or intramuscular) administration can comprise a solution or suspension of the compound or pharmaceutically acceptable salt in a sterile pharmaceutically and parenterally acceptable aqueous liquid carrier (e.g. sterile water or a sterile aqueous solution) or in a parenterally acceptable oil. Alternatively, an aqueous solution can be lyophilised to prepare the parenteral composition. A lyophilised pharmaceutical composition suitable for (e.g. adapted for) parenteral administration may, in use, optionally be reconstituted with a suitable solvent, e.g. sterile water or a sterile parenterally acceptable aqueous solution, just prior to administration. A pharmaceutical composition suitable for (e.g. adapted for) parenteral administration may optionally comprise a preservative.

As mentioned above, oral administration is generally not thought to be a preferred route of administration. However, in the event that oral administration is to be used, a pharmaceutical composition suitable for oral administration can be liquid or solid; for example it can be a syrup, suspension or emulsion, a tablet, a capsule or a lozenge.

A liquid formulation (e.g. oral) can generally consist of a suspension or solution of the compound or pharmaceutically acceptable salt in a suitable pharmaceutically acceptable liquid carrier(s), for example an aqueous solvent such as water, aqueous ethanol or aqueous glycerine, or a non-aqueous solvent, such as polyethylene glycol or an oil. The formulation may also contain a suspending agent, preservative, flavouring and/or colouring agent.

In one embodiment, the pharmaceutical composition is in unit dose form, such as a tablet or capsule for oral administration, e.g. for oral administration to a human.

A pharmaceutical composition suitable for oral administration being a tablet can comprise one or more pharmaceutically acceptable carriers and/or excipients suitable for preparing tablet formulations. The carrier can for example be or include lactose, cellulose (for example microcrystalline cellulose), or mannitol. The tablet can also or instead contain one or more pharmaceutically acceptable excipients, for example a binding agent such as hydroxypropylmethylcellulose or povidone (polyvinylpyrrolidone), a lubricant e.g. an alkaline earth metal stearate such as magnesium stearate, and/or a tablet disintegrant such as sodium starch glycollate, croscarmellose sodium, or crospovidone (cross-linked polyvinylpyrrolidone). The pharmaceutical composition being a tablet can be prepared by a method comprising the steps of: (i) mixing the compound of formula (I), as herein defined, or a pharmaceutically acceptable salt thereof, with the one or more pharmaceutically acceptable carriers and/or excipients, (ii) compressing the resulting mixture (which is usually in powder form) into tablets, and (iii) optionally coating the tablet with a tablet film-coating material.

A pharmaceutical composition suitable for oral administration being a capsule can be prepared using encapsulation procedures. For example, pellets or powder containing the active ingredient can be prepared using a suitable pharmaceutically acceptable carrier and then filled into a hard gelatin capsule. Alternatively, a dispersion or suspension can be prepared using any suitable pharmaceutically acceptable carrier, for example an aqueous gum or an oil and the dispersion or suspension then filled into a soft gelatin capsule.

Dosage Regimens

The pharmaceutical composition can optionally be in unit dose form. The unit dose form can for example be:
(a) a rupturable or peel-openable sealed dose container containing a dry powder inhalable pharmaceutical composition (e.g. a plurality of which are usually disposed inside a suitable inhalation device);
(b) a vial, ampoule or filled syringe for parenteral administration e.g. comprising a solution or suspension of the compound or pharmaceutically acceptable salt in a suitable carrier such as an aqueous carrier or e.g. containing a lyophilised parenteral pharmaceutical composition (the vial or ampoule can optionally be manufactured using a blow-fill-seal process); or
(c) a tablet or capsule for oral administration e.g. for oral administration to a human.

In the pharmaceutical composition of the invention, a or each dosage unit for inhaled or intranasal administration can for example contain from 0.005 to 10 mg, such as 0.005 to 7.5 mg (e.g. 0.01 mg, 0.05 mg, 0.1 mg, 0.5 mg or 1 mg), for example 0.02 to 2 mg (e.g. 0.05 mg, 0.1 mg, 0.25 mg, 0.4 mg, 0.5 mg, 0.875 mg or 1 mg) or 0.05 to 2 mg (e.g. 0.05 mg, 0.1 mg, 0.25 mg, 0.4 mg, 0.5 mg, 0.875 mg or 1 mg), of a compound (e.g. of formula (I)) or a pharmaceutically acceptable salt thereof, calculated as the free base. A or each dosage unit for oral or parenteral administration can for example contain from 0.02 to 1000 mg, such as 0.2 to 350 mg, of a compound (e.g. of formula (I)) or a pharmaceutically acceptable salt thereof, calculated as the free base.

When an inhalable or intranasal composition is used, a pharmaceutically acceptable compound or salt of the invention can for example be administered to a mammal (e.g. human) in a daily inhaled or intranasal dose of: 0.0003 to 0.6 mg/kg body weight/day or 0.0007 to 0.6 mg/kg body weight/day or 0.0007 to 0.1 mg/kg body weight/day, e.g. 0.0007 to 0.015 mg/kg/day or 0.004 to 0.1 mg/kg/day, of the compound (e.g. of formula (I)) or a pharmaceutically acceptable salt thereof, calculated as the free base.

A compound, e.g. of formula (I), or a pharmaceutically acceptable salt thereof of the invention can, for example, be administered to a human in a total daily inhaled or intranasal dose of: 0.005 to 10 mg per day, or 0.02 to 7.5 mg per day, or 0.05 to 7.5 mg per day, or 0.05 to 4 mg per day (e.g. 1 mg per day), or 0.25 to 2 mg per day, of the compound (e.g. of formula (I)) or a pharmaceutically acceptable salt thereof, calculated as the free base. These total daily doses can be administered as a single dose once daily, or can represent the summation of two or more separate doses administered at different times of the day (e.g. two doses per day administered every ca. 12 hours). These total daily doses can e.g. be for administration to an adult human e.g. of 50-120 kg or 60-100 kg body weight.

For example, a human inhaled or intranasal dosage regimen of 0.05 to 2 mg (e.g. 0.05 mg, 0.1 mg, 0.4 mg, 0.5 mg, 0.875 mg or 1 mg) of the compound or the salt thereof once or twice per day, or 0.2 to 2 mg (e.g. 0.4 mg, 0.5 mg, 0.875 mg or 1 mg) once or twice per day, calculated as the free base, can optionally be administered to a human, for example in the treatment and/or prophylaxis of COPD, asthma or rhinitis (e.g. allergic or non-allergic rhinitis) in the human.

When a parenteral or oral composition is used, a pharmaceutically acceptable compound or salt of the invention is optionally, for example, administered to a mammal (e.g. human) in a daily parenteral or oral dose of 0.0003 mg to 15 mg per kg body weight per day (mg/kg/day), for example 0.003 to 5 mg/kg/day, of the compound (e.g. of formula (I)) or a pharmaceutically acceptable salt thereof, calculated as the free base.

A compound, e.g. of formula (I), or pharmaceutically acceptable salt thereof of the invention is optionally, for example, administered to a human (e.g. adult human) in a total daily parenteral or oral dose of 0.02 mg to 1000 mg per day or 0.2 to 350 mg per day of the compound (e.g. of formula (I)) or a pharmaceutically acceptable salt thereof, calculated as the free base.

In a pharmaceutical composition suitable for (e.g. adapted for) external topical administration, e.g. an ointment or an oil-in-water or water-in-oil composition, the compound of formula (I) or the pharmaceutically acceptable salt thereof can be present in 0.1% to 10%, such as 0.2% to 5%, or 0.5% to 5%, or 0.5% to 3%, by weight of the composition (w/w). Typically, an external-topical pharmaceutical composition can be administered once daily, twice daily or more than twice daily, to external body part(s), e.g. to the skin such as at a site of diseased skin. The amount administered is usually such as substantially to cover the site(s) of diseased skin.

Combinations

The compounds, salts and/or pharmaceutical compositions according to the invention may also be used in combination with another therapeutically active agent, for example, a $\beta_2$ adrenoreceptor agonist, an anticholinergic compound (e.g. muscarinic (M) receptor antagonist), an anti-histamine, an anti-allergic, an anti-inflammatory agent, an antiinfective agent or an immunosuppressant.

The invention thus provides, in a further aspect, a combination comprising a compound of formula (I) or a pharmaceutically acceptable salt thereof together with another therapeutically active agent, for example, a muscarinic (M) receptor antagonist, a $\beta_2$-adrenoreceptor agonist (beta-2 adrenoreceptor agonist), an anti-histamine, an anti-allergic, an anti-inflammatory agent, an antiinfective agent or an immunosuppressant.

The invention also provides, in a further preferred aspect, a combination comprising a compound of formula (I) or a pharmaceutically acceptable salt thereof together with a muscarinic (M) receptor antagonist.

The muscarinic (M) receptor antagonist can be an $M_1$, $M_2$, $M_1/M_2$, or $M_3$ receptor antagonist, such as a $M_3$ receptor antagonist, in particular a $M_3$ receptor antagonist which selectively antagonises (e.g. antagonises 10 times or more strongly) the $M_3$ receptor over the $M_1$ and/or $M_2$ receptor.

For combinations of a muscarinic (M) receptor antagonist with PDE4 inhibitors, see for example WO 03/011274 A2 and WO 02/069945 A2/US 2002/0193393 A1 and US 2002/052312 A1, and some or all of these publications give examples of anticholinergic compounds/muscarinic (M) receptor antagonists which may be used with the compounds of formula (I) or salts, and/or suitable pharmaceutical compositions. For example, the muscarinic receptor antagonist can comprise or be an ipratropium salt (e.g. ipratropium bromide), an oxitropium salt (e.g. oxitropium bromide), or more preferably a tiotropium salt (e.g. tiotropium bromide); see e.g. EP 418 716 A1 for tiotropium.

Muscarinic antagonists which can be optionally used in the combination of the present invention include a compound (including a pharmaceutically acceptable salt thereof) defined by claim 1, 2, 3 or 4 of WO 2005/037280 A1. These compounds are stated or implied as being muscarinic (e.g. $M_3$) acetylcholine receptor antagonists.

Muscarinic antagonists which can be optionally used in the combination of the present invention include those disclosed in WO 2005/037280, WO 2005/046586 and WO 2005/104745. The muscarinic antagonist can be:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; or
(1R,5S)-3-(2-cyano-2,2-diphenylethyl)-8-methyl-8-{2-[(phenylmethyl)oxy]ethyl}-8-azoniabicyclo[3.2.1]octane bromide; or a salt of any of the foregoing.

The muscarinic (M) receptor antagonist, e.g. $M_3$ receptor antagonist, is preferably for inhaled administration, more preferably in particle-size-reduced form e.g. as defined herein. More preferably, both the muscarinic (M) receptor antagonist and the compound of formula (I) or the pharmaceutically acceptable salt thereof are for inhaled administration. Suitably, the muscarinic receptor antagonist and the compound of formula (I) or salt are for simultaneous administration. The muscarinic receptor antagonist combination is preferably for treatment and/or prophylaxis of COPD.

In one embodiment, the combination includes a $\beta_2$-adrenoreceptor agonist (beta-2 adrenoreceptor agonist) being salmeterol (e.g. as racemate or a single enantiomer such as the R-enantiomer), salbutamol, formoterol, salmefamol, fenoterol, carmoterol, indacaterol or terbutaline, or a salt thereof (e.g. pharmaceutically acceptable salt thereof), for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 12-24 hour period such as salmeterol or formoterol. Preferably, the $\beta_2$-adrenoreceptor agonist is for inhaled administration, e.g. once per day and/or for simultaneous inhaled administration; and more preferably the $\beta_2$-adrenoreceptor agonist is in particle-size-reduced form e.g. as defined herein. Preferably, the $\beta_2$-adrenoreceptor agonist combination is for treatment and/or prophylaxis of COPD or asthma. Salmeterol or a pharmaceutically acceptable salt thereof, e.g. salmeterol xinofoate, can be administered to humans at an inhaled dose of 25 to 50 micrograms twice per day (measured as the free base).

Examples of $\beta_2$-adrenoreceptor agonists e.g. long acting $\beta_2$-adrenoreceptor agonists for use in the combination include those described in WO 02/066422A, WO 03/024439, WO 02/070490, WO 02/076933, WO 03/072539, WO 03/091204, WO 2004/016578, WO2004/022547, WO 2004/037807, WO 2004/037773, WO 2004/037768, WO 2004/039762, and WO 2004/039766.

In particular, long-acting $\beta_2$-adrenoreceptor agonists (beta-2 adrenoreceptor agonists) can include compounds of formula (XX) (described in WO 02/066422):

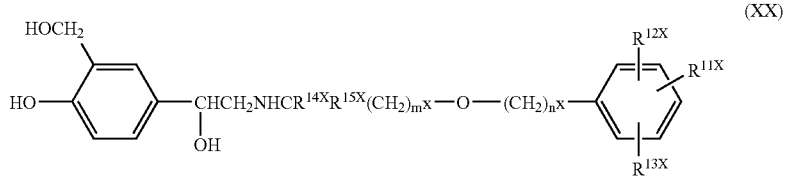

or a salt or solvate thereof, wherein in formula (XX):
$m^x$ is an integer of from 2 to 8;
$n^x$ is an integer of from 3 to 11,
with the proviso that $m^x+n^x$ is 5 to 19,
$R^{11X}$ is $-XSO_2NR^{16X}R^{17X}$ wherein X is $-(CH_2)_px-$ or $C_{2-6}$ alkenylene;
$R^{16X}$ and $R^{17X}$ are independently selected from hydrogen, $C_{1-6}$alkyl, $C_{3-7}$cycloalkyl, $C(O)NR^{18X}R^{19X}$, phenyl, and phenyl ($C_{1-4}$alkyl)-,
or $R^{16X}$ and $R^{17X}$, together with the nitrogen to which they are bonded, form a 5-, 6-, or 7-membered nitrogen containing ring, and $R^{16X}$ and $R^{17X}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, $-CO_2R^{18X}$, $-SO_2NR^{18X}R^{19x}$, $-CONR^{18X}R^{19X}$, $-NR^{18X}C(O)R^{19X}$, or a 5-, 6- or 7-membered heterocyclic ring;
$R^{18X}$ and $R^{19X}$ are independently selected from hydrogen, $C_{1-6}$alkyl,
$C_{3-6}$cycloalkyl, phenyl, and phenyl ($C_{1-4}$alkyl)-; and
$p^x$ is an integer of from 0 to 6, preferably from 0 to 4;
$R^{12X}$ and $R^{13X}$ are independently selected from hydrogen, $C_{1-6}$alkyl, $C_{1-6}$alkoxy, halo, phenyl, and $C_{1-6}$haloalkyl; and
$R^{14X}$ and $R^{15X}$ are independently selected from hydrogen and $C_{1-4}$alkyl with the proviso that the total number of carbon atoms in $R^{14X}$ and $R^{15X}$ is not more than 4.

Suitable $\beta_2$-adrenoreceptor agonists disclosed in WO 02/066422 include:
3-(4-{[6-({(2R)-2-hydroxy-2-[4-hydroxy-3-(hydroxymethyl)-phenyl]ethyl}amino)hexyl]oxy}butyl)benzenesulfonamide, or 3-(3-{[7-({(2R)-2-hydroxy-2-[4-hydroxy-3-hydroxymethyl)phenyl]ethyl}-amino)heptyl]oxy}propyl)benzenesulfonamide; or a salt thereof.

A preferred β₂-adrenoreceptor agonist disclosed in WO 03/024439 is:

4-{(1R)-2-[(6-{2-[(2,6-dichlorobenzyl)oxy]ethoxy}hexyl)amino]-1-hydroxyethyl}-2-(hydroxymethyl)phenol or a salt thereof. Suitably, this can be for inhaled administration.

Another example of β₂-adrenoreceptor agonist disclosed in WO 2004/037773 is:

4-{(1R)-2-[(6-{4-[3-(cyclopentylsulfonyl)phenyl]butoxy}hexyl)amino]-1-hydroxyethyl}-2-(hydroxymethyl)phenol or a salt thereof.

An anti-histamine usable in a combination of a compound of formula (I) or salt can for example be for oral administration (e.g. this can be as a separately-administrable tablet), and can be for treatment and/or prophylaxis of allergic rhinitis. Examples of anti-histamines for oral administration include methapyrilene, or H1 antagonists such as cetirizine, loratadine (e.g. Clarityn™), desloratadine (e.g. Clarinex™) or fexofenadine (e.g. Allegra™).

An anti-histamine usable in a combination of a compound of formula (I) or salt can for example be for intranasal administration. An anti-histamine for intranasal administration can e.g. be azelastine or a salt thereof (e.g. azelastine hydrochloride, e.g. 0.1% w/v aqueous solution), or levocabastine or a salt thereof (e.g. levocabastine hydrochloride). The anti-histamine olopatadine (e.g. as olopatadine HCl) can be used e.g. as eye drops.

Other possible combinations include, for example, a combination comprising a compound of formula (I) or a pharmaceutically acceptable salt thereof together with another anti-inflammatory agent such as an anti-inflammatory corticosteroid; or a non-steroidal anti-inflammatory drug (NSAID) such as a leukotriene antagonist (e.g. montelukast), an iNOS inhibitor, a tryptase inhibitor, a elastase inhibitor, a beta-2 integrin antagonist, a adenosine 2a agonist, or a 5-lipoxogenase inhibitor; or an antiinfective agent (e.g. an antibiotic or an antiviral). An iNOS inhibitor is optionally for oral administration. Examples of iNOS inhibitors (inducible nitric oxide synthase inhibitors) include those disclosed in WO 93/13055, WO 98/30537, WO 02/50021, WO 95/34534 and WO 99/62875.

In a combination comprising a compound of formula (I) or a pharmaceutically acceptable salt thereof together with an anti-inflammatory corticosteroid (which can for example be for treatment and/or prophylaxis of asthma, COPD, rhinitis e.g. allergic rhinitis, psoriasis or atopic dermatitis), then the anti-inflammatory corticosteroid can be fluticasone propionate (e.g. see U.S. Pat. No. 4,335,121), beclomethasone 17-propionate ester, beclomethasone 17,21-dipropionate ester, dexamethasone or an ester thereof, mometasone or an ester thereof (e.g. mometasone furoate), betamethasone valerate (for external topical administration), clobetasol propionate (for external topical administration), ciclesonide, budesonide, flunisolide, or a compound as described in WO 02/12266 A1 (e.g. as claimed in any of claims 1 to 22 therein), or a pharmaceutically acceptable salt of any of the above. If the anti-inflammatory corticosteroid is a compound as described in WO 02/12266 A1, then it can be Example 1 therein {which is 6α,9α-difluoro-17α-[(2-furanylcarbonyl)oxy]-11β-hydroxy-16α-methyl-3-oxo-androsta-1,4-diene-17β-carbothioic acid S-fluoromethyl ester} or Example 41 therein {which is 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester}, or a pharmaceutically acceptable salt thereof. The anti-inflammatory corticosteroid can for example be for inhaled, intranasal or external topical administration. Fluticasone propionate can be used and is preferably for inhaled administration to a human either (a) at a dose of 250 micrograms once per day or (b) at a dose of 50 to 250 micrograms twice per day. In a combination comprising betamethasone valerate for external topical administration, the betamethasone valerate can be present at from about 0.025% to about 0.1% w/w in an externally-topically-administrable composition such as a cream or ointment. In a combination comprising clobetasol propionate for external topical administration, the clobetasol propionate can be present at about 0.0525% w/w or about 0.05% w/w in an externally-topically-administrable composition such as a cream or ointment.

Also provided is a combination comprising a compound of formula (I) or a pharmaceutically acceptable salt thereof together with β₂-adrenoreceptor agonist and an anti-inflammatory corticosteroid, for example as described in WO 03/030939 A1. Preferably this combination is for treatment and/or prophylaxis of asthma, COPD or allergic rhinitis. The β₂-adrenoreceptor agonist and/or the anti-inflammatory corticosteroid can be as described above and/or as described in WO 03/030939 A1. In this "triple" combination, the β₂-adrenoreceptor agonist can for example be salmeterol or a pharmaceutically acceptable salt thereof (e.g. salmeterol xinafoate), and the anti-inflammatory corticosteroid can for example be fluticasone propionate.

Other examples of combinations, in particular for external topical administration (e.g. versus atopic dermatitis), include, for example, a combination comprising a compound of formula (I) or a pharmaceutically acceptable salt thereof together with an immunosuppressant, e.g. a calcineurin inhibitor such as pimecrolimus or tacrolimus. The immunosuppressant can in particular be an externally-topically administrable immunosuppressant such as pimecrolimus (e.g. pimecrolimus at ca. 1% w/w concentration in a topical composition such as a cream, and/or e.g. Elidel™) or tacrolimus (e.g. tacrolimus at from about 0.03% to about 0.1% w/w concentration in a topical composition such as an ointment, and/or e.g. Protopic™). The externally-topically administrable immunosuppressant can be administered or administrable in a external-topical composition separately from the compound or salt of the invention, or it can be contained with the compound of formula (I) or pharmaceutically acceptable salt in a combined externally-topically-administrable composition.

For external topical administration, e.g. versus an inflammatory and/or allergic skin disease such as atopic dermatitis or psoriasis, in a combination of the compound or salt of the invention together with an anti-infective agent, the anti-infective agent can include (e.g. be) an externally-topically-administrable antibacterial, such as mupiricin or a salt thereof (e.g. mupirocin calcium salt) (e.g. Bactroban™) or such as an externally-topically-administrable pleuromutilin antibacterial (e.g. retapamulin or a salt thereof, which can be present in about 1% w/w by weight of an externally-topically-administrable pharmaceutical composition, such as an ointment). Alternatively or additionally, for external topical administration, the anti-infective agent can include an externally-topically-administrable antifungal such as clotrimazole (e.g. at about 1% to about 10% w/w or at about 1% to about 2% w/w in a topical composition), or ketoconazole, or terbinafine (e.g. as HCl salt and/or at about 1% w/w).

For external topical administration, e.g. versus atopic dermatitis, a combination with an anti-itch compound may optionally be used.

The combinations referred to above may be presented for use in the form of a pharmaceutical composition and thus a pharmaceutical composition comprising a combination as defined above together with one or more pharmaceutically acceptable carriers and/or excipients represent a further aspect of the invention.

The individual compounds of such combinations may be administered either sequentially or simultaneously in separate or combined pharmaceutical composition.

In one embodiment, the combination as defined herein can be for simultaneous inhaled administration and is disposed in a combination inhalation device. Such a combination inhalation device is another aspect of the invention. Such a combination inhalation device can comprise a combined pharmaceutical composition for simultaneous inhaled administration (e.g. dry powder composition), the composition comprising all the individual compounds of the combination, and the composition being incorporated into a plurality of sealed dose containers mounted longitudinally in a strip or ribbon inside the inhalation device, the containers being rupturable or peel-openable on demand; for example such inhalation device can be substantially as described in GB 2,242,134 A (DISKUS™) and/or as described above. Alternatively, the combination inhalation device can be such that the individual compounds of the combination are administrable simultaneously but are stored separately (or wholly or partly stored separately for triple combinations), e.g. in separate pharmaceutical compositions, for example as described in PCT/EP03/00598 filed on 22 Jan. 2003, published as WO 03/061743 A1 (which discloses a medicament dispenser for use with plural elongate form medicament carriers, each having multiple distinct medicament dose portions carried thereby, e.g. as described in the claims thereof e.g. claim 1) and/or WO 2007/012871 A1 (which discloses a medicament dispenser for use with at least one medicament carrier carrying multiple distinct medicament portions, e.g. as described in the claims thereof e.g. claim 1).

The invention also provides a method of preparing a combination as defined herein, the method comprising either
 (a) preparing a separate pharmaceutical composition for administration of the individual compounds of the combination either sequentially or simultaneously, or
 (b) preparing a combined pharmaceutical composition for administration of the individual compounds of the combination simultaneously,
 wherein the pharmaceutical composition comprises the combination together with one or more pharmaceutically acceptable carriers and/or excipients.

The invention also provides a combination as defined herein, prepared by a method as defined herein.

Biological Test Methods
PDE 3, PDE 4B, PDE 4D, PDE 5, PDE 6 in Vitro Assay Methods The biological activity of the compounds or salts of the invention can be measured in the assay methods shown below, or in generally similar or generally analogous assay methods.

Some of the Examples disclosed herein and encompassed within the invention are selective PDE4 inhibitors, i.e. they inhibit PDE4 (e.g. PDE4B) more strongly than they inhibit PDE3 and/or more strongly than they inhibit PDE5 and/or more strongly than they inhibit PDE6. It is to be recognised that such selectivity is not essential to the invention.

Possible PDE Enzyme Sources and Literature References

Human recombinant PDE4B, in particular the 2B splice variant thereof (HSPDE4B2B), is disclosed in WO 94/20079 and also M. M. McLaughlin et al., "A low Km, rolipram-sensitive, cAMP-specific phosphodiesterase from human brain: cloning and expression of cDNA, biochemical characterisation of recombinant protein, and tissue distribution of mRNA", *J. Biol. Chem.*, 1993, 268, 6470-6476. For example, in Example 1 of WO 94/20079, human recombinant PDE4B is described as being expressed in the PDE-deficient yeast *Saccharomyces cerevisiae* strain GL62, e.g. after induction by addition of 150 uM $CuSO_4$, and 100,000×g supernatant fractions of yeast cell lysates are described for use in the harvesting of PDE4B enzyme.

Human recombinant PDE4D (HSPDE4D3A) is disclosed in P. A. Baecker et al., "Isolation of a cDNA encoding a human rolipram-sensitive cyclic AMP phoshodiesterase (PDE $IV_D$)", *Gene*, 1994, 138, 253-256.

Human recombinant PDE5 is disclosed in K. Loughney et al., "Isolation and characterisation of cDNAs encoding PDE5A, a human cGMP-binding, cGMP-specific 3',5'-cyclic nucleotide phosphodiesterase", *Gene*, 1998, 216, 139-147.

PDE3 can be purified from bovine aorta as described by H. Coste and P. Grondin, "Characterisation of a novel potent and specific inhibitor of type V phosphodiesterase", *Biochem. Pharmacol.*, 1995, 50,1577-1585.

PDE6 can be purified from bovine retina as described by: P. Catty and P. Deterre, "Activation and solubilization of the retinal cGMP-specific phosphodiesterase by limited proteolysis", *Eur. J. Biochem.*, 1991, 199, 263-269; A. Tar et al. "Purification of bovine retinal cGMP phosphodiesterase", *Methods in Enzymology*, 1994, 238, 3-12; and/or D. Srivastava et al. "Effects of magnesium on cyclic GMP hydrolysis by the bovine retinal rod cyclic GMP phosphodiesterase", *Biochem. J.*, 1995, 308, 653-658.

Inhibition of PDE 3, PDE 4B, PDE 4D, PDE 5 or PDE 6 Activity: Radioactive Scintillation Proximity Assay (SPA)

The ability of compounds to inhibit catalytic activity at PDE4B or 4D (human recombinant), PDE3 (from bovine aorta), PDE5 (human recombinant) or PDE6 (from bovine retina) can optionally be determined by Scintillation Proximity Assay (SPA) in a 96-well format.

Test compounds (as a solution in DMSO, suitably about 2 microliter (ul) volume of DMSO solution) are preincubated at ambient temperature (room temperature, e.g. 19-23° C.) in Wallac Isoplates (code 1450-514) with PDE enzyme in 50 mM Tris-HCl buffer pH 7.5, 8.3 mM $MgCl_2$, 1.7 mM EGTA, 0.05% (w/v) bovine serum albumin for 10-30 minutes (usually 30 minutes). The enzyme concentration is adjusted so that no more than 20% hydrolysis of the substrate defined below occurs in control wells without compound, during the incubation. For the PDE3, PDE4B and PDE4D assays, [5',8-$^3$H]Adenosine 3',5'-cyclic phosphate (Amersham Pharmacia Biotech, code TRK.559; or Amersham Biosciences UK Ltd, Pollards Wood, Chalfont St Giles, Buckinghamshire HP8 4SP, UK) is added to give 0.05 uCi per well and about 10 nM final concentration. For the PDE5 and PDE6 assays, [8-$^3$H] Guanosine 3',5'-cyclic phosphate (Amersham Pharmacia Biotech, code TRK.392) is added to give 0.05 uCi per well and about 36 nM final concentration. Plates containing assay mixture, suitably approx. 100 ul volume of assay mixture, are mixed on an orbital shaker for 5 minutes and incubated at ambient temperature for 1 hour. Phosphodiesterase SPA beads (Amersham Pharmacia Biotech, code RPNQ 0150) are added (about 1 mg per well) to terminate the assay. Plates are sealed and shaken and allowed to stand at ambient temperature for 35 minutes to 1 hour (suitably 35 minutes) to allow the beads to settle. Bound radioactive product is measured using a WALLAC TRILUX 1450 Microbeta scintillation counter. For inhibition curves, 10 concentrations (e.g. 1.5 nM-30 uM) of each compound are assayed. Curves are analysed using ActivityBase and XLfit (ID Business Solutions Limited, 2 Ocean Court, Surrey Research Park, Guildford, Surrey GU2 7QB, United Kingdom) Results are expressed as $pIC_{50}$ values.

In an alternative to the above radioactive SPA assay, PDE4B or PDE4D inhibition can be measured in the following Fluorescence Polarisation (FP) assay:

Inhibition of PDE4B or PDE4D Activity: Fluorescence Polarisation (FP) Assay

The ability of compounds to inhibit catalytic activity at PDE4B (human recombinant) or PDE4D (human recombinant) can optionally be determined by IMAP Fluorescence Polarisation (FP) assay (IMAP Explorer kit, available from Molecular Devices Corporation, Sunnydale, Calif., USA; Molecular Devices code: R8062) in 384-well format.

The IMAP FP assay is able to measure PDE activity in an homogenous, non-radioactive assay format. The FP assay uses the ability of immobilised trivalent metal cations, coated onto nanoparticles (tiny beads), to bind the phosphate group of Fl-AMP that is produced on the hydrolysis of fluorescein-labelled (Fl) cyclic adenosine mono-phosphate (Fl-cAMP) to the non-cyclic Fl-AMP form. Fl-cAMP substantially does not bind. Binding of Fl-AMP product to the beads (coated with the immobilised trivalent cations) slows the rotation of the bound Fl-AMP and leads to an increase in the fluorescence polarisation ratio of parallel to perpendicular light. Inhibition of the PDE reduces/inhibits this signal increase.

Test compounds (small volume, e.g. ca. 0.5 to 1 microliters (ul), suitably ca. 0.5 ul, of solution in DMSO) are preincubated at ambient temperature (room temperature, e.g. 19-23° C.) in black 384-well microtitre plates (supplier: NUNC, code 262260) with PDE enzyme in 10 mM Tris-HCl buffer pH 7.2, 10 mM $MgCl_2$, 0.1% (w/v) bovine serum albumin, and 0.05% $NaN_3$ for 10-30 minutes. The enzyme level is set by experimentation so that reaction is linear throughout the incubation. Fluorescein adenosine 3',5'-cyclic phosphate (from Molecular Devices Corporation, Molecular Devices code: R7091) is added to give about 40 nM final concentration (final assay volume usually ca. 20-40 ul, suitably ca. 20 ul). Plates are mixed on an orbital shaker for 10 seconds and incubated at ambient temperature for 40 minutes. IMAP binding reagent (as described above, from Molecular Devices Corporation, Molecular Devices code: R7207) is added (60 ul of a 1 in 400 dilution in binding buffer of the kit stock solution) to terminate the assay. Plates are allowed to stand at ambient temperature for 1 hour. The Fluorescence Polarisation (FP) ratio of parallel to perpendicular light is measured using an Analyst™ plate reader (from Molecular Devices Corporation). For inhibition curves, 10 concentrations (e.g. 1.5 nM-30 uM) of each compound are assayed. Curves are analysed using ActivityBase and XLfit (ID Business Solutions Limited, 2 Ocean Court, Surrey Research Park, Guildford, Surrey GU2 7QB, United Kingdom). Results are expressed as $pIC_{50}$ values.

In the FP assay, reagents can be dispensed using Multi-drop™ (available from Thermo Labsystems Oy, Ratastie 2, PO Box 100, Vantaa 01620, Finland).

For a given PDE4 inhibitor, the PDE4B (or PDE4D) inhibition values measured using the SPA and FP assays can differ slightly.

Biological Data obtained for some of the Examples (PDE4B inhibitory activity, either as one reading (n=1) or as an average of 2 or more readings (n=2 or more) are generally as follows, based on measurements only, generally using SPA and/or FP assay(s) generally as described above or generally similar or generally analogous to those described above. In each of the SPA and FP assays, absolute accuracy of measurement is not possible, and the $pIC_{50}$ readings given are generally thought to be accurate only up to very approximately ±0.5 of a log unit, depending on the number of readings made and averaged:

| Example numbers | PDE4B $pIC_{50}$ (generally in FP assay) (±about 0.5) |
|---|---|
| Example 1A1 | about 10.3 (n = 8) |
| Example 1B | about 10.2 (n = 2) |
| Example 1C | about 10.3 (n = 1) |
| Example 9 | about 10.3 (n = 1) |
| Example 11 | about 10.3 (n = 1) |
| Example 12 | about 10.5 (n = 1) |
| Example 17 | about 9.8 (n = 1) |
| Example 19 | about 10.4 (n = 2) |
| Example 20 | about 10.0 (n = 1) |
| Example 21 | about 10.2 (n = 2) |
| Example 23 | about 10.1 (n = 1) |
| Example 23A | about 10.0 (n = 1) |
| Example 26 | about 9.6 (n = 2) |
| Example 31 | about 10.1 (n = 1) |
| Example 34 | about 9.0 (n = 1) |

A majority of the Examples, namely Examples 1A1, 1B, 1C, 3, 4, 9, 11, 12, 17, 18, 19, 20, 21, 22, 23, 23A, 24, 25, 26, 30, 31, 32, 33 and 34, have been tested for PDE4B inhibition, mostly or all using the FP assay generally as described above or a generally similar or generally analogous assay. This tested majority of the Examples generally have PDE4B inhibitory activities in the range of $pIC_{50}$=about 9.0 (±about 0.5) to about 10.6 (±about 0.5), generally as measured using the FP assay generally as described above or a generally similar or generally analogous assay.

Some or all of the PDE4B-tested Examples have also been tested, for PDE3 and/or PDE5 inhibition using the above-described assays or generally similar or generally analogous assays or other assays (for example FP or SPA assays). The compound of Example 1B and the salt of Example 1A1 each exhibit a larger PDE4B $pIC_{50}$ value than any of the PDE3, PDE5 and PDE6 $pIC_{50}$ values for the same compound or salt. That is, the compound of Example 1B and the salt of Example 1A1 each inhibit PDE4B more strongly than they inhibit PDE3, PDE5 and PDE6 (as measured in whatever assays, e.g. FP or SPA assays, happen to have been used).

The PDE4D $pIC_{50}$ values of some compounds or salts of the invention are as follows, as measured using an FP assay or a generally similar assay:

the salt of Example 1A1: PDE4D $pIC_{50}$=about 10.7 (±about 0.5 or more) (n=8).

the compound of Example 1B: PDE4D $pIC_{50}$=about 10.4 (±about 0.5 or more) (n=2).

the salt of Example 9: PDE4D $pIC_{50}$>about 11.0 (±about 0.5 or more) (n=1).

the salt of Example 19: PDE4D $pIC_{50}$=about 10.7 (±about 0.5 or more) (n=2).

the salt of Example 26: PDE4D $pIC_{50}$=about 9.4 (±about 0.5 or more) (n=2).

the compound of Example 23A: PDE4D $pIC_{50}$=about 10.5 (±about 0.5 or more) (n=1).

Emesis: Some known PDE4 inhibitors can cause emesis and/or nausea to greater or lesser extents, especially after systemic exposure e.g. after oral administration (e.g. see Z. Huang et al., *Current Opinion in Chemical Biology*, 2001, 5: 432-438, see especially pages 433-434 and refs cited therein). Therefore, it would be preferable, but not essential, if a PDE4 inhibitory compound or salt of the invention were to cause only limited or manageable emetic side-effects, e.g. after inhaled or parenteral or external-topical administration. Emetic side-effects can for example be measured by the emetogenic potential of the compound or salt when administered to ferrets or monkeys; for example the time to onset, extent, frequency and/or duration of vomiting, retching and/or writhing in ferrets or monkeys is optionally measured, after intratracheal or parenteral or intraperitoneal (or oral) administration of the PDE4 inhibitor compound or salt. See for example A. Robichaud et al., "Emesis induced by inhibitors of [PDE IV] in the ferret", *Neuropharmacology*, 1999, 38, 289-297, erratum *Neuropharmacology*, 2001, 40, 465-465.

Other side effects: Some known PDE4 inhibitors can cause other side effects such as headache and/or other central nervous sytem (CNS-) mediated side effects; and/or gastrointestinal (GI) tract disturbances. Therefore, it would be preferable but not essential if a particular PDE4 inhibitory compound or salt of the invention were to cause only limited or manageable side-effects in one or more of these side-effect categories.
Other in vitro Assays:

Other assays which may also be optionally used to further profile compounds or salts of the invention include the following.
Inhibition of TNF-α (TNF-Alpha) Production in Human PBMC (Peripheral Blood Mononuclear Cell) Assay (MSD Technology)

This is an optional supplementary test, e.g. for potentially inhalably-administrable PDE4 inhibitors.

A 96-well plate (96 MicroWell™ Plates Nunclon™Δ— High Flange Design, Fisher Scientific UK, Bishop Meadow Road, Loughborough LE 11 5 RG, Leicestershire, UK) is prepared by initially adding to column 1 ca. 10 mM of test compound dissolved in DMSO. For a more potent compound, a more diluted solution in DMSO may be used. The compound is further diluted with DMSO into columns 2 to 9 by 8 successive 3-fold dilutions using the Biomek® FX Laboratory Automation Workstation (Beckman Coulter, Inc., 4300 N. Harbor Boulevard, P.O. Box 3100, Fullerton, Calif. 92834-3100, USA). Column 10 is used as a DMSO negative control (High Signal, 0% response), whilst column 11, which contains 10 mM of the PDE4 inhibitor roflumilast, is used as a positive control (Low Signal, 100% response). About 1 μl (about 1 ul) of compound is transferred to the compound plate using the Biomek® FX.

PBMC cells (peripheral blood mononuclear cells) are prepared from heparinised human blood (using 1% v/v Heparin Sodium 10001 U/ml Endotoxin Free, Leo Laboratories Ltd., Cashel Road, Dublin 12. Ireland, Cat No: PL0043/0149) from normal volunteers using the Accuspin™ System-Histopaque®-1077 essentially (Sigma-Aldrich Company Ltd., The Old Brickyard New Rd, Gillingham, Dorset SP8 4XT, UK). About 20 ml of blood is overlaid onto 15 ml Histopaque® in Accuspin™ tubes. The tube is then centrifuged at about 800 g for ca. 20 minutes. The cells are collected from the interface, washed by centrifugation (ca. 1300 g, ca. 10 minutes) and resuspended in RPMI1640 medium (Low endotoxin RPMI1640 medium, Cat No: 31870-025, Invitrogen Corporation Invitrogen Ltd, 3 Fountain Drive, Inchinnan Business Park, Paisley PA4 9RF, UK) containing 10% foetal calf serum, 1% L-glutamine (Invitrogen Corporation, Cat No: 25030024) and 1% penicillin/streptomycin (Invitrogen Corporation, Cat No: 15140-122). Viable cells are counted by trypan blue staining and diluted to $1 \times 10^6$ viable cells/ml. About 50 μl (about 50 ul) of diluted cells and about 75 μl (about 75 ul) of LPS (ca. 1 ng/ml final; Sigma Cat No: L-6386) are added to the compound plate, which is then incubated at 37° C., 5% $CO_2$, for 20 hours.

The supernatant is removed and the concentrations of TNF-α are determined by electrochemiluminescence assay using the Meso Scale Discovery (MSD) technology (Meso Scale Discovery, 9238 Gaither Road, Gaithersburg, Md. 20877, USA). See the "TNF-α (TNF-alpha) MSD Assay" described below for typical details.

Results can be expressed as pIC50 values for inhibition of TNF-α (TNF-alpha) production in PBMCs, and it should be appreciated that these results can be subject to a possibly-large variability or error.
Inhibition of TNF-α (TNF-Alpha) Production in Human PBMC (Peripheral Blood Mononuclear Cell) Assay (IGEN Technology)

This is an optional supplementary test, e.g. for potentially inhalably-administrable PDE4 inhibitors.

Test compounds are prepared as a ca. 10 mM stock solution in DMSO and a dilution series prepared in DMSO with 8 successive 3-fold dilutions, either directly from the 10 mM stock solution or from a more dilute solution in DMSO. The compound is added to assay plates using a Biomek Fx liquid handling robot.

PBMC cells (peripheral blood mononuclear cells) are prepared from heparinised human blood from normal volunteers by centrifugation on histopaque at ca. 100 g for ca. 30 minutes. The cells are collected from the interface, washed by centrifugation (ca. 1300 g, ca. 10 minutes) and resuspended in assay buffer (RPMI 1640 containing 10% foetal calf serum, 1% L-glutamine and 1% penicillin/streptomycin) at $1 \times 10^6$ cells/ml. Ca. 50 μl (ca. 50 ul) of cells are added to microtitre wells containing ca. 0.5 or ca. 1.0 μl (ul) of an appropriately diluted compound solution. Ca. 75 μl (ul) of LPS (lipopolysaccharide) (ca. 1 ng/ml final) is added and the samples are incubated at 37° C., 5% $CO_2$, for 20 hours. The supernatant is removed and the concentrations of TNF-α are determined by electrochemiluminescence assay using the IGEN technology or by ELISA (see below).

Results can be expressed as pIC50 values for inhibition of TNF-α (TNF-alpha) production in PBMCs, and it should be appreciated that these results can be subject to a possibly-large variability or error.
PBMC Assay Results:

For the following Examples, which are compounds of formula (I) or salts thereof, and generally when using the one of the above assays, or a generally similar or generally analogous assay, the measured and/or mean pIC50 values for inhibition of TNF-α (TNF-alpha) production in PBMCs are generally as follows (subject to a possibly-large variability or error):

| Example numbers | PBMC $pIC_{50}$ (MSD assay) (n = no. of measurements) |
| --- | --- |
| 1A1 | about 9.3 (n = 85) |
| 1B | about 9.2 (n = 29) |
| 9 | about 8.4 (n = 4) |
| 19 | about 9.6 (n = 12) |
| 23 | about 9.2 (n = 4) |
| 23A | about 9.1 (n = 8) |
| 26 | about 7.8 (n = 8) |

Inhibition of TNF-α (TNF-Alpha) Production in Human Whole Blood

This is an optional supplementary test. For example, as the assay may measure the effect of PDE4 inhibitors after loss by protein binding, it might possibly be relevant to externally-topically-administrable PDE4 inhibitors as protein-binding-loss of compound is possible during transport through the skin.

Test compounds are prepared as a ca. 10 mM stock solution in DMSO and a dilution series prepared in DMSO with 8 successive 3-fold dilutions, either directly from the mM stock solution or from a more dilute solution in DMSO. The compound is added to assay plates using a Biomek Fx liquid handling robot.

Heparinised blood drawn from normal volunteers is dispensed (ca. 100 μl=ca. 100 ul) into microtitre plate wells containing ca. 0.5 or ca. 1.0 μl (ul, microliters) of an appropriately diluted test compound solution. After ca. 1 hr incubation at ca. 37° C., 5% $CO_2$, ca. 25 μl (ca. 25 ul) of LPS (lipopolysaccharide) solution (S. typhosa) in RPMI 1640 (containing 1% L-glutamine and 1% Penicillin/streptomycin) is added (ca. 50 ng/ml final). The samples are incubated at ca. 37° C., 5% $CO_2$, for ca. 20 hours, and ca. 100 μl (ca. 100 ul) physiological saline (0.138% NaCl) is added, and diluted plasma is collected using a Platemate or Biomek FX liquid handling robot after centrifugation at ca. 1300 g for ca. 10 min. Plasma TNF-α content is determined by electrochemiluminescence assay using the MSD technology (see below), the IGEN technology (see below) or by enzyme linked immunosorbant assay (ELISA) (see below).

Results can be expressed as pIC50 values for inhibition of TNF-α (TNF-alpha) production in Human Whole Blood, and it should be appreciated that these results can be subject to a possibly-large variability or error.

TNF-α (TNF-alpha) MSD Assay

Using the Biomek FX, 25 μl (25 ul) of MSD Human Serum Cytokine Assay Diluent (Meso Scale Discovery, 9238 Gaither Road, Gaithersburg, Md. 20877) is added to a 96-well High-Bind MSD plate pre-coated with anti-hTNF alpha capture antibody (MA6000) and then incubated for 24 hours at 4° C. to prevent non-specific binding. About 20 μl (ul) of supernatant from the PBMC plate or about 40 μl (ul) of supernatant from the whole blood (WB) plate are then transferred from columns 1-11 to columns 1-11 of the MSD plate using the Biomek FX. About 20 μl (ul) of TNF-α standard (Cat No. 210-TA; R&D Systems Inc., 614 McKinley Place NE, Minneapolis, Minn. 55413, USA) are added to column 12 of the MSD plate to generate a standard calibration curve (about 0 to 30000 pg/ml final).

For the Whole Blood assay, plates are washed after 2 hours shaking with a Skanwasher 300 version B (Skatron Instruments AS. PO Box 8, N-3401 Lier, Norway). About 40 μl (ul) of diluted sulfo-TAG antibody (ca. 1 μg/ml final) is added, the plates are shaken at room temperature for 1 hour, and the plates washed again as above. About 150 μl (ul) of Read Buffer T (2×) is added to the plates, which are then read on a MSD Sector 6000.

For the PBMC assay, about 20 μl (ul) of diluted sulfo-TAG antibody (ca. 1 μg/ml final) is added to each well, and the plates/wells are shaken at room temperature for 2 hours.

Finally, about 90 μl (ul) of MSD Read Buffer P (diluted to 2.5 times with distilled water) is added and the plates are read on a MSD Sector 6000.

Data Analysis

Data analysis is performed with ActivityBase/XC50 module (ID Business Solutions Ltd., 2 Occam Court, Surrey Research Park, Guildford, Surrey, GU2 7QB, UK). Data are normalized and expressed as % inhibition using the formula 100*((U−C1)/(C2−C1)) where U is the unknown value, C1 is the average of the high signal (0%) control wells (column 10), and C2 is the average of the low signal (100%) control wells (column 11). Curve fitting is performed with the following equation: $y=A+((B-A)/(10^{\wedge}x(10^{\wedge}x/10^{\wedge}C)^{\wedge}D))$, where A is the minimum response, B is the maximum response, C is the log10(IC50), and D is the Hill slope. The results for each compound are recorded as pIC50 values (−C in the above equation).

TNF-α (TNF-Alpha) IGEN Assay

Ca. 50 μl supernatant from either whole blood or PBMC assay plates is transferred to a 96 well polypropylene plate. Each plate also contains a TNF-αstandard curve (ca. 0 to 30000 pg/ml: R+D Systems, 210-TA). Ca. 50 μl (ul) of streptavidin/biotinylated anti-TNF-α antibody mix, ca. 25 μl ruthenium tagged anti-TNF-α monoclonal and ca. 100 μl PBS containing 0.1% bovine serum albumin are added to each well and the plates are sealed and shaken for ca. 2 hours before being read on an IGEN instrument.

TNF-α (TNF-Alpha) ELISA Assay (Enzyme Linked Immunosorbant Assay)

Human TNF-α can be assayed using a commercial ELISA assay kit (AMS Biotechnology, 211-90-164-40) according to the manufacturers' instructions but with TNF-α calibration curves prepared using Pharmingen TNF-α (cat. No. 555212).

In Vivo Biological Assays

The in vitro enzymatic PDE4B inhibition assay(s) described above or generally similar or analogous assays should be regarded as being the primary test(s) of biological activity. However, some additional in vivo biological tests, which are optional only, and which are not an essential measure of activity, efficacy or side-effects, and which have not necessarily been carried out, are described below.

In Vivo Assay 1. LPS Induced Pulmonary Neutrophilia in Rats: Effect of Intratracheally Administered PDE4 Inhibitors This assay is an animal model of acute inflammation in the lung—specifically neutrophilia induced by lipopolysaccharide (LPS)—and allows the study of putative inhibition of such neutrophilia (anti-inflammatory effect) by an intratracheally (i.t.) administered PDE4 inhibitor ("drug"). The PDE4 inhibitors are suitably in dry powder, aqueous solution or aqueous suspension form. I.t. administration is one model of inhaled administration, allowing topical delivery to the lung.

Animals: Male CD (Sprague Dawley Derived) rats supplied by Charles River, United Kingdom are housed in groups of 5 rats per cage, acclimatised after delivery for at least 7 days with bedding/nesting material regularly changed, fed on SDS diet R1 pelleted food given ad lib, and supplied with daily-changed pasteurised animal grade drinking water.

Device for dry powder administration: For these studies, a Penn Century DP-4 dry powder intratracheal (i.t.) delivery device (insufflator) is used for administration of a dry powder blend of vehicle (inhalation grade lactose) and the PDE4 inhibitor compound or salt of the invention ("drug"). Each device is numbered and the sample loading chamber is unscrewed from the main device and weighed. The i.t. delivery needle is also weighed. The drug+lactose blend or inhalation grade lactose (vehicle control) is then added to the sample chamber and this is then re-weighed. The sample chamber is fitted back on to the main device to prevent any drug being lost. This procedure is repeated for all of the Penn century devices to be used in the study (one separate device for each animal). After dosing to the animals, the sample chambers and needles are re-weighed in order to determine the amount of sample that was expelled from the device.

Device for aqueous solution administration: A blunt dosing needle, whose forward end is slightly angled to the needle axis, is used, with a flexible plastic portex canula inserted into the needle. The portex cannula is inserted into the lumen of the blunt stainless steel dosing needle and this is carefully inserted into the back of the animal's throat and into the trachea via the larynx. A known volume (200 microliters) of the vehicle (0.2% Tween 80™ in saline) or of the solution (or suspension) drug composition is administered into the trachea using a plastic syringe that is attached to the portex cannula and dosing needle. A new internal cannula is used for each different drug group. After dosing, the needle is removed from the trachea and the animals are removed from the table and continually observed until they recover from the effects of anaesthesia. The animals are then returned to the holding cages and given free access to food and water, and are observed and any unusual behavioural changes noted. (Aqueous suspensions can be handled generally similarly.)

Drugs and Materials: Lipopolysaccharide (LPS) (Serotype:0127:B8, e.g. from Sigma, UK; e.g. L3129 prepared by phenol extraction) is dissolved in phosphate-buffered saline (PBS).

For dry powder, aqueous solution or aqueous suspension administration, PDE4 inhibitors are preferably used in size-reduced (e.g. micronised) form, for example according to the Micronisation Example(s) disclosed herein.

For dry powder administration of the drug, the PDE4 inhibitor compound or salt of the invention (drug) is administered as a dry powder blended with inhalation-grade (respiratory-grade) lactose, i.e. as a dry powder composition. The target quantity of dry powder composition administered i.t. to each animal is 2 mg. This remains constant throughout the studies. To achieve different doses, blends of the drug dry powder and lactose, containing different concentrations of the PDE4 inhibitor compound or salt of the invention (drug), are prepared. The following dry powder blends, or generally similar blends with generally analogous but nonidentical concentrations, are generally used for these studies:

Blend 1: 0.1667% w/w of drug in lactose, which can e.g. be used to dose rats at about 10 µg/kg (about 10 ug/kg), depending on the bodyweight of the rats used (e.g. ca. 300-350 g bodyweight);

Blend 2: 0.5% w/w of drug in lactose, which can e.g. be used to dose rats at about 30 µg/kg (about 30 ug/kg), depending on the bodyweight of the rats used (e.g. ca. 300-350 g bodyweight);

Blend 3: 1.667% w/w of drug in lactose, which can e.g. be used to dose rats at about 100 µg/kg (about 100 ug/kg), depending on the bodyweight of the rats used (e.g. ca. 300-350 g bodyweight);

Blend 4: 5% w/w of drug in lactose, which can e.g. be used to dose rats at about 300 µg/kg (about 300 ug/kg), depending on the bodyweight of the rats used (e.g. ca. 300-350 g bodyweight).

For dry powder administration of the drug, one suitable inhalation-grade lactose that is typically used is: lactose monohydrate; and/or lactose having about 10% fines (i.e. has about 10% of material under 15 um (15 micron) particle size, measured by Malvern particle size). Other inhalation-grade lactoses might have e.g. from about 7% to about 11% fines.

For aqueous solution compositions of the drug, a composition of 0.2% Tween 80™ (e.g. available from Sigma, e.g. 073K 00643) in phosphate buffered saline (PBS) is prepared and used as the vehicle. The Sigma catalogue 2004-2005 and The Handbook of Pharmaceutical Excipients (HPE) 4th edition 2003 pp. 479-483 define Tween 80™ as a brand of polysorbate 80 (according to HPE, polysorbate 80 is also named polyoxyethylene 20 sorbitan monooleate, i.e. having been copolymerised with about 20 moles of ethylene oxide for each mole of sorbitol and/or sorbitol anhydrides used). Solution compositions are prepared by adding the required volume of 0.2% Tween 80™ in PBS to the pre-weighed PDE4 inhibitor compound or salt of the invention (drug). The average weight of the rats generally used in these studies is approximately 350 g; the i.t. solution dose volume is 200 microliters. Thus, for a target dose of 100 µg/kg (100 ug/kg), a 0.175 mg/ml solution of the drug is prepared. Lower concentrations are achieved by preparing serial dilutions from the 0.175 mg/ml stock solution concentration. All solutions were prepared immediately prior to dosing. The formulation is usually sonicated, e.g. for approximately 2-15 minutes e.g. ca. 2 minutes, prior to use and is observed to be a solution (if it is a solution) by visual examination.

Similar to aqueous solutions, aqueous suspensions of a drug can be prepared by adding the required volume of vehicle to the pre-weighed drug; the vehicle used can for example be saline alone or preferably a mixture of saline/Tween™ (e.g. 0.2% Tween 80™ in phosphate buffered saline). The aqueous suspension is usually sonicated, e.g. for about 10-15 minutes, prior to use.

Preparation, and dosing with PDE 4 inhibitor: Rats are anaesthetised by placing the animals in a sealed Perspex chamber and exposing them to a gaseous mixture of isoflourane (4.5%), nitrous oxide (3 liters/minute) and oxygen (1 liter/minute). Once anaesthetised, the animals are placed onto a stainless steel i.t. dosing support table. They are positioned on their back at approximately a 35° angle. A light is angled against the outside of the throat to highlight the trachea. The mouth is opened and the opening of the upper airway visualised. The procedure varies for aqueous solution and dry powder administration of PDE4 inhibitors as follows:

Dosing with an aqueous solution: A portex cannula is introduced via a blunt metal dosing needle that has been carefully inserted into the rat trachea. The animals are intratracheally dosed with vehicle or PDE4 inhibitor via the dosing needle with a new internal canula used for each different drug group. The formulation is slowly (ca. 5 seconds) dosed into the trachea using a syringe attached to the dosing needle. The procedure with an aqueous suspension is generally similar.

Dosing with a Dry Powder: The intratracheal dosing device (a Penn Century dry powder insufflator, DP-4) is inserted into the rat trachea up to a pre-determined point established to be located approximately 1 cm above the primary bifurcation. Two×3 ml of air is delivered using the Penn Century dry powder insufflator device by depressing a plastic syringe (ideally coinciding with the animal inspiring), aiming to expel the entire drug quantity from the tap. After dosing, the device is removed from the airway, and then is stored in an upright position in a sealed plastic bag. At a later stage, the device is re-weighed to determine the quantity of dry powder delivered.

After dosing with either aqueous solution (or wet suspension) or dry powder, the animals are removed from the table and observed constantly until they have recovered from the effects of anaesthesia. The animals are returned to the holding cages and given free access to food and water; they are observed and any unusual behavioural changes noted.

Exposure to LPS: About 2 hours after i.t. dosing with vehicle control or the PDE4 inhibitor, the rats are placed into sealed Perspex containers and exposed to an aerosol of LPS (nebuliser concentration ca. 150 µg.ml$^{-1}$=ca. 150 ug/ml) for ca. 15 minutes. Aerosols of LPS are generated by a nebuliser (DeVilbiss, USA) and this is directed into the Perspex exposure chamber. Following the 15-minute LPS-exposure period, the animals are returned to the holding cages and allowed free access to both food and water.

In an alternative embodiment, the rats can be exposed to LPS less than 2 hours (e.g. about 30 minutes) after i.t. dosing.

In another alternative embodiment, the rats can be exposed to LPS more than 2 hours (e.g. ca. 4 hours to ca. 36 hours, such as 4 hours, 6 hours, 8 hours, 12 hours, 18 hours, 24 hours or 36 hours, in particular 4 hours or 12 hours) after i.t. dosing by vehicle or PDE4 inhibitor, to test whether or not the PDE4 inhibitor has a long duration of action (which is preferable but not essential).

Bronchoalveolar lavage: About 4 hours after LPS exposure the animals are killed by overdose of sodium pentobarbitone (i.p.). The trachea is cannulated with polypropylene tubing and the lungs are lavaged (washed out) with 3×5 ml of heparinised (25 units/ml) phosphate buffered saline (PBS).

Neutrophil cell counts: The Bronchoalveolar lavage (BAL) samples are centrifuged at ca. 1300 rpm for ca. 7 minutes. The supernatant is removed and the resulting cell pellet resuspended in ca. 1 ml PBS. A cell slide of the resuspension fluid is prepared by placing ca. 100 µl (ca. 100 ul) of resuspended BAL fluid into cytospin holders and then is spun at ca. 5000 rpm for ca. 5 minutes. The slides are allowed to air dry and then stained with Leishmans stain (ca. 20 minutes) to allow differential cell counting. The total cells are also counted from the resuspension. From these two counts, the total numbers of neutrophils in the BAL are determined. For a measure of PDE4-inhibitor-induced inhibition of neutrophilia, a comparison of the neutrophil count in rats treated with vehicle and rats treated with PDE4 inhibitors is conducted.

By varying the dose of the PDE4 inhibitor used in the dosing step (e.g. 0.3 or 0.1 mg of PDE4 inhibitor per kg of body weight, down to e.g. 0.01 mg/kg), a dose-response curve can be generated, and thence an $ED_{50}$ value. The $ED_{50}$ value is typically the dose required to achieve 50% of the maximum level of inhibition achievable for that particular PDE4 inhibitor (drug) in the particular composition used in that particular study. The $ED_{50}$ value is not usually the dose required for 50% inhibition of neutrophilia.

Results: In an assay(s), generally involving LPS-induced pulmonary neutrophilia in rats and the effect of intratracheally administered PDE4 inhibitors to those rats, which assay(s) is or are generally similar to or generally analogous to the above-mentioned assay, the following results, given below, were measured. It is noted that these results might be subject to a possibly significant margin of error; and generally results may vary as the assay or measurement method varies:

(1) N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide dihydrochloride (e.g. which can be as prepared in Example 1A1), in micronised form, showed an estimated $ED_{50}$ of very approximately 12.3 micrograms/kg body weight, for inhibition of LPS-induced pulmonary neutrophilia in rats, when administered to rats intratracheally (i.t.) as an aqueous solution in 0.2% Tween 80™ in phosphate buffered saline, the administration to the rats being about 2 hours prior to the LPS challenge. The individual values of percentage mean inhibition of LPS-induced pulmonary neutrophilia in rats at different doses, which led to this estimated $ED_{50}$ value of very approximately 12.3 micrograms/kg, were as follows (n=6-8 for each of the following four dosing groups):

about 33% mean inhibition (p>0.05) after dosing at about 10 micrograms/kg body weight;
about 56% mean inhibition (p<0.01) after dosing at about 30 micrograms/kg body weight;
about 76% mean inhibition (p<0.01) after dosing at about 100 micrograms/kg body weight; and
about 74% mean inhibition (p<0.01) after dosing at about 300 micrograms/kg body weight.

(2) N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide (e.g. which can be as prepared in Example 1B), in micronised form, showed an estimated $ED_{50}$ of very approximately 10.1 micrograms/kg body weight, for inhibition of LPS-induced pulmonary neutrophilia in rats, when administered to rats intratracheally (i.t.) as an aqueous solution in 0.2% Tween 80™ in phosphate buffered saline, the administration to the rats being about 2 hours prior to the LPS challenge. The individual values of percentage inhibition (arithmetic mean) of LPS-induced pulmonary neutrophilia in rats at different doses, which led to this estimated $ED_{50}$ value of very approximately 10.1 micrograms/kg, were as follows (using: p values are vs. LPS+Tween/PBS vehicle control; ANOVA followed by Dunnet's post test; and n=5-6 for each of the following three dosing groups):

about 29% arithmetic mean inhibition (p>0.05) after dosing at about 10 micrograms/kg body weight;
about 75% arithmetic mean inhibition (p<0.001) after dosing at about 30 micrograms/kg body weight; and
about 59% arithmetic mean inhibition (p<0.05) after dosing at about 100 micrograms/kg body weight.

(3) N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride (e.g. which can be as prepared in Example 1A2), in micronised form, gave the following arithmetic mean percentage inhibitions of LPS-induced pulmonary neutrophilia in rats, when administered to rats intratracheally (i.t.) as a dry powder composition blended in inhalation grade lactose (with about 10% fines), the administration to the rats being about 2 hours prior to the LPS challenge (using: p values are vs. LPS+vehicle control; ANOVA followed by Dunnet's post test; note these results are summations (means) derived from about 4 separate experiments each using some but not all of the following four dosing groups, and with, for each experiment, n=4 or 6 for each of the dosing groups tested):

about 29% arithmetic mean inhibition (p>0.05) after dosing at about 10 micrograms/kg body weight;
about 44% arithmetic mean inhibition (p<0.05) after dosing at about 30 micrograms/kg body weight;
about 39% arithmetic mean inhibition (p>0.05) after dosing at about 100 micrograms/kg body weight; and
about 55% arithmetic mean inhibition (p<0.05) after dosing at about 300 micrograms/kg body weight.

(4) N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride (e.g. which can be as prepared in Example 1A2), in micronised form, gave about 60% inhibition (p<0.05) of LPS-induced pulmonary neutrophilia in rats, when about 100 micrograms of the drug/kg body weight was administered to the rats intratracheally (i.t.) as a dry powder composition blended in inhalation grade lactose (with about 10% fines), the administration to the rats being about 4 hours prior to the LPS challenge.

In vivo assay 2. LPS Induced Nasal Neutrophilia in Rats: Effect of Intranasally Administered PDE4 Inhibitors This assay is an animal model of acute inflammation in the nose—specifically neutrophilia induced by lipopolysaccharide (LPS)—and allows the study of putative inhibition of such neutrophilia (anti-inflammatory effect) by an intranasally (i.n.) administered PDE4 inhibitor ("drug"). The PDE4 inhibitor is preferably in the form of an aqueous suspension or aqueous solution. Bolus, i.n. administration allows topical delivery to the nose.

Animals: Male CD rats (Sprague Dawley derived), weighing between 300-350 g are supplied by Charles River, UK and transported to the test site. On arrival at the test site, the animals are housed in groups of 4 or 5 per cage and complete a minimum acclimatisation period of 7 days. The animals are housed in solid bottomed cages using grade 8 sawdust. The bedding and nesting materials are changed 3 times per week. Diet comprises SDS diet R1 pelleted food given ad lib. Pasteurised animal grade drinking water is supplied and changed daily.

Drugs and Materials

Lipopolysaccharide (Serotype: 0127:B8, e.g. available from Sigma, UK; e.g. L3129 prepared by phenol extraction) is used for all studies and is dissolved in phosphate-buffered saline (PBS).

Tween 80™ (e.g. available from Sigma e.g. 023K 01575). A mixture of 0.2% Tween 80™ in phosphate buffered saline (PBS) is prepared as vehicle for solution compositions. The Sigma catalogue 2004-2005 and The Handbook of Pharmaceutical Excipients (HPE) 4th edition 2003 pp. 479-483 define Tween 80™ as a brand of polysorbate 80 (according to HPE, polysorbate 80 is also named polyoxyethylene 20 sorbitan monooleate, i.e. having been copolymerised with about 20 moles of ethylene oxide for each mole of sorbitol and/or sorbitol anhydrides used).

The PDE4 inhibitor compound or salt of the invention ("drug") is preferably used in size-reduced (e.g. micronised) form, for example according to the Micronisation Example(s) disclosed herein.

A solution of compound (0.7 mg/ml) is generally prepared by adding 0.2% Tween 80™ in phosphate buffered saline (PBS) to a pre-weighed micronised sample of the drug. The solution composition is sonicated, e.g. for approximately 2 min, and is observed to be a solution (if it is a solution) by visual assessment. A fixed volume of 50 microliters (25 microliters into each nostril) of either the drug-containing solution composition or a saline/Tween 80™ vehicle is administered to all animals. Each animal weighs, on average, 350 g. To achieve a dose of 100 µg/kg (100 ug/kg), each animal receives a total of 35 µg (35 ug) of the drug. The dose volume is 50 microliters (25 microliters to each nostril), and therefore a concentration of 35 µg (ug) per 50 microliters (0.7 mg/ml) is prepared. To achieve lower dose concentrations, serial dilutions are prepared in saline/Tween 80™.

Intranasal dosing with the PDE4 inhibitor (drug): Rats are anaesthetised by placing the animals in a sealed Perspex chamber and exposing them to a gaseous mixture of isofluorane (5%), nitrous oxide (2 L/min) and oxygen (1 L/min). Once anaesthetised, the animals are i.n. dosed with vehicle or PDE4 inhibitor aqueous compositions using a 10-100-microliter-range Gilson pipette and plastic disposable tip. A volume of 25 microliters is administered into each nostril by carefully inserting the pipette tip into the nostril and dispensing the required volume. When the dosing procedure is completed, the animal is returned to the cage and observed at regular intervals until it had recovered from the effects of the anaesthetic.

Exposure to LPS: Thirty minutes after i.n. dosing with vehicle or PDE4 inhibitor, the rats are anaesthetised as previously described and a 25 microliters of a solution of LPS (175 µg/kg=175 ug/kg) is administered into each nostril using the same technique described for dosing of drug or vehicle. When the dosing procedure is completed, the animal is returned to the cage and observed at regular intervals until it had recovered from the effects of the anaesthetic.

Nasal Lavage: Four hours after LPS exposure, the animals are euthanased by overdose of sodium pentobarbitone (i.p.). The trachea is exposed and a small incision made approximately 1 cm below the larynx. A polypropylene cannula is inserted into the trachea towards the larynx and into the upper airway. The nasal cavity is then lavaged with 15 ml of heparinised (10 units/ml) phosphate buffered saline. The lavage fluid is collected in a 20 ml plastic sterilin tube which is positioned against the nostrils.

Cell Counts: The nasal lavage samples are centrifuged at 1300 rpm for 7 minutes. The supernatant is removed and the resulting cell pellet is resuspended in 0.5 ml PBS. A cell slide of the resuspension fluid is prepared by placing 75 microliters of resuspended nasal lavage fluid into cytospin holders and then spun at 500 rpm for 5 min. The slides are allowed to air dry and then stained with Leishmans stain (20 minutes) to allow differential cell counting. The total cells are also counted from the resuspension. From these two counts, the total numbers of neutrophils in the nasal lavage fluid is determined. For a measure of PDE4-inhibitor-induced inhibition of neutrophilia, a comparison of the neutrophil count in rats treated with vehicle and rats treated with the PDE4 inhibitor is conducted. By varying the dose of the PDE4 inhibitor used in the dosing step (e.g. 0.3 or 0.1 mg of PDE4 inhibitor per kg of body weight, down to e.g. 0.01 mg/kg), a dose-response curve can be generated, and thence an $ED_{50}$ value.

Results: In an assay(s), generally involving LPS-induced nasal neutrophilia in rats and the effect of intranasally administered PDE4 inhibitors to those rats, which assay(s) is or are generally similar to or generally analogous to the above-mentioned assay, the following results were measured:

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride (e.g. which can be as prepared in Example 1A2), in micronised form, showed an estimated ED50 of very approximately 4.6 micrograms/kg body weight, for inhibition of LPS-induced nasal neutrophilia in rat, when administered to the rat intranasally (i.n.) as an aqueous solution in 0.2% Tween 80™ in phosphate buffered saline, the administration to the rat being about 30 minutes prior to the LPS challenge. The individual values of percentage inhibition (arithmetic mean) of LPS-induced nasal neutrophilia in rats at different doses, which led to this estimated $ED_{50}$ value of very approximately 4.6 micrograms/kg, were as follows (using: p values are vs. LPS+Tween/PBS vehicle control; ANOVA followed by Dunnet's post test; note: these data represent a summation from 2 or more separate experiments):

- essentially no inhibition after dosing at about 1 micrograms/kg body weight;
- small and non-statistically-significant inhibition after dosing at about 3 micrograms/kg body weight;
- about 62% arithmetic mean inhibition (p<0.01) after dosing at about 10 micrograms/kg body weight (for 10 ug/kg experiment, assumed rat bodyweight was ca. 350 g at time of test, rats (n=6) weighed ca. 225-300 g at delivery one month before test); and
- about 79% arithmetic mean inhibition (p<0.01) after dosing at about 100 micrograms/kg body weight (N.B. the 100 ug/kg dosing was a separate experiment with rats (n=6) weighing ca. 175-225 g at delivery nine days before test).

In Vivo Assay A:

Activity of Topically-Applied Compounds in a Pig Model of Atopic Dermatitis: Effect Of Compounds, Applied by Skin Topical Administration, on the Dinitrofluorobenzene (DNFB)-induced Delayed Type Hypersensitivity (DTH) Response in Pigs General Study Design:

The pig DTH (delayed type hypersensitivity) model of contact hypersensitivity utilizes the Th2-mediated inflammatory response in pig skin to mimic the pathology of atopic dermatitis in humans. The model measures the potential antiinflammatory effect of compounds, topically-applied to the skin, on the acute DTH (delayed type hypersensitivity) response in castrated male Yorkshire pigs.

In general in the assay, pigs (domestic Yorkshire pigs, 15-18 kg at time of sensitization, castrated males) are first sensitized by topical application of ca. 10% (w/v) dinitrofluorobenzene (DNFB) dissolved in DMSO:acetone:olive oil (ca. 1:5:3) (ca. 40 mg DNFB, 400 microliter solution total) to the ears (outer) and groin (inner). The pigs are then challenged 12 days later with ca. 0.6% (w/v) DNFB applied to randomized sites on the shaved back of the pigs (ca. 90 micrograms/site; sites are identified and numbered by grid made with marking pen).

On the day of challenge, the treatments are performed at the challenge sites at about 2 hours prior to and about 6 hours after challenge (for DMSO/acetone solutions/suspensions containing the PDE4 inhibitor, to maximize exposure to drug), or at about 30 minutes after and about 6 hours after challenge (for topical ointments or creams containing the PDE4 inhibitor, representing a more clinically relevant treatment protocol).

One day (about 24 hrs) after challenge, and optionally again at ca. 48 hrs post challenge, test sites are visually evaluated for intensity and extent of erythema by measuring the diameter of the reaction at its widest point and assigning scores of 0 to 4 for each of erythema intensity and erythema extent. Induration (a measure of swelling) is also scored 0 to 4. Scores for erythema intensity, erythema extent and induration are assigned according to the following criteria: Intensity of Erythema: 0=normal, 1=minimal, barely visible, 2=mild, 3=moderate, 4=severe. Extent of Erythema (not raised): 0=no edema, 1=macules of pin head size, 2=lentil sized macules, 3=confluent macules, 4=diffuse over entire site. Induration (palpable): 0=normal, 1=nodules of pin head size, 2=doughy lentil sized nodules, 3=confluent firm nodules, 4=diffuse hard lesion. The summed visual score at ca. 24 hours includes the individual scores for erythema intensity, erythema extent, and induration; so the maximal summed score for each site would be 12. High summed scores can generally indicate a high inflammatory response. Visual scores are subject to some inaccuracy/error.

Differences in the summed score between adjacent control (placebo) and treatment sites on the grids are calculated. This difference value is then used to determine the percent inhibition compared to the summed score for the control (placebo) sites. The more negative the difference value, the greater the calculated inhibition. Percent inhibition of (percent inhibition compared to) the mean summed score can be calculated.

About 24 hours after challenge, treatment sites can optionally also be visually evaluated for lesion area.

EXAMPLES

The various aspects of the invention will now be described by reference to the following examples. These examples are merely illustrative and are not to be construed as a limitation of the scope of the present invention.

In this section, "Intermediates" can represent syntheses of intermediate compounds intended for use in the synthesis of one or more of the "Examples", and/or "Intermediates" can represent syntheses of intermediate compounds which can possibly be used in the synthesis of compounds of formula (I) or salts thereof. "Examples" are generally examples of compounds or salts of the invention, for example compounds of formula (I) or salts thereof.

Abbreviations used herein:

| | |
|---|---|
| AcOH | acetic acid |
| $Ac_2O$ | acetic anhydride |
| BEMP | 2-t-butylimino-2-diethylamino-1,3-dimethylperhydro-1,3,2-diazaphosphazine |
| $BOC_2O$ | di tert-butyl carbonate |
| DMSO | dimethyl sulfoxide |
| DCC | N,N'-dicyclohexylcarbodiimide |
| DCM | dichloromethane |
| DMF | N,N-dimethylformamide |
| DIPEA | N,N-diisopropylethyl amine ($^iPr_2NEt$) |
| EDC | 1-(3-Dimethylaminopropyl)-3-ethylcarbodiimide hydrochloride |
| EtOAc | ethyl acetate |
| $Et_2O$ | diethyl ether |
| $Et_3N$ | triethylamine |
| EtOH | ethanol |
| HATU | O-(7-Azabenzotriazol-1-yl)-N,N,N',N'-tetramethyluronium hexafluorophosphate; also named O-(7-azabenzotriazol-1-yl)-1,1,3,3-tetramethyluronium hexafluorophosphate |
| HBTU | O-(Benzotriazol-1-yl)-N,N,N',N'-tetramethyluronium hexafluorophosphate |
| HOBT | hydroxybenzotriazole = 1-hydroxybenzotriazole |
| IPA | isopropanol (isopropyl alcohol) |
| Lawesson's reagent | 2,4-bis(4-methoxyphenyl)-1,3-dithia-2,4-diphosphetane-2,4-disulphide |
| LPS | lipopolysaccharide |
| MeCN | acetonitrile |
| MeOH | methanol |
| MDAP | mass directed autoprep HPLC |
| NMP | 1-methyl-2-pyrrolidinone (also named 1-methyl-2-pyrrolidone or N-methyl-2-pyrrolidinone) |
| PyBOP | (Benzotriazol-1-yloxy)-trispyrrolidinophosphonium hexafluorophosphate |
| TBME | tert-butyl methyl ether |
| TMS | tetramethylsilane |
| THF | Tetrahydrofuran |
| TFA | Trifluoroacetic acid |
| barg | generally, this represents the pressure relative to the prevailing atmospheric pressure (so that e.g. if the atmospheric pressure at the time is 1 atmosphere then −0.9 barg is 0.9 atmospheres below the prevailing external 1 atmosphere = 0.1 atmosphere absolute pressure). |
| HPLC | high performance liquid chromatography |
| h | hours |
| min | minutes |
| LCMS or LC/MS | liquid chromatography/mass spectroscopy |
| NMR | nuclear magnetic resonance (in which: s = singlet, d = doublet, t = triplet, q = quartet, dd = doublet of doublets, m = multiplet, H = no. of protons) |
| SPE | solid phase extraction. Unless otherwise specified, the solid phase is usually silica gel. Aminopropyl SPE, if used, typically refers to a silica SPE column with aminopropyl residues immobilised on the solid phase (e.g. IST Isolute ™ columns). It is thought that compounds isolated by SPE are usually isolated as the free base. |
| SCX | solid phase extraction (SPE) column with benzene sulfonic acid residues immobilised on the solid phase (e.g. IST Isolute ™ columns). When eluting with ammonia/methanol, it is thought that compounds isolated by SCX are usually in the free base form. |
| TLC | thin layer chromatography |
| $T_{RET}$ or $R_T$ | retention time (e.g. from LCMS) |
| $T_{int}$ | internal temperature of the reaction mixture |
| $T_{max}$ | maximum internal temperature, e.g. during an addition |
| Room temperature (ambient temperature): | this is usually in the range of about 18 to about 25° C. |

General Experimental Details

Machine Methods Used Herein:

LCMS (Liquid Chromatography/Mass Spectroscopy)
Waters ZQ mass spectrometer operating in positive ion electrospray mode, mass range 100-1000 amu.
UV wavelength: 215-330 nm
Column: 3.3 cm×4.6 mm ID (internal diameter), 3 μm (3 micrometers) ABZ+PLUS
Flow Rate: 3 ml/min
Injection Volume: 5 μl (5 microliters)
Solvent A: 0.05% v/v solution of formic acid in a mixture of [95% acetonitrile and 5% water]
Solvent B: aqueous solution of [0.1% v/v formic acid+10 mMolar ammonium acetate]
Gradient: Mixtures of Solvent A and Solvent B are used according to the following gradient profiles (expressed as % Solvent A in the mixture): 0% A/0.7 min, 0-100% A/3.5 min, 100% A/1.1 min, 100-0% A/0.2 min.

It should be noted that retention times ($T_{RET}$) quoted herein are inherently variable (e.g. the variability can be about +/−0.2 min or more.). Variability can arise e.g. when samples are run on different Waters machines, or on the same Waters machine at different times of day or under slightly different conditions, even when the same type of column and identical flow rates, injection volumes, solvents and gradients are used.

Mass Directed Automated Preparative HPLC Column, Conditions and Eluent Method A (Eluent Containing Formic Acid)

The preparative HPLC column generally used is a Supelcosil ABZplus (10 cm×2.12 cm internal diameter; particle size 5 μm=5 micrometers). A mass spectrometer attached to the end of the column can detect peaks arising from eluted compounds.
UV detection wavelength: 200-320 nm
Flow rate: 20 ml/min
Injection Volume: 0.5 to 1.0 ml
Solvent A: 0.1% v/v aqueous formic acid solution
Solvent B: 0.05% v/v solution of formic acid in a mixture of [95% acetonitrile and 5% water]
Gradient systems: mixtures of Solvent A and Solvent B are used according to a choice of 5 generic gradient profiles (expressed as % Solvent B in the mixture), ranging from a start of 0 to 50% Solvent B, with all finishing at 100% Solvent B to ensure total elution.

It is thought that compounds isolated by this method are usually isolated as formate salts.

Mass Directed Automated Preparative HPLC Column, Conditions and Eluent Method B (Eluent Containing Trifluoroacetic Acid)

The preparative HPLC column generally used is a C18 column (10 cm×2.12 cm internal diameter; particle size 5 μm=5 micrometers). A mass spectrometer attached to the end of the column can detect peaks arising from eluted compounds.
UV detection wavelength: 200-320 nm
Flow rate: 20 ml/min
Injection Volume: 0.5 to 1.0 ml
Solvent A: 0.1% v/v aqueous trifluoroacetic acid solution
Solvent B: solution of 0.1% v/v trifluoroacetic acid in acetonitrile
Gradient systems: mixtures of Solvent A and Solvent B are used according to a choice of 5 generic gradient profiles (expressed as % Solvent B in the mixture), ranging from a start of 0 to 50% Solvent B, with all finishing at 100% Solvent B to ensure total elution.

It is thought that compounds isolated by this method are usually isolated as trifluoroacetate salts.

Mass Directed Automated Preparative HPLC Column, Conditions and Eluent Method C (Eluent Containing Trifluoroacetic Acid)

The preparative HPLC column generally used is a C18 column (10 cm×2.12 cm internal diameter; particle size 5 μm=5 micrometers). A mass spectrometer attached to the end of the column can detect peaks arising from eluted compounds.
UV detection wavelength: 210-254 nm
Flow rate: 20 ml/min
Injection Volume: 0.5 to 1.0 ml
Solvent A: 0.1% v/v aqueous trifluoroacetic acid solution
Solvent B: solution of 0.1% v/v trifluoroacetic acid in acetonitrile
Gradient systems: mixtures of Solvent A and Solvent B are used according to a choice of 5 generic gradient profiles (expressed as % Solvent B in the mixture), ranging from a start of 0 to 50% Solvent B, with all finishing at 100% Solvent B to ensure total elution.

It is thought that compounds isolated by this method are usually isolated as trifluoroacetate salts.

'Hydrophobic Frit'

This generally refers to a Whatman PTFE filter medium (frit), pore size 5.0 μm (5.0 micrometers), housed in a polypropylene tube.

Evaporation of Product Fractions After Purification

Reference to column chromatography, SPE and preparative HPLC purification includes evaporation of the product containing fractions to dryness by an appropriate method.

Celite

References to celite generally refer to the filter agent Celite 545 (e.g. available from Aldrich).

Intermediates and Examples

Reagents not detailed in the text below are usually commercially available from chemicals suppliers, e.g. established suppliers such as Sigma-Aldrich. The addresses and/or contact details of the suppliers for some of the starting materials mentioned in the Intermediates and Examples below or the Assays above, or suppliers of miscellaneous chemicals in general, are as follows:

AB Chem, Inc., 547 Davignon, Dollard-des-Ormeaux, Quebec, H9B 1Y4, Canada

ABCR GmbH & CO. KG, P.O. Box 21 01 35, 76151 Karlsruhe, Germany

ACB Blocks Ltd; Kolokolnikov Per, 9/10 Building 2, Moscow, 103045, Russia

Aceto Color Intermediates (catalogue name), Aceto Corporation, One Hollow Lane, Lake Success, N.Y., 11042-1215, USA Acros Organics, A Division of Fisher Scientific Company, 500 American Road, Morris Plains, N.J. 07950, USA Aldrich (catalogue name), Sigma-Aldrich Company Ltd., Dorset, United Kingdom, telephone: +44 1202 733114; Fax: +44 1202 715460; ukcustsv@eurnotes.sial.com; or Aldrich (catalogue name), Sigma-Aldrich Corp., P.O. Box 14508, St. Louis, Mo. 63178-9916, USA; telephone: +1-314-771-5765; fax: +1-314-771-5757; custserv@sial.com; or Aldrich (catalogue name), Sigma-Aldrich Chemie GmbH, Munich, Germany; telephone: +49 89 6513 0; Fax: +49 89 6513 1169; deorders@eurnotes.sial.com.

Alfa Aesar, A Johnson Matthey Company, 30 Bond Street, Ward Hill, Mass. 01835-8099, USA Amersham Biosciences UK Ltd, Pollards Wood, Chalfont St Giles, Buckinghamshire HP8 4SP, United Kingdom Apin Chemicals Ltd., 82 C Milton Park, Abingdon, Oxon OX14 4RY, United Kingdom Apollo Scientific Ltd., Unit 1A, Bingswood Industrial Estate, Whaley Bridge, Derbyshire SK23 7LY, United Kingdom Arch Corporation, 100 Jersey Avenue, Building D, New Brunswick, N.J. 08901, USA Array Biopharma Inc., 1885 33rd Street, Boulder, Colo. 80301, USA Asinex-Reag.

AstaTech, Inc., 8301 Torresdale Ave., 19C, Philadelphia, Pa. 19136, USA

Austin Chemical Company, Inc., 1565 Barclay Blvd., Buffalo Grove, Ill. 60089, USA Avocado Research, Shore Road, Port of Heysham Industrial Park, Heysham, Lancashire LA3 2XY, United Kingdom Bayer AG, Business Group Basic and Fine Chemicals, D-51368 Leverkusen, Germany Berk Univar plc, Berk House, P.O. Box 56, Basing View, Basingstoke, Hants RG21 2E6, United Kingdom Bionet Research Ltd; Highfield Industrial Estate, Camelford, Cornwall PL32 9QZ UK Butt Park Ltd., Braysdown Works, Peasedown St. John, Bath BA2 8LL, United Kingdom Chemical Building Blocks (catalogue name), Ambinter, 46 quai Louis Bleriot, Paris, F-75016, France ChemBridge Europe, 4 Clark's Hill Rise, Hampton Wood, Evesham, Worcestershire WR11 6FW, United Kingdom ChemService Inc., P.O. Box 3108, West Chester, Pa. 19381, USA CiventiChem, PO Box 12041, Research Triangle Park, N.C. 27709, USA Combi-Blocks Inc., 7949 Silverton Avenue, Suite 915, San Diego, Calif. 92126, USA Dynamit Nobel GmbH, Germany; also available from: Saville Whittle Ltd (UK agents of Dynamit Nobel), Vickers Street, Manchester M40 8EF, United Kingdom E. Merck, Germany; or E. Merck (Merck Ltd), Hunter Boulevard, Magna Park, Lutterworth, Leicestershire LE17 4XN, United Kingdom Esprit Chemical Company, Esprit Plaza, 7680 Matoaka Road, Sarasota, Fla. 34243, USA Exploratory Library (catalogue name), Ambinter, 46 quai Louis Bleriot, Paris, F-75016, France Fluka Chemie AG, Industriestrasse 25, P.O. Box 260, CH-9471 Buchs, Switzerland Fluorochem Ltd., Wesley Street, Old Glossop, Derbyshire SK13 7RY, United Kingdom Heterocyclic Compounds Catalog (Florida Center for Heterocyclic Compounds, University of Florida, PO Box 117200, Gainsville, Fla. 32611-7200 USA ICN Biomedicals, Inc., 3300 Hyland Avenue, Costa Mesa, Calif. 92626, USA Interchim Intermediates (catalogue name), Interchim, 213 Avenue Kennedy, BP 1140, Montlucon, Cedex, 03103, France Key Organics Ltd., 3, Highfield Indusrial Estate, Camelford, Cornwall PL32 9QZ, United Kingdom Lancaster Synthesis Ltd., Newgate, White Lund, Morecambe, Lancashire LA3 3DY, United Kingdom Manchester Organics Ltd., Unit 2, Ashville Industrial Estate, Sutton Weaver, Runcorn, Cheshire WA7 3 PF, United Kingdom Matrix Scientific, P.O. Box 25067, Columbia, S.C. 29224-5067, USA Maybridge Chemical Company Ltd., Trevillett, Tintagel, Cornwall PL34 0HW, United Kingdom Maybridge Combichem (catalogue name), Maybridge Chemical Company Ltd., Trevillett, Tintagel, Cornwall PL34 0HW, United Kingdom Maybridge Reactive Intermediates (catalogue name), Maybridge Chemical Company Ltd., Trevillett, Tintagel, Cornwall PL34 0HW, United Kingdom MicroChemistry Building Blocks (catalogue name), MicroChemistry-RadaPharma, Shosse Entusiastov 56, Moscow, 111123, Russia Miteni S.p.A., Via Mecenate 90, Milano, 20138, Italy Molecular Devices Corporation, Sunnydale, Calif., USA N.D. Zelinsky Institute, Organic Chemistry, Leninsky prospect 47, 117913 Moscow B-334, Russia Oakwood Products Inc., 1741, Old Dunbar Road, West Columbia, S.C., 29172, USA OmegaChem. Inc., 8800, Boulevard de la Rive Sud, Levis, PQ, G6V 9H1, Canada Optimer Building Block (catalogue name), Array BioPharma, 3200 Walnut Street, Boulder, Colo. 80301, USA Peakdale Molecular Ltd., Peakdale Science Park, Sheffield Road, Chapel-en-le-Frith, High Peak SK23 0PG, United Kingdom Pfaltz & Bauer, Inc., 172 East Aurora Street, Waterbury, Conn. 06708, USA Qualigens Fine Chemicals Rare Chemicals (catalogue name), Rare Chemicals GmbH, Schulstrasse 6, 24214 Gettorf, Germany Rieke SALOR (catalogue name) (Sigma Aldrich Library of Rare Chemicals), Aldrich Chemical Company Inc, 1001 West Saint Paul Avenue, Milwaukee, Wis. 53233, USA Sigma (catalogue name), Sigma-Aldrich Corp., P.O. Box 14508, St. Louis, Mo. 63178-9916, USA; see "Aldrich" above for other non-US addresses and other contact details SIGMA-RBI, One Strathmore Road, Natick, Mass. 01760-1312, USA Spectrochem Synchem OHG Heinrich-Plett-Strasse 40, Kassel, D-34132, Germany Syngene International Pvt Ltd, Hebbagodi, Hosur Road, Bangalore, India.

TCI America, 9211 North Harborgate Street, Portland, Oreg. 97203, USA

TimTec Building Blocks A or B, TimTec, Inc., PO Box 8941, Newark, Del. 19714-8941, USA TimTec Overseas Stock, TimTec Inc., 100 Interchange Blvd. Newark, Del. 19711, USA TimTec Stock Library, TimTec, Inc., PO Box 8941, Newark, Del. 19714-8941, USA Trans World Chemicals, Inc., 14674 Southlawn Lane, Rockville, Md. 20850, USA Tyger Ubichem PLC, Mayflower Close, Chandlers Ford Industrial Estate, Eastleigh, Hampshire SO53 4AR, United Kingdom Ultrafine (UFC Ltd.), Synergy House, Guildhall Close, Manchester Science Park, Manchester M15 6SY, United Kingdom

TABLE 1

| Intermediate No. | Name |
|---|---|
| 1 | 1-ethyl-1H-pyrazol-5-amine |
| 2 | diethyl (1-chloropropylidene)propanedioate |
| 2A | diethyl (1-chloro-1-propen-1-yl)propanedioate and/or diethyl (1-chloropropylidene)propanedioate |
| 2B | diethyl {1-[(1-ethyl-1H-pyrazol-5-yl)amino]propylidene}propanedioate |
| 2C | ethyl 1,6-diethyl-4-hydroxy-1H-pyrazolo[3,4-b]pyridine-5-carboxylate |
| 3 | ethyl 4-chlora-1,6-diethyl-1H-pyrazolo[3,4-b]pyridine-5-carboxylate |
| 4 | ethyl 1,6-diethyl-4-(tetrahydro-2H-pyran-4-ylamino)-1H-pyrazolo[3,4-b]pyridine-5-carboxylate |
| 5 | [1,6-diethyl-4-(tetrahydro-2H-pyran-4-ylamino)-1H-pyrazolo[3,4-b]pyridin-5-yl]methanol |
| 6 | 5-(azidomethyl)-1,6-diethyl-N-(tetrahydro-2H-pyran-4-yl)-1H-pyrazolo[3,4-b]pyridin-4-amine |
| 7 | 5-(aminomethyl)-1,6-diethyl-N-(tetrahydro-2H-pyran-4-yl)-1H-pyrazolo[3,4-b]pyridin-4-amine |
| 7A | 5-(aminomethyl)-1,6-diethyl-N-(tetrahydro-2H-pyran-4-yl)-1H-pyrazolo[3,4-b]pyridin-4-amine monohydrochloride |
| 8 | 1,1-dimethylethyl{4-[({[1,6-diethyl-4-(tetrahydro-2H-pyran-4-ylamino)-1H-pyrazolo[3,4-b]pyridin-5-yl]methyl}amino)carbonyl]phenyl}carbamate |
| 9 | 4-amino-N-{[1,6-diethyl-4-(tetrahydro-2H-pyran-4-ylamino)-1H-pyrazolo[3,4-b]pyridin-5-yl]methyl}benzamide hydrochloride |
| 10 | 8-bromooctanoyl chloride |
| 11 | 4-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide |
| 13 | ethyl 4-[(1-{[(1,1-dimethylethyl)oxy]carbonyl}-4-piperidinyl)amino]-1,6-diethyl-1H-pyrazolo[3,4-b]pyridine-5-carboxylate |
| 14 | 1,1-dimethylethyl 4-{[1,6-diethyl-5-(hydroxymethyl)-1H-pyrazolo[3,4-b]pyridin-4-yl]amino}-1-piperidinecarboxylate |
| 15 | 1,1-dimethylethyl 4-{[5-(azidomethyl)-1,6-diethyl-1H-pyrazolo[3,4-b]pyridin-4-yl]amino}-1-piperidinecarboxylate |
| 16 | 4-{[5-(azidomethyl)-1,6-diethyl-1H-pyrazolo[3,4-b]pyridin-4-yl]amino}-1-piperidinecarboxamide |
| 17 | 4-{[5-(aminomethyl)-1,6-diethyl-1H-pyrazolo[3,4-b]pyridin-4-yl]amino}-1-piperidinecarboxamide |
| 19 | 1,1-dimethylethyl [4-({[(4-{[1-(aminocarbonyl)-4-piperidinyl]amino}-1,6-diethyl-1H-pyrazolo[3,4-b]pyridin-5-yl)methyl]amino}carbonyl)phenyl]carbamate |
| 20 | 4-{[5-({[(4-aminophenyl)carbonyl]amino}methyl)-1,6-diethyl-1H-pyrazolo[3,4-b]pyridin-4-yl]amino}-1-piperidinecarboxamide hydrochloride |
| 21 | 4-[(5-{[({4-[(8-bromooctanoyl)amino]phenyl}carbonyl)amino]methyl}-1,6-diethyl-1H-pyrazolo[3,4-b]pyridin-4-yl)amino]-1-piperidinecarboxamide |
| 22 | 1,1-dimethylethyl 4-(4-hydroxy-1-butyn-1-yl)benzoate |
| 23 | 1,1-dimethylethyl 4-(4-hydroxybutyl)benzoate |
| 24 | 1,1-dimethylethyl 4-{4-[(4-bromobutyl)oxy]butyl}benzoate |
| 25 | 4-{4-[(4-bromobutyl)oxy]butyl}benzoic acid |
| 26 | 4-{4-[(4-bromobutyl)oxy]butyl}benzoyl chloride |
| 27 | 4-{4-[(4-bromobutyl)oxy]butyl}-N-{[1,6-diethyl-4-(tetrahydro-2H-pyran-4-ylamino)-1H-pyrazolo[3,4-b]pyridin-5-yl]methyl}benzamide |
| 28 | 4-{[5-({[(4-{4-[(4-bromobutyl)oxy]butyl}phenyl)carbonyl]amino}methyl)-1,6-diethyl-1H-pyrazolo[3,4-b]pyridin-4-yl]amino}-1-piperidinecarboxamide |
| 29 | diethyl (1-chloroethylidene)propanedioate |
| 30 | ethyl 4-chloro-1-ethyl-6-methyl-1H-pyrazolo[3,4-b]pyridine-5-carboxylate |
| 31 | ethyl 1-ethyl-6-methyl-4-(tetrahydro-2H-pyran-4-ylamino)-1H-pyrazolo[3,4-b]pyridine-5-carboxylate |
| 32 | [1-ethyl-6-methyl-4-(tetrahydro-2H-pyran-4-ylamino)-1H-pyrazolo[3,4-b]pyridin-5-yl]methanol |
| 33 | 5-(azidomethyl)-1-ethyl-6-methyl-N-(tetrahydro-2H-pyran-4-yl)-1H-pyrazolo[3,4-b]pyridin-4-amine |
| 34 | 5-(aminomethyl)-1-ethyl-6-methyl-N-(tetrahydro-2H-pyran-4-yl)-1H-pyrazolo[3,4-b]pyridin-4-amine |
| 35 | 1,1-dimethylethyl 4-[(8-bromooctanoyl)amino]benzoate |
| 36 | 4-[(8-bromooctanoyl)amino]benzoic acid |
| 37 | 4-[(8-bromooctanoyl)amino]-N-{[1-ethyl-6-methyl-4-(tetrahydro-2H-pyran-4-ylamino)-1H-pyrazolo[3,4-b]pyridin-5-yl]methyl}benzamide |
| 38 | 1,1-dimethylethyl 4-({8-[(2-hydroxyethyl)(methyl)amino]octanoyl}amino)benzoate |
| 39 | 4-({8-[(2-hydroxyethyl)(methyl)amino]octanoyl}amino)benzoic acid |
| 39A | 4-({8-[(2-hydroxyethyl)(methyl)amino]octanoyl}amino)benzoic acid hydrogen chloride |

TABLE 1-continued

Intermediates

| Intermediate No. | Name |
|---|---|
| 40 | N-{[1,6-diethyl-4-(tetrahydro-2H-pyran-4-ylamino)-1H-pyrazolo[3,4-b]pyridin-5-yl]methyl}-4-(8-hydroxyoctyl)benzamide |
| 41 | 4-(8-bromooctyl)-N-{[1,6-diethyl-4-(tetrahydro-2H-pyran-4-ylamino)-1H-pyrazolo[3,4-b]pyridin-5-yl]methyl}benzamide |
| 42 | 1,1-dimethylethyl {2-[({[1,6-diethyl-4-(tetrahydro-2H-pyran-4-ylamino)-1H-pyrazolo[3,4-b]pyridin-5-yl]methyl}amino)carbonyl]phenyl}carbamate |
| 43 | 1,1-dimethylethyl {3-[({[1,6-diethyl-4-(tetrahydro-2H-pyran-4-ylamino)-1H-pyrazolo[3,4-b]pyridin-5-yl]methyl}amino)carbonyl]phenyl}carbamate |
| 44 | 2-amino-N-{[1,6-diethyl-4-(tetrahydro-2H-pyran-4-ylamino)-1H-pyrazolo[3,4-b]pyridin-5-yl]methyl}benzamide |
| 45 | 3-amino-N-{[1,6-diethyl-4-(tetrahydro-2H-pyran-4-ylamino)-1H-pyrazolo[3,4-b]pyridin-5-yl]methyl}benzamide |
| 46 | 2-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide |
| 47 | 3-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide |
| 48 | 5-(aminomethyl)-1-ethyl-N-(tetrahydro-2H-pyran-4-yl)-1H-pyrazolo[3,4-b]pyridin-4-amine hydrochloride |
| 49 | 4-[(6-bromohexanoyl)amino]-N-{[1,6-diethyl-4-(tetrahydro-2H-pyran-4-ylamino)-1H-pyrazolo[3,4-b]pyridin-5-yl]methyl}benzamide |
| 50 | 4-[(7-bromoheptanoyl)amino]-N-{[1,6-diethyl-4-(tetrahydro-2H-pyran-4-ylamino)-1H-pyrazolo[3,4-b]pyridin-5-yl]methyl}benzamide |
| 51 | 4-[(10-bromodecanoyl)amino]-N-{[1,6-diethyl-4-(tetrahydro-2H-pyran-4-ylamino)-1H-pyrazolo[3,4-b]pyridin-5-yl]methyl}benzamide |
| 52 | 4-[(11-bromoundecanoyl)amino]-N-{[1,6-diethyl-4-(tetrahydro-2H-pyran-4-ylamino)-1H-pyrazolo[3,4-b]pyridin-5-yl]methyl}benzamide |
| 53 | 4-[(8-bromooctanoyl)amino]benzamide |
| 54 | 4-({8-[(2-hydroxyethyl)(methyl)amino]octanoyl}amino)benzamide |
| 55 | 2-[(8-{[4-(aminocarbonyl)phenyl]amino}-8-oxooctyl)(methyl)amino]ethyl acetate |

Intermediate 1: 1-Ethyl-1H-pyrazol-5-amine

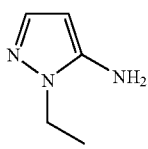

Acrylonitrile (536 g, 10.11 moles, commercially available e.g. from E. Merck) is added dropwise to hydrazine hydrate (511 g, 10.22 moles, commercially available e.g. from Qualigens Fine Chem.) maintaining the reaction temperature between 30 and 35° C. (a little exothermicity can be observed). After completion of the addition the reaction mixture is stirred at the same temperature for an additional hour. Water from the mixture is removed at 45-50° C. under reduced pressure to give the Michael addition product (2-cyanoethylhydrazine, e.g. this can be a pale yellow oil), which can be used in the next step without further purification.

A solution of acetaldehyde (561 ml, 9.99 moles, commercially available e.g. from Sigma-Aldrich) in ethanol (1008 ml) is added dropwise to a stirred solution of 2-cyanoethylhydrazine (835 g, 9.82 moles) in ethanol (700 ml) at such a rate that the temperature does not rise above 35° C. The batch is heated under reflux for 1 hour and ethanol is removed under reduced pressure to afford the Schiff's base (e.g. this can be a pale yellow oil), which can be directly used in the subsequent step.

The Schiff's base is added to a stirred mixture of sodium-tert-butoxide (908 g, 9.46 mol) in t-butanol and the reaction mixture is heated under reflux for 12 hours. The cooled reaction mixture is then poured into water (23 L), stirred for 0.5 hours and extracted with diethyl ether (1×10 L and 3×6 L). The combined organic layer is dried (Na$_2$SO$_4$) and the solution is evaporated to dryness. The residue is dissolved in dichloromethane (1.5 L) to remove impurities and the solvent is evaporated to dryness to give the title compound (e.g. this can be a red oil), which can optionally be used without further purification.

Intermediate 2: Diethyl (1-chloropropylidene)propanedioate

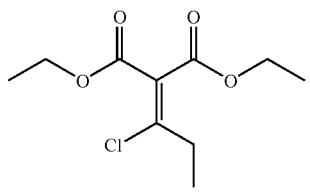

To a mixture of diethyl malonate (704 g, e.g. available from Spectrochem) and acetonitrile (3.8 L) was added anhydrous magnesium chloride immediately (419 g, e.g. available from Lancaster). Triethylamine (1222 ml) was added dropwise, maintaining the temperature at 5-10° C., followed by the dropwise addition of propionyl chloride (406 g), maintaining the temperature at or below 30° C. The reaction mixture was kept at 10-15° C. for 1 hour, and then the mixture was kept overnight at room temperature. The next day, aqueous hydrochloric acid (1 M) was added to the reaction mixture until the pH of the mixture was about 2.0 (approx. 4.8 L was required). The mixture was extracted with diethyl ether (3×800 ml). The combined ethereal extracts were washed with aqueous hydrochloric acid (1M, 2×1000 ml), followed by water (2×1000 mL) and finally with brine (2×1000 mL). Evaporation of the solvent from the ethereal extracts under reduced pressure afforded diethyl propanoylpropanedioate (845 g) as a yellow oil.

Tri-n-butylamine (316 ml) was added dropwise to a mixture of the above keto-diester derivative (300 g) in phosphorus oxychloride (POCl$_3$, 3.1 L) at room temperature. The reaction mixture was then heated under reflux for 7 hours. After cooling to room temperature, excess phosphorus oxychloride was removed by distillation under reduced pressure. The reaction mixture was then cooled to room temperature and extracted with a 1:2 mixture of hexane and diethyl ether (3×1.2 L). The combined organic extracts were washed with aqueous hydrochloric acid (1 M, 1×1 L), aqueous sodium hydroxide solution (0.1 M, 2×500 ml), brine (2×500 ml) and dried. Evaporation of the solvent under reduced pressure afforded the title compound (245 g) as a red oil which was not further purified.

Intermediate 2A:Diethyl (1-chloro-1-propen-1-yl)propanedioate and/or diethyl (1-chloropropylidene)propanedioate There are two stages to this reaction, as follows:
"Stage 1a": Preparation of Diethyl Propanoylpropanedioate

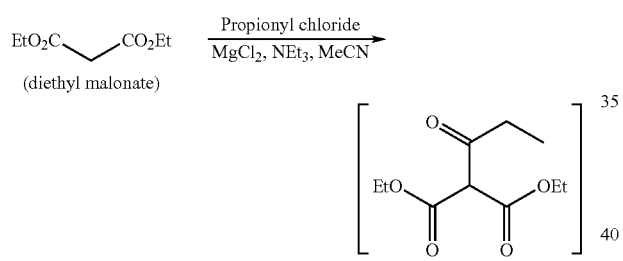

The following reaction was conducted under a nitrogen atmosphere. The volumes and equivalents stated are relative to the diethyl malonate.

Diethyl malonate (25 g, 23.7 ml, 0.156 mol, 1.0 equivalent) was charged to a clean dry reaction vessel followed by acetonitrile (125 ml, 5 volumes). The solution was cooled to 0-5° C. Anhydrous magnesium chloride (MgCl$_2$, 15.04 g, 0.158 mol, 1.01 equivalents) was added in 6 portions over 15 minutes, ensuring the internal temperature (T$_{int}$) was less than 20° C. (the maximum internal temperature during the addition (T$_{max}$) actually was 15° C.). The slurry was cooled to 0-5° C. and triethylamine (43.3 ml, 31.59 g, 0.312 mol, 2.0 equivalents) was slowly charged to the vessel from a dropping funnel over 27 minutes, maintaining T$_{int}$<20° C. (T$_{max}$ actually was 9° C.). A solution of propionyl chloride (13.7 ml, 14.59 g, 0.158 mol, 1.01 equivalents) in acetonitrile (10 ml) was added slowly via a dropping funnel to the reaction mixture over 20 minutes, maintaining T$_{int}$<20° C. (T$_{max}$ actually was 15° C.). The reaction mixture was stirred at 10-15° C. for about 54-60 minutes, and then allowed to warm to 20-25° C. (cooling removed) and stirred at 20-25° C. for about 2 hours. The reaction mixture was cooled. Toluene (50 ml) was then added in one portion, followed by 1 M aqueous hydrochloric acid (115 ml) which was added over 9 minutes via a dropping funnel (during which time an ice bath was used, with T$_{max}$ being 19° C.). The reaction mixture was stirred for 35 minutes, and then transferred to a separating funnel after standing for 5 minutes. Some grey solids were observed in the organic layer. The pH of the aqueous layer was about 6. Aqueous hydrochloric acid (2 M, 23 ml) was added, after which the pH of the aqueous layer was about 0-1. The two layers were then separated and the aqueous layer was back-extracted with toluene (50 ml). The back extraction was repeated. The combined organic layers were then washed with 1 M citric acid (50 ml) (whereupon the organic layer became milky), followed by 2 M aqueous hydrochloric acid (40 ml), water (40 ml), 15 wt % brine solution (50 ml) and a further 15 wt % brine solution (50 ml). The resulting slightly translucent opalescent organic layer was concentrated using a rotary evaporator to a volume of 100 ml. The yield of the reaction using a 1H NMR assay was calculated as about 32.3 g, about 0.149 moles, about 95.8% theory yield. This mixture of diethyl propanoylpropanedioate in toluene was used directly in the Stage 1b reaction below.

"Stage 1b": Preparation of Diethyl (1-Chloro-1-Propen-1-Yl)Propanedioate

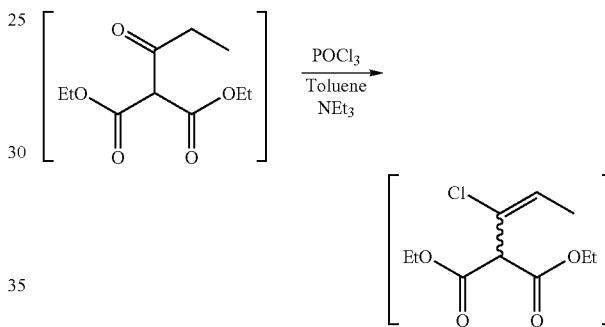

The following reaction was conducted under a nitrogen atmosphere.

Triethylamine (19.17 ml, 16.59 g, 0.1639 moles, 1.1 equivalents) was added in four portions to a reaction vessel containing the 100 ml toluene solution of diethyl propanoylpropanedioate [calculated by 1H NMR to contain about 32.3 g (about 0.149 moles, 1 equivalent) of diethyl propanoylpropanedioate] which was prepared in the Intermediate 2 (Stage 1a) process disclosed hereinabove. The reaction mixture was heated to 70° C. A mixture of phosphorus oxychloride (POCl$_3$, 20.83 ml, 34.27 g, 0.2235 moles, 1.5 equivalents) in toluene (60 ml) was slowly added to the rapidly-stirred reaction vessel, maintaining T$_{int}$<85° C. The contents were then stirred at 85° C. for about 21 hours. The reaction mixture was then cooled using an ice bath to approximately 5° C., and water (90 ml) was added over 1 hour (with the first 70 ml added very slowly), with the maximum internal temperature during the addition (T$_{max}$) being 18° C. The biphase was vigorously stirred at 5-10° C. for 15 minutes, and then the two layers were allowed to separate. The aqueous layer was separated and discarded. To the organic layer was added water (90 ml) in one portion and the mixture stirred for 15 mins and then allowed to separate. Due to slow separation and/or partial emulsification at the interface, most of the aqueous layer was removed, and then brine (20 ml) was added in an attempt to aid the separation. After 20 mins, the aqueous layer, including some emulsion and solid/scum from the interface, was separated and discarded. 1M Sodium bicarbonate solution (90 ml) was added to the organic layer and the biphase was stirred for 30 minutes. After the two layers were separated, extra toluene (60 ml) was added to the organic layer. The organic layer was concentrated to 100 ml volume in vacuo. The yield of the reaction using a 1H NMR assay was calculated as about 28.2 g, about 0.120 moles, about 80.7% theory yield.

Note: 1H NMR analysis, of a mini-worked-up sample of the crude reaction mixture and/or of the final toluene product solution, appears to suggest that the major product of the reaction is the unconjugated vinyl chloride, diethyl (1-chloro-1-propen-1-yl)propanedioate, as illustrated above.

Intermediate 2B:Diethyl {1-[(1-ethyl-1H-pyrazol-5-yl)amino]propylidene}propanedioate ("Stage 1c" preparation)

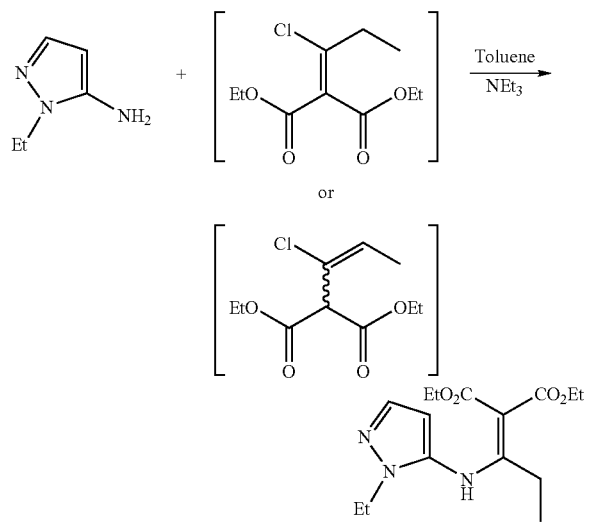

The following reaction was conducted under a nitrogen atmosphere.

5-Amino-1-ethylpyrazole (5.85 g, 0.0526 moles, 1.06 equivalents) was added in one portion to 31.35 g of a solution at room temperature, wherein the solution is of diethyl (1-chloro-1-propen-1-yl)propanedioate and/or diethyl (1-chloropropylidene)propanedioate (about 11.65 g, 0.0496 moles, 1.0 equivalent) in toluene (about 19.70 g). Triethylamine (14 ml, 10.05 g, 0.0993 moles, 2.0 equivalents) was added slowly to the reaction mixture ensuring $T_{int}$<30° C. by use of an ice bath. The reaction mixture was then heated at 90° C. for approximately 15.5 hours and then was allowed to cool to room temperature. The reaction mixture was filtered, the filter cake washed with toluene (23 ml), and then the filter cake was pulled dry. Toluene (12 ml) was added to the filtrate, and the solution was concentrated in vacuo to about 55 ml volume. Toluene (12 ml) was added to the solution which was then concentrated down to about 55 ml, and this toluene (12 ml) addition and evaporation was repeated. The toluene solution (about 55 ml) washed with 2M aqueous sodium hydroxide solution (55 ml), and the two layers were separated. The organic layer was concentrated to dryness to yield diethyl {1-[(1-ethyl-1H-pyrazol-5-yl)amino]propylidene}propanedioate as a brown liquid (11.11 g, about 72% theory yield). HPLC (5 min generic solvent gradient): $T_{RET}$ about 3.05. Mass Spectrum: Found: MH$^+$ 310.1, (M-H)$^-$ 308.1.

Intermediate 2C:Ethyl 1,6-diethyl-4-hydroxy-1H-pyrazolo[3,4-b]pyridine-5-carboxylate ("Stage 1d" preparation)

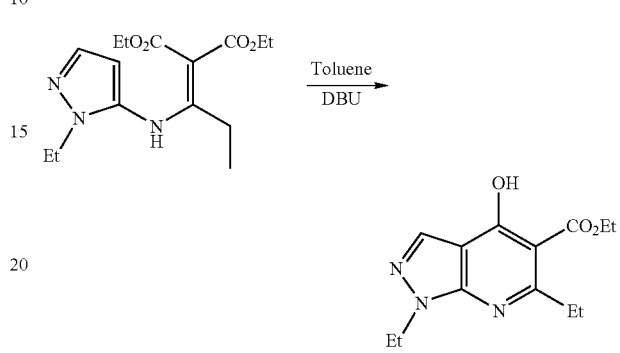

The following reaction was conducted under a nitrogen atmosphere.

Diethyl {1-[(1-ethyl-1H-pyrazol-5-yl)amino]propylidene}propanedioate (1.00 g, 3.23 mmol, e.g. which can be as prepared in Intermediate 2B) was dissolved in toluene (8 ml). To the resulting dark orange solution, 1,8-diazabicyclo[5.4.0]undec-7-ene ("DBU", 0.97 ml, 0.98 g, 6.46 mmol, 2.0 equivalents) was added, and the reaction mixture was heated at reflux for 17 hours. Further toluene (8 ml) was added to the reaction mixture, after a reduction in volume after heating had been noted. The reaction mixture was allowed to cool, and washed with water (8 ml). The two layers were separated, and the organic layer was discarded after HPLC analysis suggested that the majority of the product was in the aqueous layer. The aqueous layer, whose pH was 12, was acidified to pH 1 using concentrated aqueous hydrochloric acid (0.6 ml), whereupon gas was seen to evolve and solid precipitated spontaneously from solution. This solid was filtered and washed with water. The resulting beige solid (0.55 g) was dried in a vacuum oven at 60° C. overnight. The title compound was obtained as a beige solid (0.46 g, about 54% theory yield). HPLC (5 min generic solvent gradient): $T_{RET}$ about 2.33. Mass Spectrum: Found: MH$^+$ 264.1, (M-H)$^-$ 262.1.

Intermediate 3:Ethyl 4-chloro-1,6-diethyl-1H-pyrazolo[3,4-b]pyridine-5-carboxylate

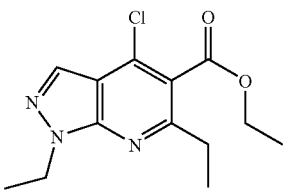

Triethylamine (230 ml) was added dropwise to a mixture of diethyl (1-chloropropylidene)propanedioate (208 g, e.g.

which can optionally be as prepared in Intermediate 2) and 1-ethyl-1H-pyrazol-5-amine (101 g, e.g. which optionally be as prepared in Intermediate 1) in toluene (2.65 L). The mixture was heated under reflux for 16 hours. The reaction mixture was then cooled to room temperature, and filtered through a sintered glass funnel to remove the solid present. The filtrate was evaporated under reduced pressure. The residue was then treated with phosphorus oxychloride (POCl$_3$, 2.65 L) and the mixture was heated under reflux for 16 hours. Excess phosphorus oxychloride was removed by distillation (e.g. under reduced pressure). The reaction mixture was then cooled and poured onto a mixture of saturated aqueous sodium hydrogen carbonate solution (4 L) and ethyl acetate (1.5 L), maintaining the temperature at 5° C. The organic layer was separated and the aqueous layer further extracted with ethyl acetate (2×1 L). The combined organic extracts were washed with aqueous sodium hydrogen carbonate solution (1×2 L, e.g. optionally a saturated solution thereof) and were dried (Na$_2$SO$_4$). Evaporation of solvent under reduced pressure afforded the crude product (202 g). The crude product was purified by chromatography (silica gel 60-120 mesh, 3.5 kg) eluting with 3% ethyl acetate in hexane. Fractions containing the product were pooled and evaporated to give the title compound (133 g) (which in one embodiment can be e.g. a pale yellow thick liquid or oil which may solidify on standing). 1H NMR (200 MHz, chloroform-d) δ (delta) ppm 1.37 (3H, t, J=7.1 Hz), 1.45 (3H, t, J=7.1 Hz), 1.57 (3H, t, J=7.2 Hz), 2.91 (2H, q, J=7.1 Hz), 4.48 (2H, q, J=7.2 Hz), 4.57 (2H, q, J=7.1 Hz) 8.05 (1H, s).

Intermediate 3 (alternative preparation):Ethyl 4-chloro-1,6-diethyl-1H -pyrazolo[3,4-b]pyridine-5-carboxylate ("Stage 2a" preparation)

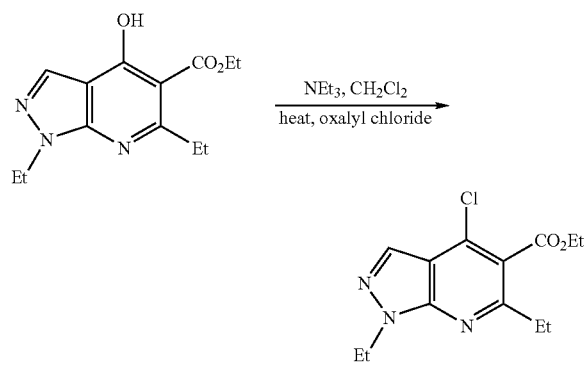

The following reaction was conducted under a nitrogen atmosphere.

Ethyl 1,6-diethyl-4-hydroxy-1H-pyrazolo[3,4-b]pyridine-5-carboxylate (0.10 g, 0.38 mmol, 1 equivalent, e.g. which can be as prepared in Intermediate 2C) was dissolved in dichloromethane (1.5 ml). Oxalyl chloride (0.07 ml, 0.10 g, 0.76 mmol, 2.0 equivalents) was added in one portion to the stirred solution. The reaction mixture, a solution, was stirred at room temperature for 2 hours, then was heated to 39° C. and stirred for 22.5 hours at this temperature, and then allowed to cool. The reaction mixture was diluted with toluene and then the solvent was removed in vacuo to give a brown oil which solidified on standing at room temperature to yield the title compound as a brown solid (0.086 g, about 80% theory yield).

HPLC (5 min generic solvent gradient): T$_{RET}$ about 3.43. Mass Spectrum: Found: MH$^+$ 282.1.

Intermediate 4:Ethyl 1,6-diethyl-4-(tetrahydro-2H-pyran-4-ylamino)-1H-pyrazolo[3,4-b]pyridine-5-carboxylate

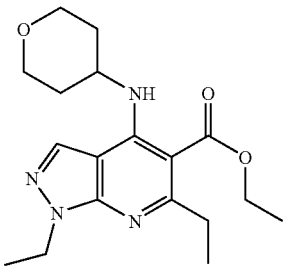

To a solution of ethyl 4-chloro-1,6-diethyl-1H-pyrazolo[3,4-b]pyridine-5-carboxylate (36.0 g, 127.8 mmol, 1 equivalent, e.g. which can optionally be as prepared in Intermediate 3) in N-methyl-2-pyrrolidinone (NMP, 300 ml) was added N,N-diisopropylethylamine (44.51 ml, 33.03 g, 255.6 mmol, 2.0 equivalents), resulting in a colour change from yellow to orange. Tetrahydro-2H-pyran-4-amine (15.51 g, 153.3 mmol, 1.2 equivalents, commercially available e.g. from Peakdale or Combi-Blocks) was added, and the reaction mixture was heated at 115° C. with stirring overnight (for about 21.5 hours). The reaction mixture was cooled to room temperature and poured into water (1200 ml), forming an oily orange mixture. This mixture was extracted with ethyl acetate (4×250 ml). The organic extracts were combined, were washed with water (50 ml) and 5% aqueous lithium chloride solution (50 ml), and were dried (brine/MgSO$_4$), filtered and evaporated to give an orange oil (46.25 g) as the residue. This residue was purified by silica gel (1 kg) chromatography, eluting with 2:1 cyclohexane:ethyl acetate (6000 ml) followed by 1:1 cyclohexane:ethyl acetate (3000 ml). The fractions containing the product only (whose RF is about 0.40 by TLC in 2:1 cyclohexane:ethyl acetate) were pooled and evaporated to give the title compound as a mobile yellow oil (33.90 g, ca. 76.6% yield) which solidified to a yellow solid on standing. LCMS m/z 347 [MH$^+$]; T$_{RET}$=3.01 min.

Intermediate 4 (alternative preparation):Ethyl 1,6-diethyl-4-(tetrahydro-2H-pyran-4-ylamino)-1H-pyrazolo[3,4-b]pyridine-5-carboxylate ("Stage 2b" preparation)

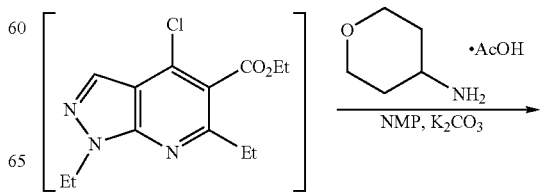

-continued

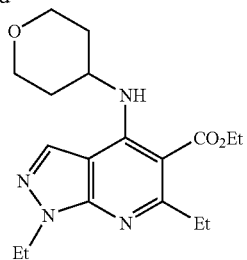

The following reaction was conducted under a nitrogen atmosphere.

Ethyl 4-chloro-1,6-diethyl-1H-pyrazolo[3,4-b]pyridine-5-carboxylate [0.75 g, 2.66 mmol, 1.0 equivalent] was dissolved in 1-methyl-2-pyrrolidinone (NMP, 4 ml). 4-Aminotetrahydro-2H-pyran acetate (0.51 g, 3.19 mmol, 1.2 equivalents) was added in one portion to the stirred solution at room temperature. The reaction mixture was stirred for 15 minutes and then potassium carbonate (1.10 g, 7.99 mmol, 3.0 equivalents) was added in one portion. The reaction mixture was heated to and at 100° C. for 16 hours, and then cooled before partitioning between ethyl acetate (25 ml) and water (25 ml) whereupon an emulsion formed. To this biphase mixture/emulsion was added brine, followed by water (20 ml) and then ethyl acetate (20 ml), to aid separation. The two layers were separated and the aqueous layer washed with ethyl acetate (20 ml). The organic layers were combined and washed with 1M aqueous hydrochloric acid (3×25 ml). To the combined aqueous layers was added ethyl acetate (25 ml); the resulting biphasic mixture was stirred vigorously, and then 10M aqueous sodium hydroxide solution (14.5 ml) was added to this stirred mixture until the pH of the now-warm mixture was measured to be about 13. The mixture was allowed to separate. The separated aqueous layer washed with ethyl acetate (20 ml). The combined organic layers were washed with water (20 ml) followed by brine (20 ml). The organic layer was concentrated to dryness to give an orange oil which visually appeared to contain sodium chloride or similar crystals. This oil was dissolved in ethyl acetate and washed with a minimal amount of water; separation was poor. The organic layer was separated and concentrated to dryness, to give the title compound as an orange oil (still containing some crystals) which solidified after standing overnight at room temperature (0.58 g, about 63% yield).

Intermediate 5: [1,6-Diethyl-4-(tetrahydro-2H-pyran-4-ylamino)-1H-pyrazolo[3,4-b]pyridin-5-yl]methanol

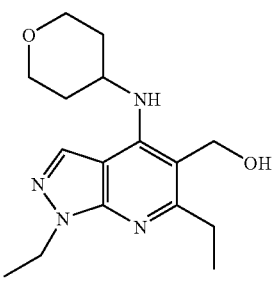

A solution of ethyl 1,6-diethyl-4-(tetrahydro-2H-pyran-4-ylamino)-1H-pyrazolo[3,4-b]pyridine-5-carboxylate (17.94 g, 51.85 mmol, e.g. which can optionally be as prepared in Intermediate 4) in dichloromethane (150 ml) was cooled to 0° C. under an atmosphere of nitrogen, and was treated with di-iso-butylaluminum hydride (100 ml of a 1.5 M solution in toluene, 150 mmol) added dropwise over 30 minutes, keeping the temperature steady at 0° C. The reaction was stirred at 0° C. for a further 30 minutes after completion of the addition. The reaction was quenched by the dropwise addition of saturated aqueous potassium sodium tartrate solution (120 ml), keeping the temperature below 5° C. The resulting mixture was diluted with ethyl acetate (300 ml) and the whole filtered through a pad of Celite, to form two layers. During this filtration the sinter funnel imploded. Material spilt on the fumehood floor was soaked up and recovered as much as possible. The organic layer was separated and dried ($MgSO_4$), the drying agent was filtered off, and the filtrate evaporated to give a first batch of product. The aqueous layer and the celite were extracted with a larger amount of ethyl acetate to give a second batch of product after evaporation. The two batches of product were combined to give the title compound (14 g) as an off-white waxy solid.

Intermediate 5 (Alternative Preparation No. 1):[1,6-Diethyl-4-(tetrahydro-2H-pyran-4-ylamino)-1H-pyrazolo[3,4-b]pyridin-5-yl]methanol

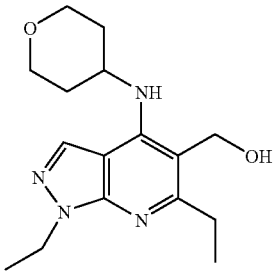

To a mixture of ethyl 1,6-diethyl-4-(tetrahydro-2H-pyran-4-ylamino)-1H-pyrazolo[3,4-b]pyridine-5-carboxylate (60.43 g, 174 mmol, 1 equivalent, e.g. which can optionally be as prepared in Intermediate 4) in dry tetrahydrofuran (300 ml) was added dry methanol (28.3 ml, 22.3 g, 698 mmol, 4 equivalents), followed by slow addition of lithium borohydride ($LiBH_4$, 2 M solution in tetrahydrofuran, 262 ml, 523 mmol, 3 equivalents) over 30 minutes. The mixture was heated as the lithium borohydride was added, reaching reflux after about 20 minutes. Further aliquots of methanol (14.1 ml, 2 equivalents, each time) were added after 1 hour and again after 1.5 hours, and the heating was continued for a further 30 minutes (for 2 hours total). The reaction mixture was cooled (ice/water bath) and was carefully treated with methanol (100 ml, non-dried) followed by cautious addition of water (200 ml) which resulted in cloudiness and then a precipitate. Addition of more water (800 ml) produced a more homogenous suspension which was stirred for 1 hour and which was then extracted with dichloromethane (about 1.5 L total volume). The organic extracts were combined, were washed with water and then brine, and were dried and evaporated to give the title compound as a white solid (49.84 g). LCMS m/z 305 [MH$^+$]; $T_{RET}$=1.79 and 1.83 min (double peak).

Intermediate 5 (Alternative Preparation No. 2, Plant Method):[1,6-Diethyl-4-(tetrahydro-2H-pyran-4-ylamino)-1H-pyrazolo[3,4-b]pyridin-5-yl]methanol

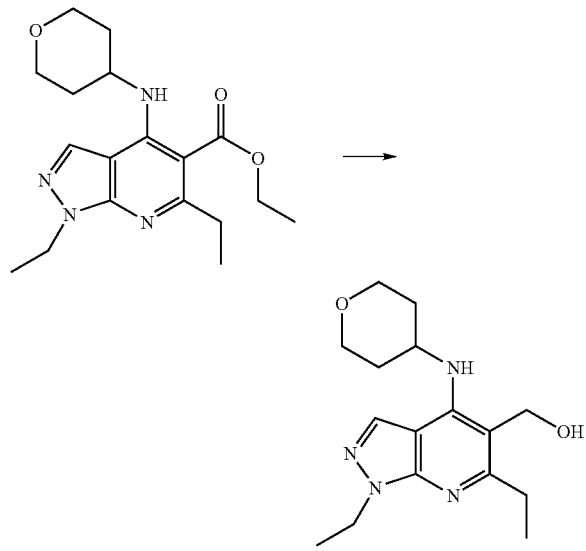

Summary of Plant Method

All weights, volumes (vol., vols) and equivalents are relative to the ethyl 1,6-diethyl-4-(tetrahydro-2H-pyran-4-ylamino)-1H-pyrazolo[3,4-b]pyridine-5-carboxylate.

The reaction is conducted under a nitrogen atmosphere, in a plant, and the organic reaction solvents are usually dry or moderately dry.

To a stirred solution of lithium borohydride (LiBH$_4$, 3 eq, 4.34 vol, 2M solution in tetrahydrofuran (THF)) and dry toluene (4 vols) at 64-68° C., is added a solution of ethyl 1,6-diethyl-4-(tetrahydro-2H-pyran-4-ylamino)-1H-pyrazolo[3,4-b]pyridine-5-carboxylate (1 wt, e.g. which can optionally be as prepared in Intermediate 4) in dry THF (1 vol.) and dry methanol (9 eq, 1.05 vol.) over at least 2.5 hours. The reaction is monitored by HPLC and is typically complete about 60 minutes (50-70 mins) after the end of the addition. The reaction mixture is then cooled down to 20±3° C., and water (3 vol.) is added dropwise over at least 30 mins followed by aqueous sodium hydroxide solution (10.8M, about 32% w/w, 6.0 vols, 8.1 wt) (dropwise over about 30-40 mins), ensuring the temperature remains below 40° C. The temperature of the reaction is then adjusted to 37±3° C. and stirred vigorously for at least 90 minutes. The organic layer and aqueous layer are separated and the aqueous layer is treated with sulphuric acid (11 vol., 13.2 wt) to remove any remaining lithium borohydride. Water (2.5 vols) is added to the organic layer over at least 30 mins followed by aqueous sodium hydroxide solution (10.8M, about 32% w/w, 2 vols, 2.7 wt) over about 30-40 mins, and the biphase is stirred vigorously at 37±3° C. for at least 30 minutes. The organic layer is again separated and the organic solution is concentrated in vacuo to 3 vols, which precipitates the product, usually as yellow solid. Toluene (3 vol.) is then added and the slurry is reconcentrated in vacuo to 3 vol. The suspension is then cooled to 10±3° C. and aged for at least 30 min. The solid is then filtered and washed with toluene (3 vol.). The product [1,6-d]ethyl-4-(tetrahydro-2H-pyran-4-ylamino)-1H-pyrazolo[3,4-b]pyridin-5-yl]methanol is then dried in vacuo at about 45° C. to constant temperature.

Step-wise Methodology Used in One Pilot Plant Batch

All weights, volumes (vol., vols) and equivalents are relative to the ethyl 1,6-diethyl-4-(tetrahydro-2H-pyran-4-ylamino)-1H-pyrazolo[3,4-b]pyridine-5-carboxylate.

The reaction was conducted under a nitrogen atmosphere, in a pilot plant.

1. Making up solution of ethyl 1,6-diethyl-4-(tetrahydro-2H-pyran-4-ylamino)-1H-pyrazolo[3,4-b]pyridine-5-carboxylate:
Dry THF (1 vol., 11 liters) was charged to a glass lined reactor followed by dry methanol (1.0 vol., 11 liters), the mixture was stirred at 20±5° C. for about 10 min at 75 rev./min, and ethyl 1,6-diethyl-4-(tetrahydro-2H-pyran-4-ylamino)-1H-pyrazolo[3,4-b]pyridine-5-carboxylate (1 wt, 11.0 kg) was added. The walls of the charge hole (for the solid ethyl 1,6-diethyl-4-(tetrahydro-2H-pyran-4-ylamino)-1H-pyrazolo[3,4-b]pyridine-5-carboxylate) were washed clean with dry methanol (0.05 vol., 0.55 liters) which went into the reactor. The contents of the glass lined reactor were stirred at 20±5° C. for about 1 hr 11 minutes at 75 rev./min.
2. Dry toluene (4 vol., 44 liters) was charged to a separate glass lined reactor and the contents were stirred.
3. A 2M solution of lithium borohydride in THF (3.89 wt, 42.8 kg) was charged to the stirred toluene-containing reactor over about 1 hour from a cylinder using a pyrophoric dispensing manifold. The contents of the reactor were heated to 66±3° C. (target range 64-68° C.) over about 50 mins.
4. The solution made up in step 1 was then charged to the stirred toluene and LiBH$_4$ solution via a peristaltic pump over 2 hrs 34 minutes, maintaining the reactor contents at a temperature of 66±3° C. (target range 64-68° C.) whilst maintaining an even paced addition rate.
5. After the addition of the ethyl 1,6-diethyl-4-(tetrahydro-2H-pyran-4-ylamino)-1H-pyrazolo[3,4-b]pyridine-5-carboxylate, the reaction contents were stirred at 66±3° C. (target range 64-68° C.) (contents temperature) at 75 rev./min for 65 minutes, and the reaction was sampled for HPLC analysis. HPLC indicated <6% a/a (about 4.7%) of the ethyl 1,6-diethyl-4-(tetrahydro-2H-pyran-4-ylamino)-1H-pyrazolo[3,4-b]pyridine-5-carboxylate remaining, and so the reaction was considered complete.
6. Straight after the sample has been taken, the contents were cooled to 20±3° C. over about 30 mins with stirring.
7. With the stirrer speed of the reactor increased to 125 rev./min, water (3 wt, 33.00 kg, 33 liters) was added to the reaction via a peristaltic pump over 33 minutes, during which the contents temperature was kept below 40° C. ($T_{max}$ of the contents was 32° C.). During this water addition the product usually precipitates forming a thick suspension.
8. After the water addition was complete the reactor contents were cooled to 20±5° C.
9. Aqueous sodium hydroxide solution (about 32% w/w, 8.1 wt, 89.10 kg) was added to the reactor via a peristaltic pump over 35 minutes.
10. After the addition of the sodium hydroxide solution, the contents of the reactor were stirred at 37±3° C. for 90 minutes.
11. The agitator was stopped and the layers were allowed to separate for at least 15 min.
12. The lower aqueous layer was separated and transferred to another vessel.

13. The upper organic layer was cooled to 20±3° C., and was held for about 9.5 hours.
13A. With the stirrer speed of the reactor increased to 125 rev./min, water (2.5 wt, 27.50 kg) was added to the organic layer via a peristaltic pump over 30 minutes, during which time the contents temperature was kept below 40° C.
14. The reactor contents were cooled to 20±5° C., and aqueous sodium hydroxide solution (about 32% ww, 2.7 wt, 29.70 kg) was added via a peristaltic pump over 35 minutes.
15. The contents of the reactor were stirred at 37±3° C. for 33 minutes.
16. The stirrer was stopped and the layers were allowed to separate for 15 minutes.
17. The lower aqueous layer was separated and transferred to another vessel.
18. The remaining reactor contents (organic layer) was stirred and cooled to 5±3° C. and then medium vacuum was applied (about −0.8 to −0.85 barg vacuum) to degas the reactor contents (to remove the hydrogen formed in the reaction).
19. The reactor contents were adjusted to 5° C. with stirring, and the reactor contents were heated under a vacuum of about −0.83 barg. Initially the reactor contents were heated to about 26° C. and eventually to about 45° C., to remove solvent by vacuum distillation until the batch was concentrated to about 33 liters (about 3 vols). The distillation is complete after 4.5 hours of heating, leaving a slurry in the reactor.
20. The vacuum was released and toluene (3 vols, 33 liters) was charged to the reactor.
21. The reactor contents were adjusted to 5° C. with stirring.
22. The reactor contents were heated, under a vacuum ranging from about −0.84 barg to about −0.91 barg. The reactor contents were heated to about 40° C. (at about −0.84 barg) and then to a maximum of 46° C. (at about −0.88 barg) and then to about 40° C. (at about −0.91 barg), to remove solvent by vacuum distillation until the batch was concentrated to about 33 liters (about 3 vols). The distillation was complete after about 4 hours 18 minutes of heating.
23. The vacuum was released and the contents were cooled to 10±3° C. and stirred at this temperature for about 6.25 hours at 75 rev./min.
24. The resulting slurry was then transferred to a 20 micron filter cloth, and filtered under nitrogen pressure (0.5-1 barg).
25. The filter cake washed with toluene (3 vol., 33 liters) under nitrogen pressure (0.5-1 barg), and then solvent was blown from the filter cake using nitrogen pressure over 11 minutes.
26. The damp filter cake was transferred to polythene lined trays, covered with muslin bags, placed in a vacuum tray dryer, and was dried by heating to 47±3° C. under vacuum (using a 5 L/min nitrogen bleed to the dryer, to minimise build-up of condensed solvents in the oven), until a constant temperature of the solid was measured for at least 4 hours. The batch was cooled to below 30° C.
27. The product [1,6-diethyl-4-(tetrahydro-2H-pyran-4-ylamino)-1H-pyrazolo[3,4-b]pyridin-5-yl]methanol was obtained as a solid (8.55 kg, 88.5% theory yield).

*Note: The remaining additional steps, below, concern the acidic quenching of the aqueous layers and mother liquors which is done for safety reasons to remove any borohydride residues left in these solutions on plant. These stages are waste management steps, separate to the core production of product, and so are not essential and may or may not be performed as is desired.

28. The aqueous layers from step 12 & 17 are stirred and cooled to 5±3° C.
29. 5M sulphuric acid (13.2 wt, 145.2 kg) is charged to the aqueous layers via peristaltic pump over 3 hrs 52 minutes maintaining a contents temperature below 40° C.
30. Post the acid addition, the contents are stirred at 5±5° C. for 2 hrs 18 minutes. The pH is checked, if the pH<3 the quench is considered complete.
31. The reactor is degassed using vacuum and purging with nitrogen before the aqueous solution is discharged and labelled as waste.
32. The mother liquors produced during the filtration steps (24 & 25) are transferred to a reactor, stirred and cooled to 5±3° C.
33. Water (5 liters) is charged to the liquors.
34. 5M sulphuric acid (1 kg) is charged to the aqueous layers via peristaltic pump over 1 hr maintaining a contents temperature below 40° C.
35. After the acid addition, the contents are stirred at 5±5° C. for 2 hrs 18 minutes. The pH is checked; if the pH<3 the quench is considered complete.
36. The reactor is degassed using vacuum and purging with nitrogen before the biphasic solution is discharged and labelled as waste.

Intermediate 6: 5-(Azidomethyl)-1,6-diethyl-N-(tetrahydro-2H-pyran-4-yl)-1H-pyrazolo[3,4-b]pyridin-4-amine

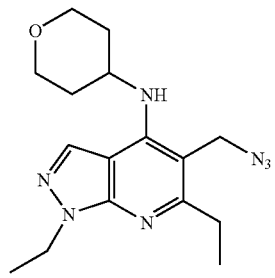

Thionyl chloride (SOCl$_2$, 50.37 ml, 82.11 g, 69 mmol) was added dropwise over 15 minutes to a suspension of [1,6-d]ethyl-4-(tetrahydro-2H-pyran-4-ylamino)-1H-pyrazolo[3,4-b]pyridin-5-yl]methanol (13.98 g, 46 mmol, e.g. which can optionally be as described in Intermediate 5) in toluene (140 ml) at room temperature. The mixture was then heated at reflux at about 85° C. for 4 hours, was allowed to cool, and then was evaporated to dryness and azeotroped with three further portions of toluene. The residue obtained was dissolved in dry dimethylsulfoxide (100 ml) and treated with sodium azide (4.49 g, 69 mmol), and the mixture was stirred at room temperature for 18 hours. The mixture was poured into saturated aqueous sodium bicarbonate solution and was extracted with 3 portions of ethyl acetate. The combined organic extracts were washed with saturated brine and water, and were then dried (Na$_2$SO$_4$), the drying agent was filtered off, and the filtrate was evaporated to dryness. The residue obtained was purified by flash chromatography, eluting with 1:1 cyclohexane:ethyl acetate. Fractions containing the product without substantial amounts of impurities were evaporated to give the title compound (5.6 g+4.75 g=10.35 g).

Intermediate 7: 5-(Aminomethyl)-1,6-diethyl-N-(tetrahydro-2H-pyran-4-yl)-1H-pyrazolo[3,4-b]pyridin-4-amine

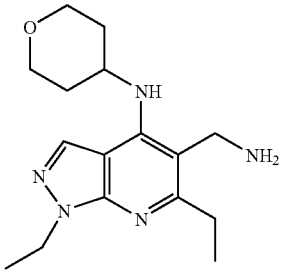

A suspension of 5-(azidomethyl)-1,6-diethyl-N-(tetrahydro-2H-pyran-4-yl)-1H-pyrazolo[3,4-b]pyridin-4-amine (10.3 g, 34 mmol, e.g. which can be as prepared in Intermediate 6) in ethanol (200 ml) was added to 10% palladium on carbon (1 g) and stirred under an atmosphere of hydrogen for 3 hours at room temperature. The catalyst was removed by filtration under nitrogen and washed well with ethanol. The filtrate was evaporated to dryness to give a dark oil. Ether was added and then evaporated to give the title compound as a foamy semi-solid (9.35 g).

Intermediate 7 (Alternative Preparation No. 1): 5-(Aminomethyl)-1,6-diethyl-N-(tetrahydro-2H-pyran-4-yl)-1H-pyrazolo[3,4-b]pyridin-4-amine In a hydrogenation flask, ethanol (300 ml) was added to 10% palladium on carbon (9.9 g, 0.2 wt. equivalents, 50% wet), followed by 5-(azidomethyl)-1,6-diethyl-N-(tetrahydro-2H-pyran-4-yl)-1H-pyrazolo[3,4-b]pyridin-4-amine (49.62 g, 151 mmol, 1 equivalent, e.g. which can be as prepared in Intermediate 6) in ethanol (900 ml). The mixture was hydrogenated overnight at room temperature and room pressure (using the Wright valve); during which the flask was vented and refilled once. The catalyst was removed by filtration and the filtrate was evaporated to give a grey solid. The residue was purified by column chromatography, using a relatively small amount of silica (1500 ml of 9385 silica), eluting initially with 5% methanol in dichloromethane (to elute some fast-moving impurities), followed by 10% and finally 15% methanol in dichloromethane to give the title compound as an almost white solid (41.25 g). LCMS m/z 304 [MH$^+$]; T$_{RET}$=1.65 and 1.69 min (split peak). NMR (d6-DMSO) showed a trace of methanol present in the product.

Intermediate 7A: 5-(Aminomethyl)-1,6-diethyl-N-(tetrahydro-2H-pyran-4-yl)-1H-pyrazolo[3,4-b]pyridin-4-amine monohydrochloride (Plant Method)

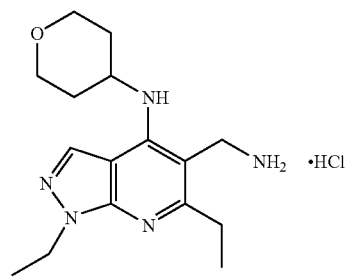

Intermediate 7A Process Scheme

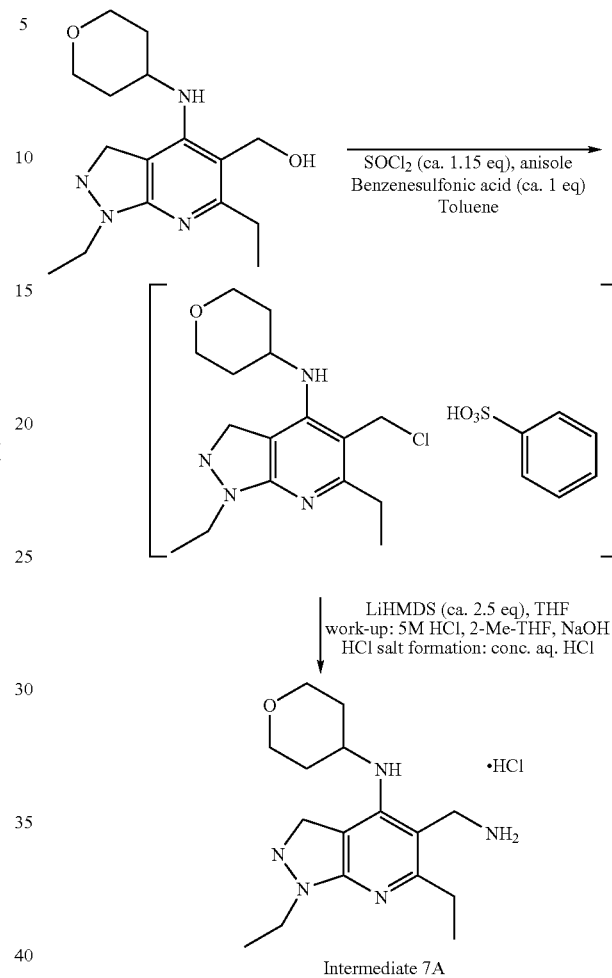

Intermediate 7A

Intermediate 7A Process Summary

All weights and volumes are relative to [1,6-d]ethyl-4-(tetrahydro-2H-pyran-4-ylamino)-1H-pyrazolo[3,4-b]pyridin-5-yl]methanol starting material, unless otherwise stated.

The reactions are conducted under an atmosphere of nitrogen in plant, and the organic reaction solvents are usually dry or moderately dry.

[1,6-Diethyl-4-(tetrahydro-2H-pyran-4-ylamino)-1H-pyrazolo[3,4-b]pyridin-5-yl]methanol (1 wt) (e.g. preferably substantially as prepared in Intermediate 5, alternative preparation no. 2, plant method) is suspended in dry anisole (5.97 wt, 6 vol) and treated with solid benzensulfonic acid (0.52 wt, about 1 equiv.). This suspension is aged at 20±5° C. for at least 30 minutes. Thionyl chloride (0.45 wt, about 1.15 equiv.) is added at 20±5° C. over at least 20 minutes, and stirred for between 20 and 30 minutes. The reaction is then sampled for HPLC. The resulting solution of 5-(chloromethyl)-1,6-diethyl-N-(tetrahydro-2H-pyran-4-yl)-1H-pyrazolo[3,4-b]pyridin-4-amine benzenesulfonate is treated with dry toluene (2 vol) and then placed under medium vacuum (about −0.85 barg, e.g. about 100-150 mbar) to remove hydrogen chloride and sulfur dioxide, and then the vacuum is increased (about −0.95 barg, e.g. about 50 mbar) to azeotrope off excess thionyl chloride and toluene.

This solution/slurry of 5-(chloromethyl)-1,6-diethyl-N-(tetrahydro-2H-pyran-4-yl)-1H-pyrazolo[3,4-b]pyridin-4-amine benzenesulfonate (ca. 7.5 vol) is added to a solution of lithium hexamethyldisilazide (LiHMDS) in tetrahydrofuran (1.3M in THF, 5.73 wt, 6.51 vol, about 2.5 equiv.) at 35±5° C. over 60-70 minutes and then stirred for a further 15 to 30 minutes.

The mixture is cooled to 10±5° C. and 5M hydrochloric acid (3.78 wt, 3.6 vol) is added. The phases are separated and the lower aqueous layer is transferred back into the vessel, and the organic phase is discarded. 2-Me-THF (2-methyl-tetrahydrofuran) (8 vol) is added and then the biphasic mixture is adjusted to pH>13 with 32% w/w aqueous sodium hydroxide solution (2.25 wt) and then warmed to 30±5° C. The layers are separated and the lower aqueous layer is back extracted with further 2-Me-THF (2 vol). The combined organic phases are washed with 15% w/w aqueous sodium chloride solution (2.2 wt).

The amount of 5-(aminomethyl)-1,6-diethyl-N-(tetrahydro-2H-pyran-4-yl)-1H-pyrazolo[3,4-b]pyridin-4-amine in solution is quantified via yieldaliser (uses a solution-based assay, using a comparator standard solution of known concentration), and an appropriate amount of 36% w/w aqueous hydrochloric acid (1.03 equivalents based on the calculated and/or measured amount of the product amine) is added at 55±5° C. The suspension is held for 2 hours at 55±5° C., and then cooled to 5±5° C. over 3 hours and held at 5±5° C. for at least 3 hours. The slurry is filtered and the separated solid is washed with 2-Me-THF (2×2 vol) and dried in vacuo at 60° C. to constant weight or batch temperature to give the product 5-(aminomethyl)-1,6-diethyl-N-(tetrahydro-2H-pyran-4-yl)-1H-pyrazolo[3,4-b]pyridin-4-amine monohydrochloride (Intermediate 7A).

Intermediate 7A: Detailed Step-wise Methodology

All weights and volumes are relative to [1,6-d]ethyl-4-(tetrahydro-2H-pyran-4-ylamino)-1H-pyrazolo[3,4-b]pyridin-5-yl]methanol starting material, _unless otherwise stated.

The reactions are conducted under an atmosphere of nitrogen in plant.

Chlorination Reaction

1. Anisole (5.97 wt, 71.6 kg) is charged to the reactor.
2. 1,6-Diethyl-4-(tetrahydro-2H-pyran-4-ylamino)-1H-pyrazolo[3,4-b]pyridin-5-yl]methanol (1 wt, 12.0 kg) (e.g. preferably substantially as prepared in Intermediate 5, alternative preparation no. 2, plant method) is charged to the reactor.
3. Benzenesulfonic acid (0.52 wt, 6.24 kg) is charged to the reactor and the contents are stirred at 20±5° C. for 34 minutes.
4. Thionyl chloride (0.45 wt, 5.4 kg) is charged to the reactor via peristaltic pump over 28 minutes, maintaining the reactor contents at 20±5° C.
5. The reactor contents are stirred at 20±5° C. for 28 minutes and then the contents are sampled for HPLC analysis. The volume of the reaction is noted.
6. Toluene (2 vols, 24 liters) is then charged to the stirred reactor.
7. The reactor contents are placed under vacuum (ca −0.85 barg) and stirred at 20±5° C. for 1 hr 6 minutes.
8. The reactor contents are then cooled to 10° C.
9. The reactor is then subjected to full vacuum for the distillation (−0.95 to −0.97 barg).
10. The batch is then heated, with an initial internal temperature of 18° C. rising to 40° C. by the end of the distillation. The end point of the distillation is the volume noted in step 5. This can be reached e.g. after 2 hrs 43 minutes of heating.
11. The vacuum is released and the contents are stirred at 20±5° C. This is the anisole slurry of 5-(chloromethyl)-1,6-diethyl-N-(tetrahydro-2H-pyran-4-yl)-1H-pyrazolo[3,4-b]pyridin-4-amine benzenesulfonate. In this example an extra charge of 15 liters of anisole is made to this slurry.

Amination Reaction

12. To a different reactor, lithium hexamethyldisilazide (LiHMDS) solution (1.3M in THF, 5.73 wt, 68.8 kg) is charged and then the contents are stirred and heated to 35±5° C.
13. The slurry of 5-(chloromethyl)-1,6-diethyl-N-(tetrahydro-2H-pyran-4-yl)-1H-pyrazolo[3,4-b]pyridin-4-amine benzenesulfonate (from step 11) is added to the LiHMDS solution in portions via a saunders valve over 46 minutes. The reactor contents temperature is maintained at 35±5° C.
14. In this example several rinses are conducted to clean the lines. A line wash of the Kammer valve line (which can become blocked) is conducted to clear residual solid using anisole (2 kg), and a vessel rinse using anisole (0.25 wt, 3.0 kg) is conducted to rinse further 5-(chloromethyl)-1,6-diethyl-N-(tetrahydro-2H-pyran-4-yl)-1H-pyrazolo[3,4-b]pyridin-4-amine benzenesulfonate into the LiHMDS solution.
15. After the residual solid is rinsed in, the amination reaction is stirred at 35±5° C. for 20 minutes.
16. The amination reaction is sampled for completion by HPLC analysis.
17. The reactor contents are then stirred and cooled to 10±5° C.
18. 5M aqueous hydrochloric acid (3.78 wt, 45.4 kg) is charged to the reactor via a peristaltic pump over 52 minutes, maintaining an internal temperature of 10±5° C.
19. The resultant biphase is stirred at 10±5° C. for at least 15 minutes.
20. The stirrer is stopped and the 2 layers are allowed to separate. The lower aqueous layer is transferred to a drum and is an aqueous solution of 5-(aminomethyl)-1,6-diethyl-N-(tetrahydro-2H-pyran-4-yl)-1H-pyrazolo[3,4-b]pyridin-4-amine hydrochloride. The pH is checked (expect pH<5).
21. The upper organic layer is discharged as waste.
22. Further line and vessel rinses are conducted running from the ex-thionyl chloride reactor vessel through the Kammer valve to the ex-amination reactor. The rinses are THF (30 liters) and water (60 liters).
23. The aqueous solution of 5-(aminomethyl)-1,6-diethyl-N-(tetrahydro-2H-pyran-4-yl)-1H-pyrazolo[3,4-b]pyridin-4-amine hydrochloride (from step 20) is charged to a reactor and stirred.
24. 2-Methyl-tetrahydrofuran (2-Me-THF) (8 vol, 96 liters) is charged to the aqueous solution.
25. Aqueous sodium hydroxide solution (32% ww, 2.25 wt, 27 kg) is charged to the reactor via a peristaltic pump over 30 minutes. Reactor contents are maintained at 10±5° C.
26. The reactor contents are heated to 30±5° C. and stirred for at least 15 minutes.
27. The stirrer is stopped and the two layers are allowed to separate. The lower aqueous layer is transferred to a drum and is an aqueous solution of the product amine. Its pH is checked (expect pH>13).
28. The upper layer is also transferred to a drum and is a 2-methyl-tetrahydrofuran solution of the product amine.

29. The aqueous solution of the product amine (from step 27) is charged to the reactor and 2-methyl-tetrahydrofuran (2-Me-THF) (2 vols, 24 liters) is added to back extract the aqueous layer further. The biphase is stirred at 30±5° C. for at least 15 minutes.

30. The stirrer is stopped and the two layers are allowed to separate. The lower aqueous layer is discharged as waste, and the upper organic layer is retained in the reactor.

31. The 2-methyl-tetrahydrofuran solution of the product amine (from step 28) is charged back into the reactor and the combined organic layers are stirred.

32. 15 wt % aqueous sodium chloride solution (2.2 wt, 26.4 kg) is charged to the reactor.

33. The biphase is heated to 30±5° C. and stirred for at least 15 minutes.

34. The stirrer is stopped and the two layers are allowed to separate. The lower aqueous layer is discharged as waste, the upper organic layer is retained in the reactor, and the volume of the solution is noted.

35. The reactor contents are sampled for HPLC analysis. An approximate yield of the product 5-(aminomethyl)-1,6-diethyl-N-(tetrahydro-2H-pyran-4-yl)-1H-pyrazolo[3,4-b]pyridin-4-amine is obtained from this analysis.

Formation and Isolation of Hydrochloride Salt of Amine

36. The contents of the reactor are heated to 55±5° C.

37. Concentrated aqueous hydrochloric acid (1.03 eq. relative to yield of 5-(aminomethyl)-1,6-diethyl-N-(tetrahydro-2H-pyran-4-yl)-1H-pyrazolo[3,4-b]pyridin-4-amine calculated in step 35, e.g. in this example this can be about 2.37 kg) is added to the reactor via a peristaltic pump over 20 minutes, maintaining the reactor contents at 55±5° C.

38. The reactor contents are stirred at 55±5° C. for 2 hrs 6 minutes.

39. The reactor contents are gradually cooled to 5±5° C. over 3 hours.

40. The slurry is then stirred at 5±5° C. for at least 3 hours. In this example, the reactor contents are stirred at 5±5° C. overnight for a stir time of 19 hrs 53 minutes.

41. The slurry is transferred to a 20 micron filter cloth, is allowed to settle for 10 mins, and is filtered under nitrogen pressure (0.5 to 1 barg).

42. The filter cake is washed with 2-methyl-tetrahydrofuran (2 vols, 24 liters) under nitrogen pressure (0.5 to 1 barg).

43. The filter cake is washed with further 2-methyl-tetrahydrofuran (2 vols, 24 liters) under nitrogen pressure (0.5 to 1 barg). Further solvent is removed from the cake by blowing under nitrogen pressure over 1 hr 40 minutes.

44. The damp filter cake is transferred to polythene lined trays, covered with muslin bags, and placed in a vacuum tray dryer. The vacuum tray dryer is put under vacuum and is heated to 60±5° C. to dry the product, using a 5 L/min nitrogen bleed to the dryer (to minimise build-up of condensed solvents in the oven). The drying is considered complete when the product temperature probe reads a constant temperature for at least 4 hours.

45. The product 5-(aminomethyl)-1,6-diethyl-N-(tetrahydro-2H-pyran-4-yl)-1H-pyrazolo[3,4-b]pyridin-4-amine monohydrochloride (Intermediate 7A) is collected as a solid, usually as a white solid.

Intermediate 8: 1,1-Dimethylethyl {4-[({[1,6-d]ethyl-4-(tetrahydro-2H-pyran-4-ylamino)-1H-pyrazolo[3,4-b]pyridin-5-yl]methyl}amino)carbonyl]phenyl}carbamate

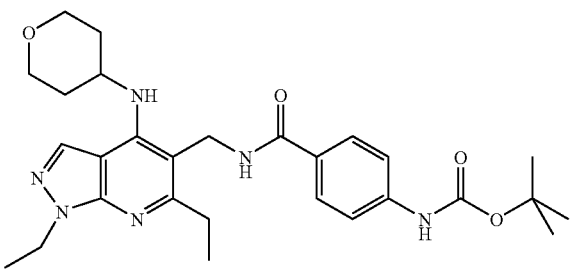

A solution of 4-({[(1,1-dimethylethyl)oxy]carbonyl}amino)benzoic acid (0.96 g, 4.05 mmol, e.g. available from Fluka) in N,N-dimethylformamide (20 ml) was treated with O-(7-azabenzotriazol-1-yl)-1,1,3,3-tetramethyluronium hexafluorophosphate (HATU, 1.7 g, 4.45 mmol, 1.1 equiv.) and then N,N-diisopropylethylamine (1.77 ml, 10.1 mmol, 2.5 equiv.). The resulting solution was allowed to stand at room temperature for 10 minutes. 5-(Aminomethyl)-1,6-diethyl-N-(tetrahydro-2H-pyran-4-yl)-1H-pyrazolo[3,4-b]pyridin-4-amine (1.24 g, 4.05 mmol, which can e.g. be as prepared in Intermediate 7) was added to this solution and the resultant mixture was allowed to stand at room temperature for 2 hours. The N,N-dimethylformamide solvent was removed by evaporation and the residue was partitioned between saturated aqueous sodium bicarbonate solution (100 ml) and dichloromethane (150 ml). The organic layer was separated and collected through a first hydrophobic frit. Meanwhile, there was some solid which did not dissolve in either the organic or aqueous layer. This solid, which contained some product, was removed by filtration, was partitioned between dichloromethane and water, and the organic layer was isolated through a second hydrophobic frit. The combined organic layers from the first and second hydrophobic frits were evaporated to dryness. The residue from the organic layers was dissolved in dichloromethane and methanol and was purified by passing through two 50 g silica SPE cartridges, eluting with a cyclohexane ethyl acetate gradient (some product eluted with 100% ethyl acetate) followed by 9:1 ethyl acetate: methanol (in which more product eluted). Fractions containing the product were combined and evaporated to dryness. Trituration with diethyl ether, and filtration and drying in vacuo of the solid gave the title compound as a cream-coloured solid (1.75 g). LCMS showed MH+=523; $T_{RET}$=2.75 min.

Intermediate 9: 4-Amino-N-{[1,6-d]ethyl-4-(tetrahydro-2H-pyran-4-ylamino)-1H-pyrazolo[3,4-b]pyridin-5-yl]methyl}benzamide hydrochloride

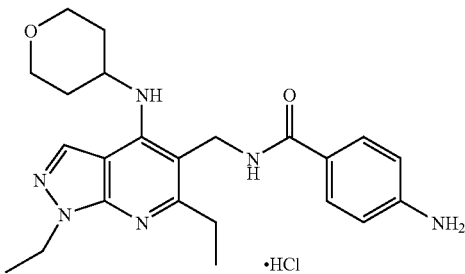

To 1,1-dimethylethyl {4-[({[1,6-d]ethyl-4-(tetrahydro-2H-pyran-4-ylamino)-1H-pyrazolo[3,4-b]pyridin-5-yl]methyl}amino)carbonyl]phenyl}carbamate (1.75 g, 3.35 mmol, which can e.g. be as prepared in Intermediate 8) was added a 4M solution of HCl in 1,4-dioxane (15 ml) resulting in a precipitate. This mixture was allowed to stand at room temperature overnight. The solvent was removed by evaporation; co-evaporation with diethyl ether (3×30 ml) gave the title compound as a pale yellow/brown foam (2.12 g, >100%, NMR showed unknown impurity present). LCMS showed MH+=423; $T_{RET}$=2.23 min.

Intermediate 10: 8-Bromooctanoyl chloride

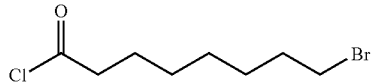

To 8-bromooctanoic acid (2.5 g, 11.2 mmol, commercially available e.g. from Aldrich) in toluene (50 ml) was added thionyl chloride (2 ml), and the mixture was stirred at room temperature overnight. The solvent was evaporated and the residue was co-evaporated with dichloromethane (2×25 ml) to give a brown oil which solidified on standing (found to be starting acid by NMR). This material was redissolved in toluene (25 ml), thionyl chloride (2 ml) was added, and the mixture was stirred at room temperature for 8 hours and then left standing overnight. The reaction mixture was evaporated to dryness and the residue was co-evaporated with dichloromethane (2×30 ml) to give the title compound as a brown oil (2.4 g), as a 3:2 mixture of product: starting acid (by NMR). 1H NMR (400 MHz, chloroform-d) δ (delta) ppm 1.37 (4H, m), 1.45 (2H, m), 1.67 (2H, m), 1.86 (2H, m), 2.90 (2H, t, J=7 Hz), 3.42 (2H, t, J=7 Hz).

Intermediate 10 (Alternative Synthesis)

8-Bromooctanoyl chloride

8-Bromooctanoic acid (2.0 g, 8.97 mmol, commercially available e.g. from Aldrich) in thionyl chloride (2 ml) was stirred at room temperature for 1 hour and then at 100° C. for 2 hours. The thionyl chloride was removed by evaporation and the residue was co-evaporated with dichloromethane (2×30 ml) to give 8-bromooctanoyl chloride as a colourless mobile oil (2.05 g).

Intermediate 11

4-[(8-Bromooctanoyl)amino]-N-{[1,6-d]ethyl-4-(tetrahydro-2H-pyran-4-ylamino)-1H-pyrazolo[3,4-b]pyridin-5-yl]methyl}benzamide

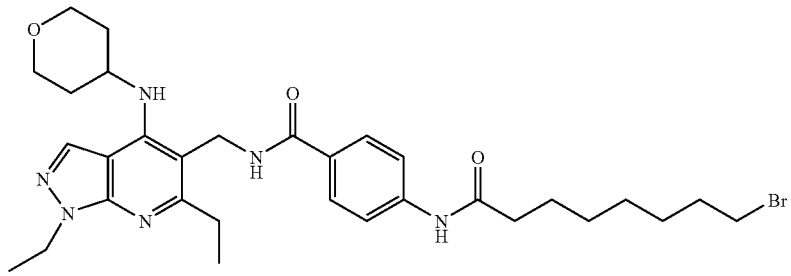

To a stirred gummy mixture of 4-amino-N-{[1,6-d]ethyl-4-(tetrahydro-2H-pyran-4-ylamino)-1H-pyrazolo[3,4-b]pyridin-5-yl]methyl}benzamide hydrochloride (2.0 g, 4.34 mmol, which can e.g. be as prepared in Intermediate 9) in dichloromethane (50 ml) cooled to 0° C. under nitrogen was added triethylamine (3.1 ml, 21.8 mmol, 5 equiv.) resulting in a white suspension. To the suspension was added, by dropwise addition over 5 minutes, a solution of 8-bromooctanoyl chloride (2.1 g, 8.69 mmol, which can e.g. be as prepared in Intermediate 10) in dichloromethane (10 ml). The mixture was then stirred at 0° C. for 1 hour, allowed to warm to room temperature and stirred for a further 18 hours. The mixture was poured into ice, diluted with dichloromethane, and the organic layer was separated and collected. The aqueous layer was extracted with more dichloromethane (50 ml). The organic layers were combined and evaporated to dryness to give a brown gum, which was triturated with diethyl ether. The resulting solid was filtered off and dried in vacuo to give the title compound as a pale yellow solid (0.98 g) containing about 15% (by LCMS) of unreacted starting material (4-amino-N-{[1,6-d]ethyl-4-(tetrahydro-2H-pyran-4-ylamino)-1H-pyrazolo[3,4-b]pyridin-5-yl]methyl}benzamide hydrochloride).

LCMS of the product showed MH+=627/629 (bromine isotopes); $T_{RET}$=3.04 min. The pyrazolo[3,4-b]pyridine starting material present showed MH+=423; $T_{RET}$=2.25 min.

A white suspension was present in the aqueous phase from the above extraction; this was extracted with ethyl acetate (3×70 ml) and the combined ethyl acetate layers were evaporated to dryness to give a pale yellow/brown gum (1.91 g). This appeared by LCMS to be very approximately 43%: 57% starting material: product. The gum was suspended in dry dichloromethane (50 ml), treated with triethylamine (0.8 ml), and cooled to about 0° C. using an ice/water bath. To this mixture was added dropwise over 3 minutes 8-bromooctanoyl chloride (0.8 g, which can e.g. be as prepared in Intermediate 10). After 10 mins at 0° C., the mixture was allowed to warm to room temperature, stirred for 5 hours and allowed to stand at room temperature overnight. The mixture was poured into ice, diluted with dichloromethane (30 ml) and the layers separated. The aqueous phase was further extracted with dichloromethane (20 ml), and the combined organic phases were passed through a hydrophobic frit and evaporated to dryness. The residue was triturated with diethyl ether, and the resulting solid was filtered off and dried in vacuo to give the title compound as a cream solid (0.66 g). LCMS showed MH$^+$=629; T$_{RET}$=3.04 min.

Intermediate 13

Ethyl 4-[(1-{[(1,1-dimethylethyl)oxy]carbonyl}-4-piperidinyl)amino]-1,6-diethyl-1H-pyrazolo[3,4-b]pyridine-5-carboxylate

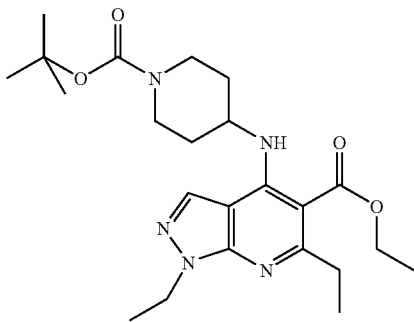

A solution of ethyl 4-chloro-1,6-diethyl-1H-pyrazolo[3,4-b]pyridine-5-carboxylate (14.8 g, 52.6 mmol, e.g. which can be as prepared in Intermediate 3, first or alternative preparation thereof) in N-methyl-2-pyrrolidinone (140 ml) was treated with N,N-diisopropylethylamine (22.9 ml, 131 mmol) followed by 1,1-dimethylethyl 4-amino-1-piperidinecarboxylate (11.6 g, 57.9 mmol, commercially available e.g. from AstaTech) and the mixture was heated at 120° C. for 24 hours. The reaction mixture was cooled and poured into aqueous lithium chloride solution (5% LiCl, 1 L) and the aqueous phase was extracted with ethyl acetate (3×250 ml). The combined organic extracts were dried (Na$_2$SO$_4$) and the solvent was evaporated. The residue, an oil, was purified by column chromatography using a column of silica gel (ART9385, 500 ml) made up in 4:1 hexane:ethyl acetate, eluting with 4:1 hexane:ethyl acetate (500 ml) and then 2:1 hexane:ethyl acetate until the product eluted. The fractions containing the product were pooled and the solvent was evaporated to give the title compound (18.55 g) as an oil which solidified on standing. LCMS m/z 446 [MH$^+$]; T$_{RET}$=3.69 min.

Intermediate 14

1,1-Dimethylethyl 4-{[1,6-d]ethyl-5-(hydroxymethyl)-1H-pyrazolo[3,4-b]pyridin-4-yl]amino}-1-piperidinecarboxylate

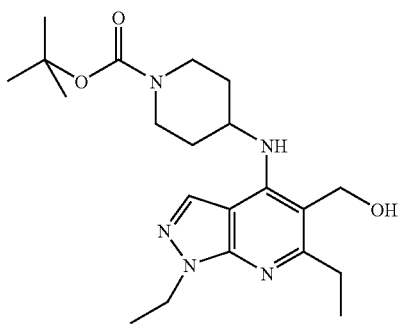

A solution of ethyl 4-[(1-{[(1,1-dimethylethyl)oxy]carbonyl}-4-piperidinyl)amino]-1,6-diethyl-1H-pyrazolo[3,4-b]pyridine-5-carboxylate (18.3 g, 41.1 mmol, e.g. which can be as prepared in Intermediate 13) in tetrahydrofuran (100 ml) was treated with lithium borohydride (LiBH$_4$, 2M in tetrahydrofuran, 40 ml, 80 mmol) followed by methanol (3.6 ml, 88.8 mmol), was heated under reflux for 3 hours, and then was cooled to about room temperature. To the cooled mixture was added a further portion of lithium borohydride (LiBH$_4$, 2M in tetrahydrofuran, 40 ml, 80 mmol) followed by methanol (3.6 ml, 88.8 mmol). The mixture was heated under reflux for 2 hours and allowed to cool to room temperature. Solid lithium borohydride (1.6 g, 73.5 mmol) was added followed by methanol (3.6 ml, 88.8 mmol), and the mixture was heated under reflux for 2 hours and allowed to cool overnight. The mixture was cooled in an ice/water bath, and treated with methanol (20 ml). After stirring for 10 min, water (10 ml) was added. When the effervescence ceased more water was added cautiously (500 ml total volume) and the mixture was stirred for 45 minutes. The mixture was partitioned between water and dichloromethane. The aqueous phase was separated and extracted with dichloromethane (×2). The combined organic extracts were washed with brine, dried (Na$_2$SO$_4$) and the solvent was evaporated. The residue was purified by column chromatography (800 ml of ART9385 silica gel, column made up using 1:1 hexane:ethyl acetate), using chloroform to load the mixture and eluting with hexane:ethyl acetate (1:1, 800 ml), hexane:ethyl acetate (1:2, 1800 ml) and finally neat ethyl acetate to complete elution of the product. The fractions containing the product were combined and the solvent was evaporated to give the title compound (12.4 g). LCMS m/z 404 [MH$^+$]; T$_{RET}$=2.40 min.

Intermediate 15

1,1-Dimethylethyl 4-{[5-(azidomethyl)-1,6-diethyl-1H-pyrazolo[3,4-b]pyridin-4-yl]amino}-1-piperidinecarboxylate

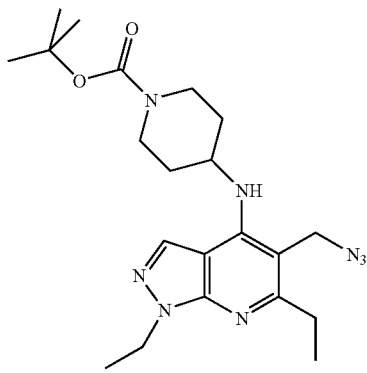

A suspension of 1,1-dimethylethyl 4-{[1,6-d]ethyl-5-(hydroxymethyl)-1H-pyrazolo[3,4-b]pyridin-4-yl]amino}-1-piperidinecarboxylate (14.0 g, 34.7 mmol, e.g. which can be as prepared in Intermediate 14) in N,N-dimethylformamide (110 ml) was treated with sodium azide (4.59 g, 70.6 mmol) and carbon tetrabromide (23.1 g, 69.7 mmol). The stirred suspension was cooled in an ice/water bath and a solution of triphenylphosphine (18.6 g, 70.9 mmol) in N,N-dimethylformamide (75 ml) was added dropwise over 30 minutes. The resulting yellow solution was allowed to warm to room temperature and was stirred for a further 3.5 hours. A solid separated during the stirring. The suspension was concentrated in vacuo to about ⅓ the original volume and partitioned between water (500 ml) and ethyl acetate (600 ml). The organic phase was separated and washed with water (×2). The combined aqueous phases were back-extracted with ethyl acetate. The combined organic extracts were then washed with 5% aqueous lithium chloride solution and were dried ($Na_2SO_4$), and the solvent was removed by evaporation. The residue was purified by column chromatography (800 ml of ART9385 silica gel, column made up in 1:1 hexane:ethyl acetate), loading the residue in dichloromethane, and eluting with 1:1 hexane:ethyl acetate. The fractions containing the product were combined and the solvent was evaporated to give the title compound as a white solid (12.6 g). LCMS m/z 429 [MH$^+$]; $T_{RET}$=2.92 min.

Intermediate 16

4-{[5-(Azidomethyl)-1,6-diethyl-1H-pyrazolo[3,4-b]pyridin-4-yl]amino}-1-piperidinecarboxamide

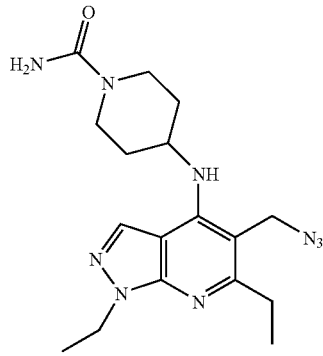

A solution of 1,1-dimethylethyl 4-{[5-(azidomethyl)-1,6-diethyl-1H-pyrazolo[3,4-b]pyridin-4-yl]amino}-1-piperidinecarboxylate (8.9 g, 20.8 mmol, e.g. which can be as prepared in Intermediate 15) in 1,4-dioxane (50 ml) was treated with 4M HCl in 1,4-dioxane (125 ml). After 2 hours the solvent was evaporated and the residue was partitioned between dichloromethane and saturated aqueous sodium bicarbonate solution. The organic phase was collected and washed with saturated aqueous sodium bicarbonate solution. The combined aqueous phases were back-extracted with dichloromethane. The combined organic phases were dried ($Na_2SO_4$) and the solvent was evaporated to give an oil (LCMS showed MH$^+$=329; $T_{RET}$=1.75 min). The oil was dissolved in dichloromethane (100 ml), and the solution was treated with N,N-diisopropylethylamine (6.1 ml, 35.0 mmol) followed by trimethylsilyl isocyanate (3.6 ml, 26.6 mmol, commercially available e.g. trimethylsilyl isocyanate 85% from Aldrich). The reaction mixture was stirred at room temperature overnight. Additional N,N-diisopropylethylamine (6.1 ml, 35.0 mmol) and trimethylsilyl isocyanate (3.6 ml, 26.6 mmol) was added. After stirring for a further 7 hours, additional trimethylsilyl isocyanate (3.6 ml) was added and stirring was continued over the weekend (e.g. this can be about 62 hours). Water (100 ml) was added and the mixture was stirred for 1 hour. The precipitated solid was collected by filtration, washed with water followed by diethyl ether, and then dried to give the title compound (2.21 g). LCMS m/z 372 [MH$^+$]; $T_{RET}$=2.08 min.

Alternative Preparation of 4-{[5-(azidomethyl)-1,6-diethyl-1H-pyrazolo[3,4-b]pyridin-4-yl]amino-}-1-piperidinecarboxamide 1,1-dimethylethyl 4-{[5-(azidomethyl)-1,6-diethyl-1H-pyrazolo[3,4-b]pyridin-4-yl]amino}-1-piperidinecarboxylate (5.14 g) is treated with a 4M solution of hydrogen chloride in dioxane (50 ml). The reaction mixture is left to stand for 2 hours. The solvent is evaporated and co-evaporated with dichloromethane (2×50 ml) then diethyl ether (2×50 ml) to give 5-(azidomethyl)-1,6-diethyl-N-4-piperidinyl-1H-pyrazolo[3,4-b]pyridin-4-amine, hydrochloride salt. This product is dissolved in dichloromethane (100 ml) and the solution is treated with DIPEA (6.3 ml) and trimethylsilyl isocyanate (1.8 ml), and then is left to stand at room temperature for 18 hours. Water (50 ml) is added and the precipitated solid is collected by filtration, washed with diethyl ether and dried to give 4-{[5-(azidomethyl)-1,6-diethyl-1H-pyrazolo[3,4-b]pyridin-4-yl]amino}-1-piperidinecarboxamide.

Intermediate 17

4-{[5-(Aminomethyl)-1,6-diethyl-1H-pyrazolo[3,4-b]pyridin-4-yl]amino}-1-piperidinecarboxamide

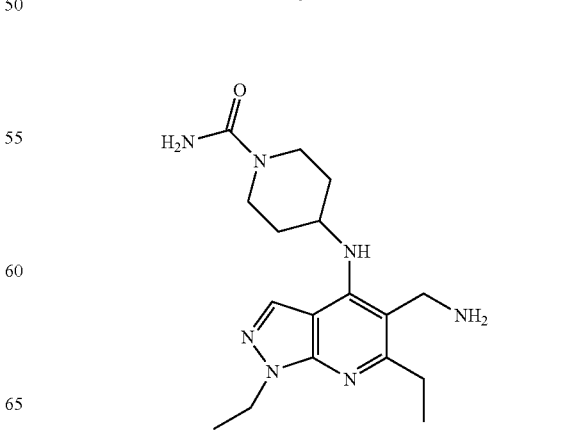

10% Palladium on carbon (0.65 g), in a flask flushed with nitrogen, was treated with water (about 2 ml), ethanol (20 ml) and a suspension of 4-{[5-(azidomethyl)-1,6-diethyl-1H-pyrazolo[3,4-b]pyridin-4-yl]amino}-1-piperidinecarboxamide (4.1 g, 11.0 mmol, e.g. which can be as prepared in Intermediate 16) in ethanol (100 ml). Additional ethanol (200 ml) was used to wash the suspension into the flask. The suspension was stirred under an atmosphere of hydrogen for 21 hours. The mixture was filtered through celite to remove catalyst, and the filtrate was evaporated to dryness to give the title compound as a grey foam (3.8 g). LCMS m/z 346 [MH$^+$]; $T_{RET}$=about 1.66 min.

Intermediate 19

1,1-Dimethylethyl [4-({[(4-{[1-(aminocarbonyl)-4-piperidinyl]amino}-1,6-diethyl-1H-pyrazolo[3,4-b]pyridin-5-yl)methyl]amino}carbonyl)phenyl]carbamate

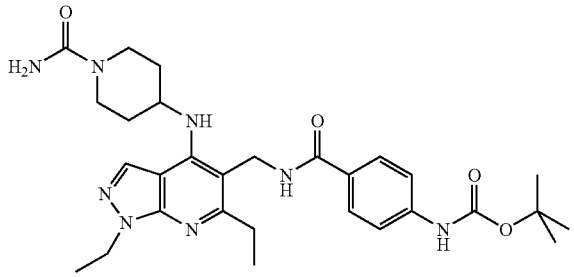

A solution of 4-({[(1,1-dimethylethyl)oxy]carbonyl}amino)benzoic acid (0.17 g, e.g. available from Aldrich) in N,N-dimethylformamide (5 ml) was treated with O-(7-azabenzotriazol-1-yl)-1,1,3,3-tetramethyluronium hexafluorophosphate (0.27 g) followed by N,N-diisopropylethylamine (0.31 ml) and the mixture allowed to stir at room temperature for 10 minutes. A suspension of intermediate 17 (0.25 g) in N,N-dimethylformamide (2 ml) was added and the resultant solution allowed to stand at room temperature for 16 h. The solvent was removed by evaporation and the residue dissolved in dichloromethane (5 ml) and applied directly to a 50 g silica SPE cartridge. Elution with a gradient of 0-100% ethyl acetate: cyclohexane followed by a gradient of 0-20% methanol: ethyl acetate gave the title compound as a cream solid (0.41 g). LCMS showed MH$^+$=565; $T_{RET}$=2.53 min.

Intermediate 20

4-{[5-({[[(4-Aminophenyl)carbonyl]amino}methyl)-1,6-diethyl-1H-pyrazolo[3,4-b]pyridin-4-yl]amino}-1-piperidinecarboxamide hydrochloride

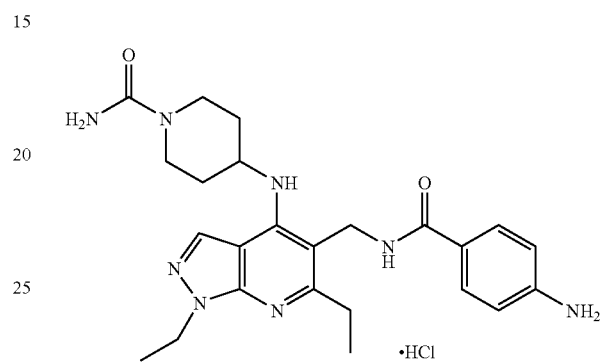

A solution of Intermediate 19 (0.41 g) in methanol (8 ml) was treated with 4M HCl in 1,4-dioxane (30 ml), resulting in a yellow solution, and stirred at room temperature for 16 hours. The solvent was evaporated to dryness, and dichloromethane (2×20 ml) added to the residue and evaporated to give the title compound as a cream solid (0.49 g). LCMS showed MH$^+$=465; $T_{RET}$=2.03 min.

Intermediate 21

4-[(5-{[({4-[(8-Bromooctanoyl)amino]phenyl}carbonyl)amino]methyl}-1,6-diethyl-1H-pyrazolo[3,4-b]pyridin-4-yl)amino]-1-piperidinecarboxamide

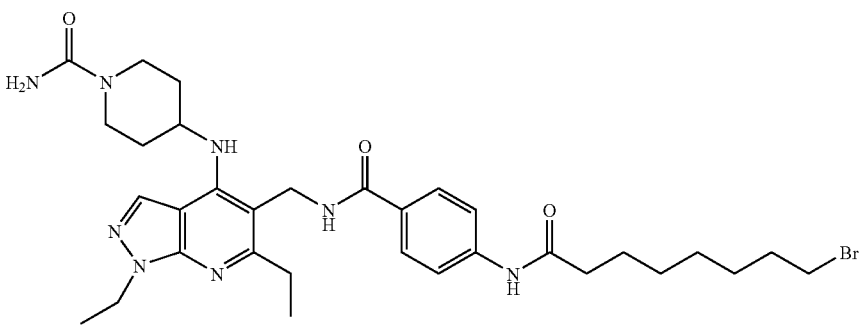

A solution of Intermediate 20 (0.49 g) and triethylamine (0.39 ml) in chloroform (20 ml) was cooled to 0° C. and treated dropwise with intermediate 10 (0.24 g). The mixture was stirred at 0° C. for 15 minutes, allowed to warm to room temperature and stirred for a further 16 hours. Water (10 ml) was added and the organic layer collected through a hydrophobic frit and evaporated to dryness. The residue was purified by passing through a 50 g silica SPE cartridge, eluting with a gradient of 0-50% methanol:dichloromethane, to give the title compound as a white solid (0.3 g). LCMS showed MH$^+$=669/671 (bromine isotope); T$_{RET}$=2.75 min.

Intermediate 22

1,1-Dimethylethyl 4-(4-hydroxy-1-butyn-1-yl)benzoate

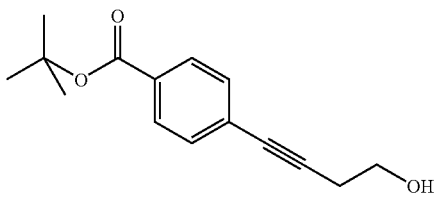

A mixture of 1,1-dimethylethyl 4-iodobenzoate (1.1 g, 3.62 mmol, e.g. which can be preparable e.g. according to E. C. Taylor, J. Org. Chem., 1995, 60(24), 7947), 3-butyn-1-ol (0.36 ml, 4.70 mmol, 1.3 equivalents), bis(triphenylphosphine)palladium(II)dichloride [(PPh$_3$)$_2$PdCl$_2$] (0.13 g, 018 mmol, 5 mol %) and copper(I)iodide (0.014 g, 0.07 mmol, 2 mol %) in triethylamine (5 ml) was stirred at room temperature for 18 hours. The mixture was diluted with dichloromethane (50 ml) and washed with water (50 ml). The organic phase was collected by passing through a hydrophobic frit and evaporated to give a dark brown oil (1.3 g). This was purified by flash chromatography on silica gel (100 g silica cartridge, FlashMaster II), eluting with a gradient of 0 to 100% ethyl acetate in cyclohexane over 20 minutes. Fractions containing product (obtained from 4:1 cyclohexane:ethyl acetate eluant) were pooled and evaporated to dryness to give the title compound as a brown gummy oil (0.9 g). 1H NMR (400 MHz, chloroform-d) δ (delta) ppm 1.60 (9H, s), 1.85 (1H, t, J=6.27 Hz), 2.73 (2H, t, J=6.27 Hz), 3.85 (2H, q, J=6.27 Hz), 7.45 (2H, d, J=8.53 Hz), 7.92 (2H, d, J=8.53 Hz).

Intermediate 23

1,1-Dimethylethyl 4-(4-hydroxybutyl)benzoate

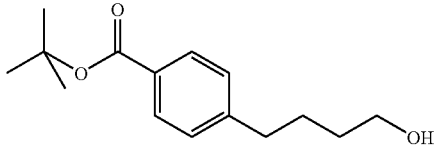

A solution of 1,1-dimethylethyl 4-(4-hydroxy-1-butyn-1-yl)benzoate (0.9 g, e.g. which can be as prepared in Intermediate 22) in a mixture of ethanol (50 ml) and ethyl acetate (5 ml) was hydrogenated over platinum(IV) oxide (PtO$_2$, 0.09 g, 10% w/w) for 18 hours at room temperature. The mixture was filtered through a bed of Celite, washing through with ethanol. The solvents were evaporated to dryness to give the title compound as a yellowy/brown oil (0.85 g). 1H NMR (400 MHz, chloroform-d) δ (delta) ppm 1.60 (14H, m), 1.70 (2H, m), 2.70 (2H, t, J=7.53 Hz & 7.78 Hz), 3.67 (2H, t, J= 6.53 Hz & 6.27 Hz) 7.23 (2H, d, J=8.28 Hz), 7.91 (2H, d, J=8.03 Hz). Extra protons at about 1.5-1.6 ppm may perhaps be due to residual H$_2$O in CDCl$_3$. LCMS showed T$_{RET}$=3.26 min with: MH$^+$ not seen, and [MH]$^+$+18 adduct=268.

Intermediate 24

1,1-Dimethylethyl 4-{4-[(4-bromobutyl)oxy]butyl}benzoate

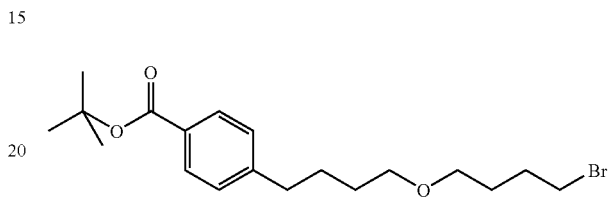

To 1,1-dimethylethyl 4-(4-hydroxybutyl)benzoate (0.85 g, 3.4 mmol, e.g. which can be as prepared in Intermediate 23) was added 1,4-dibromobutane (1.22 ml, 10.2 mmol, 3 equivalents, commercially available e.g. from Aldrich), tetra-n-butylammonium bisulphate (0.034 g, 0.1 mmol, 0.03 equivalents) and aqueous sodium hydroxide solution (50% w/v NaOH, 5 ml). The resultant biphasic mixture was stirred at room temperature over the weekend (this can be e.g. about 64 hours), diluted with water (20 ml) and extracted with diethyl ether (50 ml). The organic extract washed with water (20 ml), dried (Na$_2$SO$_4$) and evaporated to dryness. The residue was purified by passing through a 50 g silica SPE cartridge eluting with cyclohexane (100 ml), 9:1 cyclochexane:ethyl acetate (100 ml), 4:1 cyclohexane:ethyl acetate (200 ml) and 1:1 cyclohexane:ethyl acetate (100 ml). The 4:1 cyclohexane: ethyl acetate fraction containing the product was evaporated to give the title compound (1.05 g). LCMS showed T$_{RET}$=4.14 min with: MH$^+$=385 (trace), and [MH]$^+$+18 adduct=402/404 (Bromine isotope pattern).

Intermediate 25

4-{4-[(4-Bromobutyl)oxy]butyl}benzoic acid

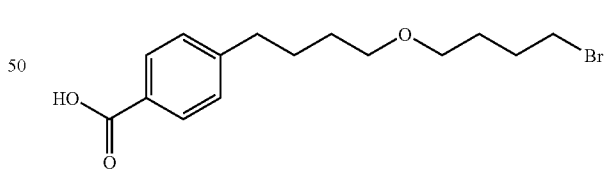

1,1-Dimethylethyl 4-{4-[(4-bromobutyl)oxy]butyl}benzoate (1.05 g, 2.72 mmol, e.g. which can be as prepared in Intermediate 24) was treated with a 4M solution of HCl in 1,4-dioxane (10 ml, 40 mmol, 15 equivalents) and the mixture was allowed to stand at room temperature overnight (about 16 hours). The solvent was evaporated in vacuo followed by several co-evaporations with dichloromethane and a trituration with diethyl ether (the material failed to solidify). The diethyl ether was evaporated off to give the title compound as greenish gum (0.91 g; product contained diethyl ether by NMR). LCMS showed MH$^+$=329/331 (Bromine isotope pattern); T$_{RET}$=3.60 min.

Intermediate 26

4-{4-[(4-Bromobutyl)oxy]butyl}benzoyl chloride

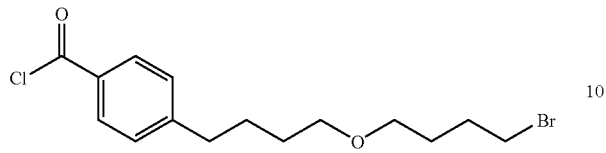

A suspension of 4-{4-[(4-bromobutyl)oxy]butyl}benzoic acid (0.91 g, 2.77 mmol, e.g. which can be as prepared in Intermediate 25) in thionyl chloride (SOCl$_2$, 2 ml) was stirred at room temperature for 1 hour and then at 100° C. for 2 hours. The reaction mixture was cooled and the excess thionyl chloride was removed by evaporation, followed by co-evaporation with dichloromethane (2×30 ml) to give the title compound as a brown oil (1.03 g). 1H NMR (400 MHz, chloroform-d) δ (delta) ppm 1.5-2.0 (10H, m); 2.75 (2H, m); 3.45 (4H, m); 7.35 (2H, d); 8.05 (2H, d). The compound was not pure by $^1$H NMR (CDCl$_3$), but it was not purified further.

Intermediate 27

4-{4-[(4-Bromobutyl)oxy]butyl}-N-{[1,6-diethyl-4-(tetrahydro-2H-pyran-4-ylamino)-1H-pyrazolo[3,4-b]pyridin-5-yl]methyl}benzamide

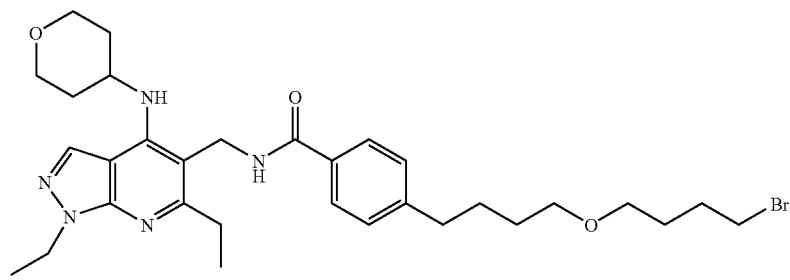

A solution of 5-(aminomethyl)-1,6-diethyl-N-(tetrahydro-2H-pyran-4-yl)-1H-pyrazolo[3,4-b]pyridin-4-amine (300 mg, 1 mmol, e.g. which can be as prepared in Intermediate 7) and triethylamine (0.34 ml, 2.5 mmol, 2.5 equivalents) in dichloromethane (20 ml) was stirred and cooled in an ice/water bath under an atmosphere of nitrogen. 4-{4-[(4-Bromobutyl)oxy]butyl}benzoyl chloride (520 mg, 1.5 mmol, 1.5 equivalents, e.g. which can be as prepared in Intermediate 26) was added portion-wise over 2 minutes, and the mixture was stirred at 0° C. for 5 minutes and then at room temperature for 3 hours. Iced water was added to the reaction mixture and the organic phase was separated and collected through a hydrophobic frit. The aqueous phase was extracted with dichloromethane (10 ml), and the organic layers were combined and evaporated to dryness to give a brown oil. The residue was purified by flash chromatography (100 g silica cartridge, FlashMaster II), eluting with a gradient of 0-100% ethyl acetate in cyclohexane over 40 minutes. The fractions containing the product were combined and evaporated to dryness to give the title compound as a glass (0.26 g). LCMS showed MH$^+$=614/616 (Bromine isotope pattern); T$_{RET}$=3.06 min.

Intermediate 28

4-{[5-({[(4-{4-[(4-Bromobutyl)oxy]butyl}phenyl)carbonyl]amino}methyl)-1,6-diethyl-1H-pyrazolo[3,4-b]pyridin-4-yl]amino}-1-piperidinecarboxamide

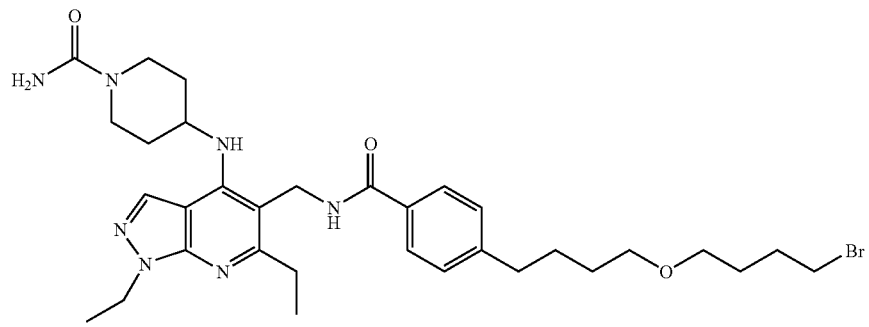

A solution of 4-{[5-(aminomethyl)-1,6-diethyl-1H-pyrazolo[3,4-b]pyridin-4-yl]amino}-1-piperidinecarboxamide (0.21 g, 0.6 mmol, e.g. which can be as prepared in Intermediate 17) and triethylamine (0.21 ml, 1.52 mmol, 2.5 equivalents) in dichloromethane (20 ml) was stirred and cooled in an ice/water bath under an atmosphere of nitrogen. 4-{4-[(4-Bromobutyl)oxy]butyl}benzoyl chloride (0.32 g, 0.91 mmol, 1.5 equivalents, e.g. which can be as prepared in Intermediate 26) was added portion-wise over 2 minutes, and the mixture was stirred at 0° C. for 10 minutes and then at room temperature overnight. Iced water was added to the reaction mixture and the organic phase was separated and collected through a hydrophobic frit. The aqueous phase was extracted with dichloromethane (50 ml), and the combined organic extracts were evaporated to dryness to give a whitish foam. The residue was purified by passing through a 20 g silica column, eluting with a gradient of cyclohexane/ethyl acetate followed by a gradient of ethyl acetate/methanol. The fractions containing the product (obtained from 9:1 ethyl acetate/methanol) were pooled and evaporated to dryness to give the title compound as a pale yellow foam (0.27 g). LCMS showed MH$^+$=656/658 (Bromine isotope pattern); $T_{RET}$=2.88 min.

Intermediate 29

Diethyl (1-chloroethylidene)propanedioate

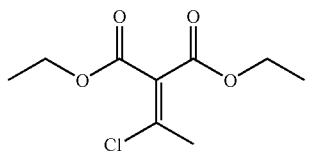

To a cooled (10° C.) suspension of diethyl malonate (200 g, 1.41 mol) in dry acetonitrile (300 mL) was added anhydrous magnesium chloride (119.37 g, 1.26 mol, e.g. available from Lancaster) maintaining the temperature below 20° C. Triethylamine (348 ml) was added dropwise to the slurry followed by the dropwise addition of a solution of acetyl chloride (98.12 g, 1.25 mol) in acetonitrile (100 ml) maintaining the temperature at 10-15° C. Stirring was continued for 1 hour at 10-15° C. and the mixture allowed to warm to room temperature overnight.

Hydrochloric acid (1M) was added to the cooled reaction mixture (10° C.) until the pH of the mixture was about 1.0 (approx. 1.1 L was required). The mixture was extracted with diethyl ether (2×800 ml). The combined ethereal extracts were washed with hydrochloric acid (1M, 1×600 ml) and brine. Evaporation of the solvent under reduced pressure afforded diethyl acetylpropanedioate as the product (233.28 g) as an orange oil.

To the above keto-diester derivative (233 g) in phosphorus oxychloride (POCl$_3$, 2.2 L) was added tri-n-butylamine (250 ml) dropwise and the solution then heated at 120° C. for 7 hours. Excess phosphorus oxychloride was removed under reduced pressure; and the cooled reaction mixture extracted with a 1:2 mixture of hexane and diethyl ether (3×1.2 L). The combined organic extracts were washed with hydrochloric acid (1M, 2×1 L), NaOH solution (0.1M, 2×1 L), with water (2×1 L), brine (2×1 L) and dried (Na$_2$SO$_4$). Evaporation of the solvent under reduced pressure afforded the title compound (158 g) as a red oil which was used without further purification.

Intermediate 30

Ethyl 4-chloro-1-ethyl-6-methyl-1H-pyrazolo[3,4-b]pyridine-5-carboxylate

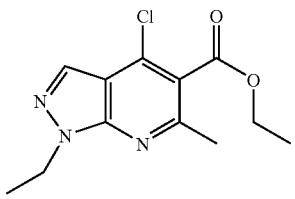

A mixture Intermediate 29 (158 g, 0.72 mol), Intermediate 1 (79 g, 0.71 mol) and triethylamine (196 ml) in toluene (2 L) was heated under reflux for 16 hrs. The reaction mixture was then cooled to room temperature, filtered and the solid residue washed thoroughly with toluene. From the combined filtrate and the washings, toluene was removed by evaporation under reduced pressure. The residue treated with phosphorus oxychloride (POCl$_3$, 2 L) and then heated under reflux for 16 hrs. Excess phosphorus oxychloride was removed under reduced pressure. The reaction mixture was diluted with ethyl acetate (1 L) and cooled to 10° C. Saturated aqueous sodium bicarbonate solution (800 ml) was added dropwise. The organic layer was separated, dried (Na$_2$SO$_4$) and evaporated to give an oil.

The crude product was purified by chromatography (silica gel, 60-120 mesh, 3 kg), eluting with 3% ethyl acetate in hexane. The desired fractions were combined and evaporated to give the title compound (76 g). 1H NMR (200 MHz, chloroform-d) δ (delta) ppm 1.42(3H,t,J=7.2 Hz), 1.50(3H,t, J=7.3 Hz), 2.68(3H,s), 4.47(2H,q,J=7.3 Hz), 4.56 (2H,q, J=7.2 Hz), 8.04 (1H,s).

Alternative Preparation of ethyl 4-chloro-1-ethyl-6-methyl-1H-pyrazolo[3,4-b]pyridine-5-carboxylate A mixture of 5-amino-1-ethylpyrazole (1.614 g, 14.5 mmol) and diethyl 2-(1-ethoxyethylidene)malonate [e.g. see *J. Am. Chem. Soc.*, 1931, 53, 1836] (3.68 g) is heated at 150° C. under Dean Stark conditions for 5 hours. Phosphorous oxychloride (25 ml) is carefully added to the mixture and the resulting solution is heated at 130° C. under reflux for 18 hours. The mixture is concentrated in vacuo and the residual oil is carefully added, with cooling, to water (100 ml). The resulting mixture is extracted with dichloromethane (3×100 ml) and the combined organic extracts are dried over anhydrous sodium sulphate and concentrated in vacuo. The residual oil is purified by Biotage chromatography (silica; 90 g) eluting with 5% ethyl acetate in petroleum ether. Fractions containing the desired product are combined and concentrated in vacuo to give ethyl 4-chloro-1-ethyl-6-methyl-1H-pyrazolo[3,4-b]pyridine-5-carboxylate.

Intermediate 31

Ethyl 1-ethyl-6-methyl-4-(tetrahydro-2H-pyran-4-ylamino)-1H-pyrazolo[3,4-b]pyridine-5-carboxylate

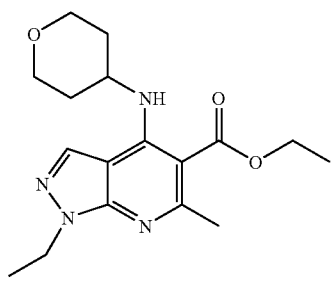

Intermediate 30 (58 g, 217 mmol) in N-methyl-2-pyrrolidinone (380 ml) was treated with N,N-diisopropylethylamine (75 ml, 433 mmol) and a solution of tetrahydro-2H-pyran-4-amine (26.2 g, 260 mmol, e.g. available from Peakdale or Combi-Blocks) in N-methyl-2-pyrrolidinone (100 ml), and was then heated at 115° C. overnight. The cooled mixture was poured into water (2500 ml) and extracted with ethyl acetate (6×250 ml). The combined organic extracts were washed with water and brine, dried and evaporated. The residue was suspended in diethyl ether (about 150 ml) and the solid collected by filtration to give the title compound (44.5 g) as a white solid. LCMS m/z 333 [MH$^+$]; T$_{RET}$=2.89 min.

The filtrate was evaporated, dissolved in ethyl acetate, washed with water and brine, dried and evaporated. Treatment with diethyl ether as described above gave a further quantity of the title compound (9.6 g). A further repeat of this procedure on the filtrate gave an additional quantity of the title compound (2.16 g).

Intermediate 32

[1-Ethyl-6-methyl-4-(tetrahydro-2H-pyran-4-ylamino)-1H-pyrazolo[3,4-b]pyridin-5-yl]methanol

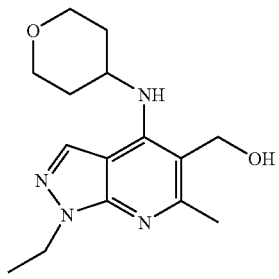

Intermediate 31 (26.9 g, 80.9 mmol) in dry dichloromethane (270 ml) under an atmosphere of nitrogen was cooled to 0° C. and treated with diisobutylaluminium hydride (162 ml of a 1.5M solution in toluene, 243 mmol). The addition took 27 minutes. The resulting pale yellow solution was stirred at 0° C. for 35 minutes and quenched by careful addition of about 20% aqueous potassium sodium tartrate solution (Rochelle's salt, 250 ml). This was exothermic and produced effervescence (temperature reached a maximum of 30° C.). After stirring for 20 min the solids were removed by filtration and washed with dichloromethane and ethyl acetate and the aqueous phase of the filtrate extracted firstly with dichloromethane then ethyl acetate. The combined organics were washed with water then brine, dried and evaporated to give 3 g of material. The aqueous phase was treated with more potassium sodium tartrate solution, concentrated and exhaustively extracted with ethyl acetate. The ethyl acetate extracts were combined, dried and evaporated to give the title compound (17.9 g) as a cream solid.

LCMS m/z 291 [MH$^+$]; T$_{RET}$=1.74, 1.81 min (split peak).

Intermediate 33

5-(Azidomethyl)-1-ethyl-6-methyl-N-(tetrahydro-2H-pyran-4-yl)-1H-pyrazolo[3,4-b]pyridin-4-amine

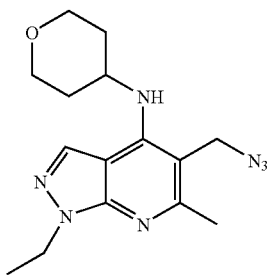

A suspension of Intermediate 32 (9.7 g, 33.4 mmol) in toluene (100 ml) was treated dropwise with thionyl chloride (SOCl$_2$, 36.6 ml, 500 mmol) over 10 minutes resulting in a gummy lump. The mixture was heated to 80° C. for 2.5 hours by which time the lump had broken down to be a pale brown suspension. The mixture was cooled, then evaporated and the residue was azeotroped with more toluene (about 20 ml). The resultant pale brown solid was suspended in dimethylsulphoxide (75 ml) and treated with sodium azide (3.25 g, 50.1 mmol); the mixture became darker and slightly more translucent. After 2 hours the mixture was partitioned between saturated aqueous sodium bicarbonate solution and ethyl acetate, the layers separated and the aqueous phase extracted with more ethyl acetate. The combined organics were washed with water then brine, dried and evaporated. The residue was purified by silica gel chromatography (800 g) eluting with 1:1 cyclohexane:ethyl acetate. The fractions containing the product were pooled and evaporated to give the title compound (7.6 g). 1H NMR (400 MHz, CDCl$_3$) δ (delta) ppm 1.51 (3H, t), 1.68 (2H, m), 2.16 (2H, m), 2.64 (3H, s), 3.61 (2H, m), 4.05 (2H, m), 4.13 (1H, m), 4.45 (2H, s), 4.47 (2H, q), 4.96 (1H, d), 7.88 (1H, s).

Intermediate 34

5-(Aminomethyl)-1-ethyl-6-methyl-N-(tetrahydro-2H-pyran-4-yl)-1H-pyrazolo[3,4-b]pyridin-4-amine

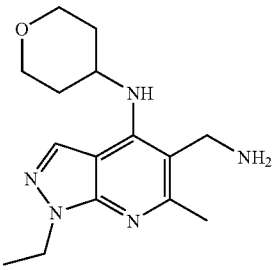

10% palladium on carbon (50% wet, 2.1 g) was treated with ethanol (20 ml) followed by a solution of Intermediate 33 (10.48 g) in ethanol (180 ml), and was hydrogenated at room temperature and pressure overnight. The catalyst was removed by filtration, washing through with more ethanol, and the solvents were removed under reduced pressure to give the title compound (9.0 g) as a grey foam: 1H NMR (400 MHz, d6 DMSO) δ (delta) ppm 1.36 (3H,t), 1.59 (2H, m), 2.0 (2H, m), 2.50 (3H, s), 3.37 (2H, br s), 3.62 (2H, m), 3.89 (2H, s), 3.91 (2H, m), 4.14 (1H, m), 4.33 (2H, q), 7.62 (1H, d), 8.02 (1H, s).

Intermediate 35

1,1-Dimethylethyl 4-[(8-bromooctanoyl)amino]benzoate

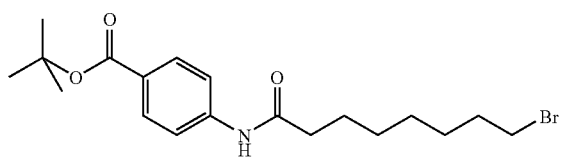

A solution of 1,1-dimethylethyl 4-aminobenzoate (0.5 g, 2.6 mmol, commercially available e.g. from Fluka) in dichloromethane (25 ml) was treated with triethylamine (1.8 ml, 12.9 mmol, 5 equivalents), and the mixture was stirred under an atmosphere of nitrogen and cooled in an ice/water bath. The cold mixture was treated with a solution of 8-bromooctanoyl chloride (0.75 g, 3.1 mmol, 1.2 equivalents, e.g. which can be as prepared in a or the alternative synthesis of Intermediate 10) in dichloromethane (1 ml) over 2 minutes. The resultant stirred mixture was allowed to warm up from ca. 10° C. to room temperature while stirring was continued for an additional 18 hours. Iced water (10 ml) was added, and the organic fraction was collected through a hydrophobic frit. The aqueous fraction was extracted again with dichloromethane (10 ml), and the organic phases were combined and evaporated to dryness. The resulting gum was purified by passing through a 50 g silica SPE cartridge, eluting with dichloromethane (400 ml) followed by 10% ethyl acetate in dichloromethane. Product was obtained from eluting with 10% ethyl acetate in dichloromethane to give the title compound as a colourless gum (0.61 g). LCMS showed MH$^+$=398/400 (Br isotope pattern); T$_{RET}$=3.82 min; with an impurity at T$_{RET}$=2.95 min. NMR (CDCl$_3$) suggested that the material was about 75% pure; this was not purified further.

Intermediate 36

4-[(8-Bromooctanoyl)amino]benzoic acid

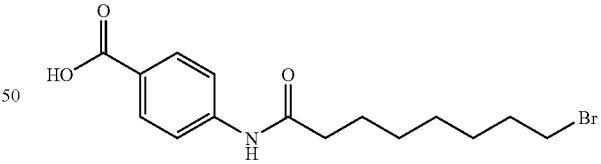

To a solution of 1,1-dimethylethyl 4-[(8-bromooctanoyl)amino]benzoate (0.61 g, 1.5 mmol, as prepared in Intermediate 35) in dichloromethane (2 ml) was added a 4M solution of HCl in 1,4-dioxane (4 ml, about 10 equivalents), and the mixture was left to stand at ambient temperature for 18 hours. The mixture was evaporated to dryness and the residue was co-evaporated with dichloromethane (20 ml) to give the title compound as a white solid (0.51 g). LCMS showed MH$^+$=342/344 (Br isotope pattern); T$_{RET}$=3.34 min. NMR
LCMS m/z 291 [MH$^+$]; T$_{RET}$=1.74, 1.81 min (split peak). (d6-DMSO) suggested that the material was again about 75% pure and that the impurity from the previous reaction (Intermediate 35) was still present. The mixture was used without further purification.

Intermediate 37

4-[(8-Bromooctanoyl)amino]-N-{[1-ethyl-6-methyl-4-(tetrahydro-2H-pyran-4-ylamino)-1H-pyrazolo[3,4-b]pyridin-5-yl]methyl}benzamide

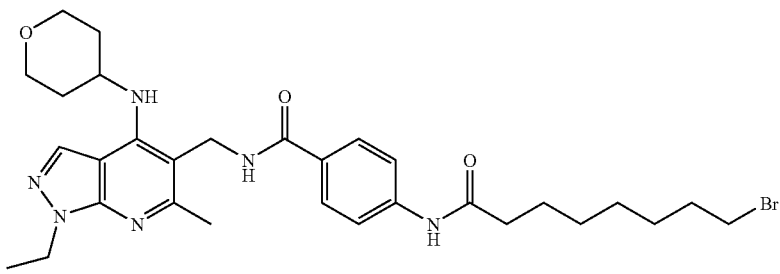

A solution of 4-[(8-bromooctanoyl)amino]benzoic acid (0.25 g, 0.73 mmol, e.g. which can be as prepared in Intermediate 36) in thionyl chloride (2 ml) was stirred under an atmosphere of nitrogen for 1 hour, then heated at 100° C. for 2 hours. The thionyl chloride was evaporated and the residue co-evaporated with dichloromethane (2×20 ml) to give a black gum. This was used without further purification.

To a solution of 5-(aminomethyl)-1-ethyl-6-methyl-N-(tetrahydro-2H-pyran-4-yl)-1H-pyrazolo[3,4-b]pyridin-4-amine (0.14 g, 0.49 mmol, e.g. which can be as prepared in Intermediate 34) in dichloromethane (10 ml) under an atmosphere of nitrogen was added triethylamine (0.34 ml, 2.5 mmol) and the mixture cooled in an ice/water bath. To this mixture was added a solution of the acid chloride intermediate prepared above in dichloromethane (10 ml) dropwise over 3-5 minutes. The resultant solution was stirred at 0-10° C. for 2 hours. The mixture was diluted with dichloromethane (10 ml), iced water (about 20 ml) was added and the organic fraction collected through a hydrophobic frit. The aqueous fraction was extracted with a further portion of dichloromethane (10 ml), the organic layer collected through a hydrophobic frit, and the combined organic extracts evaporated to dryness. The resulting gum was purified flash chromatography on silica gel, eluting with a gradient of 0-100% ethyl acetate/cyclohexane followed by a gradient of 0-20% methanol/ethyl acetate. Fractions containing the product were pooled and evaporated to give the title compound as a yellow foam (0.1 g). LCMS showed MH$^+$=613/615 (Br isotope pattern); T$_{RET}$=2.91 min. An impurity (ca. 15% by LC) was also seen with T$_{RET}$3.35 min, MH$^+$=755/757—the material was used without further purification.

Intermediate 38

1,1-Dimethylethyl 4-({8-[(2-hydroxyethyl)(methyl)amino]octanoyl}amino)benzoate

To a solution of 2-(methylamino)ethanol (10.7 g, 11.5 ml, 144 mmol, 1.5 equivalents, commercially available e.g. from Aldrich) in dry N,N-dimethylformamide (300 ml) was added N,N-diisopropylethylamine (25 ml, 18.5 g, 144 mmol, 1.5 equivalents). To this mixture was added 1,1-dimethylethyl 4-[(8-bromooctanoyl)amino]benzoate (38.1 g, 96 mmol, 1 equivalent) in dry N,N-dimethylformamide (250 ml) over 12 minutes. The mixture was then heated to and at about 60° C. for 4.25 hours. The mixture was then cooled and the solvent was removed by evaporation using high vacuum to give a golden oil. An attempt to partition this oil between water and ethyl acetate gave a cloudy organic phase and phase separation was poor; an oil separated out as a third layer, some of which was collected and evaporated to give crude product (16.69 g). The remaining emulsion was allowed to stand overnight, giving a clear organic layer which was decanted off, dried (MgSO$_4$) and evaporated to give further crude product as a golden oil (28.11 g). Attempts to further extract the aqueous phase with ethyl acetate or dichloromethane gave an emulsion again, from which further crude product (about 10 g) was finally isolated. The combined crude product was purified by chromatography on silica gel (about 1400 ml of 7734 silica), eluting with 5% methanol in dichloromethane, then 8% methanol in dichloromethane, then 10% methanol in dichloromethane, and finally 20% and 30% methanol in dichloromethane, to afford the title compound as a white foam (28.4 g). LCMS showed MH$^+$=393; T$_{RET}$=2.52 min.

Intermediate 39

4-({8-[(2-Hydroxyethyl)(methyl)amino]octanoyl}amino)benzoic acid

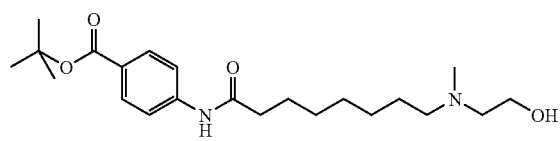

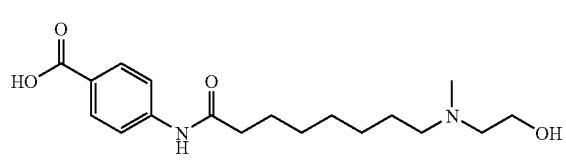

To a mixture of 4-[(8-bromooctanoyl)amino]benzoic acid (50 mg, 0.15 mmol, as prepared in Intermediate 36) in N,N-dimethylformamide (2 ml) was added 2-(methylamino)ethanol (24 microliters, 0.3 mmol, 2 equivalents, commercially available e.g. from Aldrich) followed by N,N-diisopropylethylamine (0.13 mL, 0.8 mmol, about 5 equivalents), and the resulting solution was heated at 60° C. for 16 hours. The solvent was removed by evaporation, and the residue was purified by Mass Directed Automated Preparative HPLC (Method A). Fractions containing product were pooled and evaporated to dryness to give the title compound (25.4 mg) as a pale brown solid. LCMS showed MH$^+$=337; T$_{RET}$=2.03 min.

Intermediate 39A 4-({8-[(2-hydroxyethyl)(methyl)amino]octanoyl}amino)benzoic acid hydrogen chloride

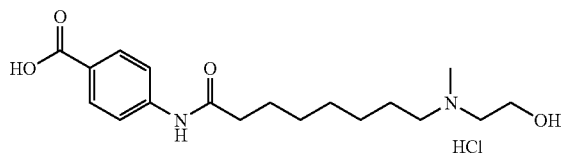

To a solution of 1,1-dimethylethyl 4-({8-[(2-hydroxyethyl)(methyl)amino]octanoyl}amino)-benzoate (28.4 g, 72.4 mmol, e.g. which can be as prepared in Intermediate 38) in dry dichloromethane (225 ml) was added a 4M hydrogen chloride solution in 1,4-dioxane (145 ml, 579 mmol, 8 equivalents). The mixture quickly became cloudy and was stirred overnight resulting in a uniform white suspension. The solvents were evaporated off in vacuo, using a high vacuum at the end, to give the title compound (23.45 g) as a white solid. LCMS showed positive ion at m/z 336; T$_{RET}$=2.01 min. NMR (d6-DMSO) appeared to show a trace of dichloromethane and 1,4-dioxane in the product.

Intermediate 40

N-{[1,6-diethyl-4-(tetrahydro-2H-pyran-4-ylamino)-1H-pyrazolo[3,4-b]pyridin-5-yl]methyl}-4-(8-hydroxyoctyl)benzamide

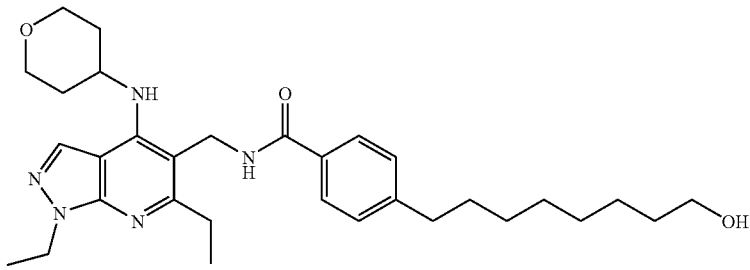

A solution of Intermediate 7 (182 mg, 0.6 mmol), 4-(8-hydroxyoctyl)benzoic acid (100 mg, 0.4 mmol, e.g. preparable according to K. Fukai JP11174621), (1H-1,2,3-benzotriazol-1-yloxy)(tri-1-pyrrolidinyl)phosphonium hexafluorophosphate (PyBOP, 208 mg, 0.4 mmol, e.g. available from Aldrich) and N,N-diisopropylethylamine (0.276 ml, 1.6 mmol) in dry N,N-dimethylformamide (3 ml) was allowed to stir at room temperature for 4 hours. The solvent was evaporated and the residue partitioned between chloroform (10 ml) and saturated aqueous sodium bicarbonate solution (10 ml); the organic fraction was collected by passing through a hydrophobic frit and evaporated. The residue was dissolved in chloroform (20 ml), and the solution passed through a 10 g aminopropyl SPE cartridge under gravity. The cartridge was further eluted with 10% methanol in chloroform, and product containing fractions evaporated to give the title compound (330 mg). LCMS showed MH$^+$=536; T$_{RET}$=2.92 min.

Intermediate 41

4-(8-Bromooctyl)-N-{[1,6-diethyl-4-(tetrahydro-2H-pyran-4-ylamino)-1H-pyrazolo[3,4-b]pyridin-5-yl]methyl}benzamide

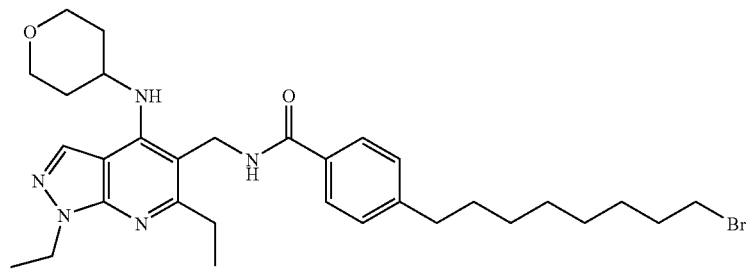

Triphenylphosphine (197 mg, 0.75 mmol) was added dropwise in dichloromethane (3 ml) to a mixture of Intermediate 40 (330 mg, 0.62 mmol) and carbon tetrabromide (247 mg, 0.74 mmol) in dichloromethane (7 ml) at 0° C. under an atmosphere of nitrogen. The mixture was allowed to reach ambient temperature and stirred for 3 hours, then allowed to stand for a further 16 hours. The solvent was evaporated and the residue purified by flash chromatography (20 g silica cartridge), eluting with a gradient of 0 to 100% ethyl acetate in cyclohexane over 30 minutes. Fractions containing product were combined and evaporated to give the title compound (60 mg) as a colourless oil. LCMS showed MH$^+$=598/600 (bromine isotopes); T$_{RET}$=3.42 min.

Intermediate 42

1,1-Dimethylethyl {2-[({[1,6-diethyl-4-(tetrahydro-2H-pyran-4-ylamino)-1H-pyrazolo[3,4-b]pyridin-5-yl]methyl}amino)carbonyl]phenyl}carbamate

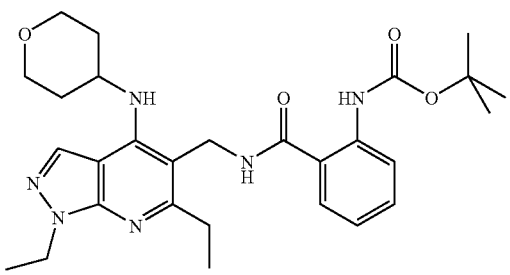

A mixture of Intermediate 7 (250 mg, 0,83 mmol) and 2-({[(1,1-dimethylethyl)oxy]carbonyl}amino)benzoic acid (196 mg, 0.83 mmol, e.g. available from Fluka) in N,N-dimethylformamide (4 ml) was treated with N,N-diisopropylethylamine (0.569 ml, 3.3 mmol) and (1H-1,2,3-benzotriazol-1-yloxy)(tri-1-pyrrolidinyl)phosphonium hexafluorophosphate (472 mg, 0.91 mmol) and allowed to stir at room temperature for 4 hours. An additional portion of (1H-1,2,3-benzotriazol-1-yloxy)(tri-1-pyrrolidinyl)phosphonium hexafluorophosphate (0.5 equiv., 0.41 mmol) was added and the mixture stirred for an additional hour. The solvent was evaporated and the residue dissolved in ethyl acetate (50 ml) and washed with aqueous sodium bicarbonate solution (2×50 ml); the organic fraction was dried (Na$_2$SO$_4$) and evaporated. The residue was purified by chromatography on silica gel (50 g SPE cartridge), eluting with a gradient of 0-100% ethyl acetate/cyclohexane followed by a gradient of 0-20% methanol/ethyl acetate over 40 minutes. Fractions

Intermediate 43

1,1-Dimethylethyl {3-[({[1,6-diethyl-4-(tetrahydro-2H-pyran-4-ylamino)-1H-pyrazolo[3,4-b]pyridin-5-yl]methyl}amino)carbonyl]phenyl}carbamate

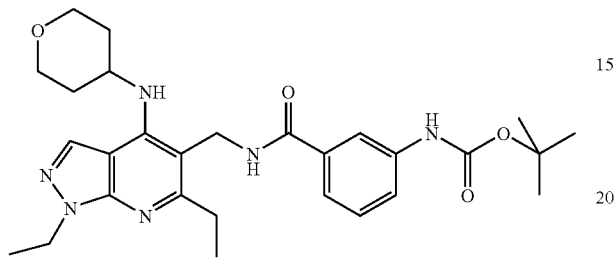

A mixture of Intermediate 7 (250 mg, 0,83 mmol) and 3-({[(1,1-dimethylethyl)oxy]carbonyl}amino)benzoic acid (196 mg, 0.83 mmol, e.g. available from Fluka) in N,N-dimethylformamide (4 ml) was treated with N,N-diisopropylethylamine (0.569 ml, 3.3 mmol) and (1H-1,2,3-benzotriazol-1-yloxy)(tri-1-pyrrolidinyl)phosphonium hexafluorophosphate (472 mg, 0.91 mmol) and allowed to stir at room temperature for 4 hours. An additional portion of (1H-1,2,3-benzotriazol-1-yloxy)(tri-1-pyrrolidinyl)phosphonium hexafluorophosphate (0.5 equivalents, 0.41 mmol) was added and the mixture stirred for an additional hour. The solvent was evaporated and the residue partitioned between ethyl acetate (50 ml) and aqueous sodium bicarbonate solution (50 ml); saturated sodium chloride solution was added and the layers allowed to separate overnight. The aqueous layer was further extracted with ethyl acetate (50 ml), and the organic fractions collected, dried ($Na_2SO_4$) and evaporated; however the residue contained very little product. A white solid was filtered off from the aqueous layer and dried to give the title compound (193 mg). LCMS showed $MH^+$=523; $T_{RET}$=2.99 min.

Intermediate 44

2-Amino-N-{[1,6-diethyl-4-(tetrahydro-2H-pyran-4-ylamino)-1H-pyrazolo[3,4-b]pyridin-5-yl]methyl}benzamide

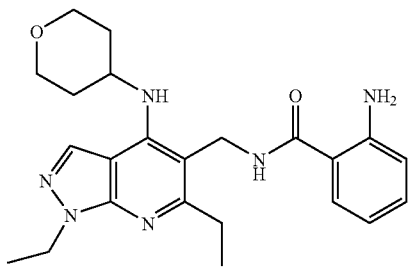

A solution of Intermediate 42 (292 mg, 0.56 mmol) in methanol (8 ml) was treated with a 4M hydrogen chloride solution in 1,4-dioxane (24 ml) and allowed to stir at ambient temperature for 16 hours. The solvent was evaporated and co-evaporation with dichloromethane (2×20 ml) gave the title compound (182 mg) as a gold powder. LCMS showed $MH^+$=423; $T_{RET}$=2.16 min.

Intermediate 45

3-Amino-N-{[1,6-diethyl-4-(tetrahydro-2H-pyran-4-ylamino)-1H-pyrazolo[3,4-b]pyridin-5-yl]methyl}benzamide

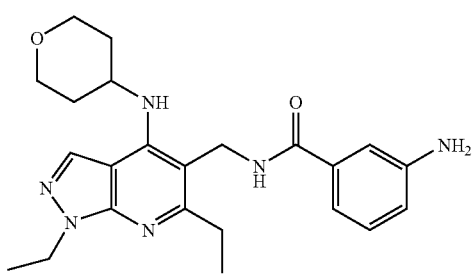

A solution of Intermediate 43 (193 mg, 0.37 mmol)) in methanol (8 ml) was treated with a 4M hydrogen chloride solution in 1,4-dioxane (24 ml) and allowed to stir at ambient temperature for 16 hours. The solvent was evaporated and co-evaporation with dichloromethane (2×20 ml) gave the title compound (224 mg) as a gold powder. LCMS showed $MH^+$=423; $T_{RET}$=2.36 min.

Intermediate 46

2-[(8-Bromooctanoyl)amino]-N-{[1,6-diethyl-4-(tetrahydro-2H-pyran-4-ylamino)-1H-pyrazolo[3,4-b]pyridin-5-yl]methyl}benzamide

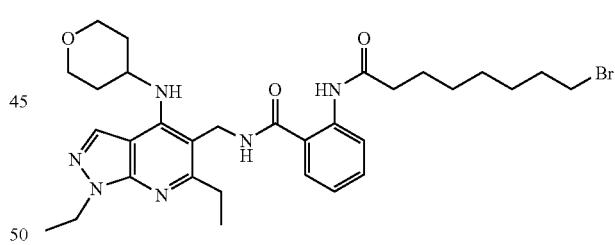

To a solution of Intermediate 44 (182 mg, 0.43 mmol) in dichloromethane (4 ml) at 0° C. was added triethylamine (0.282 ml) followed by dropwise addition of Intermediate 10 (191 mg, 0.79 mmol) over 5 minutes. The mixture was stirred for 1 hour at 0° C., allowed to warm to room temperature, and stirring was continued for a further 18 hours. Dichloromethane (50 ml) was added, the mixture poured into iced water and the organic fraction collected. The aqueous layer was extracted with more dichloromethane (50 ml), and the combined organic layers were evaporated to dryness. The residue was purified by passing through a 10 g silica SPE cartridge eluting with a gradient of 0-100% ethyl acetate/cyclohexane over 40 minutes. Fractions containing product were pooled and evaporated to give the title compound (68 mg) as a colourless oil. LCMS showed $MH^+$=627/629 (bromine isotopes); $T_{RET}$=3.14 min.

Intermediate 47

3-[(8-Bromooctanoyl)amino]-N-{[1,6-diethyl-4-(tetrahydro-2H-pyran-4-ylamino)-1H-pyrazolo[3,4-b]pyridin-5-yl]methyl}benzamide

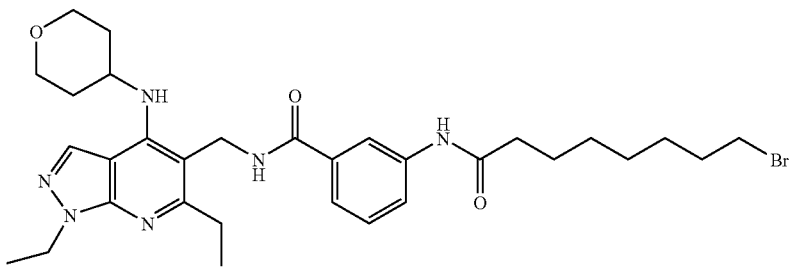

To a solution of Intermediate 45 (224 mg, 0.53 mmol) in dichloromethane (5 ml) at 0° C. was added triethylamine (0.347 ml) followed by dropwise addition of Intermediate 10 (235 mg, 0.97 mmol) over 5 minutes. The mixture was stirred for 1 hour at 0° C., allowed to warm to room temperature, and stirring was continued for a further 18 hours. Dichloromethane (50 ml) was added, the mixture poured into iced water, and the organic fraction collected. The aqueous layer was extracted with more dichloromethane (50 ml), and the combined organic layers were evaporated to dryness. The residue was purified by passing through a 10 g silica SPE cartridge, eluting with a gradient of 0-100% ethyl acetate/cyclohexane over 40 minutes. Fractions containing product were pooled and evaporated to give the title compound (42 mg) as a colourless oil. LCMS showed $MH^+=627/629$ (bromine isotopes); $T_{RET}=3.15$ min.

Intermediate 48

5-(Aminomethyl)-1-ethyl-N-(tetrahydro-2H-pyran-4-yl)-1H-pyrazolo[3,4-b]pyridin-4-amine hydrochloride

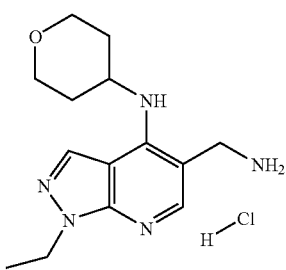

1-Ethyl-4-(tetrahydro-2H-pyran-4-ylamino)-1H-pyrazolo[3,4-b]pyridine-5-carboxamide (0.59 g, 2.04 mmol, e.g. preparable according to WO2004/056823) was suspended in dry tetrahydrofuran (20 ml) and borane-tetrahydrofuran complex (10.2 ml, 1M soln in tetrahydrofuran) was added. The reaction was heated under reflux under nitrogen for 4 hours. The mixture was cooled, quenched with methanol (20 ml), and allowed to stand at room temperature over the weekend. The solvent was evaporated in vacuo and the residue dissolved in methanol and applied to a 20 g SCX cartridge, eluting with methanol followed by 2M ammonia/methanol. The ammonia/methanol fractions were combined and evaporated to gave a yellow oil (0.38 g). The oil was dissolved in methanol, 2M hydrochoric acid (5 ml) was added, and the mixture was heated at 70° C. for 2 hours. The mixture was cooled and solvent evaporated to give an orange oil (0.4 g).

Purification by flash chromatography, eluting with 0-30% methanol and 1% triethylamine in dichloromethane over 20 minutes, gave the title compound as an impure oil (0.32 g). LCMS showed $MH^+=276$; $T_{RET}=1.72$ min.

The impure intermediate (0.31 g) was dissolved in methanol (10 ml) and di-t-butyldicarbonate (0.25 g, 1.13 mmol) and triethylamine (0.16 ml, 1.13 mmol) were added. The mixture was left standing at room temperature for 16 hours. The solvent was evaporated and the residue partitioned between dichloromethane (10 ml) and water (10 ml). The organic phase was collected by passing through a hydrophobic frit and the solvent evaporated to give the impure BOC-protected amine intermediate as an orange oil (0.26 g), which was used without further purification. LC/MS showed $MH^+=376$; $T_{RET}=2.39$ mins.

The BOC-protected intermediate (58 mg, including material from another preparation) was treated with a 4M solution of HCl in 1,4-dioxane (1 ml) and the resulting mixture was left standing at room temperature for 16 hours. The solvent was removed by evaporation to give the title compound as a beige coloured solid (55 mg). LCMS showed $MH^+=276$; $T_{RET}=1.66$ min.

Intermediates 49 to 52

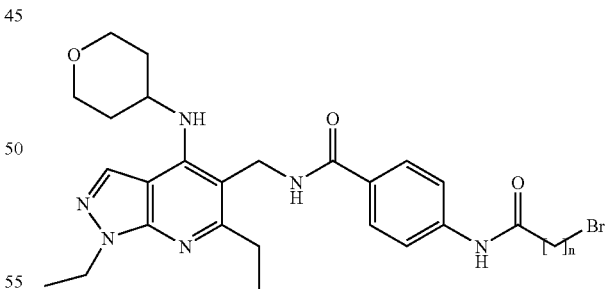

A solution of Intermediate 9 (0.10 g, 0.22 mmol) in dichloromethane (5 ml) was treated with triethylamine (0.15 ml, 1.1 mmol) and the mixture was cooled to 0° C. To the mixture was added the appropriate acid chloride (see Table 2 below, 0.33 mmol). After 5 minutes at 0° C., the mixture was allowed to reach room temperature and the reaction continued for a further 2 hours.

The mixture was treated with ice/water (2 ml). In the case of Intermediate 49, this product precipitated out and was isolated by filtration to give the title compound (74 mg; used without further purification).

For isolation of Intermediates 50, 51 and 52, the organic phase was separated by passing through a hydrophobic frit. The aqueous phase was extracted further with dichloromethane (2×2 ml), and the organic phases were combined and evaporated to give the crude product. Intermediate 51 was obtained as a brown oil (312 mg; generally used without further purification). Intermediate 52 was obtained as a brown oil (366 mg; generally used without further purification). Intermediate 50 was purified by mass directed preparative HPLC (Method A) to give the title compound as a white solid (76 mg).

TABLE 2

| Intermediate number formed | Acid chloride reagent | One possible Source of, or one possible publication mentioning, the acid chloride | M+ ion | $T_{RET}$ (min) |
|---|---|---|---|---|
| 49 | n = 5 | Aldrich | 599, 601 | 2.72 |
| 50 | n = 6 | Advanced Synthesis Technologies | 613, 615 | 2.85 |
| 51 | n = 9 | Chem & Pharm Bull; 31(2), 454-65 | 655, 657 | 3.22 |
| 52 | n = 10 | Advanced Synthesis Technologies | 669, 671 | 3.31 |

Intermediate 53

4-[(8-bromooctanoyl)amino]benzamide

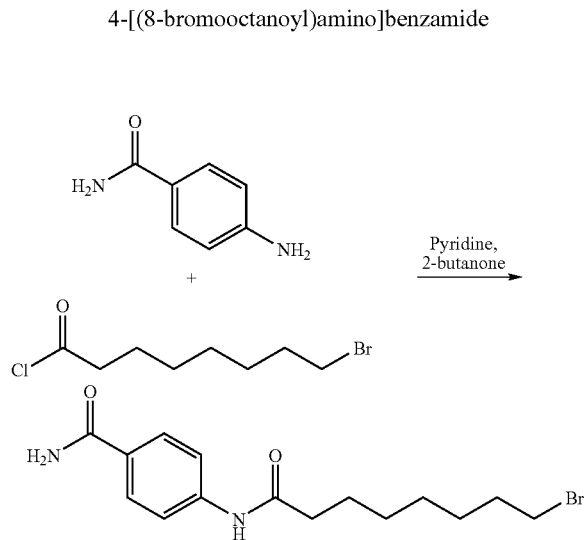

This preparation is an embodiment of the "Stage 4a" preparation within Process 1C described herein. The following reaction was conducted under a nitrogen atmosphere. All volumes ("vol.") and equivalents are relative to the 4-aminobenzamide.

Pyridine (1.6 mL, 20 mmol, 1.1 equivalents) was added to a slurry of 4-aminobenzamide (2.5 g, 18 mmol) in 2-butanone (40 mL, 16 vol.) with mechanical stirring. After about 2 hours, a solution of 8-bromooctanoyl chloride* (3.7M, 5.5 mL, 20 mmol, 1.1 equivalents) in 2-butanone (10 mL, 4 vol.) was added dropwise over 18 min. The resulting mixture, a very viscous slurry, was stirred at room temperature for 19 to 19.5 hours and then filtered through two 42.5 mm diameter filter papers in a filter funnel. The reaction vessel was rinsed with the filtrate and filtered through the same filter funnel and filter papers. Water (25 mL, 10 vol.) was then added to the filtration cake which was stirred well and filtered. The washing process was repeated with more water (25 mL), and the resultant filtration cake was then displacement washed with methanol (10 mL, 4 vol.) and then tert-butyl methyl ether (TBME, 10 mL, 4 vol.). The residual solvents in the cake were removed under suction, the damp solid was dried in vacuo at 50° C. overnight to yield the title compound as a white solid (5.99 g, about 95-96% yield based on the amount of 4-aminobenzamide used). HPLC (5 mins generic solvent gradient): $T_{RET}$ about 3.01 min. Mass spectrum: Found: MH+ 341/343, (M-H)− 339/341.

* 8-Bromooctanoyl chloride can optionally be prepared: (i) substantially as described in this reference: Xue, F.; Seto, C. T. "Structure-activity studies of cyclic ketone inhibitors of the serine protease plasmin: design, synthesis, and biological activity", *Bioorganic & Medicinal Chemistry*, 2006, 14(24), 8467-8487; and/or (ii) as described in Intermediate 10 herein (using the first or the alternative synthesis given).

Intermediate 53 (Alternative Preparation)

4-[(8-bromooctanoyl)amino]benzamide

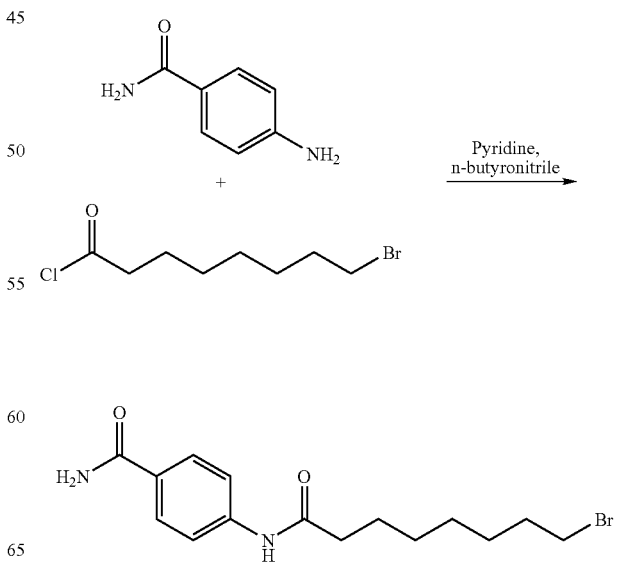

The following reaction is conducted under a nitrogen atmosphere.

Pyridine (1.6 mL, 1.1 equivalents) is added to a mixture of 4-aminobenzamide (2.5 g, 18 mmol) and n-butyronitrile (65 mL) at 20° C. under an atmosphere of nitrogen. The mixture is stirred for 15 minutes before a solution of 8-bromooctanoyl chloride (3.7M in toluene, 5.5 mL, 20 mmol, 1.1 equivalents) in n-butyronitrile (10 mL) is added over 20 minutes. The mixture is then stirred at 20° C. for 22 hours. Upon complete reaction the mixture is filtered. The resulting product is washed with methanol (10 mL), water (2×25 mL), methanol (10 mL) and tert-butyl methyl ether (TBME, 10 mL) before being dried in vacuo to yield the title compound, generally as a solid.

Intermediate 54

4-({8-[(2-hydroxyethyl)(methyl)amino]octanoyl}amino)benzamide

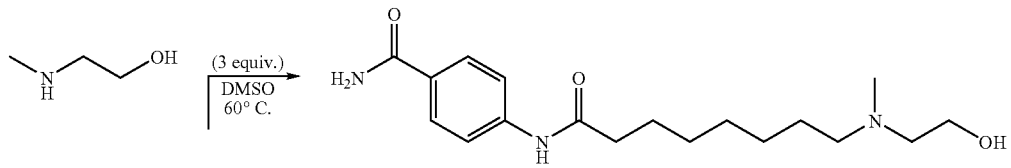

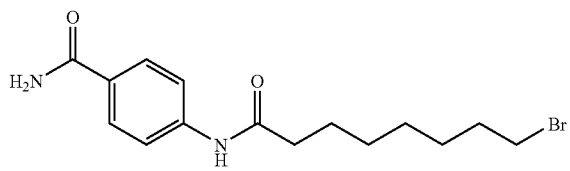

This preparation is an embodiment of the "Stage 4b" preparation within Process 1C described herein. The following reaction was conducted under a nitrogen atmosphere.

2-(Methylamino)ethanol (4.07 mL, 50.6 mmol, 3 equivalents) was added to a stirred slurry of 4-[(8-bromooctanoyl)amino]benzamide (5.76 g, 16.9 mmol, e.g. which can be as prepared in Intermediate 53 (first or alternative preparation thereof)) in dimethyl sulfoxide (30 mL). The mixture was heated at 60° C. for 2 hours, cooled to room temperature, quenched with ice (150 g), stirred for about 30 mins and filtered. Filtration, through a Whatman hardened filter paper, was very slow, taking about 2 hours. The resultant wet white paste was dissolved in methanol (about 130 mL) and filtered through a SCX-2 SPE cartridge (70 g), eluting with methanol (about 500 mL) and then 10% concentrated ammonia-methanol (about 700 mL). Fractions from the ammonia-methanol eluate containing UV active component were pooled together and evaporated to dryness to give the title compound as a white solid (5.15 g after drying at 60° C. for 19 hours, about 91% yield based on the amount of 4-[(8-bromooctanoyl)amino]benzamide used). HPLC (5 mins generic solvent gradient): $T_{RET}$ about 1.95 min. Mass spectrum: Found: MH$^+$ 336, (M-H)$^-$334.

Intermediate 54 (Alternative Preparation)

4-({8-[(2-hydroxyethyl)(methyl)amino]octanoyl}amino)benzamide

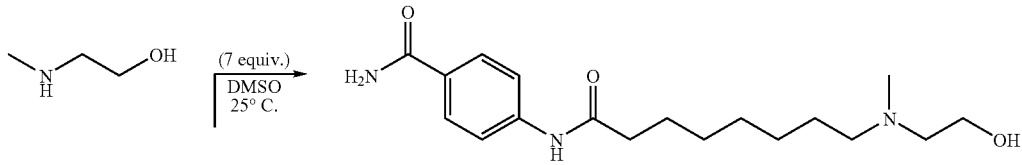

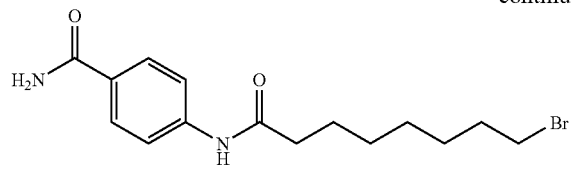

The following reaction is conducted under a nitrogen atmosphere.

2-(Methylamino)ethanol (9.5 g, 7 equivalents) is added to a stirred mixture of 4-[(8-bromooctanoyl)amino]benzamide (5.76 g, 16.9 mmol, e.g. which can be as prepared in Intermediate 53 (first or alternative preparation thereof)) and dimethyl sulfoxide (30 mL). The mixture is stirred at 25° C. until the reaction is substantially complete and is then diluted with acetonitrile (115 mL). After stirring for 1 hour the mixture is filtered, washed with ethyl acetate (15 mL) and tert-butyl methyl ether (TBME, 15 mL) before being dried in vacuo to yield the title compound, generally as a solid.

Intermediate 55

2-[(8-{[4-(aminocarbonyl)phenyl]amino}-8-oxooctyl)(methyl)amino]ethyl acetate

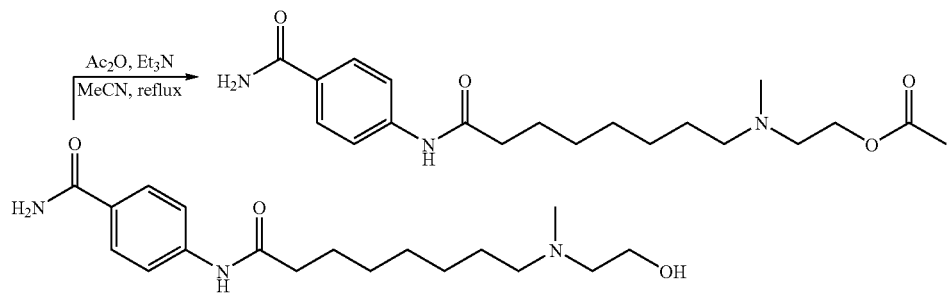

This preparation is an embodiment of the "Stage 5" preparation within Process 1C described herein. The following reaction was conducted under a nitrogen atmosphere.

A mixture of 4-({8-[(2-hydroxyethyl)(methyl)amino] octanoyl}amino)benzamide (6.05 g, 18 mmol, e.g. which can be as prepared in Intermediate 54), acetic anhydride (4.25 mL, 45 mmol, 2.5 equivalents) and triethylamine (7.5 mL, 54 mmol, 3 equivalents) in dry acetonitrile (100 mL) was stirred at room temperature for 66 hours. Additional acetic anhydride (3.40 mL, 36 mmol, 2 equivalents) was then added. The mixture was heated under reflux for 2.5 hours and cooled to room temperature with magnetic stirring. The resultant slurry was filtered, washed with acetonitrile (12 mL then 6 mL) and the residual solvents in the filter cake removed under suction. The cake was then dried in vacuo at 50° C. for 15 hours to afford the title compound as a greyish brown solid (5.4 g, about 79% yield based on the amount of 4-({8-[(2-hydroxyethyl)(methyl)amino]octanoyl}amino)benzamide used). HPLC (5 mins generic solvent gradient): $T_{RET}$ about 2.05 min. Mass spectrum: Found: MH$^+$ 378, (M-H)$^-$ 376.

Optional Intermediates

In this Optional Intermediates section, "Intermediates" generally represent syntheses of intermediate compounds which (in some cases) might theoretically be usable in the synthesis of compounds of formula (I) or salts thereof, but which have not necessarily been used to prepare specific compounds of formula (I) or salts thereof (and in most or all cases they have not been so used).

Optional Intermediate 60

[1-ethyl-4-(tetrahydro-2H-pyran-4-ylamino)-1H-pyrazolo[3,4-b]pyridin-5-yl]methanol

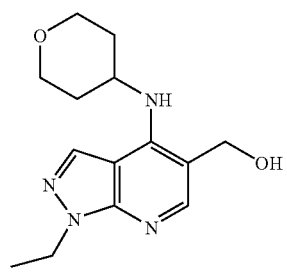

A solution of 1M diisobutylaluminium hydride in dichloromethane (80 ml) is added dropwise to a stirred solution of ethyl 1-ethyl-4-(tetrahydro-2H-pyran-4-ylamino)-1H-pyrazolo[3,4-b]pyridine-5-carboxylate [e.g. see Intermediate 32 and/or Example 3 of WO 2004/024728 A2] (13.8 g) in dichloromethane (75 ml) at 0° C. under nitrogen. The reaction mixture is maintained below 5° C. during the addition, and is then stirred for 0.5 h at 0° C. The mixture is then quenched by addition of aqueous potassium sodium tartrate (10% solution), diluted with water (150 ml) and the organic phase separated. The aqueous phase is extracted with ethyl acetate (2×250 ml) and the combined organics are dried (magnesium sulphate) and evaporated. The residue is purified by column chromatography on silica gel eluting with a gradient of 0-100% ethyl acetate in cyclohexane followed by 0-20% methanol in ethyl acetate to give Intermediate 60.

Optional Intermediate 61

5-(chloromethyl)-1-ethyl-N-(tetrahydro-2H-pyran-4-yl)-1H-pyrazolo[3,4-b]pyridin-4-amine

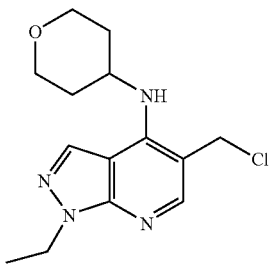

Intermediate 60 (80 mg) is treated with thionyl chloride (1 ml) and heated at 80° C. for 1 h then allowed to cool. The orange solution is evaporated to dryness and the residue azeotroped with toluene (2×5 ml) to give Intermediate 61.

Optional Intermediate 62

5-(azidomethyl)-1-ethyl-N-(tetrahydro-2H-pyran-4-yl)-1H-pyrazolo[3,4-b]pyridin-4-amine

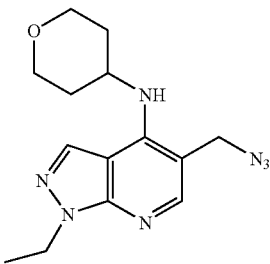

A solution of Intermediate 61 (50 mg) in anhydrous dimethylsulphoxide (0.2 ml) is treated with lithium azide (9 mg) and the solution is stirred at room temperature for 20 h. A further portion of lithium azide (15 mg) is then added, and after a further day stirring at room temperature, water (0.25 ml) is added. The solution is extracted with dichloromethane (2×5 ml) and the combined organic extracts are passed through a hydrophobic frit (6 ml) and then are blown to dryness. The residue is dissolved in dichloromethane (0.5 ml) and applied to an SPE cartridge (silica; 1 g). The cartridge is eluted with 50% ethyl acetate in cyclohexane and fractions containing the desired material are combined and blown to dryness to give Intermediate 62.

Optional Intermediate 63

1-ethyl-$N^4$-(tetrahydro-2H-pyran-4-yl)-1H-pyrazolo[3,4-b]pyridine-4,5-diamine

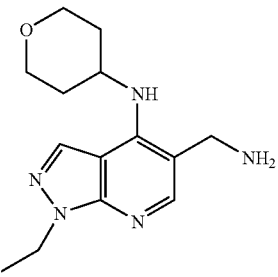

A solution of Intermediate 62 (0.351 g) in ethanol (30 ml) is added to palladium on carbon (5% wet, 0.050 g) and the mixture is stirred at room temperature for 20 hours under an atmosphere of hydrogen. The mixture is filtered through a glass fibre filter and through celite, which is then washed with ethanol (50 ml). The combined filtrates and washings are concentrated in vacuo to give Intermediate 63.

| Optional Intermediate Number | Structure of compound | One or two possible published reference(s) to (e.g. synthetic reference to), or one possible source of, the compound |
|---|---|---|
| 100 | 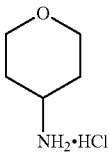 | Intermediate 8A of WO 2004/024728 A2 (Glaxo Group Limited) |
| 101 | 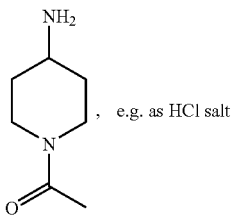, e.g. as HCl salt | Intermediate 6 of WO 2004/024728 A2 (Glaxo Group Limited), which refers to WO 00/42011 |
| 102 | 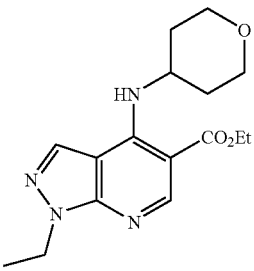 | Intermediate 32 and/or Example 3 of WO 2004/024728 A2 (Glaxo Group Limited); or Intermediate 4 of WO 2005/058892 A1 (Glaxo Group Limited) |
| 103 | 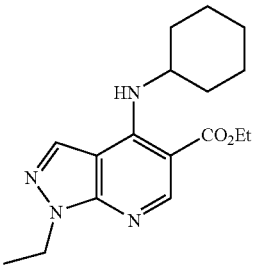 | Intermediate 5 of WO 2005/058892 A1 (Glaxo Group Limited) |
| 104 | 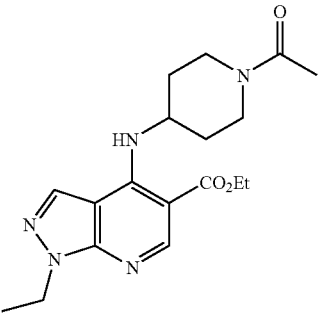 | Example 207 of WO 2004/024728 A2 (Glaxo Group Limited); or Intermediate 6 of WO 2005/058892 A1 (Glaxo Group Limited) |

-continued

| Optional Intermediate Number | Structure of compound | One or two possible published reference(s) to (e.g. synthetic reference to), or one possible source of, the compound |
|---|---|---|
| 105 | 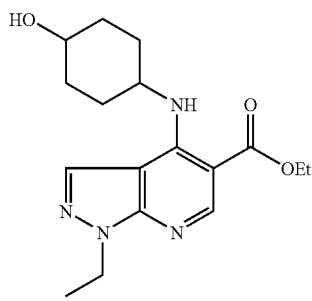 | Example 204 of WO 2004/024728 A2 (Glaxo Group Limited) |
| 106 | 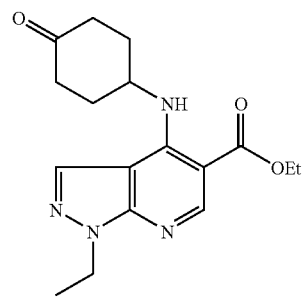 | Example 205 of WO 2004/024728 A2 (Glaxo Group Limited) |
| 107 | 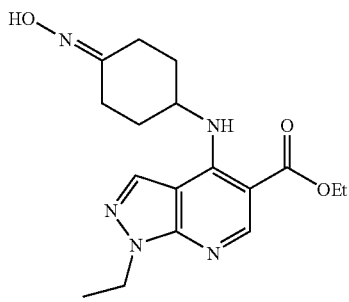 | Example 652 of WO 2004/024728 A2 (Glaxo Group Limited) |
| 108 | 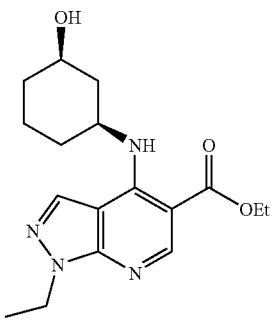<br>[cis-(3-hydroxycyclohex-1-yl)amino group, racemic] | Intermediate 12 of WO 2005/058892 A1 (Glaxo Group Limited) |

| Optional Intermediate Number | Structure of compound | One or two possible published reference(s) to (e.g. synthetic reference to), or one possible source of, the compound |
|---|---|---|
| 109 | 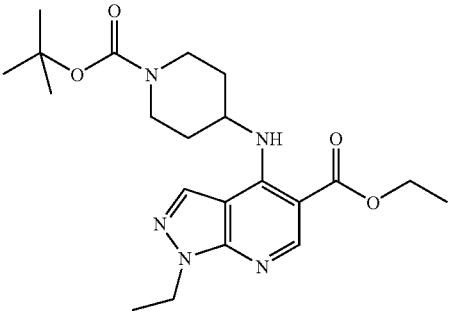 | Intermediate 102 of WO 2005/058892 A1 (Glaxo Group Limited) |
| 110 | 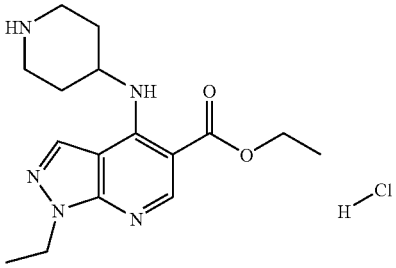 | Intermediate 103 of WO 2005/058892 A1 (Glaxo Group Limited) |
| 111 | 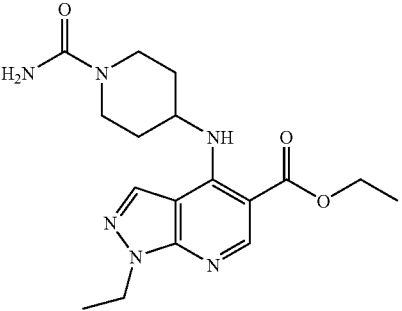 | Intermediate 104 of WO 2005/058892 A1 (Glaxo Group Limited) |
| 112 | 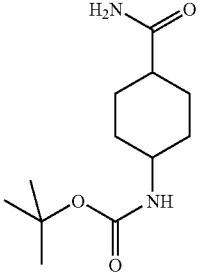 | Intermediate 112 of WO 2005/058892 A1 (Glaxo Group Limited) |
| 113 | 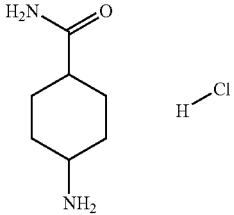 | Intermediate 113 of WO 2005/058892 A1 (Glaxo Group Limited) |

-continued

| Optional Intermediate Number | Structure of compound | One or two possible published reference(s) to (e.g. synthetic reference to), or one possible source of, the compound |
|---|---|---|
| 114 | 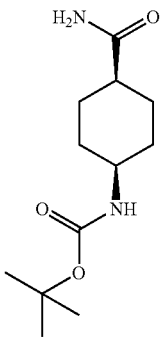 | Intermediate 114 of WO 2005/058892 A1 (Glaxo Group Limited) |
| 115 | 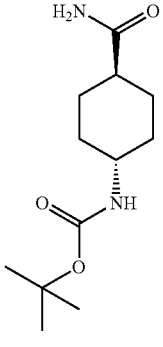 | Intermediate 115 of WO 2005/058892 A1 (Glaxo Group Limited) |
| 116 | 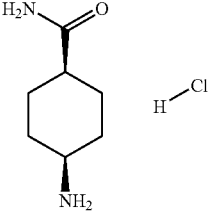 | Intermediate 116 of WO 2005/058892 A1 (Glaxo Group Limited) |
| 117 | 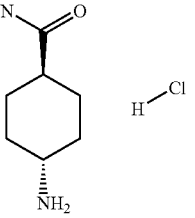 | Intermediate 117 of WO 2005/058892 A1 (Glaxo Group Limited) |
| 118 | 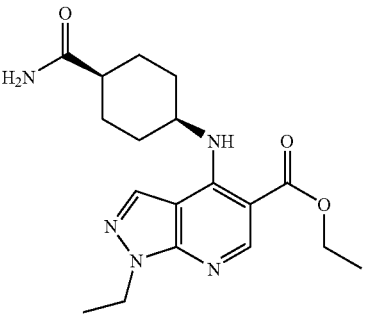 | Intermediate 118 of WO 2005/058892 A1 (Glaxo Group Limited) |

| Optional Intermediate Number | Structure of compound | One or two possible published reference(s) to (e.g. synthetic reference to), or one possible source of, the compound |
|---|---|---|
| 119 | 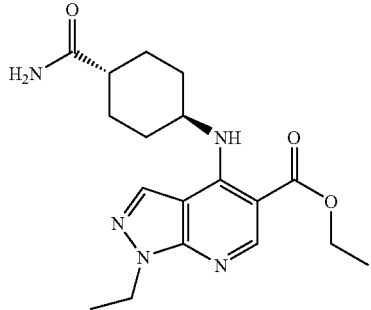 | Intermediate 119 of WO 2005/058892 A1 (Glaxo Group Limited) |
| 120 | 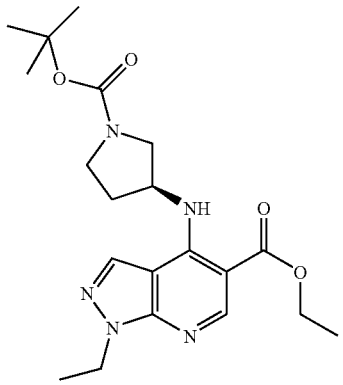 | Intermediate 146 of WO 2005/058892 A1 (Glaxo Group Limited) |
| 121 | 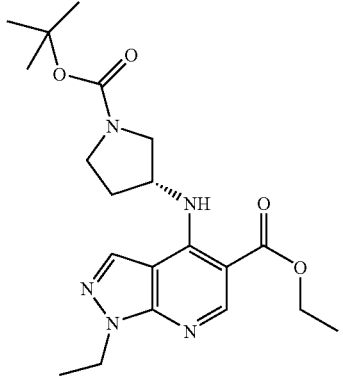 | Intermediate 147 of WO 2005/058892 A1 (Glaxo Group Limited) |
| 122 | 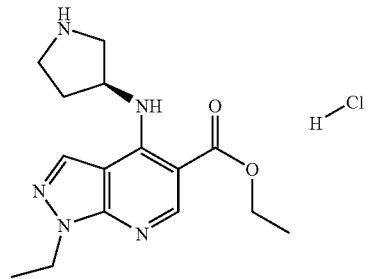 | Intermediate 148 of WO 2005/058892 A1 (Glaxo Group Limited) |

-continued

| Optional Intermediate Number | Structure of compound | One or two possible published reference(s) to (e.g. synthetic reference to), or one possible source of, the compound |
|---|---|---|
| 123 | 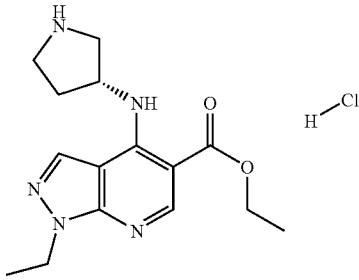 | Intermediate 149 of WO 2005/058892 A1 (Glaxo Group Limited) |
| 124 | 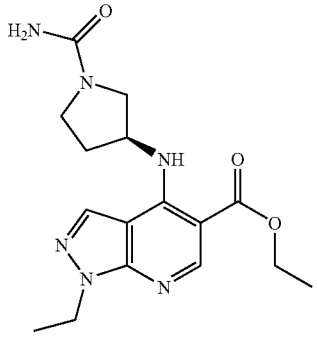 | Intermediate 150 of WO 2005/058892 A1 (Glaxo Group Limited) |
| 125 | 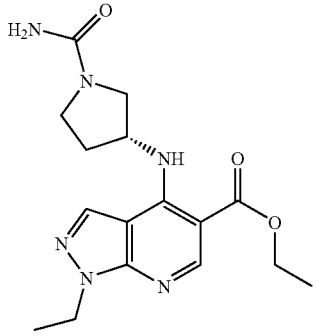 | Intermediate 151 of WO 2005/058892 A1 (Glaxo Group Limited) |
| 126 | 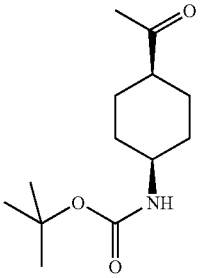 | Intermediate 155 of WO 2005/058892 A1 (Glaxo Group Limited) |
| 127 | 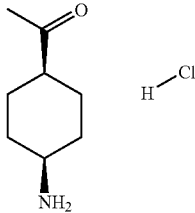 | Intermediate 156 of WO 2005/058892 A1 (Glaxo Group Limited) |

| Optional Intermediate Number | Structure of compound | One or two possible published reference(s) to (e.g. synthetic reference to), or one possible source of, the compound |
|---|---|---|
| 128 | 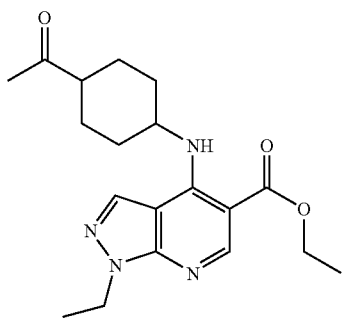<br>(mixture of cis and trans isomers) | Intermediate 157 of WO 2005/058892 A1 (Glaxo Group Limited) |
| 129 | 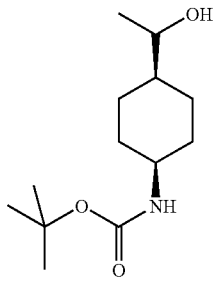 | Intermediate 159 of WO 2005/058892 A1 (Glaxo Group Limited) |
| 130 | 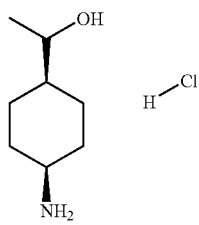 | Intermediate 160 of WO 2005/058892 A1 (Glaxo Group Limited) |
| 131 | 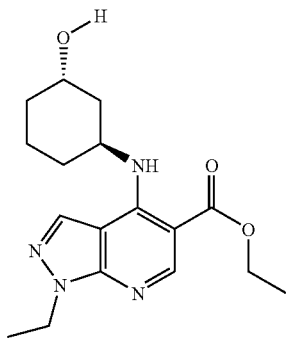<br>[contains trans-(3-hydroxycyclohex-1-yl)amino group, racemic] | Intermediate 161 of WO 2005/058892 A1 (Glaxo Group Limited) |

| Optional Intermediate Number | Structure of compound | One or two possible published reference(s) to (e.g. synthetic reference to), or one possible source of, the compound |
|---|---|---|
| 132 | 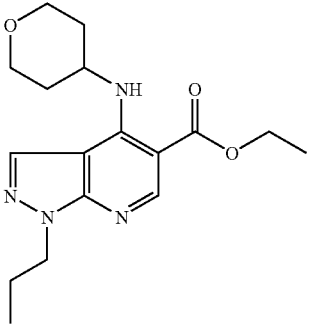 | Example 185 of WO 2004/024728 A2 (Glaxo Group Limited); or Intermediate 171 of WO 2005/058892 A1 (Glaxo Group Limited) |
| 133 | 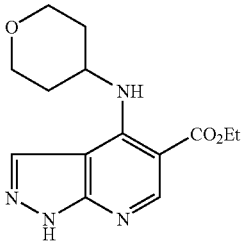 | Example 20 of WO 2004/024728 A2 (Glaxo Group Limited) |
| 134 | 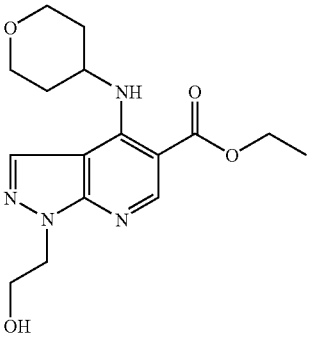 | Example 186 of WO 2004/024728 A2 (Glaxo Group Limited) |
| 135 | 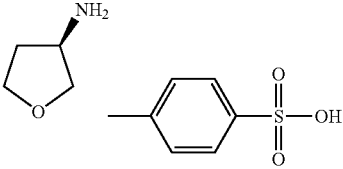 | Fluka Chemie AG, Germany (CAS 111769-27-8) |
| 136 | 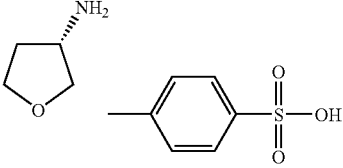 | E. Merck, Germany; or E. Merck (Merck Ltd), Hunter Boulevard, Magna Park, Lutterworth, Leicestershire LE17 4XN, United Kingdom (CAS 104530-80-5) |
| 137 | 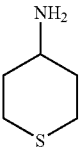 | Intermediate 11 of WO 2004/024728 A2, and optionally reference cited therein |

| Optional Intermediate Number | Structure of compound | One or two possible published reference(s) to (e.g. synthetic reference to), or one possible source of, the compound |
|---|---|---|
| 138 | 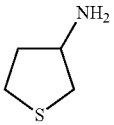 | Intermediate 12 of WO 2004/024728 A2, and optionally references cited therein |
| 139 | 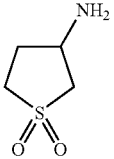 | Sigma Aldrich Library of Rare Chemicals (SALOR) (CAS-6338-70-1) |
| 140 | 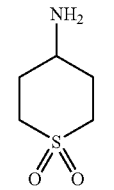 | Intermediate 14 of WO 2004/024728 A2, and optionally references cited therein |
| 141 | 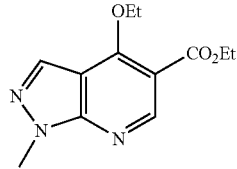 | Intermediate 3 of WO 2004/024728 A2 (Glaxo Group Limited) |
| 142 | 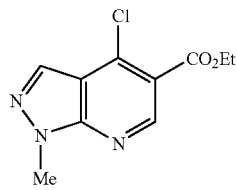 | Intermediate 25 of WO 2004/024728 A2 (Glaxo Group Limited) |
| 143 | 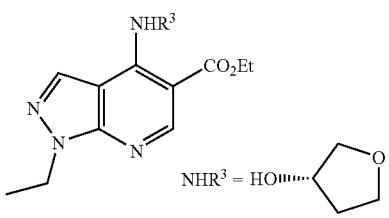 | Example 8 of WO 2004/024728 A2 (Glaxo Group Limited) |
| 144 | 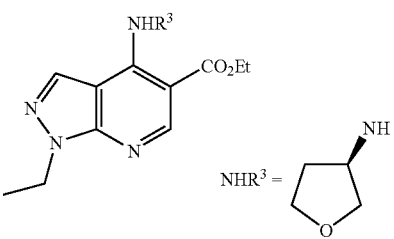 | Example 9 of WO 2004/024728 A2 (Glaxo Group Limited) |

| Optional Intermediate Number | Structure of compound | One or two possible published reference(s) to (e.g. synthetic reference to), or one possible source of, the compound |
|---|---|---|
| 145 | 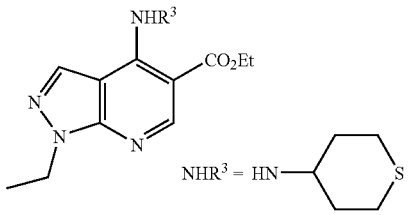 | Example 10 of WO 2004/024728 A2 (Glaxo Group Limited) |
| 146 | 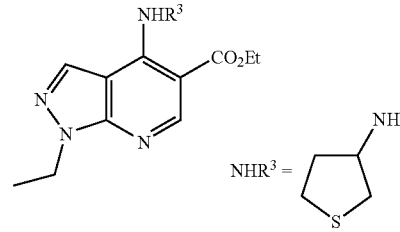 | Example 11 of WO 2004/024728 A2 (Glaxo Group Limited) |
| 147 | 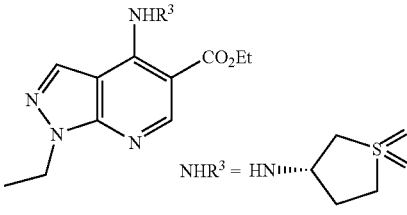 | Example 13 of WO 2004/024728 A2 (Glaxo Group Limited) |
| 148 | 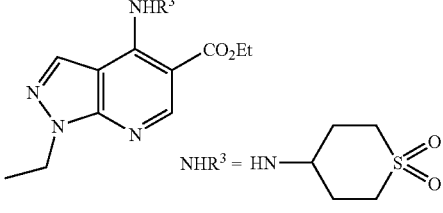 | Example 14 of WO 2004/024728 A2 (Glaxo Group Limited) |
| 149 | 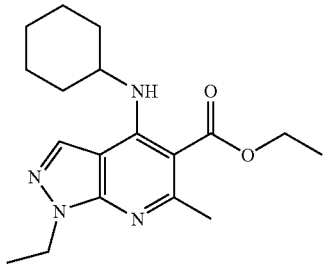 | Example 190 of WO 2004/024728 A2 (Glaxo Group Limited) |
| 150 | 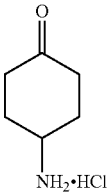 | Intermediate 54 of WO 2004/024728 A2 (Glaxo Group Limited) |

-continued

| Optional Intermediate Number | Structure of compound | One or two possible published reference(s) to (e.g. synthetic reference to), or one possible source of, the compound |
|---|---|---|
| 151 | 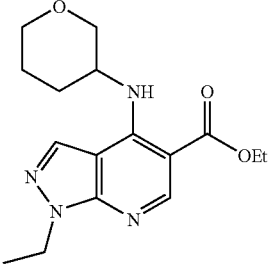 | Intermediate 58A of WO 2004/024728 A2 (Glaxo Group Limited) |
| 152 | 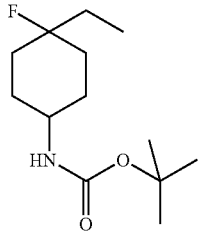<br>[sample containing 1,1-dimethylethyl (4-fluoro-3-cyclohexen-1-yl)carbamate as an impurity] | Intermediate 62 of WO 2004/024728 A2 (Glaxo Group Limited) |
| 153 | 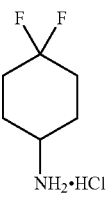<br>[sample containing 4-fluoro-3-cyclohexen-1-amine) as an impurity] | Intermediate 63 of WO 2004/024728 A2 (Glaxo Group Limited) |
| 154 | 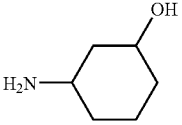 | AB Chem, Inc., Canada (mixture of cis and trans); or J. Chem. Soc., Perkin Trans. 1, 1994, 537 |
| 155 | as Intermediate 154, but racemic cis-isomer, i.e. racemic cis-(3-hydroxy-cyclohex-1-yl)-amine | J. Chem. Soc., Perkin Trans 1, 1994, 537 (discloses a 3.3:1 cis:trans mixture) |
| 156 |  | Aldrich, or TCI-America |
| 157 | 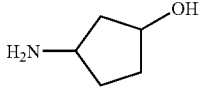 | U.S. Pat. No. 4,219,660 |
| 158 | 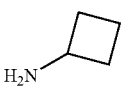 | Aldrich |
| 159 | 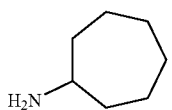 | Aldrich |

-continued
| Optional Intermediate Number | Structure of compound | One or two possible published reference(s) to (e.g. synthetic reference to), or one possible source of, the compound |
|---|---|---|
| 160 | 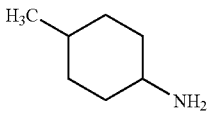 | Aldrich |
| 161 | 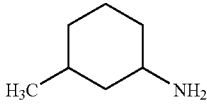 | Pfaltz-Bauer |
| 162 |  | J. Org. Chem., 1985, 50(11), 1859 |
| 163 | 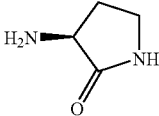 | WO 99/12933 |
| 164 | 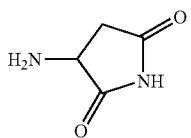 | EP 1188744 |
| 165 | 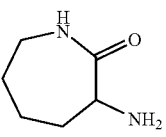  (3-Aminoazepan-2-one) | Sigma-Aldrich Company Ltd |
| 166* |  | J. Med. Chem., 1994, 37(17), 2360 |
| 167* |  | Aldrich |
| 168* | 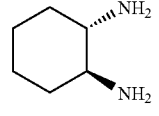  (trans isomer, e.g. optionally racemic) | Aldrich |
| 169* | 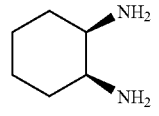 | Aldrich |
| 170* | 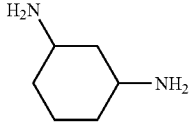 | Peakdale Molecular Ltd |

| Optional Intermediate Number | Structure of compound | One or two possible published reference(s) to (e.g. synthetic reference to), or one possible source of, the compound |
|---|---|---|
| 171 | 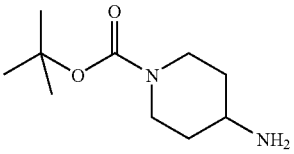<br>1,1-dimethylethyl 4-amino-1-piperidinecarboxylate | AstaTech |
| 172 | 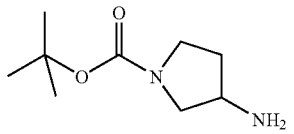 | |
| 173 | 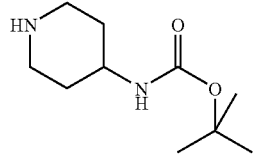<br>1,1-dimethylethyl 4-piperidinylcarbamate | Syngene or AstaTech |
| 174 | 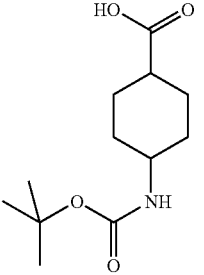<br>4-({[(1,1-dimethylethyl)oxy]carbonyl}amino)cyclohexane carboxylic acid | Fluka |
| 175 | 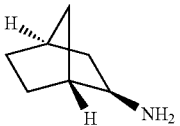 | Aldrich |
| 176 | 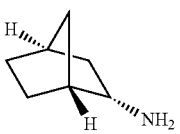 | Aldrich |

EXAMPLES

Table of Examples

| Example No. | Name |
|---|---|
| 1A1 | N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}-amino)benzamide dihydrochloride |
| 1A2 | N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}-amino)benzamide monohydrochloride |
| 1A3 | N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}-amino)benzamide monohydrochloride (recrystallised) |
| 1B | N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide |
| 1C | N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide trifluoroacetate (salt) |
| 1D | N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrobromide |
| 1E | N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide hemisuccinate |
| 1F | N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide hemifumarate |
| 1G | N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide mono-xinafoate (mono-1-hydroxy-2-naphthoate) |
| 1H1 and 1H2 | N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide phosphate |
| 1J1 and 1J2 | N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide mono-(+)-camphorsulfonate |
| 3 | 4-[(1,6-diethyl-5-{[({4-[(8-{(2R)-2-[(methyloxy)methyl]-1-pyrrolidinyl}octanoyl)amino]phenyl}carbonyl)amino]methyl}-1H-pyrazolo[3,4-b]pyridin-4-yl)amino]-1-piperidinecarboxamide trifluoroacetate |
| 4 | 4-[(1,6-diethyl-5-{[({4-[(8-{(2S)-2-[(methyloxy)methyl]-1-pyrrolidinyl}octanoyl)amino]phenyl}carbonyl)amino]methyl}-1H-pyrazolo[3,4-b]pyridin-4-yl)amino]-1-piperidinecarboxamide trifluoroacetate |
| 9 | 4-({1,6-diethyl-5-[({[4-({8-[(2-hydroxyethyl)(methyl)amino]octanoyl}amino)phenyl]carbonyl}amino)methyl]-1H-pyrazolo[3,4-b]pyridin-4-yl}amino)-1-piperidinecarboxamide trifluoroacetate (salt) |
| 11 | N-{[1,6-diethyl-4-(tetrahydro-2H-pyran-4-ylamino)-1H-pyrazolo[3,4-b]pyridin-5-yl]methyl}-4-[(8-{(2R)-2-[(methyloxy)methyl]-1-pyrrolidinyl}octanoyl)amino]benzamide trifluoroacetate |
| 12 | N-{[1,6-diethyl-4-(tetrahydro-2H-pyran-4-ylamino)-1H-pyrazolo[3,4-b]pyridin-5-yl]methyl}-4-[(8-{(2S)-2-[(methyloxy)methyl]-1-pyrrolidinyl}octanoyl)amino]benzamide trifluoroacetate |
| 17 | formate salt of N-{[1,6-diethyl-4-(tetrahydro-2H-pyran-4-ylamino)-1H-pyrazolo[3,4-b]pyridin-5-yl]methyl}-4-{[8-(4-morpholinyl)octanoyl]amino}benzamide |
| 18 | formate salt of N-{[1,6-diethyl-4-(tetrahydro-2H-pyran-4-ylamino)-1H-pyrazolo[3,4-b]pyridin-5-yl]methyl}-4-{[8-(1-pyrrolidinyl)octanoyl]amino}benzamide |
| 19 | formate salt of N-{[1,6-diethyl-4-(tetrahydro-2H-pyran-4-ylamino)-1H-pyrazolo[3,4-b]pyridin-5-yl]methyl}-4-[4-({4-[(2-hydroxyethyl)(methyl)amino]butyl}oxy)butyl]benzamide |
| 20 | formate salt of N-{[1,6-diethyl-4-(tetrahydro-2H-pyran-4-ylamino)-1H-pyrazolo[3,4-b]pyridin-5-yl]methyl}-4-(4-{[4-(4-morpholinyl)butyl]oxy}butyl)benzamide |
| 21 | formate salt of N-{[1,6-diethyl-4-(tetrahydro-2H-pyran-4-ylamino)-1H-pyrazolo[3,4-b]pyridin-5-yl]methyl}-4-(4-{[4-(1-pyrrolidinyl)butyl]oxy}butyl)benzamide |

-continued

| Example No. | Name |
|---|---|
| 22 | formate salt of 4-[(1,6-diethyl-5-{[({4-[4-({4-[(2-hydroxyethyl)(methyl)amino]butyl}oxy)butyl]phenyl}carbonyl)amino]methyl}-1H-pyrazolo[3,4-b]pyridin-4-yl)amino]-1-piperidinecarboxamide |
| 23 | formate salt of 4-({1,6-diethyl-5-[({[4-(4-{[4-(4-morpholinyl)butyl]oxy}butyl)phenyl]carbonyl}amino)methyl]-1H-pyrazolo[3,4-b]pyridin-4-yl}amino)-1-piperidinecarboxamide |
| 23A | 4-({1,6-diethyl-5-[({[4-(4-{[4-(4-morpholinyl)butyl]oxy}butyl)phenyl]carbonyl}amino)methyl]-1H-pyrazolo[3,4-b]pyridin-4-yl}amino)-1-piperidinecarboxamide |
| 24 | formate salt of 4-({1,6-diethyl-5-[({[4-(4-{[4-(1-pyrrolidinyl)butyl]oxy}butyl)phenyl]carbonyl}amino)methyl]-1H-pyrazolo[3,4-b]pyridin-4-yl}amino)-1-piperidinecarboxamide |
| 25 | formate salt of N-{[1-ethyl-6-methyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide |
| 26 | formate salt of N-{[1-ethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide |
| 27 | N-{[1,6-diethyl-4-(tetrahydro-2H-pyran-4-ylamino)-1H-pyrazolo[3,4-b]pyridin-5-yl]methyl}-4-[8-(4-morpholinyl)octyl]benzamide |
| 28 | N-{[1,6-diethyl-4-(tetrahydro-2H-pyran-4-ylamino)-1H-pyrazolo[3,4-b]pyridin-5-yl]methyl}-4-{8-[(2-hydroxyethyl)(methyl)amino]octyl}benzamide |
| 29 | N-{[1,6-diethyl-4-(tetrahydro-2H-pyran-4-ylamino)-1H-pyrazolo[3,4-b]pyridin-5-yl]methyl}-3-({8-[(2-hydroxyethyl)(methyl)amino]octanoyl}amino)benzamide |
| 30 | N-{[1,6-diethyl-4-(tetrahydro-2H-pyran-4-ylamino)-1H-pyrazolo[3,4-b]pyridin-5-yl]methyl}-2-({8-[(2-hydroxyethyl)(methyl)amino]octanoyl}amino)benzamide |
| 31 | N-{[1,6-diethyl-4-(tetrahydro-2H-pyran-4-ylamino)-1H-pyrazolo[3,4-b]pyridin-5-yl]methyl}-4-({6-[(2-hydroxyethyl)(methyl)amino]hexanoyl}amino)benzamide |
| 32 | N-{[1,6-diethyl-4-(tetrahydro-2H-pyran-4-ylamino)-1H-pyrazolo[3,4-b]pyridin-5-yl]methyl}-4-({7-[(2-hydroxyethyl)(methyl)amino]heptanoyl}amino)benzamide |
| 33 | N-{[1,6-diethyl-4-(tetrahydro-2H-pyran-4-ylamino)-1H-pyrazolo[3,4-b]pyridin-5-yl]methyl}-4-({10-[(2-hydroxyethyl)(methyl)amino]decanoyl}amino)benzamide |
| 34 | N-{[1,6-diethyl-4-(tetrahydro-2H-pyran-4-ylamino)-1H-pyrazolo[3,4-b]pyridin-5-yl]methyl}-4-({11-[(2-hydroxyethyl)(methyl)amino]undecanoyl}amino)benzamide |

Example 1A1

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide dihydrochloride

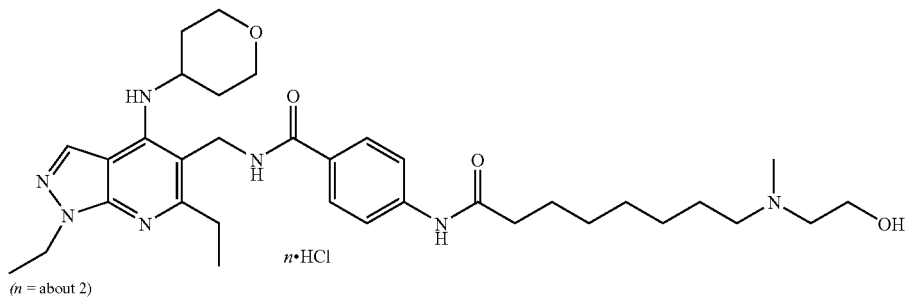

(n = about 2)

To a solution of 4-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide (0.98 g, 1.56 mmol, e.g. which can be as prepared in Intermediate 11) in N,N-dimethylformamide (50 ml) was added N,N-diisopropylethylamine (0.54 ml, 3.12 mmol) followed by 2-(methylamino)ethanol (0.2 ml, 2.34 mmol, commercially available e.g. from Aldrich) and the resulting solution was heated at 80° C. for 16 hours. The mixture was cooled, evaporated to dryness and the residue partitioned between dichloromethane (30 ml) and saturated aqueous sodium bicarbonate solution (30 ml). The aqueous portion was extracted with more dichloromethane (30 ml) and the combined organic extracts were passed through a hydrophobic frit and evaporated to dryness to give an amber oil (1.3 g). The residue was purified by passing through a 50 g silica SPE cartridge, loading using dichloromethane, and eluting with dichloromethane (100 ml), 5% methanol/dichloromethane (100 ml), 10% methanol/dichloromethane (200 ml), 20% methanol/dichloromethane (200 ml), 20% methanol/1% triethylamine/dichloromethane (200 ml) and 25% methanol/1% triethylamine/dichloromethane (400 ml). Fractions containing the product (generally obtained from the 25% methanol/1% triethylamine/dichloromethane elution) were combined and evaporated to dryness. Co-evaporation with dichloromethane and diethyl ether to remove excess triethylamine gave the product as a cream-coloured foamy solid (0.54 g). Attempts to recrystallise the foam from various solvents including ethyl acetate, ethyl acetate/diethyl ether, isopropanol/water, and ethanol/diethyl ether, were unsuccessful (material failed to crystallise). Hence the foam was dissolved in dichloromethane, treated with a 4M solution of HCl in 1,4-dioxane (5 ml), and allowed to stand at room temperature overnight. Evaporation of the solvent followed by co-evaporation with diethyl ether and ethanol gave a foam. Attempts to recrystallise this foam from various solvent combinations including diethyl ether/ethyl acetate/ethanol were unsuccessful (material failed to crystallise). The foam was triturated with diethyl ether, filtered and dried to give the title compound as a cream solid (0.45 g). LCMS showed MH$^+$=622; T$_{RET}$=2.24 min. Under the microscope this material appeared to be partially crystalline.

The $^1$H NMR spectrum for this or a similar sample of the title compound was as follows:

$^1$H NMR (400 MHz, DMSO-d$_6$) δ (delta) ppm 13.90 (1 H, br. s.), 10.27 (1 H, s.), 9.63 (1H, br. s.), 9.22 (1 H, br. s.), 9.14 (1 H, br. s.), 8.40 (1 H, br. s.), 7.87 (2 H, d, J=8.5 Hz), 7.71 (2 H, d, J=8.5 Hz), 5.31 (1 H, br. s.), 4.49-4.62 (4 H, m), 4.24-4.39 (1 H, m), 3.90 (2 H, d, J=11.0 Hz), 3.72 (2 H, t, J=5.0 Hz), 3.62 (2 H, t, J=11.0 Hz), 2.91-3.28 (6 H, m), 2.74 (3 H, d, J=4.5 Hz), 2.34 (2 H, t, J=7.0 Hz), 1.95 (2 H, d, J=12.0 Hz), 1.54-1.77 (6H, m), 1.37 (3 H, t, J=7.0 Hz), 1.25-1.33 (9 H, m).

This compound is thought to be the dihydrochloride salt, e.g. based on a comparison of its $^1$H NMR spectrum with that of Example 1A2 (e.g. that given below).

Example 1A2

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride under nitrogen. The slurry mixture was stirred and was heated from 21° C. to 65° C. over 40 minutes (the starting material dissolving at about 60° C.), and when at 65° C. the mixture was treated with concentrated hydrochloric acid (2.82 ml, 1.05 equivalents). This acid was rinsed into the vessel with further isopropanol (5 ml).

The temperature was adjusted to 56° C. and then seeds of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide hydrochloride (about 2 mg) (e.g. monohydrochloride or dihydrochloride) were added. After cooling to 51° C. over 1.25 h, the batch was held at 51° C. for 5 minutes and then cooled to 0-2° C. over about 2 hours. Crystallisation occurred during this cool.

The slurry was held at ca. 0-2° C. for about one hour and then heated to 45° C. (Jacket temperature) over 2 hours, and then cooled to 0° C. over 2 hours. This 'temperature cycling' was repeated three further times, before holding at 0° C. for very approximately half an hour to one hour. The batch was filtered, and the solid washed with chilled (ca. 5° C.) isopropanol (2×30 ml) and dried in vacuo at 40-45° C. to give the title compound as a solid (17.5 g).

$^1$H NMR (500 MHz, DMSO-d$_6$) δ (delta) ppm 10.31 (s, 1 H), 10.01 (br. s., 1 H), 8.86 (br. s., 1 H), 8.02 (br. s., 1 H), 7.85 (d, J=8.5 Hz, 2 H), 7.70 (d, J=8.5 Hz, 2 H), 7.19 (br. s., 1 H), 5.30-5.35 (m, 1 H), 4.53 (d, J=5.5 Hz, 2 H), 4.30-4.39 (m, 2 H), 4.12 (br. s., 1 H), 3.85-3.90 (m, J=11.0 Hz, 2 H), 3.71-3.78 (m, J=4.9 Hz, 2 H), 3.53-3.59 (m, J=11.0, 11.0 Hz, 2 H), 2.91-3.24 (m, 6 H), 2.73 (s, 3 H), 2.32-2.37 (m, 2 H), 1.89-1.94 (m, J=12.2 Hz, 2 H), 1.48-1.73 (m, 6 H), 1.25-1.34 (m, 12 H).

This compound is thought to be the monohydrochloride salt, e.g. based on a comparison of its $^1$H NMR spectrum with that of Example 1A1 (e.g. that given above).

It is also thought that there are at least two solid (e.g. crystalline) forms of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride, with a first solid (e.g. crystalline) form (named "Form 1") being a preferred substantially-anhydrous solid (e.g. crystalline) form (named "anhydrate") and with a second solid (e.g. crystalline) form (named "Form 2") being a less-preferred hydrated solid (e.g.

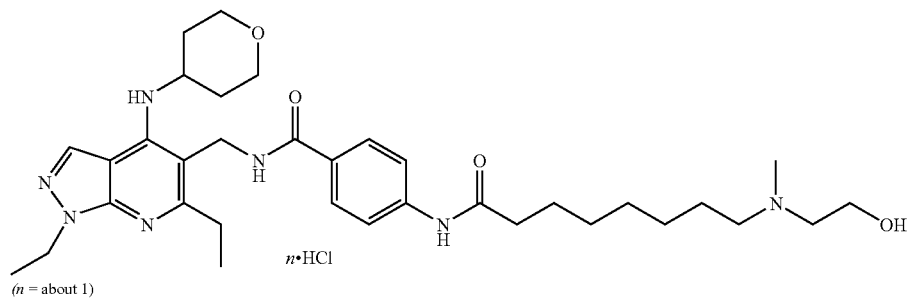

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide (the "free base", 20.3 g, e.g. which can be as prepared in Example 1B) was charged to a 500 ml jacketed temperature-controlled laboratory reactor and was suspended in isopropanol (203 ml)

crystalline) form (named "hydrate"). The solid (e.g. crystalline) monohydrochloride salt prepared in the above-described synthesis (Example 1A2) is thought to be substantially the Form 1 anhydrate.

A sample of N-{[1,6-diethyl-4-(tetrahydro-2H-pyran-4-ylamino)-1H-pyrazolo[3,4-b]pyridin-5-yl]methyl}-4-({8-

[(2-hydroxyethyl)(methyl)amino]octanoyl}amino)benzamide monohydrochloride Form 1 anhydrate, prepared in the above-described synthesis (Example 1A2), has substantially the following X-ray powder diffraction (XRPD) characteristics. The X-ray powder diffraction (XRPD) data were acquired on a PANalytical X.Pert Pro powder diffractometer, model PW3040/60, serial number DY1850 using an XCelerator detector. The acquisition conditions were: radiation: Cu Kα (copper K-alpha), generator tension: 40 kV, generator current: 45 mA, start angle: 2.0°. 2.θ, end angle: 40.0°. 2θ, step size: 0.0167° 2θ, time per step: 31.75 seconds. The sample was prepared by mounting a few milligrams of sample on Si wafer (zero background) plate(s), resulting in a thin layer of powder. Characteristic XRPD peak positions (angles) and calculated d-spacings for the monohydrochloride Form 1 anhydrate, calculated from the raw data using Highscore software, are shown in the following table, with a margin of error of approximately ±0.1° 2θ for each of the peak assignments:

| degrees 2θ (2-theta) | approximate d-spacing in Å (Angstroms) |
|---|---|
| 5.1 | 17.3 |
| 7.8 | 11.4 |
| 10.3 | 8.6 |
| 10.7 | 8.3 |
| 14.3 | 6.2 |
| 15.2 | 5.8 |
| 17.5 | 5.1 |
| 18.6 | 4.8 |
| 18.8 | 4.7 |
| 19.7 | 4.5 |
| 20.3 | 4.4 |
| 21.4 | 4.1 |
| 21.9 | 4.1 |
| 22.4 | 4.0 |
| 23.1 | 3.9 |
| 23.5 | 3.8 |
| 24.0 | 3.7 |

The following four XRPD peaks of the monohydrochloride Form 1 anhydrate, from the above list of XRPD peaks, are thought to distinguish this Form 1 anhydrate from the Form 2 hydrate: 5.1±0.1° 2θ (d-spacing ca. 17.3 Å), 10.7±0.1° 2θ (d-spacing ca. 8.3 Å), 23.1±0.1° 2θ (d-spacing ca. 3.9 Å), 23.5±0.1° 2θ (d-spacing ca. 3.8 Å).

The following two XRPD peaks of the monohydrochloride Form 1 anhydrate are thought also partially to distinguish this Form 1 anhydrate from the Form 2 hydrate, but there are shoulders or low intensity peaks of another form in fairly close proximity that make these peaks slightly less distinguishing than the above four peaks: 10.3±0.1° 2θ (d-spacing ca. 8.6 Å), 17.5±0.1° 2θ (d-spacing ca. 5.1 Å).

The IR (infrared) spectrum of the solid product, the monohydrochloride Form 1 anhydrate, was recorded using a Nicolet Avatar 360 FT-IR spectrometer fitted with a diamond/ZnSe ATR accessory. The FT-IR data were recorded over 64 scans at 4 cm$^{-1}$ resolution. For the monohydrochloride Form 1 anhydrate product, solid-form IR bands were observed at: 3252, 2938, 2857, 1688, 1639, 1598, 1571, 1526, 1503, 1437, 1407, 1355, 1304, 1254, 1185, 1162, 1139, 1123, 1086, 1035, 1014, 988, 964, 860, 820 and 770 cm$^{-1}$ (with some variation or error possible for each peak, e.g. of ±2 cm$^{-1}$ or ±1 cm$^{-1}$). It is thought that the solid-form IR spectrum of the monohydrochloride Form 1 anhydrate includes a characteristic band at 1639 (±2 or ±1) cm$^{-1}$. In comparison, a solid-form sample (not prepared in this Example) of the monohydrochloride Form 2 hydrate appears to include a characteristic band at ca. 1623 (±2 or ±1) cm$^{-1}$.

Example 1A2

Alternative Preparation No. 1, Plant Method: N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride (n=1)

The monohydrochloride salt may be prepared directly from 5-(aminomethyl)-1,6-diethyl-N-(tetrahydro-2H-pyran-4-yl)-1H-pyrazolo[3,4-b]pyridin-4-amine monohydrochloride e.g. Intermediate 7A. For example, the following process may be used, e.g. in plant:

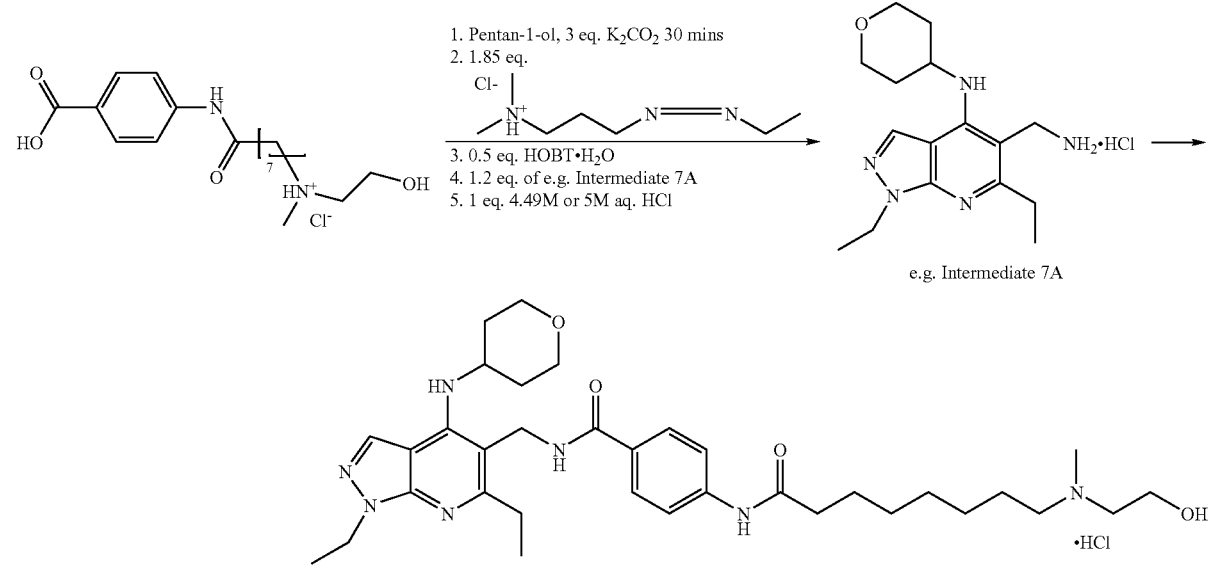

Example 1A2 (Alternative Preparation No. 1, Plant Method)

Summary of Plant Method

The following reaction is carried out under a nitrogen atmosphere, in plant. All weights, volumes and equivalents are relative to the 5-(aminomethyl)-1,6-diethyl-N-(tetrahydro-2H-pyran-4-yl)-1H-pyrazolo[3,4-b]pyridin-4-amine monohydrochloride.

To stirred n-pentanol (pentan-1-ol, 15 vol, 105 L) in a glass-lined reactor at 18° C. under nitrogen is added 4-({8-[(2-hydroxyethyl)(methyl)amino]octanoyl}amino)benzoic acid hydrogen chloride (0.95 wt, 6.65 kg) (e.g. which can be as prepared in Intermediate 39A, or which can be specially ordered from Sigma-Aldrich) and potassium carbonate [325 mesh particle size (quite a fine particle size), 1.02 wt, 7.14 kg]. After stirring at 90 rpm for 10 minutes at 20±5° C., 1-(3-dimethylaminopropyl)-3-ethylcarbodiimide hydrochloride (EDC) (0.87 wt, 6.09 kg), 1-hydroxybenzotriazole hydrate (HOBT.H$_2$O) (0.19 wt, 1.33 kg) and 5-(aminomethyl)-1,6-diethyl-N-(tetrahydro-2H-pyran-4-yl)-1H-pyrazolo[3,4-b]pyridin-4-amine monohydrochloride (1 wt, 7.0 kg) (e.g. which is preferably substantially as prepared in Intermediate 7A) are added sequentially. The heterogeneous reaction mixture is warmed to 20±5° C., and is stirred at 90-160 rpm under nitrogen at 20±5° C. for 9 hours 20 minutes (90 minutes at 90 rpm, 90 minutes at 125 rpm, and 6 hours 20 minutes at 160 rpm). Water (10 vol, 70 L) is added and the mixture is stirred for 16 minutes while maintaining the current batch temperature; the layers are allowed to settle for 15 minutes and separated. To the upper organic layer is added 32% w/w aqueous sodium hydroxide solution (2.5 wt, 17.5 kg) over a period of 37 minutes, while maintaining the reactor contents at 20±5° C. The mixture is then heated to 45±5° C. and stirred at 75 rpm at 45±5° C. for 2 hours. The mixture is cooled to 20±5° C. and water (8 vol, 56 L) is added. The mixture is stirred for 15 minutes and allowed to settle for 15 minutes. The lower aqueous layer is removed and the remaining organic layer is held overnight without stirring. 6.5% w/w aqueous sodium chloride solution (10.4 wt, 72.8 kg) is added to the organic layer. Aqueous hydrochloric acid (17% w/w) is added over 83 minutes, while maintaining the reactor contents at 20±5° C., with the amount of 17% w/w hydrochloric acid used (e.g. about 7.0 kg to about 19.20 kg) being such as to ensure that the pH is adjusted finally to 5.75±0.25, with a final pH of less than 5.5 being avoided to minimise loss of the product (as hydrochloride) to the aqueous layer. The mixture is stirred for 30 minutes and allowed to settle for 30 minutes. The organic layer is separated, is stirred with 4% aqueous sodium hydroxide solution (10.4 wt, 72.8 kg) for 15 minutes while maintaining the current batch temperature, and is allowed to settle for 30 minutes. The lower aqueous layer is removed. Water (10 vol, 70 L) is added to the organic layer and stirred for at least 15 minutes while maintaining the current batch temperature. The agitator is then switched off. The reactor contents are heated to 25±5° C., allowed to settle for 30 minutes and then cooled to 20±5° C. The lower aqueous layer is removed. The organic layer is transferred from the reactor, the reactor is washed with n-pentanol (pentan-1-ol, 2 vol, 14 L), and the combined organic mixture is filtered to remove any insoluble matters while being returned to the reactor. The organic mixture is allowed to settle for about 1 hour, after which a lower aqueous layer forms which is removed. The separated organic layer is allowed to settle overnight, after which a lower aqueous layer forms which is removed. A solution yield is obtained on the organic solution using a calibrated HPLC system and 4.49M aqueous hydrochloric acid (1 equivalent, 3.80 kg) is added, maintaining the reactor contents at 20 ±5° C. The mixture is concentrated in vacuo to 10 volumes (70 L), by vacuum distillation at about −0.901 to −0.912 barg, at internal temperatures starting from 46.5° C. and rising to about 78° C. (jacket temperature 60° C., rising to 90° C., and rising again to 100° C.). The mixture is then adjusted to 85±5° C. under an atmospheric pressure of nitrogen. A slurry of seed crystals (0.007 kg, 0.001 wt) of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride (preferably the Form 1 anhydrate thereof) in n-pentanol (pentan-1-ol, 0.07 L, 0.01 vol) is added. The mixture is cooled to 60±5° C., stirred for 2 hours at 60±5° C., and then adjusted to 55±5° C. Tert-butyl methyl ether (TBME) (4.3 vol, 30.1 L) is added over 5 minutes, maintaining the reactor contents at 50±5° C. The resultant mixture is cooled to 20±5° C. over about 1 hour, and then is stirred for about 14 hours at 20±5° C. The resultant slurry is filtered under 0.5 to 1 barg of nitrogen pressure using a 20 micron filter cloth. The reactor and then the filter cake is washed with n-pentanol (pentan-1-ol, 2.5 vol, 17.5 L), and the filter cake is then washed with TBME (2.5 vol, 17.5 L), the filter cake washes being under 0.5 to 1 barg of nitrogen pressure. Residual solvent in the filter cake is removed under nitrogen pressure. Then the filtered solid is dried at 55±5° C. in vacuo in a vacuum tray dryer under a bleed of 5 L/min nitrogen until the product achieves a constant temperature for at least 4 hours, and then is cooled to <30° C., to yield the desired product N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride.

The solid compound preparable by the above alternative preparation no. 1 (Plant Method) is substantially in the form of the crystalline monohydrochloride Form 1 anhydrate (see Example 1A2, first synthesis, for discussion of this form).

Example 1A2 Alternative Preparation No. 1

Plant Method—Detailed Step-Wise Methodology

This reaction is for carrying out in a 400 L glass lined reactor; the reaction is carried out under a nitrogen atmosphere.

All weights, volumes and equivalents are relative to 5-(aminomethyl)-1,6-diethyl-N-(tetrahydro-2H-pyran-4-yl)-1H-pyrazolo[3,4-b]pyridin-4-amine monohydrochloride.

1. Purge the reactor with nitrogen.
2. Add n-pentanol (pentan-1-ol, 15 vol, 105 L) to the 400 L glass lined reactor.
3. Run the agitator at 90 rpm (revolutions per minute).
4. Cool the contents to 18° C.
5. Charge the reactor with 4-({8-[(2-hydroxyethyl)(methyl)amino]octanoyl}amino)benzoic acid hydrogen chloride (0.95 wt, 6.65 kg) and then potassium carbonate (325 mesh particle size (quite a fine particle size), 1.02 wt, 7.14 kg).
6. Stir the contents at 20±5° C. for 10 minutes at 90 rpm.
7. Add 1-(3-dimethylaminopropyl)-3-ethylcarbodiimide hydrochloride (EDC) (0.87 wt, 6.09 kg), 1-hydroxybenzotriazole hydrate (HOBT.H$_2$O) (0.19 wt, 1.33 kg) and 5-(aminomethyl)-1,6-diethyl-N-(tetrahydro-2H-pyran-4-yl)-1H-pyrazolo[3,4-b]pyridin-4-amine monohydrochloride (1 wt, 7.0 kg) to the reactor.

8. Heat the contents of the reactor to 20±5° C., and then stir the contents of the reactor at 20±5° C. for 90 minutes at 90 rpm.
9. Adjust agitator speed to 125 rpm and stir the reactor contents for a further 90 minutes.
10. Adjust agitator speed to 160 rpm and stir the heterogeneous reactor contents at 20±5° C. for a further 6 hours 20 minutes.
11. Add water (10 vol, 70 L) to the reactor.
12. Stir the contents of the reactor for 16 minutes, maintaining the current batch temperature.
13. Stop the agitator and allow the layers of the contents to settle for 15 minutes.
14. Remove the lower aqueous layer.
15. Add 32% w/w aqueous sodium hydroxide solution (2.5 wt, 17.5 kg) to the reactor over a period of 37 minutes, maintaining the reactor contents at 20±5° C.
16. Heat the contents of the reactor to 45±5° C. over a period of 12 minutes, and stir at 45±5° C. for 2 hours at 75 rpm.
17. Cool the contents of the reactor to 20±5° C. over a period of 18 minutes.
18. Add water (8 vol, 56 L) to the reactor.
19. Stir the contents of the reactor for 15 minutes, maintaining the current batch temperature, before allowing the layers to settle for 15 minutes.
20. Remove the lower aqueous layer. The reactor contents are held overnight with the agitator off.
21. Charge the reactor with 6.5% w/w aqueous sodium chloride solution (10.4 wt, 72.8 kg).
22. Calibrate a pH probe using pH 7.0, 2.0 and 10.0 buffers.
23. Add 17% w/w aqueous hydrochloric acid to the stirred reactor over a period of 83 minutes (using a slower addition rate towards the end of the addition), maintaining the reactor contents at 20±5° C., with the amount of 17% w/w hydrochloric acid used being such as to ensure that the pH of the contents is adjusted to a final pH of 5.75±0.25. A final pH of less than 5.5 is avoided to minimise loss of the product (as hydrochloride) to the aqueous layer. [Note: If some alkaline aqueous phase is still present in or together with the organic layer after step 20, e.g. due to some emulsion formation, and if this alkaline aqueous phase is not separated off before the aqueous sodium chloride solution addition in step 21, then more than the theoretically-required about 7.0 kg amount of 17% w/w hydrochloric acid will be required, e.g. 19.20 kg may be required, to achieve a final pH of 5.75±0.25.]
24. Stir the contents of the reactor for 30 minutes, maintaining the current batch temperature, before stopping the agitator and allowing the layers to settle for 30 minutes.
25. Remove the lower aqueous layer.
26. Add 4% aqueous sodium hydroxide solution (10.4 wt, 72.8 kg) to the reactor.
27. Stir the contents of the reactor for 15 minutes, maintaining the current batch temperature, before stopping the agitator and allowing the layers to settle for 30 minutes.
28. Remove the lower aqueous layer.
29. Add water (10 vol, 70 L) to the reactor.
30. Stir the contents of the reactor for at least 15 minutes, maintaining the current batch temperature, and then stop the agitator.
31. Warm the contents of the reactor to 25±5° C. (jacket temperature 40±5° C.).
32. Allow the contents of the reactor to settle for 30 minutes.
33. Cool the contents of the reactor to 20±5° C. over 6 minutes.
34. Remove the lower aqueous layer.
35. Transfer the organic mixture from the reactor into earthed polylined steel drums, add pentan-1-ol (2 vol, 14 L) to the reactor, and discharge these pentan-1-ol washings into the drum containing the organic mixture. Transfer the combined organic mixture from the drum back into the reactor through a filter, in order to filter the organic layer (to remove any insoluble matters).
36. Allow the organic mixture in the reactor to settle for about 1 hour, to allow the organic mixture to separate into an upper organic layer and a further lower aqueous layer. Remove the lower aqueous layer.
37. Allow the organic mixture to settle overnight, with the agitator off, to allow further separation, and then remove the lower aqueous layer.
38. Determine the solution yield using a calibrated HPLC system.
39. Add 4.49M aqueous hydrochloric acid (3.80 kg, 1 equivalent) to the stirred reactor over 8 minutes, maintaining the reactor contents at 20±5° C.
40. Adjust the contents (about 140 liters) of the reactor to 35° C. with stirring, and partly concentrate the reactor contents via vacuum distillation (whereupon the batch temperature can fall, e.g. to about 26° C.). Release the vacuum and stop distillation. Re-establish a vacuum with a jacket temperature of about 60° C. and an intended internal (batch) temperature of about 45° C., and then concentrate the reactor contents to 70 liters (10 vol) via vacuum distillation at pressures ranging from −0.901 to −0.912 barg, and with internal (batch) temperatures starting from 46.5° C. and rising to from 78.44° C. to 77.56° C. (jacket temperature 60° C., rising to 90° C., and rising again to 100° C.).
41. Adjust the contents of the reactor to 85±5° C.
42. Add a slurry of seed crystals (0.007 kg, 0.001 wt) of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate in n-pentanol (pentan-1-ol, 0.07 L, 0.01 vol) to the contents of the reactor.
43. Cool the contents of the reactor to 60±5° C.
44. Stir the contents of the reactor at 60±5° C. for 2 hours at 75 rpm.
45. Adjust the temperature of the reactor contents to 55±5° C.
46. Add tert-butyl methyl ether (TBME) (4.3 vol, 30.1 L) to the reactor over 5 minutes whilst keeping the temperature of the reactor contents at 50±5° C.
47. Cool the contents of the reactor to 20 ±5° C. over about 1 hour.
48. Age the contents of the reactor at 20 ±5° C. for approximately 14 hours with stirring at 75 rpm.
49. Transfer the reactor contents onto a 20 micron filter cloth, allow the slurry to settle for about 10 minutes, and filter off the solid under 0.5 to 1 barg nitrogen pressure.
50. Wash the reactor with n-pentanol (pentan-1-ol, 2.5 vol, 17.5 L) with 75 rpm stirring at 20±5° C. for 13 minutes, transfer the pentan-1-ol washings onto the filter cake, and wash the filter cake under 0.5 to 1 barg nitrogen pressure.
51. Wash the filter cake with tert-butyl methyl ether (TBME) (2.5 vol, 17.5 L) under 0.5 to 1 barg nitrogen pressure, and blow solvent from the cake under nitrogen pressure for 6 minutes.
52. Transfer the damp filtered solid onto polythene lined trays, cover with muslin bags, and place in a vacuum tray dryer. Dry the solid in vacuo at 55±5° C. under a bleed of 5 L/min nitrogen until the temperature of a probe in the product remains constant for at least 4 hours, and then cool the solid to <30° C. to give the product N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride, substantially in the form of the monohydrochloride Form 1 anhydrate thereof.

When a method substantially as described in the above detailed steps 1 to 52 was performed, a yield of 9.15 kg of solid N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride, substantially in the form of the monohydrochloride Form 1 anhydrate, was obtained.

Example 1A2 Alternative Preparation No. 2

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride

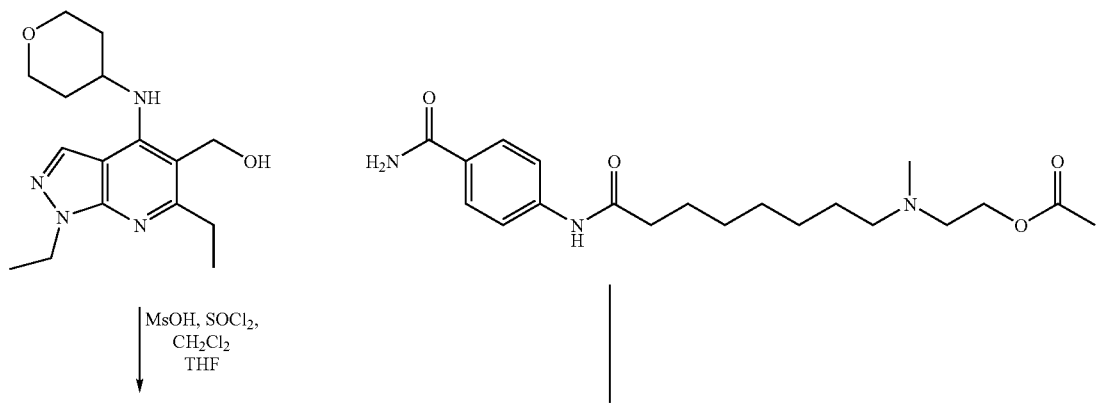

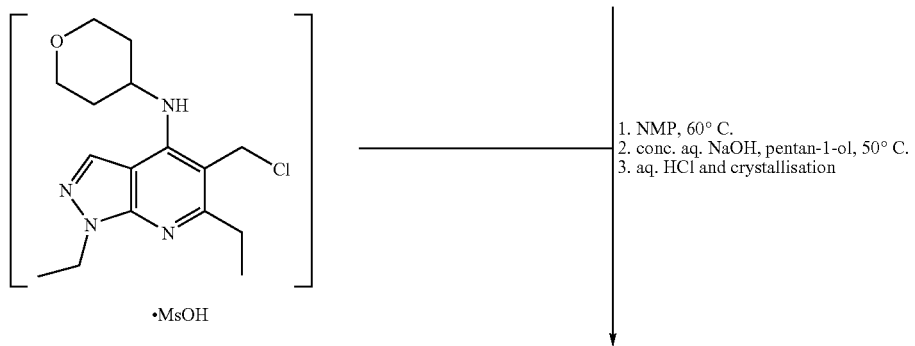

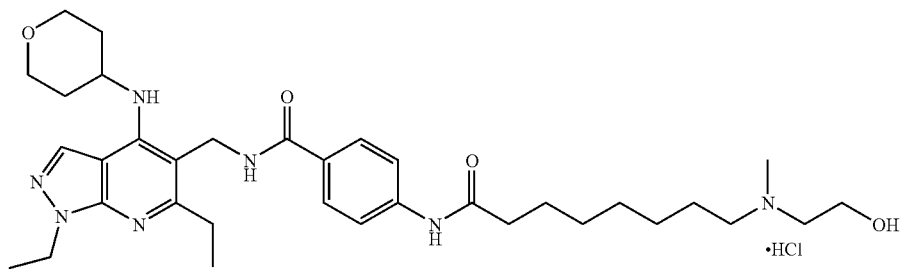

This preparation represent embodiment(s) of "Stage 6a (chlorination), Stage 6b (coupling to form amide), and Stage 7 (acetyl deprotection)" preparations within Process 1C described herein.

The following reactions were conducted under a nitrogen atmosphere.

A solution of methanesulfonic acid (0.79 mL, 11 mmol, 1 equivalent) in dry dichloromethane (3.5 mL) was added dropwise over 3 minutes to a stirred solution of [1,6-diethyl-4-(tetrahydro-2H-pyran-4-ylamino)-1H-pyrazolo[3,4-b]pyridin-5-yl]methanol [3.4 g, 11 mmol, 1 equivalent, e.g. which can be as prepared in Intermediate 5 (alternative preparation no. 2, plant method)] in dry dichloromethane (13.5 mL) under nitrogen. The mixture was cooled in a water bath. A solution of thionyl chloride (1.1 mL, 15 mmol, 1.35 equivalents) in dry dichloromethane (3.5 mL) was added dropwise whilst keeping the reaction temperature to <25° C. by addition of dry ice pellets into the water bath. After the addition was complete, the reaction mixture was stirred for 40 mins. This mixture is thought to contain 5-(chloromethyl)-1,6-diethyl-N-(tetrahydro-2H-pyran-4-yl)-1H-pyrazolo[3,4-b]pyridin-4-amine methanesulfonate salt, from LC analysis during or at the end of the 40 min period which showed the 5-(methoxymethyl)-derivative derived from a methanol quench of the 5-(chloromethyl)-compound.

The reaction mixture was then concentrated to about half of its original volume. Dry dichloromethane (15 mL) was added and the mixture was then evaporated in vacuo to about half of its original volume. Dry tetrahydrofuran (15 mL) was then added and the mixture was evaporated in vacuo to about 10 mL. 2-[(8-{[4-(Aminocarbonyl)phenyl]amino}-8-oxooctyl)(methyl)amino]ethyl acetate (4 g, 11 mmol, 1 equivalent, e.g. which can be as prepared in Intermediate 55) was added to the resultant solution which was evaporated, removing most of the solvent, to form a syrupy slurry. Dry 1-methyl-2-pyrrolidinone (NMP, 30 mL) was added and the mixture was stirred at 60° C. for 3.75 hours (all the material dissolved when the temperature reached about 50° C.). Additional 5-(chloromethyl)-1,6-diethyl-N-(tetrahydro-2H-pyran-4-yl)-1H-pyrazolo[3,4-b]pyridin-4-amine methanesulfonate salt (0.44 g, 1.06 mmol, e.g. which can be as prepared in a generally analogous manner to that described above) was added, and the reaction mixture was heated for a further 1 hour at 60° C. and was then allowed to stand at room temperature for 17 hours. The reaction micture was quenched with an aqueous potassium carbonate solution (5% w/v, 300 mL), whereupon effervescence occurred and an exotherm was noted. The reaction mixture was extracted with isopropyl acetate (2×100 mL). The combined organic extracts were washed with water (100 mL). n-Pentanol (pentan-1-ol, 34 mL) was added. The organic mixture was evaporated in vacuo to remove most of the isopropyl acetate. The resultant solution was treated with aqueous sodium hydroxide solution (10M, 7 mL), heated at 50° C. for 1.5 hours and allowed to cool to room temperature. Water (28 mL) was added, and the mixture was stirred, allowed to settle and the layers were separated. The resultant organic solution was washed with water (34 mL), the biphase mixture was allowed to settle for 1.5 hours and the aqueous layer was separated. The concentration of the product, N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide (the "free base"), in the resultant organic solution was determined quantitatively by HPLC to be about 133.6 to about 135.4 mg/mL, with a total volume of 43 mL, leading to an estimated yield of the free base of about 5.78 g (estimated "solution yield" of about 87.8%).

Aqueous hydrochloric acid (5M, 1.86 mL, amount estimated for preparation of monohydrochloride salt) was then added. The mixture was concentrated in vacuo at about 90° C. (bath temperature) to about 34 mL volume. (9.5 mL solvent was removed, including about 5.5 mL water as a lower layer). A microspatula of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride seed crystals (e.g. substantially in the form of the Form 1 anhydrate thereof) was added. No crystallisation occurred. Another 1.8 mL of solvent (including 0.6 ml of water as a lower layer) was removed in vacuo at ca. 110° C. (bath temperature). The solution became hazy, and the mixture was cooled to about 90° C. (bath temperature). Another microspatula of seed crystals was added. The hazy mixture was cooled to 60° C. and was aged for 1.5 hours. tert-Butyl methyl ether (TBME, 14.4 mL) was added. The mixture was allowed to cool to room temperature and was stirred at room temperature, for 15.5 hours in total. The resultant slurry was filtered, displacement washed with n-pentanol (7 mL) and then TBME (7 mL). Residual solvents in the filter cake were removed under suction for about 15 mins, and then the resultant wet white filter cake (7.14 g) was dried in vacuo at 70° C. for 22.25 hours to afford the title product, substantially in the form of the monohydrochloride Form 1 anhydrate, as a white solid (4.75 g, molecular weight about 658.3, so about 65-66% yield based on amount of [1,6-diethyl-4-(tetrahydro-2H-pyran-4-ylamino)-1H-pyrazolo[3,4-b]pyridin-5-yl]methanol used). HPLC (5 mins generic solvent gradient): $T_{RET}$ about 2.45 min. Mass spectrum: Found: MH$^+$ 622, (M-H)$^-$ 620. A preliminary analysis suggests a purity of about 97.7%.

Example 1A3

Recrystallisation of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate (e.g. as prepared in Example 1A2 such as alternative Plant preparation no. 1 thereof) is preferably recrystallised from dry (e.g. anhydrous) n-propanol. An alternative suitable recrystallisation solvent is anhydrous ethanol, though it is thought this gives lower recrystallisation yields than anhydrous n-propanol.

Generally, for the recrystallisation, it is considered preferable not to conduct the recrystallisation in a water-containing solvent, in order to reduce the risk of forming the undesired monohydrochloride Form 2 hydrate.

One possible embodiment of Example 1A3 is as follows:

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohy drochloride Form 1 anhydrate is dissolved in about 7 volumes of anhydrous n-propanol at about 85° C., e.g. under nitrogen. The temperature is adjusted to about 70° C. The mixture is seeded with a small amount of N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate product. The mixture is then held at about 70° C. for about two hours (e.g. with stirring), cooled to 0° C. over about 3 to 16 hours (e.g. for about 12 hours) (e.g. with stirring), is aged at 0° C. for about 2 to about 8 hours (e.g. with stirring), and the resulting solid product is separated by filtration. The filtered solid product can optionally be dried in vacuo with heating e.g. at 55±5° C.

Example 1A3 Alternative Preparation

Recrystallisation of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate n-Propanol (propan-1-ol, 7.8 L, 6 vol) was added to N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride Form 1 anhydrate (1.304 kg, 1 wt, which e.g. can be as prepared in Example 1A2 (Alternative preparation no. 1, Plant Method) or Example 1A2 (Alternative Preparation no. 2)), in a first vessel, and the resulting suspension was heated under nitrogen to 90±3° C. (e.g. 90-92° C.) until complete dissolution of the solid had been achieved. The resulting solution (having reached 96° C.) was then transferred over about 20 minutes through a 5 micron filter into a second vessel pre-heated to 85±3° C. under nitrogen. The first vessel washed with n-propanol (1.3 L, 1 vol) which was heated to 90° C., and these hot n-propanol washings were then passed through the previously-used lines and filter into the second vessel over about 2 minutes. The resulting combined solution in the second vessel was cooled to 70±3° C. and was seeded with a slurry of micronised N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)-benzamide monohydrochloride Form 1 anhydrate (about 1.3 g, 0.001 wt) in n-propanol (10 ml). The resulting mixture was aged at 70±3° C. for 2 hours and then was cooled to 0±3° C. over 12 hours (approx. 0.1 degree/minute cooling rate), all under nitrogen. The resulting slurry was then aged at 0±3° C. for 5 hours 10 minutes with stirring at 110 rpm. The solid was collected by filtration under vacuum (using a ca. 24 cm PTFE mini filter fitted with Whatman No. 113 wet strengthened filter paper with rough side up, and using a ca. 600 mbar vacuum regulated by a Buchi vacuum controller). The filter cake washed twice with prefiltered n-propanol (2×2.6 L, 2×2 vol) under suction to free the product of most of the solvent. The resulting filtered solid was transferred to polythene lined steel trays, covered with mono filament cloth, and transported to an oven in a sealed polythene bag. After removal of the bag once in the oven, the solid product was dried in vacuo at 60° C. to a constant probe temperature and/or to a constant weight, using a ca. 70 mbar vacuum regulated by a Buchi vacuum controller, to give the title product as the Form 1 anhydrate and as a white solid (1.096 kg; yield: 84% theory, 84% w/w).

Example 1B

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide

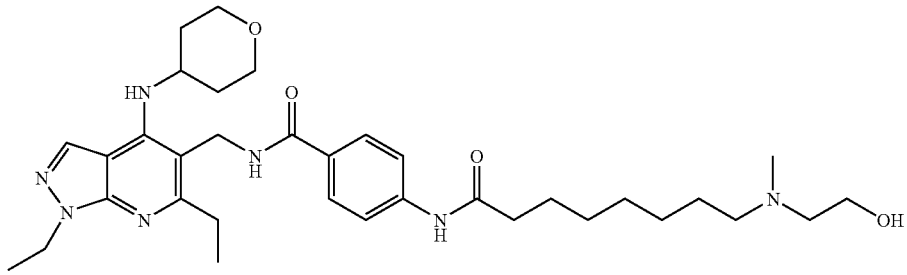

A suspension of 4-({8-[(2-hydroxyethyl)(methyl)amino]octanoyl}amino)benzoic acid (7.38 g, 19.8 mmol, 1.2 equivalents, e.g. which can be as prepared in Intermediate 39) in N,N-dimethylformamide (75 ml, about 10 volumes cf. the weight of the acid) was treated with N,N-diisopropylethylamine (4.89 ml, 3.62 g, 28.1 mmol, 1.7 equivalents) resulting in a clear yellow solution. N,N'-Dicyclohexylcarbodiimide (4.42 g, 21.45 mmol, 1.3 equivalents) and then 1-hydroxybenzotriazole hydrate (3.28 g, 21.45 mmol, 1.3 equivalents) were added, and the mixture was stirred at room temperature for 15 minutes. 5-(Aminomethyl)-1,6-diethyl-N-(tetrahydro-2H-pyran-4-yl)-1H-pyrazolo[3,4-b]pyridin-4-amine (5 g, 16.5 mmol, 1 equivalent, e.g. which can optionally be as prepared in Intermediate 7 including alternative preparation no. 1 thereof) was then added, resulting in a cloudy yellow/orange solution which was allowed to stir at room temperature overnight. As much N,N-dimethylformamide as possible was evaporated off, the residue was partitioned between dichloromethane and sodium bicarbonate solution, and then the separated aqueous phase was extracted with more dichloromethane. The combined organic extracts were washed with lithium chloride solution, water and brine, were dried (MgSO₄), and were concentrated by evaporation, to give the crude product (15.5 g). 1.73 g of this crude product was removed. The remainder of the crude product was purified by column chromatography on silica gel (about 600 g), eluting with 10% methanol in dichloromethane, followed by 20% methanol in dichloromethane, 20% methanol in dichloromethane containing triethylamine, and finally 30% methanol in dichloromethane containing triethylamine. The majority of the fractions containing the product were combined and evaporated to give the title compound (6.68 g) as a white foam. LCMS showed MH⁺=622; T$_{RET}$=2.21 min. The apparently-more-pure fractions containing the product were combined and evaporated to give more of the title compound (0.48 g).

Example 1B Alternative Preparation No. 1A

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide

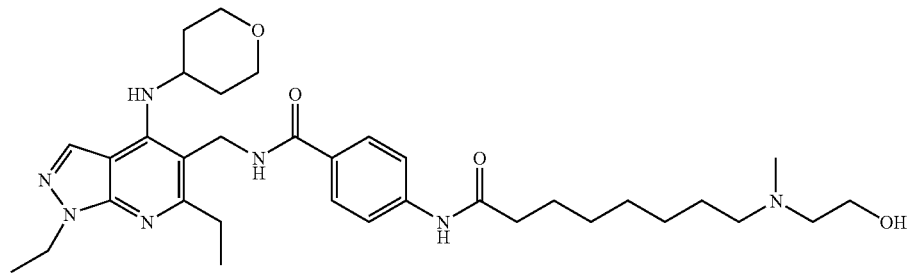

O-(7-Azabenzotriazol-1-yl)-N,N,N',N'-tetramethyluronium hexafluorophosphate (HATU, 2.4 g, 6.3 mmol) was added to a solution of 4-[(8-bromooctanoyl)amino]benzoic acid (2.1 g, 6.1 mmol) in N,N-dimethylformamide (20 ml) followed by N,N-diisopropylethylamine (2.5 g, 19 mmol). The solution was stirred at room temperature for 15 min, and 5-(aminomethyl)-1,6-diethyl-N-(tetrahydro-2H-pyran-4-yl)-1H-pyrazolo[3,4-b]pyridin-4-amine (1.7 g, 5.6 mmol. e.g. which can be substantially as prepared in Intermediate 7 including alternative preparation no. 1 thereof) was added as a solid. The solution was stirred at room temperature for 3 hours, and then was added to aqueous sodium bicarbonate solution (200 ml) and extracted with dichloromethane (2×100 ml). The dried (sodium sulphate) organic extract was evaporated gently to leave crude 4-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide mixed with N,N-dimethylformamide (about 5 ml).

2-(Methylamino)ethanol (3 ml, 35 mmol, commercially available e.g. from Aldrich) was added to this crude mixture and the solution was heated in a sealed microwave vessel (split between three 10 ml vessels) at 150° C. for 15 min. The resulting mixture was evaporated and the residue purified on a 100 g silica cartridge, eluting with a gradient starting with dichloromethane and finishing with 30% methanol in dichloromethane containing 1% triethylamine, to give a yellow gum (2.5 g) containing small amounts of impurities. The gum was dissolved in 19:1 ethyl acetate/methanol (100 ml) and washed with aqueous sodium carbonate solution. The organic phase was evaporated onto silica and applied to a column of silica (300 ml), eluting with 9:1 ethyl acetate: 2M ammonia in methanol to give a gum (1.75 g). Trituration with diethyl ether (30 ml) gave a white solid (1.5 g). LCMS showed MH⁺=622; T$_{RET}$=2.1 min. This product was used in the preparation of Example 1B (Alternative preparation no. 1B), as described below.

Example 1B Alternative Preparation No. 1B

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide

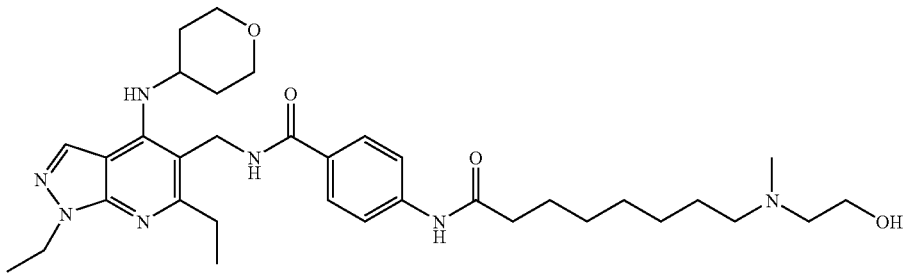

A mixture of 4-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide (2.2 g, 3.5 mmol, e.g. which can be as prepared in Intermediate 11) and 2-(methylamino)ethanol (2 ml, 22 mmol, commercially available e.g. from Aldrich,) in N,N-dimethylformamide (4 ml), was split between two 10 ml sealed microwave vessels, and was heated at 140° C. under microwave irradiation for 15 minutes. The combined reaction mixtures were poured into aqueous sodium carbonate solution (Na$_2$CO$_3$, 100 ml) and extracted with ethyl acetate (2×75 ml). The organic phase washed with water (100 ml) and evaporated. The residue was purified by column chromatography on silica gel (700 ml), eluting with 19:1 dichloromethane: 2M ammonia in methanol, to give a gum (1.2 g). The gum was triturated with diethyl ether (20 ml) to give a solid (1.1 g).

This 1.1 g of solid was combined with the white solid material (1.5 g) prepared by Example 1B (Alternative preparation no. 1A), see above for the method. The two batches of product were blended by stirring in diethyl ether (50 ml) for 2 hours. Filtration gave the title compound as a white powder (2.4 g). LCMS showed MH$^+$=622; T$_{RET}$=2.14 min.

Example 1B Alternative Preparation No. 2

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide

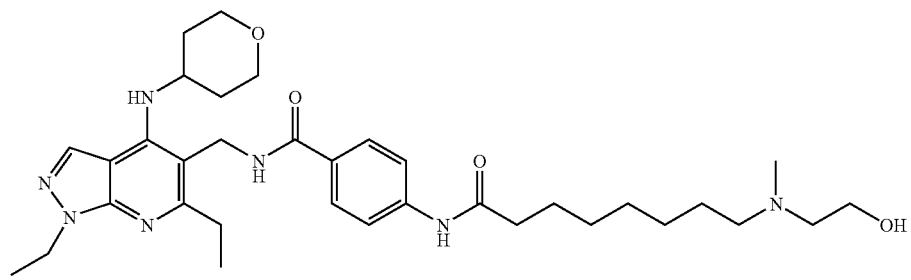

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride (20.0 g, 0.0304 mol, e.g. optionally the Form 1 anhydrate thereof) was suspended in ethyl acetate (150 ml). Potassium carbonate (7.5 g in 50 ml water) was added dropwise, and the mixture was stirred vigorously for 3 hours. The solid was filtered off, washed with ethyl acetate (30 ml), and dried at 50° C. Analysis indicates that this product contains about 1.5% of chloride. The product was suspended in isopropanol (160 ml), and Dowex 550A resin (10 g) was added. The suspension was heated to 60° C. for 1 hour, and was filtered while hot. The filtrate was concentrated to leave a white foam. Dichloromethane (100 ml) was added and the resulting mixture was concentrated to dryness to give the title compound (the "free base"). Analysis indicates about 0.3% of chloride remaining; NMR analysis indicates about 0.3% of water present.

The product free base made by this "Example 1B (alternative preparation no. 2)" procedure is thought, from a preliminary analysis, to be present as a substantially amorphous form (i.e. a substantially non-crystalline form), e.g. as ascertained by substantially a lack of or minimal birefringence under microscopy and/or as ascertained by X-ray powder diffraction.

Example 1B1

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, or a salt thereof 4-[(8-Bromooctanoyl)amino]-N-{[1,6-diethyl-4-(tetrahydro-2H-pyran-4-ylamino)-1H-pyrazolo[3,4-b]pyridin-5-yl]methyl}benzamide (100 mg, 0.16 mmol, e.g. which can optionally be as prepared in Intermediate 11) was dissolved in N,N-dimethylformamide (4 ml). To one-quarter of this solution, i.e. containing 4-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide (25 mg, 0.04 mmol) in N,N-dimethylformamide (1 ml), was added 2-(methylamino)ethanol (0.0064 ml (6.4 microliters), 0.08 mmol, 2 equivalents, commercially available e.g. from Aldrich) followed by N,N-diisopropylethylamine (0.04 ml, about 6 equivalents). The reaction mixture was heated at 85° C. for 16 hours. The solvent was evaporated and the residue was purified by eluting through a 5 g silica SPE cartridge, with dichloromethane containing 20% methanol and 1% triethylamine as the eluent, to give the title compound (18.7 mg), in the form of a cream foam, initially thought to be in the form of the "free base".

LCMS showed MH$^+$=622; T$_{RET}$=2.20 min. However, later re-inspection of the $^1$H NMR spectrum suggests that the product was isolated as a salt e.g. a mono-salt (presumed to be a hydrobromide salt), e.g. from the signals of protons adjacent to the (2-hydroxyethyl)(methyl)amino group.

Example 1D

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrobromide Isopropanol (15 ml) was added to N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide (the "free base", 1.5 g, e.g. which can be as prepared in Example 1B) and the mixture was heated at 60° C. for 1 hour to dissolve the free base. 48% Aqueous hydrobromic acid (0.273 ml, 1 equiv.) was added, and the mixture was left to temperature cycle between 0° C. and 40° C. over the weekend (about 3 days). The resulting solid was isolated by filtration, washed with isopropanol (about 5 ml), left on the filter for a while, and then dried under vacuum at 40° C. in a vacuum oven overnight to give the title compound (1.286 g). NMR appeared to show some isopropanol present (e.g. very approx. 0.89% w/w). XRPD appeared to suggest product was partly crystalline material.

Ion chromatography of the product appears to confirm that the stoichiometry of the salt is that of a monohydrobromide.

Example 1E

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide hemisuccinate Isopropanol (10 ml) was added to N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide (the "free base", 1 g, e.g. which can be as prepared in Example 1B) and the mixture was heated at 60° C. for 0.5 hour to dissolve the free base. A solution of succinic acid (199 mg, 1.05 equiv.) in isopropanol (2 ml) was added to the solution of the free base, and the mixture was left to temperature cycle between 0° C. and 40° C. for about 3 days. The resulting solid was isolated by filtration, washed with isopropanol (about 2 ml), left on the filter paper for a while, and dried under vacuum at 40° C. in an oven overnight to give the title compound (0.833 g). NMR appeared to show approximately 1:0.471 stoichiometry of free base: succinate, and some isopropanol present (e.g. approximately 0.73% w/w). XRPD appeared to suggest the product was mainly crystalline material.

Example 1F

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide hemifumarate N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide [the "free base", 100 mg, about 0.161 mmol, as a substantially amorphous form thereof, as prepared in Example 1B (alternative preparation no. 2)] was dissolved in isopropanol (1 ml) at room temperature. The resulting solution was added to fumaric acid (18.7 mg±1 mg, 1 equivalent) and heated to 40° C. The reaction mixture was left to temperature cycle between 0° C. and 40° C. overnight. The next day, the reaction mixture was a slurry, and the solid from this was isolated by filtration, washed with isopropanol (0.5 ml) and dried at ambient temperature under vacuum overnight. 54.4 mg of dried solid was obtained. NMR data appears to support a stoichiometry consistent with the solid product being substantially a hemifumarate salt.

Example 1G

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide mono-xinafoate (mono-1-hydroxy-2-naphthoate)

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide [the "free base", 100 mg, about 0.161 mmol, as a substantially amorphous form thereof, as prepared in Example 1B (alternative preparation no. 2)] was dissolved in isopropanol (1 ml) at room temperature. The resulting solution was added to xinafoic acid (1-hydroxy-2-naphthoic acid) (30.3 mg±1 mg, 1 equivalent) and heated to 40° C. The reaction mixture was left to temperature cycle between 0° C. and 40° C. overnight. The next day, it remained a solution. Cyclohexane (0.5 ml) was added and the resulting solution was left to temperature cycle between 0° C. and 40° C. overnight. The next day, the reaction mixture was a slurry, and the solid from this was isolated by filtration, washed with 1:1 isopropanol: cyclohexane (1 ml) and dried at ambient temperature under vacuum over the weekend. 58.6 mg of dried solid was obtained. NMR data appears to support a stoichiometry consistent with the solid product being substantially a mono-xinafoate (mono-1-hydroxy-2-naphthoate) salt.

Example 1H1

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide phosphate N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide [the "free base", 100 mg, about 0.161 mmol, as a substantially amorphous form thereof, as prepared in Example 1B (alternative preparation no. 2)] was suspended in methyl isobutyl ketone (MIBK, 1 ml), producing a slightly turbid solution. Phosphoric acid ($H_3PO_4$, 85 wt % solution in water (commercially available e.g. from Aldrich), 7.9 microliters, 1 equivalent) was added. Methyl isobutyl ketone (MIBK, 0.5 ml) was added. A gum appeared at the bottom of the vial, which was left to temperature cycle between 0° C. and 40° C. for about 2 days. A suspension had formed, and from this the resulting solid was isolated by filtration, washed with isopropanol (0.5 ml) and dried at 40° C. under vacuum overnight. 74.4 mg of dried solid was obtained.

Example 1H2

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide phosphate N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide [the "free base", 100 mg, about 0.161 mmol, as a substantially amorphous form thereof, as prepared in Example 1B (alternative preparation no. 2)] was dissolved in isopropanol (1 ml) at room temperature. Phosphoric acid ($H_3PO_4$, 85 wt % solution in water (commercially available e.g. from Aldrich), 3.95 microliters, 0.5 equivalents) was added. A gum formed, which dissolved on heating to 60° C. No precipitation occurred after cooling to ambient temperature and about 30 minutes at ambient temperature. Phosphoric acid ($H_3PO_4$, 85 wt % solution in water (commercially available e.g. from Aldrich), 3.95 microliters, 0.5 equivalents) was added. A gum formed, which did not dissolve on heating to 60° C. The reaction mixture was left to temperature cycle between 0° C. and 40° C. for about 2 days. A suspension had formed, and from this the resulting solid was isolated by filtration, washed with isopropanol (0.5 ml) and dried at 40° C. under vacuum overnight. 68.3 mg of dried solid was obtained.

Example 1J1

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide mono-(+)-camphorsulfonate N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide [the "free base", 100 mg, about 0.161 mmol, as a substantially amorphous form thereof, as prepared in Example 1B (alternative preparation no. 2)] and (+)-camphorsulfonic acid (37.4 mg±1 mg, 1 equivalent) were suspended in methyl isobutyl ketone (MIBK, 5 ml). The resulting solution/suspension was left to temperature cycle between 0° C. and 40° C. overnight. The next day, a suspension had formed, and from this the resulting solid was isolated by filtration, washed with methyl isobutyl ketone (MIBK, 1 ml) and dried at 40° C. under vacuum overnight. 111.4 mg of dried solid was obtained. NMR data appears to support a stoichiometry consistent with the solid product being substantially a mono-(+)-camphorsulfonate.

Example 1J2

N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide mono-(+)-camphorsulfonate N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide [the "free base", 100 mg, about 0.161 mmol, as a substantially amorphous form thereof, as prepared in Example 1B (alternative preparation no. 2)] and (+)-camphorsulfonic acid (37.4 mg±1 mg, 1 equivalent) were suspended in ethyl acetate (6 ml). The resulting suspension was left to temperature cycle between 0° C. and 40° C. overnight. The next day, a suspension had formed, from which the resulting solid was isolated by filtration, washed with ethyl acetate (1 ml) and dried at 40° C. under vacuum overnight. 82.2 mg of dried solid was obtained. NMR data appears to support a stoichiometry consistent with the solid product being substantially a mono-(+)-camphorsulfonate.

Examples 1C, 3, 4, 9, 11 and 12

0.04 mmol of the appropriate (8-bromooctanoyl)amino-alkylating agent (selected from those listed below) in N,N-dimethylformamide (0.5 ml) was treated with a solution of the appropriate amine (HNR$^5$R$^6$ wherein NR$^5$R$^6$ is as defined in the table below; 0.08 mmol) in N,N-dimethylformamide (0.5 ml) followed by N,N-diisopropylethylamine (0.04 ml). The reaction mixture was heated at 80° C. for 16 hours and the solvent was removed in vacuo. The residue was purified by mass directed preparative HPLC (Method B) to give the appropriate title compound (with a structure as shown in the table below) as a trifluoroacetate salt.

(8-Bromooctanoyl)amino-alkylating agents and amounts used:

4-[(8-Bromooctanoyl)amino]-N-{[1,6-diethyl-4-(tetrahydro-2H-pyran-4-ylamino)-1H-pyrazolo[3,4-b]pyridin-5-yl]methyl}benzamide (200.8 mg/8=25.10 mg, 0.04 mmol, e.g. which can be as prepared in Intermediate 11); and 4-[(5-{[({4-[(8-bromooctanoyl)amino]phenyl}carbonyl)amino]methyl}-1,6-diethyl-1H-pyrazolo[3,4-b]pyridin-4-yl)amino]-1-piperidinecarboxamide (214.3 mg/8=26.79 mg, 0.04 mmol, e.g. which can be as prepared in Intermediate 21).

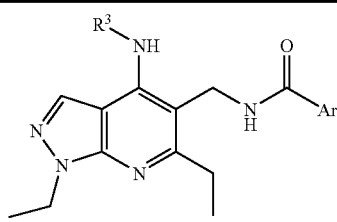

| Example No. | R$^3$ | Ar | Q$^1$, Q$^2$ | Starting material can be as prepared in | NR$^5$R$^6$ (wherein the connecting nitrogen atom is underlined) | One possible Source of HNR$^5$R$^6$ | M-H ion | T$_{RET}$ (min) |
|---|---|---|---|---|---|---|---|---|
| 1C | (tetrahydropyran-4-yl) | (x1a) | Q$^1$ is NH; Q$^2$ is —C(O)— | Intermediate 11 | Me-N-CH$_2$CH$_2$-OH | Aldrich | 620 | 2.24 |
| 3 | (4-carbamoylpiperidin-1-yl) | (x1a) | Q$^1$ is NH; Q$^2$ is —C(O)— | Intermediate 21 | (S)-2-methoxymethylpyrrolidine | Aldrich | 702 | 2.24 |

-continued

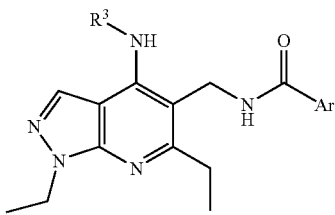

| Example No. | R³ | Ar Q¹, Q² | Starting material can be as prepared in | NR⁵R⁶ (wherein the connecting nitrogen atom is underlined) | One possible Source of HNR⁵R⁶ | M-H ion | T_RET (min) |
|---|---|---|---|---|---|---|---|
| 4 | H₂N-C(O)-N(piperidin-4-yl)- | (x1a) Q¹ is NH; Q² is —C(O)— | Intermediate 21 | (S)-2-(methoxymethyl)pyrrolidine | Aldrich | 702 | 2.24 |
| 9 | H₂N-C(O)-N(piperidin-4-yl)- | (x1a) Q¹ is NH; Q² is —C(O)— | Intermediate 21 | Me-N(H)-CH₂CH₂-OH | Aldrich | 662 | 2.15 |
| 11 | tetrahydro-2H-pyran-4-yl | (x1a) Q¹ is NH; Q² is —C(O)— | Intermediate 11 | (S)-2-(methoxymethyl)pyrrolidine | Aldrich | 660 | 2.34 |
| 12 | Me-N(H)-CH₂CH₂-OH | (x1a) Q¹ is NH; Q² is —C(O)— | Intermediate 11 | (S)-2-(methoxymethyl)pyrrolidine | Aldrich | 660 | 2.34 | where Ar is (x1a):

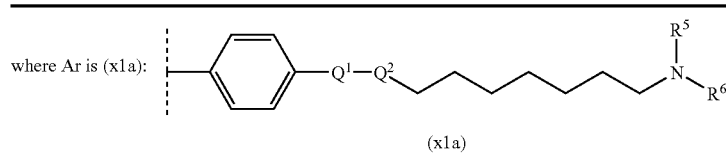

(x1a)

The salt prepared in Example 1C above is named N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide trifluoroacetate.

Examples 17, 18, 19, 20, 21, 22, 23 and 24

To a solution of the appropriate bromo alkylating agent (0.04 mmol) (selected from those listed below) in N,N-dimethylformamide (1 ml) were added the appropriate amine HNR⁵R⁶ (wherein NR⁵R⁶ is as defined in the table below) (0.08 mmol, 2 equivalents) followed by N,N-diisopropylethylamine (0.04 ml, about 6 equivalents). The reaction mixture was heated at 85° C. for 16 hours. The solvent was evaporated and the residue was purified by mass directed preparative HPLC (Method A, using formic acid) to give the title compound (with a structure as shown in the table below) as a formate salt. In all cases, the product was present as a foam.

Bromo Alkylating Agents and Amounts Used:

4-[(8-Bromooctanoyl)amino]-N-{[1,6-diethyl-4-(tetrahydro-2H-pyran-4-ylamino)-1H-pyrazolo[3,4-b]pyridin-5-yl]methyl}benzamide (100 mg/4=25 mg, 0.04 mmol, e.g. which can be as prepared in Intermediate 11);

4-{4-[(4-Bromobutyl)oxy]butyl}-N-{[1,6-diethyl-4-(tetrahydro-2H-pyran-4-ylamino)-1H-pyrazolo[3,4-b]pyridin-5-yl]methyl}benzamide (98 mg/4=24.5 mg, 0.04 mmol, e.g. which can be as prepared in Intermediate 27); and 4-{[5-({[(4-{4-[(4-Bromobutyl)oxy]butyl}phenyl)carbonyl]amino}methyl)-1,6-diethyl-1H-pyrazolo[3,4-b]pyridin-4-yl]amino}-1-piperidinecarboxamide (105 mg/4=26.25 mg, 0.04 mmol, e.g. which can be as prepared in Intermediate 28).

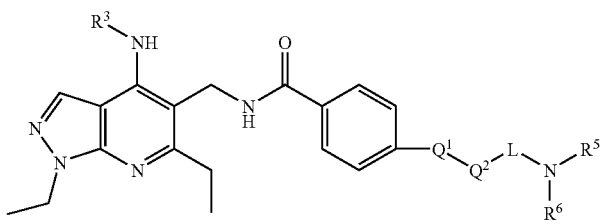

| Example No. | R³ | Q¹, Q² | L | Starting material can be as prepared in | NR⁵R⁶ (wherein the connecting nitrogen atom is underlined) | One possible Source of HNR⁵R⁶ | MH⁺ ion | T$_{RET}$ (min) |
|---|---|---|---|---|---|---|---|---|
| 17 | tetrahydropyran-4-yl | Q¹ is NH; Q² is —C(O)— | —(CH₂)₇— | Intermediate 11 | morpholine | Aldrich | 634 | 2.20 |
| 18 | tetrahydropyran-4-yl | Q¹ is NH; Q² is —C(O)— | —(CH₂)₇— | Intermediate 11 | pyrrolidine | Aldrich | 618 | 2.25 |
| 19 | tetrahydropyran-4-yl | Q¹ and Q² are a bond | —(CH₂)₄—O—(CH₂)₄— | Intermediate 27 | Me-N(H)-CH₂CH₂-OH | Aldrich | 609 | 2.27 |
| 20 | tetrahydropyran-4-yl | Q¹ and Q² are a bond | —(CH₂)₄—O—(CH₂)₄— | Intermediate 27 | morpholine | Aldrich | 621 | 2.28 |
| 21 | tetrahydropyran-4-yl | Q¹ and Q² are a bond | —(CH₂)₄—O—(CH₂)₄— | Intermediate 27 | pyrrolidine | Aldrich | 605 | 2.28 |
| 22 | 4-(aminocarbonyl)piperidin-1-yl | Q¹ and Q² are a bond | —(CH₂)₄—O—(CH₂)₄— | Intermediate 28 | Me-N(H)-CH₂CH₂-OH | Aldrich | 651 | 2.12 |

-continued

| Example No. | R³ | Q¹, Q² | L | Starting material can be as prepared in | NR⁵R⁶ (wherein the connecting nitrogen atom is underlined) | One possible Source of HNR⁵R⁶ | MH⁺ ion | $T_{RET}$ (min) |
|---|---|---|---|---|---|---|---|---|
| 23 | (piperidine-4-yl with N-C(O)NH₂) | Q¹ and Q² are a bond | —(CH₂)₄—O—(CH₂)₄— | Intermediate 28 | morpholine | Aldrich | 663 | 2.14 |
| 24 | (piperidine-4-yl with N-C(O)NH₂) | Q¹ and Q² are a bond | —(CH₂)₄—O—(CH₂)₄— | Intermediate 28 | pyrrolidine | Aldrich | 647 | 2.17 |

The specific procedure used for Example 23 was as follows:

Example 23

Formate salt of 4-({1,6-diethyl-5-[({[4-(4-{[4-(4-morpholinyl)butyl]oxy}butyl)phenyl]carbonyl}amino)methyl]-1H-pyrazolo[3,4-b]pyridin-4-yl}amino)-1-piperidinecarboxamide

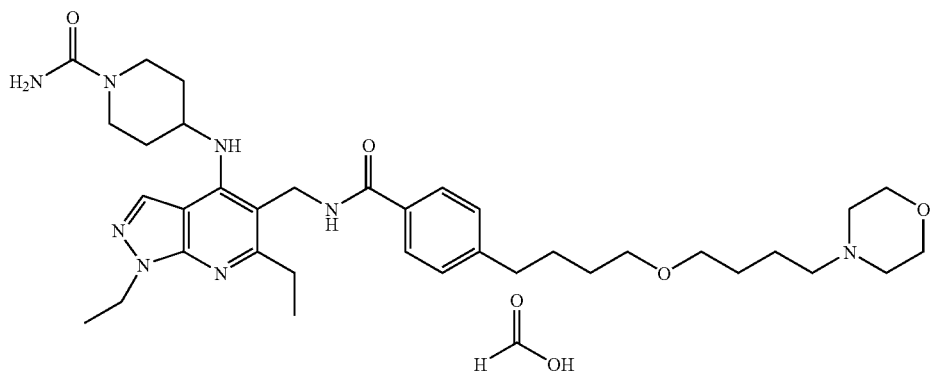

To a solution of 4-{[5-({[(4-{4-[(4-bromobutyl)oxy]butyl}phenyl)carbonyl]amino}methyl)-1,6-diethyl-1H-pyrazolo[3,4-b]pyridin-4-yl]amino}-1-piperidinecarboxamide (105 mg/4=26.25 mg, 0.04 mmol, e.g. which can be as prepared in Intermediate 28) in N,N-dimethylformamide (1 ml) were added morpholine (0.007 ml, 0.08 mmol, 2 equivalents) followed by N,N-diisopropylethylamine (0.04 ml, about 6 equivalents). The reaction mixture was heated at 85° C. for 16 hours. The solvent was evaporated and the residue was purified by mass directed preparative HPLC (Method A, using formic acid) to give the title compound as a cream foam (7.9 mg). LCMS showed MH$^+$=663; T$_{RET}$=2.14 min.

Example 23A 4-({1,6-Diethyl-5-[({[4-(4-{[4-(4-morpholinyl)butyl]oxy}butyl)phenyl]carbonyl}amino)methyl]-1H-pyrazolo[3,4-b]pyridin-4-yl}amino)-1-piperidinecarboxamide

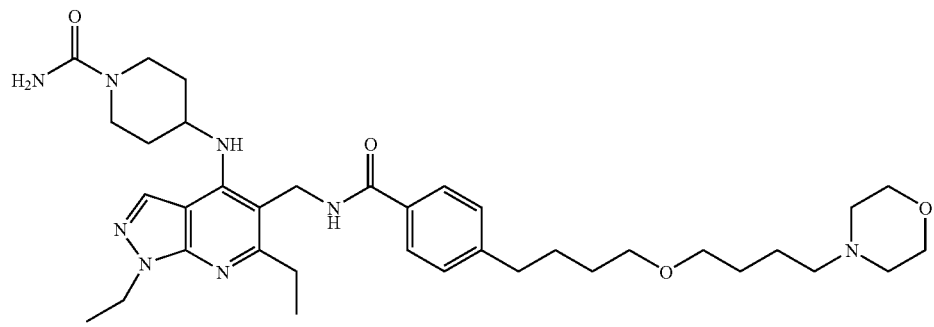

A mixture of 4-{[5-({[(4-{4-[(4-bromobutyl)oxy]butyl}phenyl)carbonyl]amino}methyl)-1,6-diethyl-1H-pyrazolo[3,4-b]pyridin-4-yl]amino}-1-piperidinecarboxamide (1.1 g, 1.67 mmol, e.g. which can be as prepared in Intermediate 28) in N,N-dimethylformamide (20 ml) was treated with N,N-diisopropylethylamine (0.567 ml) and morpholine (0.300 ml, 3.3 mmol) and heated at 65° C. The solvent was removed under vacuum and the residue was applied directly to a 100 g silica SPE cartridge and eluted with a gradient of from 0% to 50% methanol in dichloromethane over 40 mins. Fractions containing product were pooled and evaporated to give a pale orange foam which appeared to be about 85% pure by analytical HPLC. The residue was further purified by mass directed preparative HPLC (Method C, using 0.1% trifluoroacetic acid) in 50 mg portions, and, following evaporation of the solvent from the appropriate fractions, the residual material was dissolved in dichloromethane and washed with saturated aqueous sodium bicarbonate solution (NaHCO$_3$). The organic fraction was collected by passing through a hydrophobic frit and evaporated to give the title compound (0.300 g) as a white foam. LCMS showed MH$^+$=663; T$_{RET}$=2.09 min.

Example 25

Formate salt of N-{[1-ethyl-6-methyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide

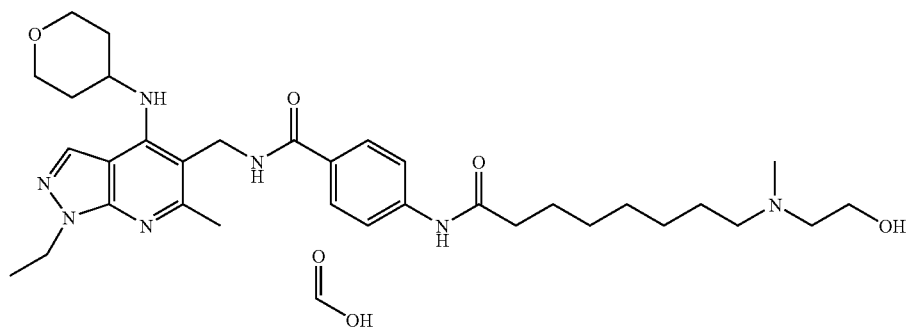

To a solution of 4-[(8-bromooctanoyl)amino]-N-{[1-ethyl-6-methyl-4-(tetrahydro-2H-pyran-4-ylamino)-1H-pyrazolo[3,4-b]pyridin-5-yl]methyl}benzamide (50 mg, 0.08 mmol, e.g. which can be as prepared in Intermediate 37) in N,N-dimethylformamide (1 ml) was added N,N-diisopropylethylamine (0.085 ml, 0.49 mmol) and 2-(methylamino)ethanol (0.008 ml, 0.1 mmol, commercially available e.g. from Aldrich), and the resulting solution was heated at 60° C. for 2 hours. The solvent was evaporated and the residue purified by mass directed preparative HPLC (Method A). Evaporation of the solvent gave the title compound as a cream foamy solid (22.2 mg). LCMS showed $MH^+=608$; $T_{RET}=2.16$ min.

Example 26

Formate salt of N-{[1-ethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide

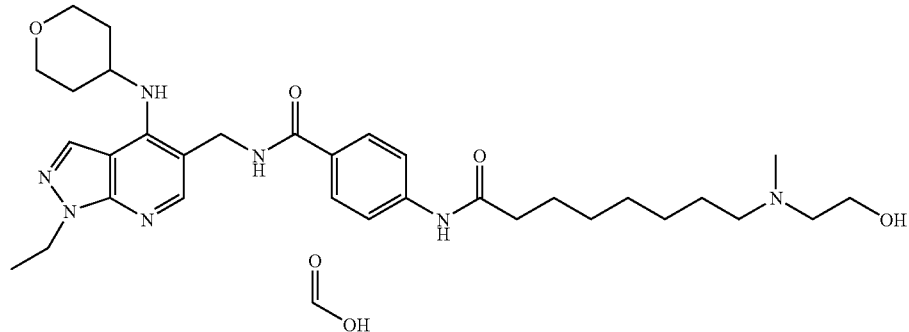

A solution of 4-({8-[(2-hydroxyethyl)(methyl)amino]octanoyl}amino)benzoic acid (24 mg, 0.06 mmol, e.g. which can be as prepared in Intermediate 39) in N,N-dimethylformamide (1 ml) was treated with 5-(aminomethyl)-1-ethyl-N-(tetrahydro-2H-pyran-4-yl)-1H-pyrazolo[3,4-b]pyridin-4-amine hydrochloride (20 mg, 0.065 mmol, e.g. which can be as prepared in Intermediate 48), N,N-diisopropylethylamine (0.036 ml, 0.21 mmol) and O-(7-azabenzotriazol-1-yl)-1,1,3,3-tetramethyluronium hexafluorophosphate (25 mg, 0.065 mmol) and the resultant mixture was allowed to stand at ambient temperature for 18 hours. The solvent was evaporated and the residue partitioned between dichloromethane (5 ml) and saturated aqueous sodium bicarbonate solution (5 ml). The organic fraction was collected through a hydrophobic frit, evaporated and purified by mass directed preparative HPLC (Method A). Fractions containing the product were pooled and evaporated to give the title compound (8.3 mg) as a pale yellow solid. LCMS showed $MH^+=594$; $T_{RET}=2.16$ min.

Example 27

N-{[1,6-diethyl-4-(tetrahydro-2H-pyran-4-ylamino)-1H-pyrazolo[3,4-b]pyridin-5-yl]methyl}-4-[8-(4-morpholinyl)octyl]benzamide

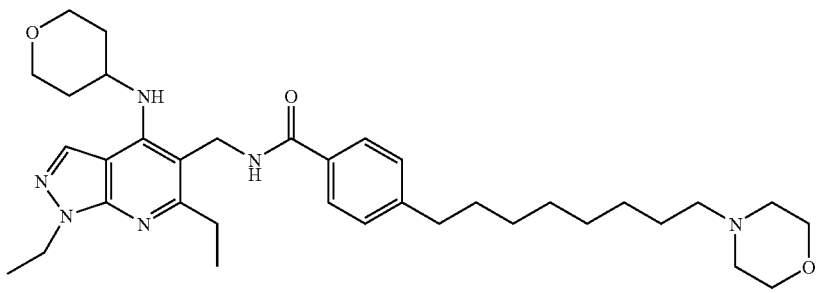

A solution of 4-(8-bromooctyl)-N-{[1,6-diethyl-4-(tetrahydro-2H-pyran-4-ylamino)-1H-pyrazolo[3,4-b]pyridin-5-yl]methyl}benzamide (36.3 mg, 0.06 mmol, e.g. which can be as prepared in Intermediate 41) in N,N-dimethylformamide (6 ml) was treated with morpholine (0.021 ml, 0.24 mmol) and N,N-diisopropylethylamine (0.042 ml, 0.24 mmol) and heated at 60° C. for 16 hours. The solvent was evaporated and the residue purified by mass directed preparative HPLC (Method A). Fractions containing product were pooled and evaporated to give the title compound (11 mg). LCMS showed MH$^+$=605; T$_{RET}$=2.39 min.

Example 28

N-{[1,6-diethyl-4-(tetrahydro-2H-pyran-4-ylamino)-1H-pyrazolo[3,4-b]pyridin-5-yl]methyl}-4-{8-[(2-hydroxyethyl)(methyl)amino]octyl}benzamide

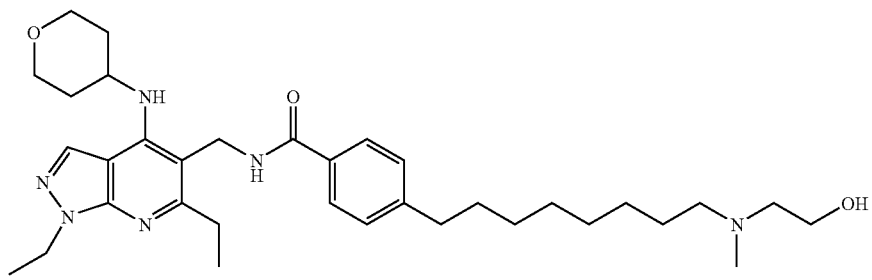

A solution of 4-(8-bromooctyl)-N-{[1,6-diethyl-4-(tetrahydro-2H-pyran-4-ylamino)-1H-pyrazolo[3,4-b]pyridin-5-yl]methyl}benzamide (36.3 mg, 0.06 mmol, e.g. which can be as prepared in Intermediate 41) in N,N-dimethylformamide (6 ml) was treated with 2-(methylamino)ethanol (0.0195 ml, 0.24 mmol, commercially available e.g. from Aldrich) and N,N-diisopropylethylamine (0.042 ml, 0.24 mmol) and heated at 60° C. for 16 hours. The solvent was evaporated and the residue purified by mass directed preparative HPLC (Method A). Fractions containing product were pooled and evaporated to give the title compound (7 mg). LCMS showed MH$^+$=593; T$_{RET}$=2.37 min.

Example 29

N-{[1,6-diethyl-4-(tetrahydro-2H-pyran-4-ylamino)-1H-pyrazolo[3,4-b]pyridin-5-yl]methyl}-3-({8-[(2-hydroxyethyl)(methyl)amino]octanoyl}amino)benzamide

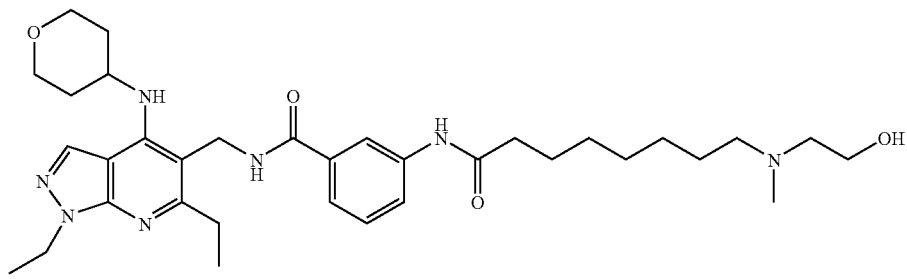

A solution of 3-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide (42 mg, 0.067 mmol, e.g. which can be as prepared in Intermediate 47) in N,N-dimethylformamide (3 ml) was treated with 2-(methylamino)ethanol (0.011 ml, 0.13 mmol, commercially available e.g. from Aldrich) and N,N-diisopropylethylamine (0.0235 ml, 0.13 mmol) and heated at 60° C. for 16 hours. The solvent was evaporated and the residue purified by mass directed preparative HPLC (Method A). Fractions containing product were pooled and evaporated to give the title compound (33 mg). LCMS showed MH$^+$=622; T$_{RET}$=2.21 min.

Example 30

N-{[1,6-diethyl-4-(tetrahydro-2H-pyran-4-ylamino)-1H-pyrazolo[3,4-b]pyridin-5-yl]methyl}-2-({8-[(2-hydroxyethyl)(methyl)amino]octanoyl}amino)benzamide

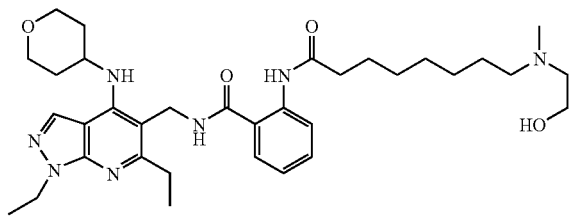

A solution of 2-[(8-bromooctanoyl)amino]-N-{[1,6-diethyl-4-(tetrahydro-2H-pyran-4-ylamino)-1H-pyrazolo[3,4-b]pyridin-5-yl]methyl}benzamide (68 mg, 0.11 mmol, e.g. which can be as prepared in Intermediate 46) in N,N-dimethylformamide (5 ml) was treated with 2-(methylamino)ethanol (0.0175 ml, 0.22 mmol, commercially available e.g. from Aldrich) and N,N-diisopropylethylamine (0.038 ml, 0.22 mmol) and heated at 60° C. for 16 hours. The solvent was evaporated and the residue purified by mass directed preparative HPLC (Method A). Fractions containing product were pooled and evaporated to give the title compound (5 mg). LCMS showed MH$^+$=622; T$_{RET}$=2.15 min.

Examples 31 to 34

Example 31

N-{[1,6-diethyl-4-(tetrahydro-2H-pyran-4-ylamino)-1H-pyrazolo[3,4-b]pyridin-5-yl]methyl}-4-({6-[(2-hydroxyethyl)(methyl)amino]hexanoyl}amino)benzamide

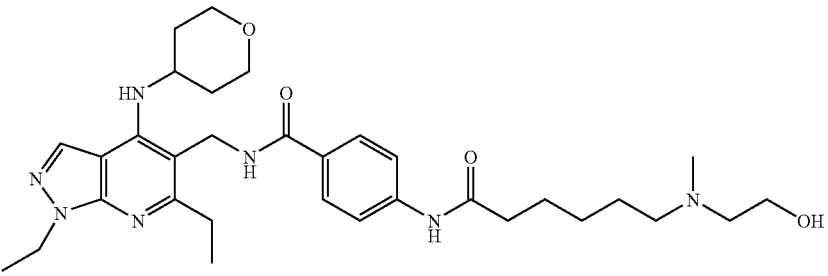

To a solution of 4-[(6-bromohexanoyl)amino]-N-{[1,6-diethyl-4-(tetrahydro-2H-pyran-4-ylamino)-1H-pyrazolo[3,4-b]pyridin-5-yl]methyl}benzamide (74 mg, 0.12 mmol, e.g. which can be as prepared in Intermediate 49) in N,N-dimethylformamide (3 ml) was added 2-methylamino)ethanol (0.019 ml, 0.24 mmol, commercially available e.g. from Aldrich) and N,N-diisopropylethylamine (0.042 ml, 0.24 mmol), and the mixture was heated at 85° C. with stirring for 3 hours. On cooling the solvent was removed by evaporation and the residue purified by mass directed preparative HPLC (Method A) to give a yellow gum (50 mg). This gum was dissolved in dichloromethane (5 ml) and washed with saturated aqueous sodium bicarbonate solution (3 ml), and the organic phase was isolated by passing through a hydrophobic frit. The aqueous phase was further extracted with dichloromethane (3 ml), and the combined organic phases evaporated to give the title compound as a white residue (33 mg). LCMS showed MH$^+$=594; T$_{RET}$=2.02 min.

Examples 32 to 34 were prepared in a generally similar manner:

| Example number | Starting material can e.g. be as prepared in: | n | M$^+$ ion | T$_{RET}$(min) |
|---|---|---|---|---|
| 32 | Intermediate 50 | n = 6 | 608 | 2.12 |
| 33 | Intermediate 51 | n = 9 | 650 | 2.32 |
| 34 | Intermediate 52 | n = 10 | 664 | 2.40 |

INTRANASAL COMPOSITION EXAMPLE

The following solution, a pharmaceutical composition intended for intranasal administration to a mammal, such as a human or dog or rat or monkey, (and/or for intranasal delivery of the active drug substance), may be prepared.

A 1% w/w aqueous solution for intranasal administration is as follows:

| | Quantity mg/g | % w/w |
|---|---|---|
| N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino) benzamide monohydrochloride (e.g. this can e.g. be as prepared in Example 1A2, or in Example 1A2 alternative preparation no. 1), Micronized Active Drug Substance | 10 mg | 1 |
| Xylitol, EP and/or USP and/or JP (used as an isotonicity adjusting agent) Not Animal Origin | 45 mg | 4.5 |
| Xanthan Gum, EP and/or USP (used as thickening agent) Not Animal Origin, Powder | 2 mg | 0.2 |
| Potassium Sorbate, EP and/or USP Not Animal Origin | 3 mg | 0.3 |
| Edetate Disodium, Dihydrate (EDTA), EP and/or USP And/or JP, Not Animal Origin, Crystalline Powder | 0.15 mg | 0.015 |
| Sodium Citrate, Dihydrate, USP Not Animal Origin, Crystalline Powder | 11.8 mg | 1.18 |
| Citric Acid Anhydrous, EP and/or USP Not Animal Origin, Granular Powder | 7.6 mg | 0.76 |
| Water for Injection BP, 100 Percent PL08828/0047, 1000 ml | to 1 g | to 100 |

METHOD OF MANUFACTURE

1. To prepare the 4.5 pH Citrate Buffer solution: Dissolve Sodium Citrate in the minimum amount of water, heat if necessary to 50-60° C. to aid dissolution. Dissolve the Citric Acid in the minimum amount of water, heat if necessary to 50-60° C. to aid dissolution. Pour the Sodium Citrate and Citric Acid into a beaker and make up to 50% of the target mass of water required to make the bulk solution.
2. Divide the Citrate Buffer solution from step 1 into two halves (pour equal quantities into two separate beakers).
3. To one half of the prepared Citrate Buffer solution (prepared in step 1) add the N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride micronized active drug substance, heat if necessary to 50-60° C. to aid dissolution, and dissolve with the aid of a stirrer.
4. In a separate beaker, add the Xylitol to approximately 20% of the target mass of water and mix until dissolved at 3000 rpm using a Silverson mixer.
5. Add the Xanthan Gum to the Xylitol solution and mix at 3000 rpm until dissolved.
6. Dissolve the Edetate Disodium Dihydrate (EDTA) in the minimum quantity of water. Heat to 50-60° C. to aid dissolution if required and add to the bulk, mixing at 3000 rpm.
7. Gradually add the remaining Citrate Buffer solution (prepared in step 1) to the Xylitol, Xanthan Gum, and EDTA solution.
8. Gradually incorporate the N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide monohydrochloride previously dissolved in the Citrate Buffer solution (prepared in step 3), to the solution (prepared in step 7) and mix for a further 3 mins.
9. Dissolve the Potassium Sorbate in the minimum quantity of water and add to the bulk, and mix for a further 3 mins.
10. Add water to make up to the target mass solution and mix at 4200 rpm for 5 mins.

This formulation is preferably be stored under a nitrogen headspace (and/or stored at about 5° C.).

Alternative variations of this intranasal composition example include the following:

1. Add polysorbate 80 (polyoxyethylene 20 sorbitan monooleate, e.g. about 1% to about 5% w/w) as a solubilising agent, in order to reduce the amount of precipitation of, and/or to slow down the rate of precipitation of, the drug substance from solution.

and/or

2. Vary the concentration of the active drug substance used within the range of 0.05% w/w to 1% w/w, for example about 0.5% w/w.

The invention claimed is:

1. N-{[1,6-diethyl-4-(tetrahydro-2H-pyran-4-ylamino)-1H-pyrazolo [3,4-b]pyridin-5-yl]methyl}-4-({8-[(2-hydroxyethyl)(methyl)amino]octanoyl}amino)benzamide, whose formula is

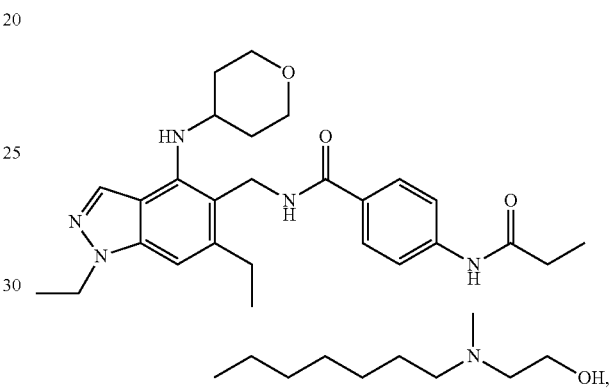

or a pharmaceutically acceptable salt thereof.

2. A compound or salt as claimed in claim 1, wherein the compound or salt is N-{[1,6-diethyl-4-(tetrahydro-2H-pyran-4-ylamino)-1H-pyrazolo[3,4-b]pyridin-5-yl ]methyl}-4-({8-[(2-hydroxyethyl)(methyl)amino]octanoyl}amino)benzamide or a hydrochloride, hydrobromide, or succinate salt thereof.

3. A hydrochloride salt of N-{[1,6-diethyl-4-(tetrahydro-2H-pyran-4-ylamino)-1H-pyrazolo[3,4-b]pyridin-5-yl]methyl-4-({8-[(2-hydroxyethyl)(methyl)amino]-octanoyl } amino)benzamide.

4. N-{[1,6-Diethyl-4-(tetrahydro-2H-pyran-4-ylamino)-1H-pyrazolo[3,4- b]pyridin-5-yl]methyl}-4-({8-[(2-hydroxyethyl)(methyl)amino]octanoyl}amino)-benzamide monohydrochloride.

5. A phosphate, fumarate, 1-hydroxy-2-naphthoate (xinafoate), or (+)-camphorsulfonate salt of N-{[1,6-diethyl-4-(tetrahydro-2H-pyran-4-ylamino)-1H-pyrazolo[3,4-b ]pyridin-5-yl]methyl}-4-({8-[(2-hydroxyethyl)(methyl)amino]octanoyl}amino)benzamide.

6. A pharmaceutical composition comprising a N-{[1,6-diethyl-4-(tetrahydro-2H-pyran-4-ylamino)-1H-pyrazolo[3,4-b]pyridin-5-yl]methyl1-4-({8-[(2-hydroxyethyl)(methyl)amino]octanoyl}amino)benzamide or a pharmaceutically acceptable salt thereof, and one or more pharmaceutically acceptable carriers and/or excipients.

7. A pharmaceutical composition as claimed in claim 6, comprising N-{[1,6-Diethyl-4-(tetrahydro-2H-pyran-4-ylamino)-1H-pyrazolo[3,4-b]pyridin-5-yl]methyl}-4-({8-[(2-hydroxyethyl)(methyl) amino]octanoyl}amino)benzamide monohydrochloride, and one or more pharmaceutically acceptable carriers and/or excipients.

8. A pharmaceutical composition as claimed in claim 6, comprising a phosphate, fumarate, 1-hydroxy-2-naphthoate (xinafoate), or (+)-camphorsulfonate salt of N-{[1,6-diethyl-4-(tetrahydro-2H-pyran-4-ylamino)-1H-pyrazolo[3,4-b]pyridin-5-yl]methyl}-4-({8-[(2-hydroxyethyl)(methyl)amino]octanoyl}amino)benzamide, and one or more pharmaceutically acceptable carriers and/or excipients.

* * * * *